United States Patent
Irlapati et al.

(10) Patent No.: US 9,725,463 B2
(45) Date of Patent: Aug. 8, 2017

(54) SUBSTITUTED HETEROCYCLIC COMPOUNDS AS CRAC MODULATORS

(71) Applicant: LUPIN LIMITED, Mumbai, Maharashtra (IN)

(72) Inventors: Nageswara Rao Irlapati, Maharashtra (IN); Nilesh Raghunath Khedkar, Maharashtra (IN); Ravindra Babanrao Jape, Maharashtra (IN); Rahul Shripad Nandurdikar, Maharashtra (IN); Zubair Abdul Wajid Shaikh, Maharashtra (IN); Neelima Sinha, Maharashtra (IN); Venkata P. Palle, Maharashtra (IN); Rajender Kumar Kamboj, Maharashtra (IN)

(73) Assignee: LUPIN LIMITED, Mumbai (IN)

( * ) Notice: Subject to any disclaimer, the term of this patent is extended or adjusted under 35 U.S.C. 154(b) by 0 days.

(21) Appl. No.: 14/899,719

(22) PCT Filed: Jun. 20, 2014

(86) PCT No.: PCT/IB2014/062482
§ 371 (c)(1),
(2) Date: Dec. 18, 2015

(87) PCT Pub. No.: WO2014/203217
PCT Pub. Date: Dec. 24, 2014

(65) Prior Publication Data
US 2016/0145268 A1    May 26, 2016

(30) Foreign Application Priority Data

Jun. 21, 2013 (IN) .......................... 2105/MUM/2013
Mar. 20, 2014 (IN) ............................ 917/MUM/2014

(51) Int. Cl.
| C07D 498/04 | (2006.01) |
| C07D 263/58 | (2006.01) |
| C07D 265/36 | (2006.01) |
| C07D 413/04 | (2006.01) |
| C07D 413/12 | (2006.01) |
| C07D 413/14 | (2006.01) |
| C07D 417/04 | (2006.01) |
| A61K 31/5377 | (2006.01) |

(52) U.S. Cl.
CPC ........ C07D 498/04 (2013.01); A61K 31/5377 (2013.01); C07D 263/58 (2013.01); C07D 265/36 (2013.01); C07D 413/04 (2013.01); C07D 413/12 (2013.01); C07D 413/14 (2013.01); C07D 417/04 (2013.01)

(58) Field of Classification Search
CPC .. C07D 498/04; C07D 263/58; C07D 265/36; C07D 413/04; C07D 413/12; C07D 413/14; C07D 417/04; A61K 31/5377
See application file for complete search history.

(56) References Cited

U.S. PATENT DOCUMENTS

| 2010/0152241 A1 | 6/2010 | Whitten |
| 2011/0082165 A1 | 4/2011 | Ellsworth et al. |
| 2012/0088764 A1 | 4/2012 | Cai et al. |
| 2014/0249306 A1 | 9/2014 | Iwaki et al. |
| 2014/0336376 A1 | 11/2014 | Nakagawa et al. |

FOREIGN PATENT DOCUMENTS

| GB | 2497806 A | 6/2013 |
| WO | 2005009539 A2 | 2/2005 |
| WO | 2005009954 A2 | 2/2005 |
| WO | 2006034402 A2 | 3/2006 |
| WO | 2006061379 A1 | 6/2006 |
| WO | 2006/081391 A2 | 8/2006 |
| WO | 2006081389 A1 | 8/2006 |
| WO | 2006083477 A2 | 8/2006 |
| WO | 2007/042906 A1 | 4/2007 |
| WO | 2007/087441 A2 | 8/2007 |
| WO | 2007087429 A2 | 8/2007 |

(Continued)

OTHER PUBLICATIONS

International Search Report and Written Opinion for corresponding International Patent Application No. PCT/IB2014/062482 (mailed Sep. 26, 2014).
Fabien Vanden Abeele et al.: "Bcl-2-dependent modulation of Ca2+ homeostasis and store-operated channels in prostate cancer cells", Cancer Cell, vol. 1, Mar. 1, 2002, pp. 169-179.
Attila Braun et al.: "Orai1 (CRACM1) is the platelet SOC channel and essential for pathological thrombus formation", Blood, vol. 113, No. 9, Feb. 26, 2009, pp. 2056-2063.
Antonio Di Sabatino et al.: "Targeting Gut T Cell Ca2+ Release-Activated Ca2+ Channels Inhibits T Cell Cytokine Production and T-Box Transcription Factor T-Bet in Inflammatory Bowel Disease", The Journal of Immunology, vol. 183, Jul. 31, 2009, pp. 3454-3462.
Marc Fahrner et al.: "Mechanistic View on Domains Mediating STIM1-Orai Coupling", Immunological Reviews, vol. 231, Issue 1, Sep. 10, 2009, pp. 99-112.

(Continued)

*Primary Examiner* — Rebecca Anderson
(74) *Attorney, Agent, or Firm* — Merchant & Gould P.C.

(57) ABSTRACT

The invention relates to compounds of Formula (I) and their pharmaceutically acceptable salts, wherein the substituents are as described herein, and their use in medicine for the treatment of diseases, disorders associated with the modulation of calcium release-activated calcium (CRAC) channel. The invention also relates to pharmaceutical compositions containing such compounds in treating diseases disorders associated with calcium release-activated calcium (CRAC) channel modulators. wherein, ring D is Formula (a) or Formula (b): A and B, which may be same or different, are independently $CR_3$ or N; Y is $CR_3$ or N; L is selected from —$NR_2C(O)$—, —$C(O)NR_2$— and —$NR_2CR_aR_b$—; $R_a$ and $R_b$ are independently hydrogen, halogen or substituted or unsubstituted alkyl; ring E is selected from the Formula (i) to (vii).

19 Claims, No Drawings

(56) References Cited

FOREIGN PATENT DOCUMENTS

| | | | |
|---|---|---|---|
| WO | 2007087442 | A2 | 8/2007 |
| WO | 2007089904 | A2 | 8/2007 |
| WO | 2009017819 | A1 | 2/2009 |
| WO | 2009035818 | A1 | 3/2009 |
| WO | 2009062285 | A1 | 5/2009 |
| WO | 2009076454 | A2 | 6/2009 |
| WO | 2010025295 | A2 | 3/2010 |
| WO | 2010027875 | A2 | 3/2010 |
| WO | 2010039238 | A1 | 4/2010 |
| WO | 2010128324 | A1 | 11/2010 |
| WO | 2010130794 | A1 | 11/2010 |
| WO | 2011034962 | A2 | 3/2011 |
| WO | 2011048112 | A1 | 4/2011 |
| WO | 2011151434 | A1 | 12/2011 |
| WO | 2012/028629 | A1 | 3/2012 |
| WO | 2012/056478 | A | 5/2012 |
| WO | 2012/151355 | A1 | 11/2012 |
| WO | 2012/170931 | A2 | 12/2012 |
| WO | 2013059666 | A1 | 4/2013 |
| WO | 2013059677 | A1 | 4/2013 |
| WO | 2013/062028 | A1 | 5/2013 |
| WO | 2013065835 | A1 | 5/2013 |
| WO | 2013164769 | A1 | 11/2013 |
| WO | 2014059333 | A1 | 4/2014 |

OTHER PUBLICATIONS

Karen Gilio et al.: "Roles of Platelet STIM1 and Orai1 in Glycoprotein VI- and Thrombin-dependent Procoagulant Activity and Thrombus Formation", Journal of Biological Chemistry, vol. 285, No. 31, Jul. 30, 2010, pp. 23629-23638.

Rajender K. Motiani et al.: "A Novel Native Store-operated Calcium Channel Encoded by Orai3", The Journal of Biological Chemistry, vol. 285, No. 25, Jun. 18, 2010, pp. 19173-19181.

Anant B. Parekh: "Store-operated CRAC channels: function in health and disease", Nature Reviews, Drug Discovery, vol. 9, May 1, 2010, 399-410 pages.

Anant B. Parekh et al.: "Store-Operated Calcium Channels", Physiological Reviews, vol. 85, Issue 2, Apr. 1, 2005, pp. 757-810.

David Varga-Szabo et al.: "The calcium sensor STIM1 is an essential mediator of arterial thrombosis and ischemic brain infarction", The Journal of Experimental Medicine, vol. 205, No. 7, Jun. 16, 2008, pp. 1583-1591.

Peter G. M. Wuts et al: "Greene's Protective Group in Organic Synthesis", Fourth Edition, John Wiley & Sons, Inc., 2007, 1112 pages.

Shengyu Yang et al.: "Orai1 and STIM1 are Critical for Breast Tumor Cell Migration and Metastasis", Cancer Cell, vol. 15, Feb. 3, 2009, pp. 124-134.

International Search Report from International Patent Application No. PCT/IB2014/062538, mailed Sep. 10, 2014.

Brynmor Jones et al.: "The Halogenation of Phenolic Ethers and Anilides. Part XVII.* An Investigation Into the Additive Effects of Substituents in Benzyl Phenyl Ethers", 1955, pp. 2772-2775.

Yoshikazu Uto et al.: "Synthesis and Evaluation of Novel Stearoyl-CoA Desaturase 1 Inhibitors: 1'-}6-[5-(pyridin-3-ylmethyl)-1,3,4-oxadiazol-2-yl]pyridazin-3-yl}-3, 4-dihydrospiro[chromene-2,4'-piperidine] Analogs", European Journal of Medicinal Chemistry, vol. 45, Issue 11, Nov. 2010, pp. 4788-4796.

SUBSTITUTED HETEROCYCLIC COMPOUNDS AS CRAC MODULATORS

RELATED APPLICATIONS

The present application is a National Stage Application of international Patent Application No. PCT/IB2014/062482, filed Jun. 20, 2014, which claims benefit of Indian Provisional Patent Application Nos. 2105/MUM/2013, filed on Jun. 21, 2013 and 917/MUM/2014, filed on Mar. 20, 2014 and which applications are incorporated herein by reference. To the extent appropriate, a claim of priority is made to each of the above disclosed applications.

TECHNICAL FIELD OF THE INVENTION

The invention relates to substituted heterocyclic compounds, pharmaceutically acceptable salts thereof and pharmaceutical compositions for the treatment, management, and/or lessening of severity of diseases, disorders, syndromes or conditions associated with the modulation of calcium release-activated calcium (CRAC) channel. The invention also relates to methods of treating, managing and/or lessening the severity of the diseases disorders, syndromes or conditions associated with the modulation of CRAC. The invention also relates to processes for the preparation of the compounds of the invention.

BACKGROUND OF THE INVENTION

Inflammation is the response by the body to infection, irritation or injury; wherein the immune cells of the body are activated in response to any of these stimuli. Inflammation plays a key role in many diseases not only of the immune cells such as allergy, asthma, arthritis, dermatitis, multiple sclerosis, systemic lupus but also organ transplant, diabetes, cardiovascular disease, Alzheimer's disease, Parkinson's disease, inflammatory and/or irritable bowel syndrome (Di Sabatino et. al., J. Immunol., 183, 3454-3462, 2009), psoriasis, and cancer. An initial inflammatory response to pathogens or injury is necessary and required to fight infection or heal the wound, but sustained or persistent inflammation can lead to any of the chronic disorders; characterized by the production of inflammatory cytokines as, specified above.

Inflammation is characterized by the production of different cytokines such as IL-2, IL-4, IL-10, IL-13, IL-17, IL-21, IL-23, IL-28, IFN-γ, TNF-α, etc., that have been implicated in playing a role in different diseases. Any drug which can modulate the production of these cytokines would help to alleviate the disease symptoms and may also cure it.

$Ca^{+2}$ signals have been shown to be essential for diverse cellular functions in different cell types including differentiation, effector functions, and gene transcription in cells of the immune system as well as regulating the cytokine signaling pathway through calcineurin and nuclear factor of activated T cells (NFAT).

In immune cells, sustained $Ca^{+2}$ influx has been shown to be necessary for complete and long-lasting activation of calcineurin-NFAT pathways, essential for cytokine production. Engagement of receptors such as T-cell antigen receptor (TCR), the B-cell antigen receptor (BCR), and the Fc receptors (FcR) on mast cells, macrophages, and NK cells, leads to the tyrosine phosphorylation and activation of phospholipase C-γ (PLC-γ). PLC-γ hydrolyzes phosphatidylinositol-3,4-biphosphate ($PIP_2$) to the second messengers, inositol-1,4,5-triphosphate ($IP_3$) and diacylglycerol (DAG). $IP_3$ binds to $IP_3$ receptors ($IP_3R$) in the membrane of the endoplasmic reticulum (ER) and induces the release of ER $Ca^{+2}$ stores into the cytoplasma. The decrease in the $Ca^{+2}$ concentration in the ER induces store-operated $Ca^{+2}$ entry (SOCE) through plasma membrane $Ca^{+2}$ channels. SOCE through highly $Ca^{+2}$-selective $Ca^{+2}$ release-activated $Ca^{+2}$ (hereinafter, CRAC) channels constitutes the major pathway of intracellular $Ca^{+2}$ entry in T cells, B cells, macrophages, mast cells, and other cell types (Parekh and Putney, Physiol. Rev., 85, 757-810, 2005).

The CRAC channel is comprised of two family proteins, one which functions in sensing $Ca^{+2}$ levels in the ER—the stromal interacting molecules (STIM)-1 and -2 and the other which is a pore-forming protein—Orai1, 2 and 3. The STIM proteins are single transmembrane proteins localized on the ER membrane with their N-termini oriented toward the lumen and containing an EF-hand $Ca^{+2}$ binding motif. Depletion of $Ca^{+2}$ from the ER causes $Ca^{+2}$ to dissociate from STIM, which causes a conformational change that promotes oligomerization and migration of STIM molecules to closely apposed ER-plasma membrane junctions. At the junctions, the STIM oligomers interact with the Orai proteins. In resting cells, Orai channels are dispersed across the plasma membrane and on depletion of $Ca^{+2}$ from the stores, they aggregate in the vicinity of the STIM punctae. The eventual increase in intracellular $Ca^{+2}$ concentration activates the calcineurin-NFAT pathway. NFAT activates transcription of several genes including cytokine genes such as IL-2, etc along with other transcription factors such as AP-1, NFκB and Foxp3 (Fahmer et. al., Immuno. Rev., 231, 99-112, 2009).

The role of CRAC channel in different diseases such as allergy, inflammatory bowel disease, thrombosis and breast cancer has been reported in literature (Parekh, Nat. Rev., 9, 399-410, 2010). It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai1 proteins potential targets for cancer therapy (Yang et. al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

Recent literature reports the role of STIM1 and Orai1 in collagen dependent arterial thrombosis in mice in vivo and that deficiency in either protects against collagen dependent arterial thrombus formation as well as brain infarction (Varga-Szabo et. al., J. Exp. Med., 205, 1583-1591, 2008; Braun et. al., Blood, 113, 2056-2063, 2009). The role of STIM1-Orai1 mediated SOCE in thrombus formation makes Orai1 a potential target for treatment of thrombosis and related conditions (Gillo et. al., JBC, 285; 31, 23629-23638, 2010).

As the Orai pore channel proteins have been shown to be essential for transmitting the signal induced by the binding of antigens to the cellular receptors on the immune cells, a potential Orai channel interacting drug would be able to modulate the signaling thereby impacting the secretion of the cytokines involved in, as mentioned herein before, inflammatory conditions, cancer, allergic disorders, immune disorders, rheumatoid arthritis, cardiovascular diseases, thrombocytopathies, arterial and/or venous thrombosis and associated or related conditions which can be benefitted by the CRAC channel modulatory properties of the compounds described herein.

Several compounds have been reported in the art as CRAC channel modulators. For Example, patent application publications WO2005009539, WO2005009954, WO2006081391, WO2006081389, WO2006034402, WO2006083477, WO2007087441, WO2007087442, WO2007087429, WO2007089904, WO2009017819, WO2009076454, WO2009035818, US20100152241, WO2010039238, WO2010025295, WO2010027875, WO2011034962, WO2012151355, WO2013059666, WO2013059677, WO2013164769, WO2014059333 disclose the compounds for modulating CRAC channels.

SUMMARY OF THE INVENTION

In accordance with one aspect, the invention provides the compounds of Formula (I):

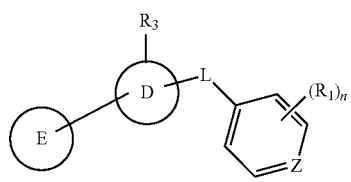

(I)

wherein,
ring D is Formula (a) or Formula (b):

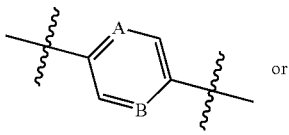

(a)

or

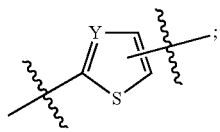

(b)

A and B, which may be same or different, are independently $CR_3$ or N;
Y is $CR_3$ or N;
L is selected from $-NR_2C(O)-$, $-C(O)NR_2-$ and $-NR_2CR_aR_b-$;
$R_a$ and $R_b$ are independently hydrogen, halogen or substituted or unsubstituted alkyl;
ring E is selected from the Formula (i) to (vii):

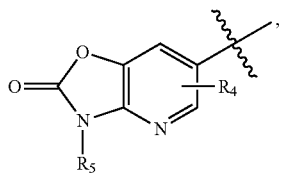

(i)

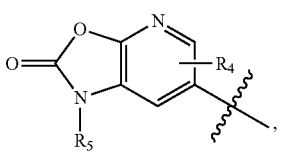

(ii)

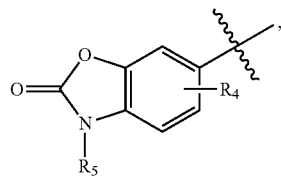

(iii)

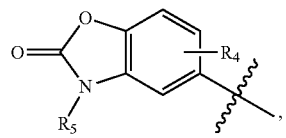

(iv)

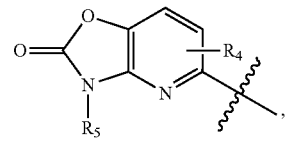

(v)

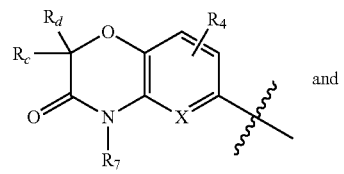

(vi)

and

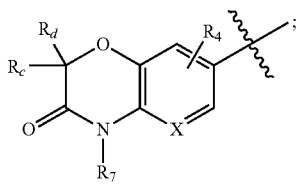

(vii)

X is N or $CR_4$;
Z is N or CR where R is selected from hydrogen, halogen or substituted or unsubstituted alkyl;
$R_1$, which may be same or different at each occurrence, is independently selected from halogen, cyano, nitro, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl and substituted or unsubstituted cycloalkoxy;
$R_2$ is hydrogen or substituted or unsubstituted alkyl;
$R_3$ is independently selected from hydrogen, halogen, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl and $-C(O)OR_6$;
$R_4$, which may be same or different at each occurrence, is independently selected from hydrogen, halogen, cyano, nitro, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl, substituted or unsubstituted cycloalkoxy, $-NR_8R_9$, $-COOR_6$ and $CONH_2$;
$R_5$ is selected from substituted or unsubstituted alkyl, substituted or unsubstituted haloalkyl, substituted or unsubstituted hydroxyalkyl, substituted or unsubstituted alkoxyalkyl, substituted or unsubstituted cycloalkyl and substituted or unsubstituted cycloalkylalkyl;

$R_6$ is a hydrogen or substituted or unsubstituted alkyl;

$R_7$ is selected from hydrogen, substituted or unsubstituted alkyl, substituted or unsubstituted haloalkyl, substituted or unsubstituted hydroxyalkyl, substituted or unsubstituted alkoxyalkyl, substituted or unsubstituted cycloalkyl, and substituted or unsubstituted cycloalkylalkyl;

$R_8$ and $R_9$ are independently selected from hydrogen, substituted or unsubstituted alkyl, substituted or unsubstituted haloalkyl, and substituted or unsubstituted cycloalkyl;

$R_c$, and $R_d$ are independently selected from hydrogen or substituted or unsubstituted alkyl, substituted or unsubstituted cycloalkylalkyl, substituted or unsubstituted hydroxyalkyl, and substituted or unsubstituted alkoxyalkyl; and 'n' is an integer ranging from 0 to 4, both inclusive;

or a pharmaceutically acceptable salt thereof.

According to one embodiment, there are provided compounds having the structure of Formula (II):

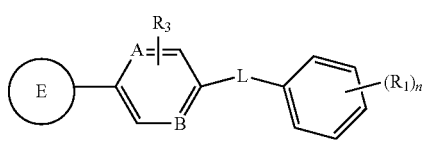
(II)

wherein,

A and B, which may be same or different, are independently $CR_3$ or N, wherein $R_3$ is selected from hydrogen, halogen and substituted or unsubstituted alkyl;

L is selected from —NHC(O)—, —C(O)NH— and —NHCH$_2$—;

ring E is selected from the Formula (i) to (v):

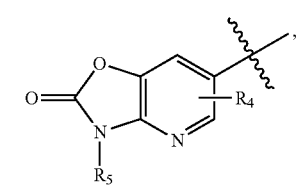
(i)

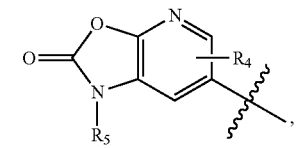
(ii)

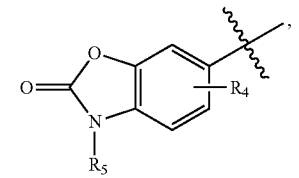
(iii)

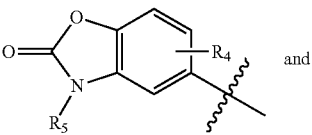
(iv)

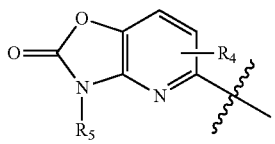
(v)

$R_1$, which may be same or different at each occurrence, is independently selected from halogen, substituted or unsubstituted alkyl and substituted or unsubstituted haloalkyl;

$R_3$ is selected from hydrogen, halogen, or substituted or unsubstituted alkyl;

$R_4$ is selected from hydrogen, halogen, substituted or unsubstituted alkyl and substituted or unsubstituted cycloalkyl;

$R_5$ is selected from substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl; and 'n' is an integer ranging from 1 to 2, both inclusive;

or a pharmaceutically acceptable salt thereof.

According to one embodiment, there are provided compounds having the structure of Formula (III):

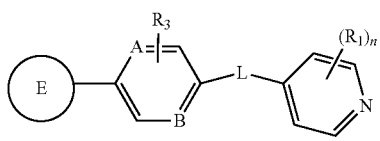
(III)

wherein,

A and B, which may be same or different, are independently $CR_3$ or N, where $R_3$ is selected from hydrogen, halogen and substituted or unsubstituted alkyl;

L is selected from —NHC(O)—, —C(O)NH— and —NHCH$_2$—;

ring E is selected from the Formula (i) to (v):

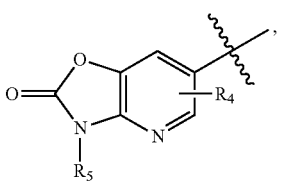
(i)

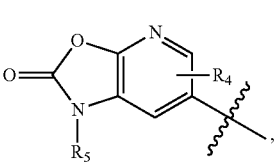
(ii)

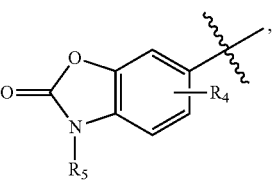
(iii)

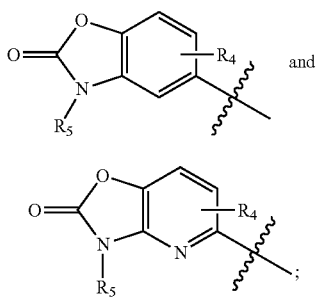

R₁, which may be same or different at each occurrence, is independently selected from halogen, substituted or unsubstituted alkyl and substituted or unsubstituted haloalkyl;

R₃ is selected from hydrogen, halogen and substituted or unsubstituted alkyl;

R₄ is selected from hydrogen, halogen, substituted or unsubstituted alkyl and substituted or unsubstituted cycloalkyl;

R₅ is selected from substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl; and 'n' is an integer ranging from 1 to 2, both inclusive; or a pharmaceutically acceptable salt thereof.

According to another embodiment, there are provided compounds having the structure of Formula (II):

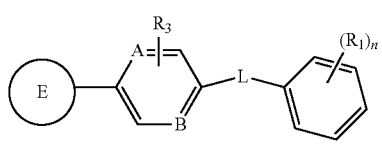

wherein,

A and B, which may be same or different, are independently CR₃ or N, where R₃ is selected from hydrogen, halogen and substituted or unsubstituted alkyl;

L is selected from —NHC(O)—, —C(O)NH— and —NHCH₂—;

ring E is Formula (vi) or (vii):

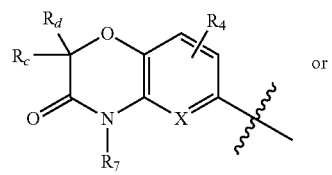

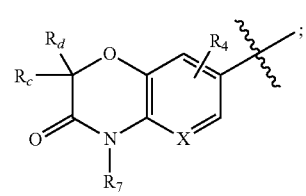

X is N or CR₄ where R₄ is selected from hydrogen, halogen, substituted or unsubstituted alkyl, and substituted or unsubstituted cycloalkyl;

R₁, which may be same or different at each occurrence, is independently selected from halogen, substituted or unsubstituted alkyl and substituted or unsubstituted haloalkyl;

R₃ is selected from hydrogen, halogen and substituted or unsubstituted alkyl;

R₄, which may be same or different at each occurrence, is independently selected from hydrogen, halogen, substituted or unsubstituted alkyl and substituted or unsubstituted cycloalkyl;

R₇ is selected from hydrogen, substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl;

$R_c$, and $R_d$ are hydrogen or substituted or unsubstituted alkyl; and

'n' is an integer ranging from 1 to 2, both inclusive; or a pharmaceutically acceptable salt thereof.

According to another embodiment, there are provided compounds having the structure of Formula (III):

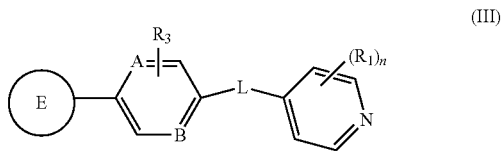

wherein,

A and B, which may be same or different, are independently CR₃ or N, where R₃ is selected from hydrogen, halogen or substituted or unsubstituted alkyl;

L is selected from —NHC(O)—, —C(O)NH— and —NHCH₂—;

ring E is Formula (vi) or (vii):

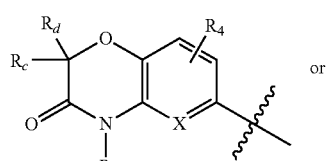

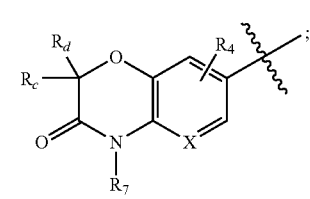

X is N or CR₄ where R₄ is selected from hydrogen, halogen, substituted or unsubstituted alkyl, and substituted or unsubstituted cycloalkyl;

R₁, which may be same or different at each occurrence, is independently selected from halogen, substituted or unsubstituted alkyl and substituted or unsubstituted haloalkyl;

R$_3$ is selected from hydrogen, halogen and substituted or unsubstituted alkyl;

R$_4$, which may be same or different at each occurrence, is independently selected from hydrogen, halogen, substituted or unsubstituted alkyl and substituted or unsubstituted cycloalkyl;

R$_7$ is selected from hydrogen, substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl;

R$_c$, and R$_d$ are hydrogen or substituted or unsubstituted alkyl; and

'n' is an integer ranging from 1 to 2, both inclusive;

or a pharmaceutically acceptable salt thereof.

According to another embodiment, there are provided compounds having the structure of Formula (IV):

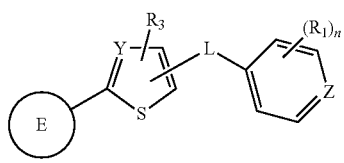

(IV)

wherein,

Y is CR$_3$ or N, where R$_3$ is selected from hydrogen, halogen and substituted or unsubstituted alkyl;

Z is CH or N;

L is —NHC(O)— or —C(O)NH—;

ring E is selected from the Formula (i) to (v):

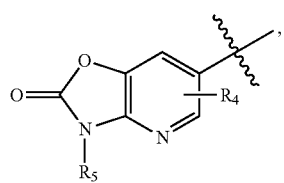

(i)

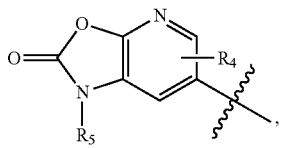

(ii)

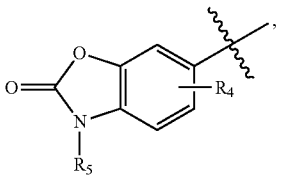

(iii)

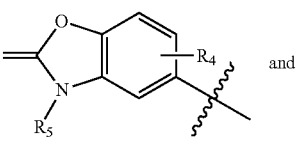

(iv)

and

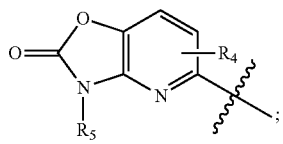

(v)

R$_1$, which may be same or different at each occurrence, is independently selected from halogen, substituted or unsubstituted alkyl and substituted or unsubstituted haloalkyl;

R$_3$ is selected from hydrogen, halogen and substituted or unsubstituted alkyl;

R$_4$ is selected from hydrogen, halogen, substituted or unsubstituted alkyl and substituted or unsubstituted cycloalkyl;

R$_5$ is selected from substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl; and 'n' is an integer ranging from 1 to 2, both inclusive;

or a pharmaceutically acceptable salt thereof.

It should be understood that the Formula (I), Formula (II), Formula (III) and Formula (IV) structurally encompasses all tautomers, stereoisomers, enantiomers and diastereomers, including isotopes wherever applicable and pharmaceutically acceptable salts that may be contemplated from the chemical structure of the genera described herein.

The details of one or more embodiments of the invention set forth in the below are illustrative in nature only and not intended to limit to the scope of the invention. Other features, objects and advantages of the inventions will be apparent from the description and claims.

According to another embodiment there are provided compounds of Formula (I) wherein L is selected from —NHC(O)—, —C(O)NH— and —NHCH$_2$—.

According to another embodiment there are provided compounds of Formula (I) wherein Z is N or CH;

According to another embodiment there are provided compounds of Formula (I) wherein ring D is selected from Formula (a) or Formula (b):

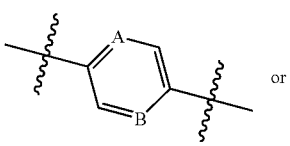

(a)

or

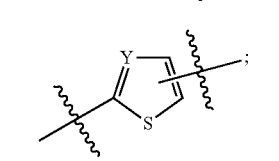

(b)

wherein A and B, which may be same or different, are independently CR$_3$ or N; Y is CR$_3$ or N; wherein each of R$_3$ is selected from hydrogen, halogen and substituted or unsubstituted alkyl.

According to another embodiment there are provided compounds of Formula (I) wherein ring E selected from the Formula (i) to (v):

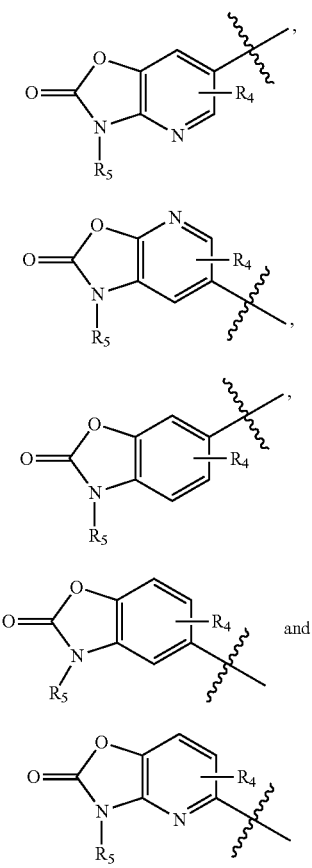

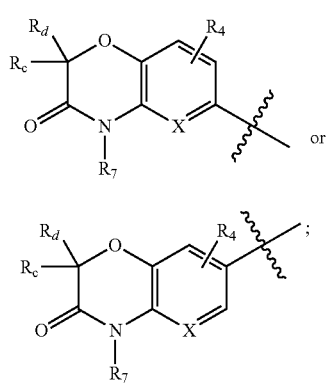

wherein $R_4$ is independently selected from hydrogen, halogen, substituted or unsubstituted alkyl, substituted or unsubstituted haloalkyl, and substituted or unsubstituted cycloalkyl; $R_5$ is selected from substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl.

According to another embodiment there are provided compounds of Formula (I) wherein ring E is Formula (vi) or (vii):

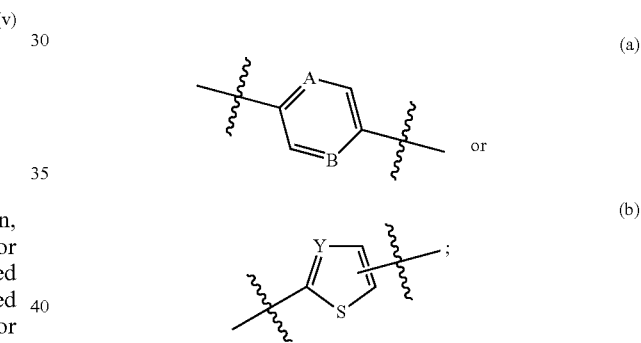

wherein X is N or $CR_4$ where $R_4$ is hydrogen, halogen or substituted or unsubstituted alkyl; $R_c$ and $R_d$ are hydrogen or substituted or unsubstituted alkyl; $R_4$ is selected from hydrogen, halogen, substituted or unsubstituted alkyl, substituted or unsubstituted haloalkyl, and substituted or unsubstituted cycloalkyl; and $R_7$ is selected from hydrogen, substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl.

According to another embodiment there are provided compounds of Formula (I)

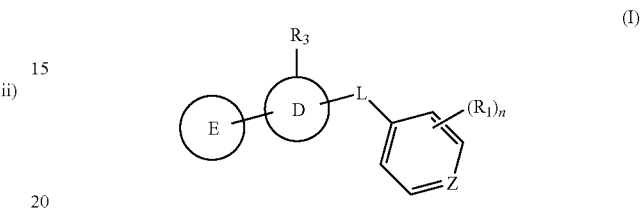

or a pharmaceutically acceptable salt thereof;

wherein L is selected from —NHC(O)—, —C(O)NH— and —NHCH$_2$—; Z is N or CH; $R_1$ is halogen or substituted or unsubstituted alkyl; 'n' is 1 or 2; ring D is Formula (a) or Formula (b):

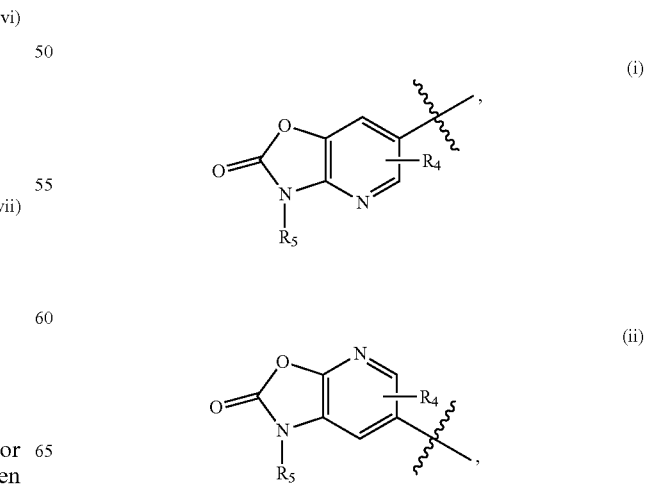

A and B are independently $CR_3$ or N; Y is $CR_3$ or N; each of $R_3$ is independently hydrogen, substituted or unsubstituted alkyl; and ring E is selected from (i) to (v)

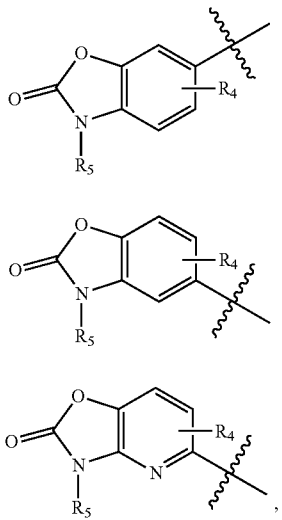

(iii)

(iv)

(v)

R₄ is selected from hydrogen, substituted or unsubstituted alkyl and substituted or unsubstituted cycloalkyl; R₅ is selected from substituted or unsubstituted alkyl, substituted or unsubstituted haloalkyl, substituted or unsubstituted hydroxyalkyl and substituted or unsubstituted cycloalkylalkyl.

According to another embodiment there are provided compounds of Formula (I)

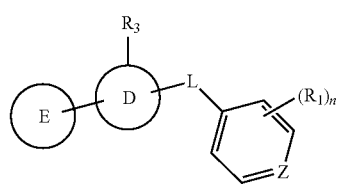

(I)

wherein L is selected from —NHC(O)—, —C(O)NH— and —NHCH₂—; Z is N or CH; each of R₁ is halogen or substituted or unsubstituted alkyl; 'n' is 1 or 2; ring D is Formula (a) or Formula (b):

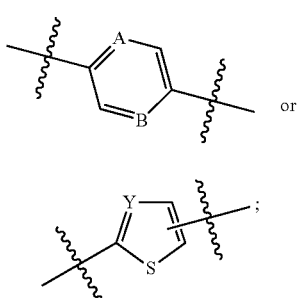

(a)

(b)

A and B are independently CR₃ or N; Y is CR₃ or N; each of R₃ is selected from hydrogen or substituted or unsubstituted alkyl; and ring E is (vi) or (vii)

(vi)

(vii)

X is N or CR₄; R₄ is selected from hydrogen, substituted or unsubstituted alkyl and substituted or unsubstituted cycloalkyl; R_c, and R_d are hydrogen or substituted or unsubstituted alkyl; and R₇ hydrogen, substituted or unsubstituted alkyl.

In another aspect, the invention provides a pharmaceutical composition comprising at least one compound of Formula (I) and at least one pharmaceutically acceptable excipient.

In another aspect of the invention, there is provided a compound of Formula (I) useful in treating, managing and/or lessening the severity of the diseases, disorders, syndromes or conditions associated with the modulation of CRAC channel.

In another aspect, the invention provides a pharmaceutical composition of a compound of Formula (I) useful in treating, managing and/or lessening the severity of the diseases disorders, syndromes or conditions associated with the modulation of CRAC channel in a subject in need thereof by administering to the subject, one or more compounds described herein in therapeutic effective amount.

In another aspect, the invention provides a method of modulating ion channel activity, for Example, CRAC channel, by administering effective amount of a compound of Formula (I) and/or pharmaceutically acceptable salts.

In another aspect, the invention provides a method of modulating the secretion of cytokines, for Example IL-2, IL-4, IL-10, IL-13, IL-17, IL-21, IL-23, IL-28, IFN-γ and TNF-α and the like, by regulating the cytokine signalling pathway through calcineurin and NFAT cells.

In another aspect, there are provided processes for the preparation compounds of Formula (I):

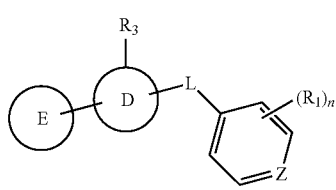

(I)

where ring D, ring E, L, Z, R₁, R₃, and 'n' are as described herein above;
the process comprising any of the method (A) to (D):
method (A):
reacting a borate compound of Formula (1) with various halobenzamides of Formula (2) where X' is halogen or OTf, to give compound of Formula (I) by using suitable reagents Pd(PPh$_3$)$_2$Cl$_2$, Pd$_2$dba$_3$, Pd(PPh$_3$)$_4$, or Pd(OAc)$_2$ and suitable ligand 2,2'-bis(diphenylphosphino)-1,1'-binaphthyl (BINAP), xanthophos, or triphenylphosphine

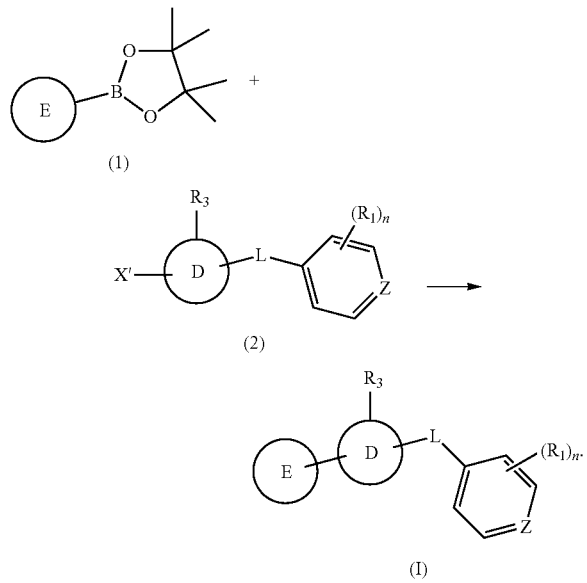

method (B)

reacting a compound of Formula (3) where X' is halogen or OTf, with compound of Formula (4) where P is pinacolatoboronate or stannane, to give compound of Formula (I) by using suitable reagents Pd(PPh$_3$)$_2$Cl$_2$, Pd$_2$dba$_3$, Pd(PPh$_3$)$_4$, or Pd(OAc)$_2$ and a suitable ligand 2,2'-bis(diphenylphosphino)-1,1'-binaphthyl (BINAP), xanthophos, or triphenylphosphine

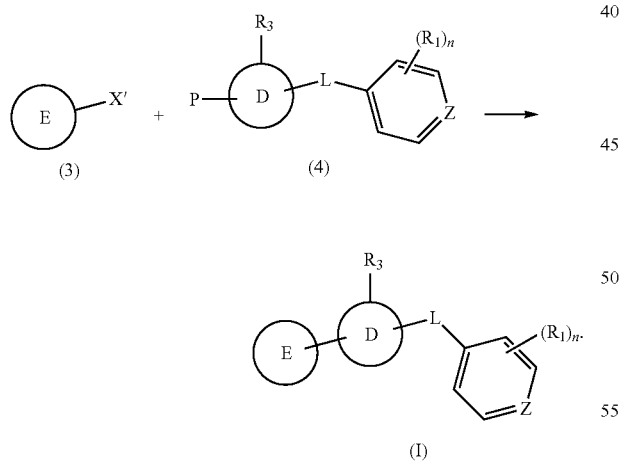

method (C), which comprises the steps of
a) reacting a borate derivative of Formula (1) with compound of Formula (5) where X' is halogen or OTf, and Y' is NHR$_2$, or COOH, COOalkyl or COCl, to give compound of Formula (7) by using suitable reagents Pd(PPh$_3$)$_2$Cl$_2$, Pd$_2$dba$_3$, Pd(PPh$_3$)$_4$, or Pd(OAc)$_2$ and suitable ligand 2,2'-bis(diphenylphosphino)-1,1'-binaphthyl (BINAP), xanthophos, or triphenylphosphine

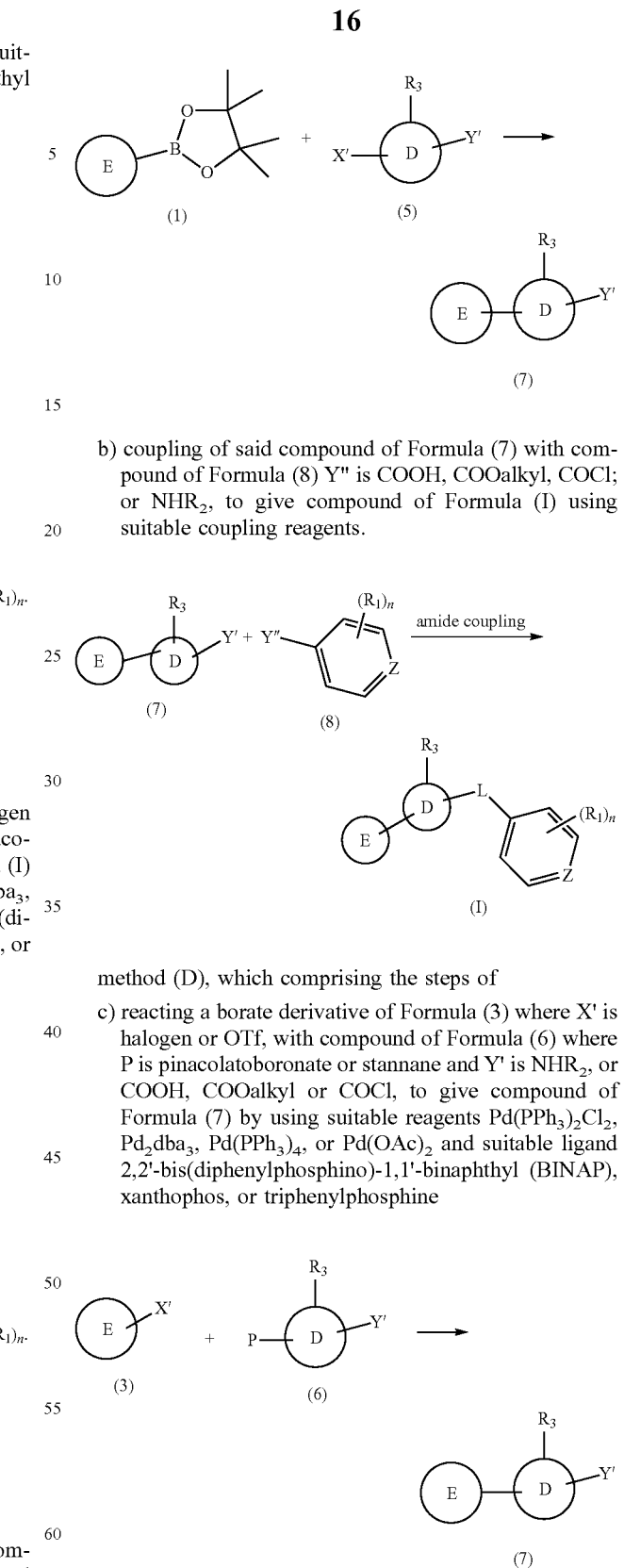

b) coupling of said compound of Formula (7) with compound of Formula (8) Y'' is COOH, COOalkyl, COCl; or NHR$_2$, to give compound of Formula (I) using suitable coupling reagents.

method (D), which comprises the steps of
c) reacting a borate derivative of Formula (3) where X' is halogen or OTf, with compound of Formula (6) where P is pinacolatoboronate or stannane and Y' is NHR$_2$, or COOH, COOalkyl or COCl, to give compound of Formula (7) by using suitable reagents Pd(PPh$_3$)$_2$Cl$_2$, Pd$_2$dba$_3$, Pd(PPh$_3$)$_4$, or Pd(OAc)$_2$ and suitable ligand 2,2'-bis(diphenylphosphino)-1,1'-binaphthyl (BINAP), xanthophos, or triphenylphosphine d) coupling of said compound of Formula (7) with compound of Formula (8) where Y'' is COOH, COOalkyl, COCl; or NHR$_2$, to give compound of Formula (I) using suitable coupling reagents

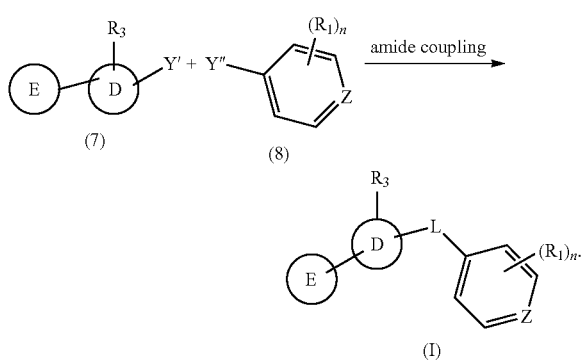

DETAILED DESCRIPTION OF THE INVENTION

Definitions and Abbreviations

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting Examples of alkenyl groups include ethenyl, 1-propenyl, 2-propenyl(allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting Examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting Examples of such groups are methoxy, ethoxy and propoxy and the like. Unless set forth or recited to the contrary, all alkoxy groups described or claimed herein may be straight chain or branched, substituted or unsubstituted.

The term "alkoxyalkyl" refers to an alkoxy group as defined above directly bonded to an alkyl group as defined above, e.g., —$CH_2$—O—$CH_3$, —$CH_2$—O—$CH_2CH_3$, —$CH_2CH_2$—O—$CH_3$ and the like. Unless set forth or recited to the contrary, all alkoxyalkyl groups described or claimed herein may be substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronapththyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkoxy" refers to an cycloalkyl, defined herein, group attached via an oxygen linkage. Non-limiting Examples of such groups are cyclopropoxy, cyclobutoxy, cyclopentoxy, cyclohexyloxy and the like. Unless set forth or recited to the contrary, all alkoxy groups described or claimed herein may be straight chain or branched, substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting Examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms.

The term "haloalkoxy" refers to an haloalkyl, defined herein, group attached via an oxygen linkage. Non-limiting Examples of such groups are monohaloalkoxy, dihaloalkoxy or polyhaloalkoxy including perhaloalkoxy. Unless set forth or recited to the contrary, all haloalkoxy groups described or claimed herein may be straight chain or branched, substituted or unsubstituted.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting Examples of a hydroxyalkyl include 2-hydroxyethyl, 3-hydroxypropyl, 2-hydroxypropyl, and the like.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —CH$_2$C$_6$H$_5$ and —C$_2$H$_4$C$_6$H$_5$. Unless set forth or recited to the contrary, all arylalkyl groups described or claimed herein may be substituted or unsubstituted.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ring systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —CF$_2$—, —C(O)—, —S(O)—, S(O)$_2$, —C(=N-alkyl)-, or —C(=N-cycloalkyl), etc. In addition heterocyclic ring may also be fused with aromatic ring. Non-limiting Examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisoquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached by any atom of the heterocyclic ring that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached by any atom of the heteroaryl ring that results in the creation of a stable structure. Non-limiting Examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$C(O)R$^y$, —NR$^x$C(S)R$^y$, —NR$^x$C(S)NR$^y$R$^z$, —S(O)$_2$NR$^x$R$^y$, —OR$^x$, —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, and —S(O)$_2$R$^x$; wherein R$^x$, R$^y$ and R$^z$ are independently selected from hydrogen, halogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl. The aforementioned "substituted" groups cannot be further substituted. For Example, when the substituent on "substituted alkyl" is "aryl" or "alkenyl", the aryl or alkenyl cannot be substituted aryl or substituted alkenyl, respectively.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "Tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of Formula (I).

The term "treating" or "treatment" of a state, disease, disorder, condition or syndrome includes: (a) delaying the appearance of clinical symptoms of the state, disease, disorder, condition or syndrome developing in a subject that may be afflicted with or predisposed to the state, disease, disorder, condition or syndrome but does not yet experience or display clinical or subclinical symptoms of the state, disease, disorder, condition or syndrome; (b) inhibiting the state, disease, disorder, condition or syndrome, i.e., arresting or reducing the development of the disease or at least one clinical or subclinical symptom thereof; c) lessening the severity of a disease disorder or condition or at least one of its clinical or subclinical symptoms thereof; and/or (d) relieving the disease, i.e., causing regression of the state, disorder or condition or at least one of its clinical or subclinical symptoms.

The term "modulate" or "modulating" or "modulation" refers to a decrease or inhibition in the amount, quality, or effect of a particular activity, function or molecule; by way of illustration that block or inhibit calcium release-activated calcium (CRAC) channel. Any such modulation, whether it be partial or complete inhibition is sometimes referred to herein as "blocking" and corresponding compounds as "blockers". For Example, the compounds of the invention are useful as modulators of the CRAC channel.

The term "subject" includes mammals, preferably humans and other animals, such as domestic animals; e.g., household pets including cats and dogs.

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

Unless otherwise stated, in the present application "protecting group" refers to the groups intended to protect an otherwise labile group, e.g., an amino group, a carboxy group and the like, under specific reaction conditions. Various protecting groups along with the methods of protection and deprotection are generally known to a person of ordinary skilled in the art. Incorporated herein in this regard as reference is *Greene's Protective Groups in Organic Synthesis*, 4th Edition, John Wiley & Sons, New York. In the invention, preferred amino protecting groups are t-butoxycarbonyl, benzyloxycarbonyl, acetyl and the like; while preferred carboxy protecting groups are esters, amides and the like.

Pharmaceutically Acceptable Salts:

The compounds of the invention may form salts with acid or base. The compounds of invention may be sufficiently basic or acidic to form stable nontoxic acid or base salts, administration of the compound as a pharmaceutically acceptable salt may be appropriate. Non-limiting Examples of pharmaceutically acceptable salts are inorganic, organic acid addition salts formed by addition of acids including hydrochloride salts. Non-limiting Examples of pharmaceutically acceptable salts are inorganic, organic base addition salts formed by addition of bases. The compounds of the invention may also form salts with amino acids. Pharmaceutically acceptable salts may be obtained using standard procedures well known in the art, for Example by reacting a sufficiently basic compound such as an amine with a suitable acid affording a physiologically acceptable anion.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereospecific or asymmetric synthesis or chiral HPLC (high performance liquid chromatography). Tautomeric forms and mixtures of compounds described herein are also contemplated.

Pharmaceutical Compositions

The invention relates to pharmaceutical compositions containing the compound of Formula (I). In particular, the pharmaceutical compositions contain a therapeutically effective amount of at least one compound of Formula (I) and at least one pharmaceutically acceptable excipient (such as a carrier or diluent). Preferably, the pharmaceutical compositions include the compound(s) described herein in an amount sufficient to modulate the calcium release-activated calcium (CRAC) channel to treat CRAC channel mediated diseases such as inflammatory diseases, autoimmune diseases, allergic disorders, organ transplant, cancer and cardiovascular disorders when administered to a subject.

The compound of the invention may be incorporated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes a pharmaceutical agent that does not itself induce the production of antibodies harmful to the individual receiving the composition, and which may be administered without undue toxicity.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For Example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for Example, in a sachet.

The pharmaceutical compositions may be administered in conventional forms, for Example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral Formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid Formulations include, but are not limited to, syrups, emulsions, suspensions, solutions, soft gelatin and sterile injectable liquids, such as aqueous or non-aqueous liquid suspensions or solutions. For parenteral application, particularly suitable are injectable solutions or suspensions, preferably aqueous solutions with the active compound dissolved in polyhydroxylated castor oil.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

For administration to human patients, the total daily dose of the compounds of the invention depends, of course, on the mode of administration. For Example, oral administration may require a higher total daily dose, than an intravenous (direct into blood). The quantity of active component in a unit dose preparation may be varied or adjusted from 0.1 mg to 10000 mg, more typically 1.0 mg to 1000 mg, and most typically 10 mg to 500 mg, according to the potency of the active component or mode of administration.

Suitable doses of the compounds for use in treating the diseases disorders, syndromes and conditions described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects for the patient. For Example, the daily dosage of the CRAC channel modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Method of Treatment

In a further embodiment, the invention is directed to the treatment or prophylaxis of inflammatory conditions by administering an effective amount of a compound of the invention.

Inflammation is part of the normal host response to infection and injury or exposure to certain substances prone to cause it. Inflammation begins with the immunologic process of elimination of invading pathogens and toxins to repair damaged tissue. Hence, these responses are extremely ordered and controlled. However, excessive or inappropriate inflammation contributes to a range of acute and chronic human diseases and is characterized by the production of inflammatory cytokines, arachidonic acid-derived eicosanoids (prostaglandins, thromboxanes, leukotrienes, and other oxidized derivatives), other inflammatory agents (e.g., reactive oxygen species), and adhesion molecules. As used herein, the term "inflammatory conditions" is defined as a disease or disorder or abnormality characterized by involvement of inflammatory pathways leading to inflammation, and which may result from, or be triggered by, a dysregulation of the normal immune response.

The compound(s) of the invention are useful in treatment of inflammatory conditions including, but not limited to, diseases of many body systems such as (musculoskeletal) arthritis, myositis, rheumatoid arthritis, osteoarthritis, gout, gouty arthritis, acute pseudogout, Reiter's syndrome, ankylosing spondylitis, psoriatic arthritis, dermatomyositis; (pulmonary) pleuritis, pulmonary fibrosis or nodules, restrictive lung disease, chronic obstructive pulmonary disease (COPD), acute respiratory distress syndrome (ARDS), (cardiovascular) aortic valve stenosis, restenosis, arrhythmias, coronary arteritis, myocarditis, pericarditis, Raynaud's phenomenon, systemic vasculitis, angiogenesis, atherosclerosis, ischaemic heart disease, thrombosis, myocardial infarction; (gastrointestinal) dysmotility, dysphagia, inflammatory bowel diseases, pancreatitis, (genitourinary) interstitial cystitis, renal tubular acidosis, urosepsis, (skin) purpura, vasculitis scleroderma, eczema, psoriasis, (neurologic) central nervous system disorders, cranial and peripheral neuropathies, peripheral neuropathy, radiculopathy, spinal cord or cauda equina compression with sensory and motor loss, multiple sclerosis (MS) (mental) cognitive dysfunction, Alzheimer's disease, (neoplastic) lymphoma, inflammation associated with cancer, (ophthalmologic) iridocyclitis, keratoconjunctivitis sicca, uveitis, (hematologic) chronic anemia, thrombocytopenia, (renal) amyloidosis of the kidney, glomerulonephritis, kidney failure and other diseases such as tuberculosis, leprosy, sarcoidosis, syphilis, SjOgren's syndrome, cystitis, fibromyalgia, fibrosis, septic shock, endotoxic shock, surgical complications, systemic lupus erthymotosus (SLE), transplantation associated arteriopathy, graft vs. host reaction, allograft rejection, chronic transplant rejection.

The inflammatory bowel diseases also include Crohn's disease, ulcerative colitis, indeterminate colitis, necrotizing enterocolitis, and infectious colitis.

"Allergic disorders" are defined as disorders/diseases that are caused by a combination of genetic and environmental factors resulting in a hypersensitivity disorder of the immune system. Allergic diseases are characterized by excessive immunoglobulin E (IgE) production, mast cell degranulation, tissue eosinophilia and mucus hypersecretion, resulting in an extreme inflammatory response. These responses also take place during infection with multicellular parasites, and are linked to the production of a characteristic set of cytokines by T helper (Th) 2 cells. For Example asthma is a chronic inflammatory condition of the lungs, characterized by excessive responsiveness of the lungs to stimuli, in the form of infections, allergens, and environmental irritants. Allergic reactions can also result from food, insect stings, and reactions to medications like aspirin and antibiotics such as penicillin. Symptoms of food allergy include abdominal pain, bloating, vomiting, diarrhea, itchy skin, and swelling of the skin during hives. Food allergies rarely cause respiratory (asthmatic) reactions, or rhinitis. Insect stings, antibiotics, and certain medicines produce a systemic allergic response that is also called anaphylaxis. The main therapeutic interest around CRAC in allergic disorders, originates from its role in lymphocytes and mast cells, CRAC activation being a requirement for lymphocyte activation.

The compound(s) of the invention are useful in treatment of allergic disorders including, but not limited to, atopic dermatitis, atopic eczema, Hay fever, asthma, urticaria (including chronic idiopathic urticaria), vernal conjunctivitis, allergic rhinoconjunctivitis, allergic rhinitis (seasonal and perennial), sinusitis, otitis media, allergic bronchitis, allergic cough, allergic bronchopulmonary aspergillosis, anaphylaxis, drug reaction, food allergies and reactions to the venom of stinging insects.

In yet another embodiment, the invention is directed to the treatment of "immune disorders" by administering an effective amount of a compound of the invention.

The compounds of this invention can be used to treat subjects with immune disorders. As used herein, the term "immune disorder" and like terms mean a disease, disorder or condition caused by dysfunction or malfunction of the immune system as a whole or any of its components including autoimmune disorders. Such disorders can be congenital or acquired and may be characterized by the component(s) of the immune system getting affected or by the immune system or its components getting overactive. Immune disorders include those diseases, disorders or conditions seen in animals (including humans) that have an immune component and those that arise substantially or entirely due to immune system-mediated mechanisms. In addition, other immune system mediated diseases, such as graft-versus-host disease and allergic disorders, will be included in the definition of immune disorders herein.

Because a number of immune disorders are caused by inflammation or lead to inflammation, there is some overlap between disorders that are considered immune disorders and inflammatory disorders. For the purpose of this invention, in the case of such an overlapping disorder, it may be considered either an immune disorder or an inflammatory disorder. An autoimmune disorder is a condition that occurs when the immune system mistakenly attacks and destroys its own body cells, tissues and/or organs. This may result in temporary or permanent destruction of one or more types of body tissue, abnormal growth of an organ, changes in organ function, etc. For Example, there is destruction of insulin producing cells of the pancreas in Type 1 diabetes mellitus. Different autoimmune disorders can target different tissues, organs or systems in an animal while some autoimmune disorders target different tissues, organs or systems in different animals. For Example, the autoimmune reaction is directed against the gastrointestinal tract in Ulcerative colitis and the nervous system in multiple sclerosis whereas in systemic lupus erythematosus (lupus), affected tissues and organs may vary among individuals with the same disease. For Example, one person with lupus may have affected skin and joints whereas another may have affected kidney, skin and lungs.

Specific autoimmune disorders that may be ameliorated using the compounds and methods of this invention include without limitation, autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland), autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome), autoimmune disorders of the nervous system (e.g., multiple sclerosis, myasthenia gravis, autoimmune neuropathies such as Guillain-Barre, and autoimmune uveitis), autoimmune disorders of the blood (e.g., autoimmune hemolytic anemia, pernicious anemia, and autoimmune thrombocytopenia) and autoimmune disorders of the blood vessels (e.g., temporal arteritis, anti-phospholipid syndrome, vasculitides such as Wegener's granulomatosis, and Behcet's disease).

"Treatment of an immune disorder" herein refers to administering a compound or a composition of the invention alone or in combination with other agents to a subject, who has an immune disorder, a sign or symptom of such a disease or a risk factor towards such a disease, with a purpose to cure, relieve, alter, affect, or prevent such disorder or sign or symptom of such a disease, or the predisposition towards it.

In another embodiment, the invention is directed to the treatment of cancer by administering an effective amount of a compound of the invention.

It has been reported in the art that STIM1 and Orai1 are essential in in vitro tumor cell migration and in vivo tumor metastasis. Thus the involvement of store operated $Ca^{2+}$ entry in tumor metastasis renders STIM1 and Orai1 proteins potential targets for cancer therapy (Yang et. al., Cancer Cell, 15, 124-134, 2009). Additional literature available on the involvement of CRAC channel in cancer are Abeele et. al., Cancer Cell, 1, 169-179, 2002, Motiani et al., J. Biol. Chem., 285; 25, 19173-19183, 2010.

The compound(s) of the invention may be useful in treatment of cancers and/or its metastasis including, but not limited to, breast cancer, lung cancer, pancreatic cancer, ovarian cancer, colon cancer, neck cancer, kidney cancer, bladder cancer, thyroid, blood cancer, skin cancer and the like.

In yet another embodiment, the invention is directed to the treatment or prophylaxis of allergic disorders by administering an effective amount of a compound of the invention.

In yet another embodiment, the invention is directed to the treatment or prophylaxis of cardiovascular diseases or disorders by administering an effective amount of a compound of the invention.

The compounds of this invention can be used to treat subjects with cardiovascular disorders. "Cardiovascular disorder" refers to a structural and functional abnormality of the heart and blood vessels, comprised of diseases including but not limited to, atherosclerosis, coronary artery disease, arrhythmia, heart failure, hypertension, diseases of the aorta and its branches, disorders of the peripheral vascular system, aneurysm, endocarditis, pericarditis, heart valve disease. It may be congenital or acquired. One of the main pathological feature of all these diseases is clogged and hardened arteries, obstructing the blood flow to the heart. The effects differ depending upon which vessels are clogged with plaque. The arteries carrying oxygen rich blood, if clogged, result in coronary artery disease, chest pain or heart attack. If the arteries reaching the brain are affected, it leads to transient ischemic attack or stroke. If the vessels in arms or legs are affected, leads to peripheral vascular disease. Because a number of cardiovascular diseases may also be related to or arise as a consequence of thrombocytopathies, there is some overlap between disorders that are considered under heading cardiovascular disorders and thrmobocytopathies. For the purpose of this invention, in the case of such an overlapping disorder, it may be considered either a cardiovascular disorder or a thrombocytopathy.

STIM1 is located on the endoplasmic reticulum (ER) and functions as a calcium sensor. Orai1 is a pore forming subunit of calcium channel located on the plasma membrane, the depletion of calcium in the endoplasmic reticulum is sensed by STIM1, and calcium enters via Orai1 to refill the endoplasmic reticulum. This pathway of filling the calcium is called store operated calcium entry (SOCE), which plays an important role in calcium homeostasis, cellular dysfunction and has a significant importance in cardiovascular diseases. In cardiomyocytes, calcium is not only involved in excitation-contraction coupling but also acts as a signalling molecule promoting cardiac hypertrophy. Hypertrophic hearts are susceptible to abnormalities of cardiac rhythm and have impaired relaxation. Vascular smooth muscle cells (VSMCs) are responsible for the maintenance of vascular tone. VSMCs disorders, usually manifested as a phenotype change, are involved in the pathogenesis of major vascular diseases such as atherosclerosis, hypertension and restenosis. SOCE was also found increased in metabolic syndrome (MetS) swine coronary smooth muscle cells. The compound of this invention can be used to treat neointimal hyperplasia, occlusive vascular diseases, MetS—which is a combination of medical disorders including coronary artery disease, stroke and type 2 diabetes, abdominal aortic aneurysm, angina, transient ischemic attack, stroke, peripheral artery occlusive disease which includes inflammation, complement activation, fibrinolysis, angiogenesis and/or diseases related to FXII-induced kinin formation such as hereditary angioedema, bacterial infection of the lung, trypanosome infection, hypotensive shock, pancreatitis, chagas disease, thrombocytopenia or articular gout, myocardial infarction, portal vein thrombosis which leads to hypertension, pulmonary hypertension, deep vein thrombosis, jugular vein thrombosis, systemic sepsis, pulmonary embolism, and papilledema, Budd-Chiari syndrome, Paget-Schroetter disease, cerebral venous sinus thrombosis ischemic cardiomyopathy, hypertrophic cardiomyopathy, arrhythmogenic right ventricular cardiomyopathy, Prinzmetal angina, angina pectoris, chronic venous insufficiency, acute coronary syndrome, endocarditis, conceptual apraxia, pulmonary valve stenosis, thrombophlebitis, ventricular tachycardia, temporal arteritis, tachycardia, paroxysmal atrial fibrillation, persistent atrial fibrillation, permanent atrial fibrillation, respiratory sinus arrhythmia, carotid artery dissection, cerebrovascular diseases include, hemorrhagic stroke and ischemic stroke (where the thrombo-inflammatory cascade results in infarct growth), cardiomegaly, endocarditis, pericarditis, pericardial effusion. Valvular heart disease, vascular diseases or vascular inflammation is the result of ruptured atherosclerotic plaque which initiates thrombus formation. Platelet activation play an important role in vascular inflammation leading to myocardial infarction and ischaemic stroke, the compound of this invention will prevent platelet activation and plaque formation and would also be useful to treat all peripheral vascular diseases (PVD), pulmonary thromboembolism, and venous thrombosis.

"Treatment of cardiovascular disorders" herein refers to administering a compound or a composition of the invention alone or in combination with other agents to a subject, who has a cardiovascular disease, a sign or symptom of such a disease or a risk factor towards such a disease, with a purpose to cure, relieve, alter, affect, or prevent such disorder or sign or symptom of such a disease, or the predisposition towards it.

In yet another embodiment, the invention is directed to the treatment of "thrombocytopathies" by administering an effective amount of a compound of the invention.

Thrombocytopathies: The compounds of this invention can be used to treat subjects with thrombocytopathies. Thrombocytopathy is an abnormality of platelets or its functions. It may be congenital or acquired. It may cause a thrombotic or a bleeding tendency or may be part of a wider disorder such as myelodysplasia. Thrombocytopathies include such vascular disorders that arise due to dysfunction of platelets or coagulation system or diseases or complications that arise as a result of partial or complete restriction of blood flow to different organs or systems due to such thrombocytopathies. Thrombocytopathies will thus include without limitation diseases due to superficial vein thrombosis, diseases due to deep vein thrombosis, diseases due to arterial thrombosis, peripheral vascular diseases, thrombophilia, thrombophlebitis, embolisms, thromboembolism, ischemic cardiovascular diseases including but not limited to myocardial ischemia, angina, ischemic cerebrovascular diseases including but not limited to stroke, transient ischemia attack, cerebral venous sinus thrombosis (CVST) and complications arising due to thrmobocytopathies. Besides this, the disorder related to venous or arterial thrombus formation can be inflammation, complement activation, fibrinolysis, angiogenesis and/or diseases related to FXII-induced kinin formation such as hereditary angioedema, bacterial infection of the lung, trypanosome infection, hypotensitive shock, pancreatitis, chagas disease, thrombocytopenia or articular gout.

Under normal circumstances, when the endothelial cells lining blood vessels are breached, platelets interact with von Willebrand factor (vWF) via the membrane glycoprotein 1b complex to help seal the breach. Glycoprotein IIb/Ia complex attracts other platelets, which combine to form aggregates. The platelets contain granules which break down to release fibrinogen, vWF, platelet-derived growth factor adenosine 5'-diphosphate (ADP), calcium and 5-hydroxytryptamine (5-HT)-serotonin. All this helps to promote the formation of a haemostatic plug (primary haemostasis). Activated platelets also synthesise thromboxane A2 from arachidonic acid as well as presenting negatively charged phospholipids on the outer leaflet of the platelet membrane bilayer. This negative surface provides binding sites for enzymes and cofactors of the coagulation system. The total effect is therefore to stimulate the coagulation system to form a clot (secondary haemostasis).

Thus physiological platelet activation and thrombus formation are essential to stop bleeding in case of vascular injury, whereas under pathological conditions this may lead to vessel occlusion due to inadequate triggering of the same process in diseased vessels leading to thrombosis, thromboembolism or tissue ischemia of vital organs. A central step in platelet activation is agonist-induced elevation of the intracellular Ca(2+) concentration. This happens on the one hand through the release of Ca(2+) from intracellular stores and on the other hand through Ca(2+) influx from the extracellular space. In platelets, the major Ca(2+) influx pathway is through store operated Ca(2+) entry (SOCE), induced by store depletion. STIM1 is the the Ca(2+) sensor in the endoplasmic reticulum (ER) membrane, whereas Orai1 is the major store operated Ca(2+) (SOC) channel in the plasma membrane, which play a key role in platelet SOCE.

"Treatment of thrombocytopathy" herein refers to administering a compound or a composition of the invention alone or in combination with other agents to a subject, who has a thrombocytopathy, a sign or symptom or complication of such a disease or a risk factor towards such a disease, with the purpose to cure, relieve, alter, affect, or prevent such a disorder or sign or symptom, or the predisposition towards it.

General Methods of Preparation

The compounds of the invention, including compounds of general Formula (I) and specific Examples are prepared through the reaction sequences illustrated in synthetic Schemes-1 and Scheme-2. Starting materials are commercially available or may be prepared by the procedures described herein or by the procedures known in the art. Furthermore, in the following synthetic schemes, where specific acids, bases, reagents, coupling agents, solvents, etc., are mentioned, it is understood that other bases, acids, reagents, coupling agents, solvents etc., known in the art may also be used and are therefore included within the scope of the invention. Variations in reaction conditions and parameters like temperature, pressure, duration of reaction, etc., which may be used as known in the art are also within the scope of the invention. All the isomers of the compounds described in these schemes, unless otherwise specified, are also encompassed within the scope of this invention.

The compounds obtained by using the general reaction sequences may be of insufficient purity. These compounds can be purified by using any of the methods for purification of organic compounds known in the art, for Example, crystallization or silica gel or alumina column chromatography using different solvents in suitable ratios. Unless mentioned otherwise, room temperature (RT) refers to a temperature in the range of 22 to 27° C.

$^1$H-NMR spectra of the compounds of the invention were recorded using a BRUCKNER instrument (model: Avance-III), 400 MHz. Liquid chromatography-mass spectra (LCMS) of the compounds of the invention were recorded using Agilent ion trap model 6320 and Thermo Scientific Single Quad model MSQ plus instruments. IUPAC nomenclature for the compounds of the invention was used according to ChemBioDraw Ultra 12.0 software.

Scheme-1

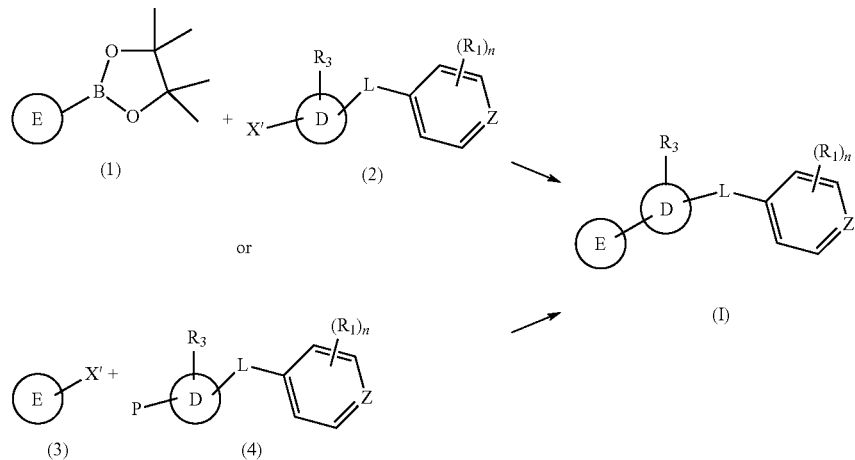

X' is halogen or OTf; P is pinacolatoboronate or stannane;

The compounds of Formula (I), where ring D, ring E, Z, L, $R_1$, $R_3$ and 'n' are as defined herein above, can be prepared as depicted in Scheme-1 thus, the reaction of borate derivative of Formula (1) with various halobenzamides of Formula (2) to give compound of Formula (I).

Alternatively, the compounds of the Formula (I) can also be prepared by the reaction of halo/triflate derivatives of the Formula (3) with borate/stannane derivatives of the Formula (4) as shown in Scheme-1. The said reaction can be mediated by a suitable catalyst known in the art such as $Pd(PPh_3)_2Cl_2$, $Pd_2dba_3$, $Pd(PPh_3)_4$, $Pd(OAc)_2$ or mixture(s) thereof; a suitable ligand known in the art such as 2,2'-bis(diphenylphosphino)-1,1'-binaphthyl (BINAP), xanthophos, triphenylphosphine or mixture(s) thereof; in the presence of a suitable base and suitable solvent(s) such as tetrahydrofuran, dioxane, toluene, DCM, DMSO, DMA, DMF their mixture(s) thereof to afford the compounds of the Formula (I).

The compounds of the Formula (2) and (4) can be prepared by following the methods known in the art.

Scheme-2

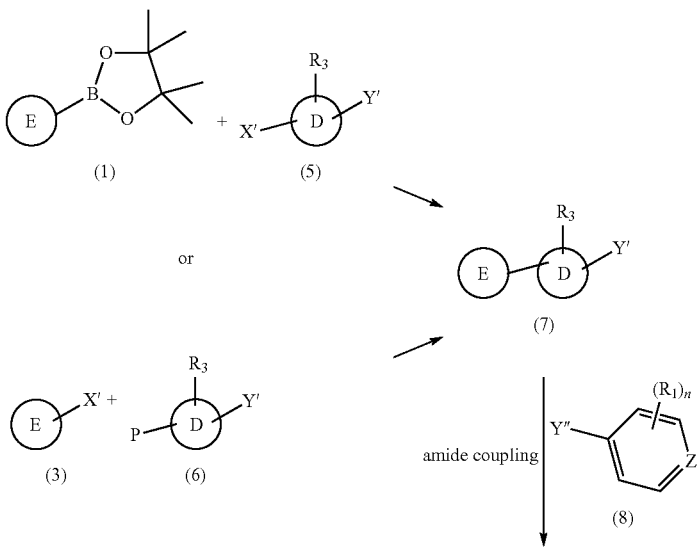

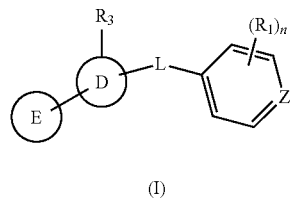

(I)

X' is halogen or OTf; P is pinacolatoboronate or stannane;
Y' is either NHR₂; or COOH, COOalkyl or COCl
Y" is either COOH, COOalkyl, COCl; or NHR₂;
R₂ is as defined herein above Compound of Formula (I) where ring D, ring E, Z, $R_1$, $R_3$ and 'n' are as defined herein above, can also be prepared by an alternative approach as shown in Scheme 2. The borate compound of the Formula (1) is reacted with halo compound of the Formula (5) followed by amide coupling reaction with Formula (8) to give compound of Formula (I). Alternatively, halo derivatives of the Formula (3) are reacted with stannane/borate derivatives of the Formula (6) followed by amide coupling reaction with Formula (8) using the amide coupling methods known in the art to result compound of Formula (I).

INTERMEDIATES

Intermediate-1a: 6-Bromo-3,7-dimethyloxazolo[4,5-b]pyridin-2(3H)-one and

Intermediate-1b: 3,7-Dimethyl-6-(4,4,5,5-tetramethyl-1,3,2-dioxaborolan-2-yl)oxazolo[4,5-b]pyridin-2(3H)-one

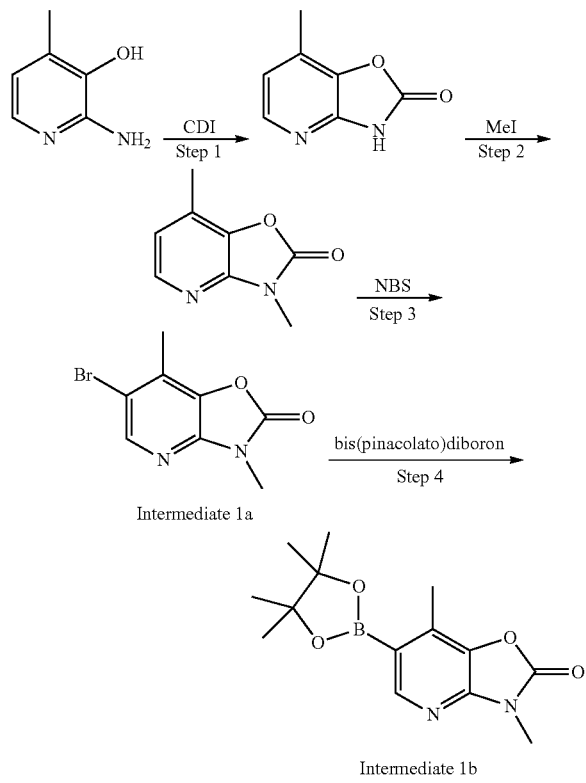

Step-1:
7-Methyloxazolo[4,5-b]pyridin-2(3H)-one: A mixture of 2-amino-4-methylpyridin-3-ol (4.80 g, 38.7 mmol) and carbonyldiimidazole (9.40 g, 58.0 mmol) in THF (50 mL) was stirred at 80° C. for 6 h. Then the reaction was allowed to room temperature and diluted with water (50 mL) followed by ethyl acetate (50 mL). The layers were separated and the aqueous layer was extracted with ethyl acetate (2×50 mL). The combined organic layers were washed with water (50 mL), brine (50 mL), dried ($Na_2SO_4$) and filtered. The filtrate was evaporated and the crude product obtained was purified by flash column chromatography (silica gel, ethyl acetate-hexanes system as eluent) to yield 2.0 g (35%) of the title compound as white solid. ¹HNMR (400 MHz, DMSO-$d_6$) δ 12.34 (s, 1H, $D_2O$ exchangeable), 7.90 (d, J=5.5 Hz, 1H), 6.97 (d, J=5.5 Hz, 1H), 2.31 (s, 3H); GC-MS (m/z) 150 (M)⁺.

Step-2:
3,7-Dimethyloxazolo[4,5-b]pyridin-2(3H)-one: To a solution of Step-1 Intermediate (1.80 g, 11.9 mmol) in DMF (10 mL) was added potassium carbonate (2.48 g, 17.9 mmol) at 0° C., followed by methyl iodide (1.12 mL, 17.9 mmol). The resulting mixture was stirred at RT for 3 h. The reaction was then diluted with ice-water, and the resultant precipitate was filtered and the residue was washed with water and dried to afford 1.08 g (55%) of the desired product as white solid. ¹HNMR (400 MHz, DMSO-$d_6$) δ 7.99 (d, J=5.0 Hz, 1H), 7.03 (d, J=5.0 Hz, 1H), 3.33 (s, 3H), 2.34 (s, 3H); GC-MS (m/z) 164 (M)⁺.

Step-3:
6-Bromo-3,7-dimethyloxazolo[4,5-b]pyridin-2(3H)-one: To an ice-cold solution of Step-2 Intermediate (1.10 g, 6.70 mmol) in acetic acid (12 mL) was added sodium acetate (0.660 g, 8.04 mmol) followed by drop-wise addition of bromine (0.34 mL, 6.70 mmol). The resulting mixture was stirred at RT for 12 h then diluted with water (50 mL) followed by ethyl acetate (50 mL). Organic layer separated and aqueous layer was further extracted with ethyl acetate (2×50 mL). The combined organic layers were washed with water (50 mL), 5% $NaHCO_3$ solution (50 mL), brine (50 mL), dried ($Na_2SO_4$) and filtered. The filtrate was rotary evaporated and the crude product was purified by flash column purification (silica gel, 50% ethyl acetate in hexanes system as eluent) to afford 1.0 g (61%) of the desired product as white solid. ¹HNMR (400 MHz, CDCl₃) δ 8.22 (s, 1H), 3.47 (s, 3H), 2.44 (s, 3H); GC-MS (m/z) 242, 244 [(M)⁺ Br⁷⁹, ⁸¹].

Step-4:
3,7-Dimethyl-6-(4,4,5,5-tetramethyl-1,3,2-dioxaborolan-2-yl)oxazolo[4,5-b]pyridin-2(3H)-one Step 4: In a sealed tube, to a nitrogen purged solution of Step-3 Intermediate (0.800 g, 3.29 mmol) and 4,4,4',4',5,5,5',5'-octamethyl-2,2'- bi(1,3,2-dioxaborolane) (1.0 g, 3.95 mmol) in 1,4-dioxane (15 mL) was added potassium acetate (0.485 g, 4.94 mmol) and PdCl$_2$(dppf)-CH$_2$Cl$_2$ adduct −1 (0.182 g, 0.329 mmol). The resulting mixture was throughly deoxygenated by purging nitrogen gas for another 5 min and then stirred at 110° C. for 3 h. The reaction mixture was allowed to room temperature then diluted with ethyl acetate (20 mL) and filtered through celite pad. The residue was washed with ethyl acetate (20 mL) and the combined filtrates were concentrated under reduced pressure. The crude product was purified by flash column chromatography (silica gel, 50% ethyl acetate in hexanes system as eluent) to obtain 0.700 g (73%) of the desired product as white solid. $^1$H-NMR (400 MHz, CDCl$_3$) δ 8.44 (s, 1H), 3.72 (s, 3H), 2.55 (s, 3H), 1.36 (s, 12H); ESI-MS (m/z) 291 (MH)$^+$.

The below Intermediates given in Table-1 were prepared by following the similar procedure as described in Intermediate-1.

Intermediate-4a:
6-Bromo-3,7-dimethylbenzo[d]oxazol-2(3H)-one
and

Intermediate-4b: 3,7-Dimethyl-6-(4,4,5,5-tetramethyl-1,3,2-dioxaborolan-2-yl)benzo[d]oxazol-2(3H)-one

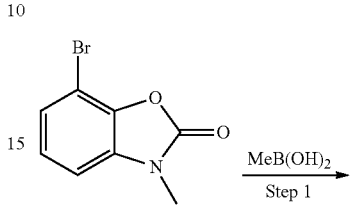

Step 1

TABLE 1

| Intermediate No. | Structure/IUPAC name | $^1$HNMR/ESI-MS |
|---|---|---|
| 2a | 6-Bromo-7-ethyl-3-methyloxazolo[4,5-b]pyridin-2(3H)-one | $^1$HNMR (400 MHz, CDCl$_3$) δ 8.22 (s, 1H), 3.48 (s, 3H), 2.93 (q, J = 7.5 Hz, 2H), 1.32 (t, J = 7.5 Hz, 3H); GC-MS (m/z) 256, 258 [(M)$^+$ Br$^{79,81}$] |
| 2b | 7-Ethyl-3-methyl-6-(4,4,5,5-tetramethyl-1,3,2-dioxaborolan-2-yl)oxazolo[4,5-b]Pyridine-2(3H)-one | $^1$HNMR (400 MHz, CDCl$_3$) δ 8.47 (s, 1H), 3.49 (s, 3H), 3.03 (q, J = 7.5 Hz, 2H), 1.37 (s, 12H), 1.24 (t, J = 7.5 Hz, 3H); ESI-MS (m/z) 305 (MH)$^+$ |
| 3 | 6-Bromo-7-cyclopropyl-3-methyloxazolo[4,5-b]pyridin-2(3H)-one | $^1$HNMR (400 MHz, CDCl$_3$) δ 8.20 (s, 1H), 3.44 (s, 3H), 2.16-2.09 (m, 1H), 1.40-1.29 (m, 2H), 1.23-1.12 (m, 2H); GC-MS (m/z) 268, 270 [(M)$^+$ Br$^{79,81}$] |

-continued

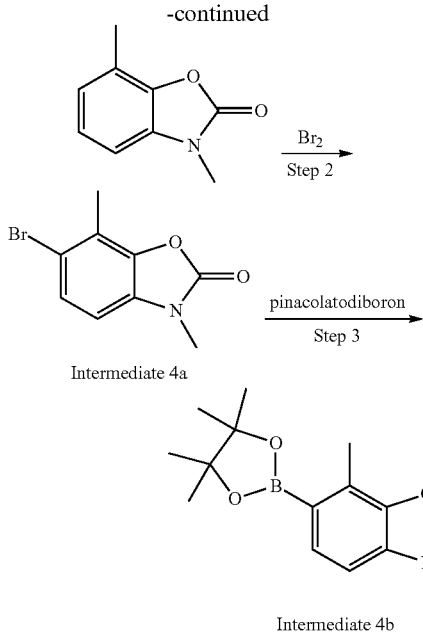

Intermediate 4a

Intermediate 4b

Step-1:

3,7-Dimethylbenzo[d]oxazol-2(3H)-one: In a sealed tube, to a stirred and nitrogen purged solution of 7-bromo-3-methyloxazolo[4,5-b]pyridin-2(3H)-one (prepared by following the procedure as described in WO2006061379; 200 mg, 0.87 mmol), RuPhos (0.600 g, 1.29 mmol) and methylboronic acid (0.924 g, 15.43 mmol) in toluene/water (50 mL, 4:1) was added potassium phosphate (5.46 g, 25.7 mmol) and Pd(OAc)$_2$ (290 mg, 1.29 mmol). After stirring the resulting mixture at 100° C. for 12 h, the reaction was allowed to cool to room temperature, diluted with ethyl acetate (10 mL). This was filtered through celite bed and washed with ethyl acetate (10 mL) and concentrated the filtrate under reduced pressure. The crude product was purified by flash column chromatography (silica gel, 50% ethyl acetate in hexanes system as eluent) to afford 150 mg (8%) of the desired product as white solid. $^1$H NMR (400 MHz, CDCl$_3$) δ 7.10 (t, J=7.5 Hz, 1H), 6.95 (d, J=7.5 Hz, 1H), 6.81 (d, J=7.5 Hz, 1H), 3.41 (s, 3H), 2.40 (s, 3H); GC-MS 163 (m/z) (M)$^+$ Step-2:

6-Bromo-3,7-dimethylbenzo[d]oxazol-2(3H)-one: To an ice-cooled and stirred solution of Step-1 Intermediate (110 mg, 0.67 mmol) in acetic acid (2 mL) was added bromine (35 µL, 0.67 mmol). The resulting solution was stirred at room temperature for 12 h. Then solvent was then evaporated under reduced pressure and the residual mass was diluted with ethyl acetate (10 mL). The organic layer was then washed with 5% NaHCO$_3$ solution (5 mL), dried (Na$_2$SO$_4$) and rotary evaporated. The crude product was purified by flash column chromatography (silica gel, hexane-ethylacetate system as eluent, 3:1) to afford 90 mg (55%) of the desired product as white solid. $^1$H NMR (400 MHz, CDCl$_3$) δ 7.40 (d, J=8.5 Hz, 1H), 6.71 (d, J=8.5 Hz, 1H), 3.40 (s, 3H), 2.43 (s, 3H); GC-MS (m/z) 241, 243 (M, Br$^{79, 81}$).

Step-3:

3,7-Dimethyl-6-(4,4,5,5-tetramethyl-1,3,2-dioxaborolan-2-yl)benzo[d]oxazol-2(3H)-one: The title compound was prepared from step-2 Intermediate by following the similar procedure as described in step-4 of Intermediate-1. $^1$HNMR (400 MHz, CDCl$_3$) δ 7.67 (d, J=8.0 Hz, 1H), 6.80 (d, J=8.0 Hz, 1H), 3.41 (s, 3H), 2.57 (s, 3H), 1.36 (s, 12H); GCMS (m/z) 289 (M)$^+$.

Intermediate-5:
5-Bromo-3,4-dimethylbenzo[d]oxazol-2(3H)-one

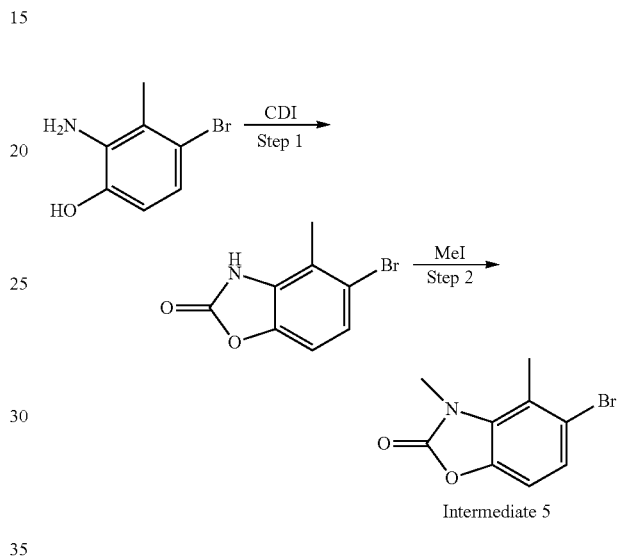

Intermediate 5

Step-1:

5-Bromo-4-methylbenzo[d]oxazol-2(3H)-one: To a stirred solution of 2-amino-4-bromo-3-methylphenol (prepared by following the procedure as described in WO2009062285; 1.0 g, 4.95 mmol) in THF (20 mL) was added CDI (0.88 g, 5.44 mmol) at room temperature. The reaction was stirred at 80° C. for 12 h. Then the reaction was allowed to room temperature and diluted with water (10 mL) followed by ethyl acetate (10 mL). The layers were separated and the aqueous layer was extracted with ethyl acetate (2×10 mL). The combined organic layers were washed with brine (10 mL), dried (Na$_2$SO$_4$) and filtered. The filtrate was evaporated and the crude product was purified by flash column chromatography (silica gel, hexanes-ethyl acetate system as eluent, 2:1) to yield 0.700 g (62%) as white solid. $^1$H-NMR (400 MHz, DMSO-d$_6$) δ 11.96 (s, 1H, D$_2$O exchangeable), 7.30 (d, J=8.5 Hz, 1H), 7.10 (d, J=8.5 Hz, 1H), 2.31 (s, 3H); GC-MS (m/z) 227, 229 (M. Br$^{79}$. 81).

Step-2:

5-Bromo-3,4-dimethylbenzo[d]oxazol-2(3H)-one: To a solution of Step-1 Intermediate (250 mg, 1.10 mmol) in DMF (5 mL) was added potassium carbonate (303 mg, 2.19 mmol) at 0° C., followed by methyl iodide (0.14 mL, 2.19 mmol). After stirring the resulting mixture at room temperature for 3 h, the reaction was diluted with ice-water. The resultant precipitate was filtered and washed with water (5 mL) and dried to afford 180 mg (68%) as white solid. $^1$H-NMR (400 MHz, CDCl$_3$) δ 7.34 (d, J=8.5 Hz, 1H), 6.98 (d, J=8.5 Hz, 1H), 3.64 (s, 3H), 2.65 (s, 3H); GC-MS (m/z) 241, 243 (M$^+$, Br$^{79, 81}$).

Intermediate-6:
6-Bromo-1-methyloxazolo[5,4-b]pyridin-2(1H)-one

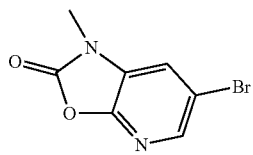

The title compound was prepared from 3-amino-5-bromopyridin-2-ol by following the similar procedure as described in step-1 and step-2 of Intermediate-1.

Intermediate-7:
6-Bromo-3-methylbenzo[d]oxazol-2(3H)-one

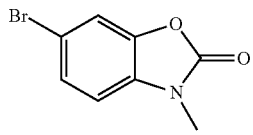

The title compound was prepared by following the similar procedure as described in WO2010130794.

The below Intermediate-8 to Intermediate-11 were prepared by following procedure as reported in WO2012056478.

Intermediate-8:
N-(5-Bromopyrazin-2-yl)-2,6-difluorobenzamide

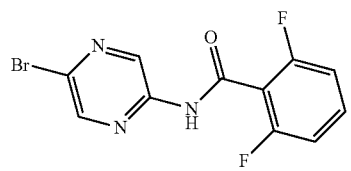 [SMILES: O=C(Nc1cnc(Br)cn1)c1c(F)cccc1F]

Intermediate-9:
N-(5-Bromopyridin-2-yl)-2,6-difluorobenzamide

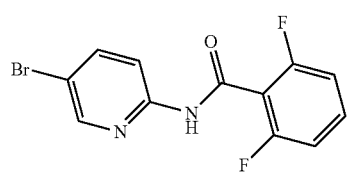

Intermediate-10a:
N-(4-Bromophenyl)-2,6-difluorobenzamide

And

Intermediate-10b: 2,6-Difluoro-N-(4-(4,4,5,5-tetramethyl-1,3,2-dioxaborolan-2-yl)phenyl)benzamide Intermediate 10a
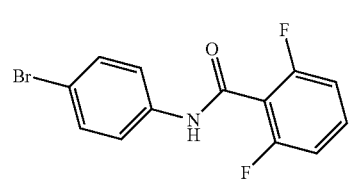 [SMILES: O=C(Nc1ccc(Br)nc1)c1c(F)cccc1F]

Intermediate 10b
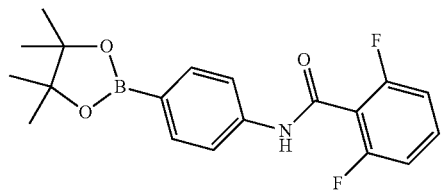

Intermediate-11:
N-(6-Bromopyridin-3-yl)-2,6-difluorobenzamide

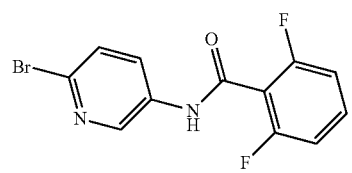

Intermediate-12:
6-Bromo-3-methyloxazolo[4,5-b]pyridin-2(3H)-one

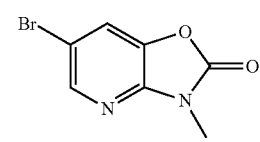

The title compound was prepared by following the procedure as described in WO2011151434.

Intermediate-13:
6-Bromo-7-ethyl-3-methylbenzo[d]oxazol-2(3H)-one

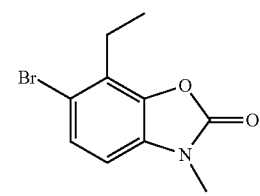

The title compound was prepared by following the similar procedure as described in Intermediate 4a. $^1$HNMR (400 MHz, CDCl$_3$) δ 7.39 (d, J=8.5 Hz, 1H), 6.71 (d, J=8.5 Hz, 1H), 3.40 (s, 3H), 2.90 (q, J=7.5 Hz, 2H), 1.23 (t, J=7.5 Hz, 3H); GC-MS (m/z) 255, 257 [(M)$^+$ Br$^{79, 81}$].

Intermediate-14: 6-Bromo-7-cyclopropyl-3-methyl-benzo[d]oxazol-2(3H)-one

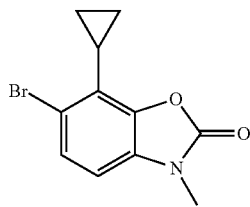

The title compound was prepared by following the similar procedure as described in Intermediate-4a. $^1$HNMR (400 MHz, CDCl$_3$) δ 7.46-7.35 (m, 1H), 6.67 (d, J=8.5 Hz, 1H), 3.37 (s, 3H), 2.06-1.98 (m, 1H), 1.17-0.98 (m, 4H); GC-MS (m/z) 267, 269 [M$^+$, Br$^{79, 81}$].

Intermediate-15: 6-Bromo-1,7-dimethyloxazolo[5,4-b]pyridin-2(1H)-one

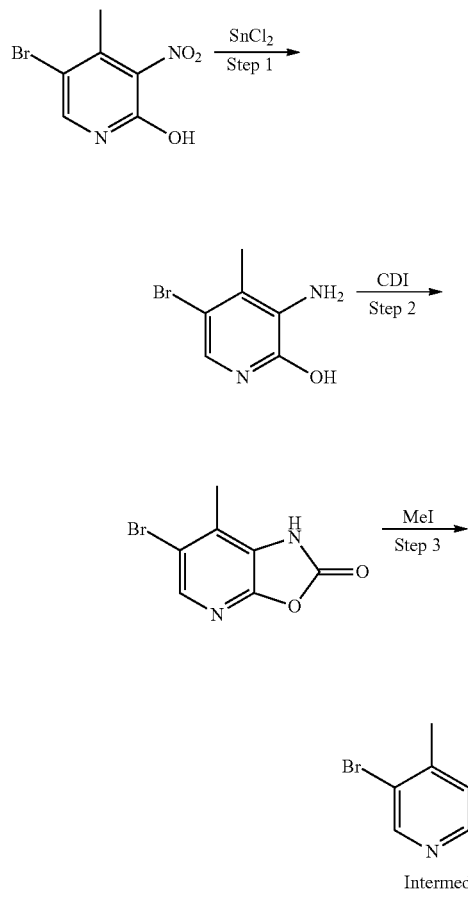

Intermediate 15

Step-1:
3-Amino-5-bromo-4-methylpyridin-2-ol: To a solution of 5-bromo-4-methyl-3-nitropyridin-2-ol (1.0 g, 4.29 mmol) in ethanol (20 mL), at room temperature was added tin (II) chloride (2.44 g, 12.87 mmol). The resulting mixture was stirred at reflux temperature for 12 h. Then the reaction was allowed to room temperature and the solvent was removed under reduced pressure. The residue was basified with aqueous ammonia and filtered through celite. The filtrate was evaporated under vacuum to afford 180 mg (21%) of the desired product which was used for the next step without further purification. $^1$HNMR (400 MHz, DMSO-d$_6$) δ 11.56 (s, 1H), 6.91 (s, 1H), 5.16 (s, 2H, D$_2$O exchangeable), 2.06 (s, 3H); GC-MS (m/z) 202, 204 [M$^+$, Br$^{79, 81}$].

Step-2:
6-Bromo-7-methyloxazolo[5,4-b]pyridin-2(1H)-one: To a stirred solution of step-1 Intermediate (100 mg, 0.493 mmol) in THF (5 mL) was added CDI (120 mg, 0.739 mmol) at room temperature and then the reaction was heated at 80° C. for 2 h. The reaction was allowed to room temperature and diluted with water (10 mL) followed by ethyl acetate (10 mL). The layers were separated and the aqueous layer was extracted with ethyl acetate (2×10 mL). The combined organics were washed with water (10 mL), brine (10 mL), dried (Na$_2$SO$_4$) and filtered. The filtrate was concentrated under vacuum and the crude product was purified by column chromatography (silica gel, ethyl acetate-hexane system as eluent) to yield 100 mg (89%) of the desired product as white solid. $^1$HNMR (400 MHz, CDCl$_3$) δ 9.76 (s, 1H, D$_2$O exchangeable), 8.19 (s, 1H), 2.47 (s, 3H); GC-MS (m/z) 228, 230 [M$^+$, Br$^{79, 81}$]

Step-3:
6-Bromo-1,7-dimethyloxazolo[5,4-b]pyridin-2(1H)-one: To a (0° C.) cooled solution of Step-2 Intermediate (110 mg, 0.48 mmol) in DMF (5 mL), was added potassium carbonate (100 mg, 0.72 mmol) followed by methyl iodide (0.05 mL, 0.72 mmol). The reaction mixture was stirred for 3 h at room temperature. The reaction mixture was diluted with ice-water, and the resultant precipitate was filtered. The residue was washed with water and dried to afford 88 mg (75%) of the desired product as white solid. $^1$HNMR (400 MHz, CDCl$_3$) δ 8.16 (s, 1H), 3.67 (s, 3H), 2.65 (s, 3H); GC-MS (m/z) 242, 244 [M$^+$, Br$^{79, 81}$].

Intermediate-16:
5-Bromo-3,6-dimethylbenzo[d]oxazol-2(3H)-one

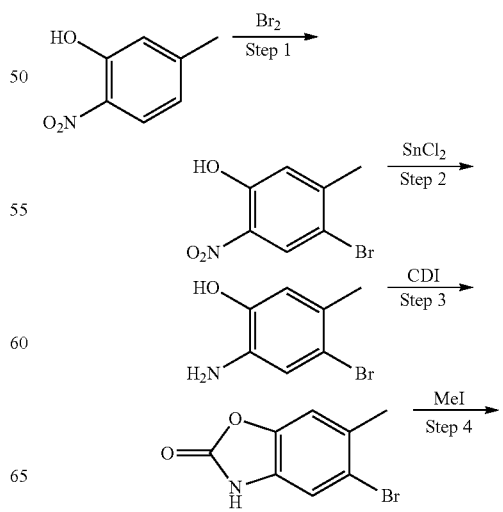

-continued

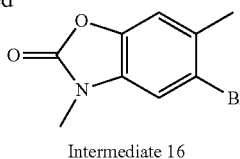
Intermediate 16

Step-1:

4-Bromo-5-methyl-2-nitrophenol: To a stirred solution of 5-methyl-2-nitrophenol (6.0 g, 39.2 mmol) in acetic acid (60 mL) was added a solution of bromine (4.04 mL, 78 mmol) in acetic acid (10 mL) at 0° C. over a period of 30 min. The resulting mixture was stirred at room temperature for 2 h. The solvent was then evaporated under reduced pressure and the residue was diluted with ethyl acetate (300 mL). The resulting organic layer was washed with saturated solution of sodium thiosulphate (2×50 mL), water (50 mL) and brine (50 mL). The organic layer was then dried ($Na_2SO_4$) and filtered. The filtrate was rotary evaporated to afford 9.0 g (99%) of the title product as a yellow solid. $^1$HNMR (400 MHz, CDCl3) δ 10.46 (s, 1H), 8.29 (s, 1H), 7.08 (s, 1H), 2.46 (s, 3H); GC-MS (m/z) 232, 234 [$M^+$. $Br^{79, 81}$].

Step-2:

2-Amino-4-bromo-5-methylphenol: To a stirred solution of step-1 Intermediate (1.8 g, 7.76 mmol) in methanol (20 mL) were added tin(II) chloride dihydrate (5.88 g, 31.0 mmol) followed by the addition of concentrated HCl (1.65 mL, 54.3 mmol) at room temperature. The resulting mixture was heated at 75° C. for 2 h. Then the reaction was allowed to room temperature and the solvent was removed under reduced pressure. The crude mass was diluted with ethyl acetate (100 mL), basified with aqueous ammonia (pH 14) and the resulting solid suspension was filtered through Celite bed. The residue was washed with ethyl acetate (2×50 mL). The combined filtrates were washed with water (50 mL), brine (50 mL), dried ($Na_2SO_4$) and filtered. The filtrate was evaporated under reduced pressure to afford 1.3 g (83%) of the title product as a white solid. $^1$HNMR (400 MHz, $CDCl_3$) δ 6.96 (s, 1H), 6.64 (s, 1H), 3.61 (bs, 2H, $D_2O$ exchangeable), 2.26 (s, 3H); GC-MS (m/z) 201, 203 [$M^+$, $Br^{79, 81}$].

Step-3:

5-Bromo-6-methylbenzo[d]oxazol-2(3H)-one: To a stirred solution of step-2 Intermediate (10 g, 49.5 mmol) in THF (100 mL) was added CDI (9.63 g, 59.4 mmol) at room temperature. The resulting mixture was stirred at 80° C. for 2 h. The reaction was then cooled back down to room temperature and then diluted with ethyl acetate (500 mL). The organic layer was washed with water (2×100 mL), brine (100 mL), dried ($Na_2SO_4$) and filtered. The filtrate was concentrated under vacuum and the crude product was purified by flash column chromatography (silica gel, ethyl acetate-hexanes system as eluent) to obtain 7.0 g (62%) of the title product as a white solid. $^1$HNMR (400 MHz, $CDCl_3$) δ 7.14 (s, 1H), 7.09 (s, 1H), 8.68 (bs, 1H, $D_2O$ exchangeable), 2.42 (s, 3H); GC-MS (m/z) 227, 229 [$M^+$, $Br^{79, 81}$].

Step-4:

5-Bromo-3,6-dimethylbenzo[d]oxazol-2(3H)-one: To a stirred solution of step-3 Intermediate (6.90 g, 30.3 mmol) in DMF (50 mL) was added $K_2CO_3$ (6.27 g, 45.4 mmol) followed by methyl iodide (2.84 ml, 45.4 mmol) at room temperature. The resulting mixture was stirred at room temperature for 16 h and then poured into ice cold water (100 mL). The separated solid product was filtered off and dried to afford 7.0 g (96%) of the title product as a white solid. $^1$HNMR (400 MHz, CDCl3) δ 7.15 (s, 1H), 7.11 (s, 1H), 3.38 (s, 3H), 2.43 (s, 3H); GC-MS (m/z) 241, 243 [$M^+$, $Br^{79, 81}$].

The below Intermediates (17-25) given in Table-2 were prepared by following the similar procedure as described in Intermediate-16.

TABLE 2

| Intermediate No. | Structure/IUPAC name | $^1$HNMR/ESI-MS |
|---|---|---|
| Intermediate-17 | 5-Bromo-3-ethyl-6-methylbenzo[d]oxazol-2(3H)-one | HNMR (400 MHz, $CDCl_3$) δ 7.18 (s, 1H), 7.12 (s, 1H), 3.86 (q, J = 7.0 Hz, 2H), 2.43 (s, 3H), 1.38 (t, J = 7.0 Hz, 3H); ESI-MS (m/z) 256, 258 [$(MH)^+$, $Br^{79,81}$]. |
| Intermediate-18 | 5-Bromo-3-(cyclopropylmethyl)-6-methylbenzo[d]oxazol-2(3H)-one | $^1$HNMR (400 MHz, $CDCl_3$) δ 7.22 (s, 1H), 7.12 (s, 1H), 3.68 (d, J = 7.0 Hz, 2H), 1.24-1.16 (m, 1H), 0.63-0.59 (m, 2H), 0.47-0.43 (m, 2H); ESI-MS (m/z) 282, 284 [$(MH)^+$, $Br^{79,81}$]. |
| Intermediate-19 | 5-Bromo-3-(2-fluoroethyl)-6-methylbenzo[d]oxazol-2(3H)-one | $^1$HNMR (400 MHz, $CDCl_3$) δ 7.27 (s, 1H), 7.13 (s, 1H), 4.75 (dt, J = 47.0, 4.5 Hz, 2H), 4.10 (dt, J = 27.0, 4.5 Hz, 2H), 2.43 (s, 3H).; ESI-MS (m/z) 274, 276 [$(MH)^+$, $Br^{79,81}$]. |
| Intermediate-20 | 5-Bromo-3-isopropyl-6-methylbenzo[d]oxazol-2(3H)-one | $^1$HNMR (400 MHz, $CDCl_3$) δ 7.25 (s, 1H), 7.11 (s, 1H), 4.62-4.44 (m, 1H), 2.42 (s, 3H), 1.54 (s, 6H); ESI-MS (m/z) 270, 272 [$(MH)^+$, $Br^{79,81}$]. |
| Intermediate-21 | 5-Bromo-3-(difluoromethyl)-6-methylbenzo[d]oxazol-2(3H)-one | $^1$HNMR (400 MHz, $CDCl_3$) δ 7.55 (s, 1H), 7.19 (t, J = 57.0 Hz, 1H), 7.18 (s, 1H), 2.46 (s, 3H); ESI-MS (m/z) 278, 280 [$(MH)^+$, $Br^{79,81}$]. |

TABLE 2-continued

| Intermediate No. | Structure/IUPAC name | ¹HNMR/ESI-MS |
|---|---|---|
| Intermediate-22 | 5-Bromo-6-methyl-3-(3,3,3-trifluoropropyl)benzo[d]oxazol-2(3H)-one | ¹HNMR (400 MHz, CDCl$_3$) δ 8.04 (s, 1H), 7.14 (s, 1H), 4.06 (d, J = 7.0 Hz, 2H), 2.98 (s, 3H), 2.72-2.56 (m, 2H); ESI-MS (m/z) 324, 326 [(MH)$^+$, Br$^{79,81}$]. |
| Intermediate-23 | 5-Bromo-6-methyl-3-propylbenzo[d]oxazol-2(3H)-one | ¹HNMR (400 MHz, CDCl$_3$) δ 7.16 (s, 1H), 7.11 (s, 1H), 3.78-3.74 (m, 2H), 1.86-1.81 (m, 2H), 1.01 (t, J = 7.5 Hz, 3H); ESI-MS (m/z) 270, 272 [(MH)$^+$, Br$^{79,81}$]. |
| Intermediate-24 | 5-Bromo-3-isobutyl-6-methylbenzo[d]oxazol-2(3H)-one | ¹HNMR (400 MHz, CDCl$_3$) δ 7.15 (s, 1H), 7.11 (s, 1H), 3.59 (d, J = 7.5 Hz, 2H), 2.43 (s, 3H), 2.28-2.13 (m, 1H), 1.00 (d, J = 6.5 Hz, 6H); ESI-MS (m/z) 284, 286 [(MH)$^+$, Br$^{79,81}$]. |
| Intermediate-25 | 5-Bromo-3-(2-((tert-butyldimethylsilyl)oxy)ethyl)-6-methylbenzo[d]oxazol-2(3H)-one | ¹HNMR (400 MHz, CDCl$_3$) δ 7.32 (s, 1H), 7.09 (s, 1H), 3.92 (s, 4H), 2.42 (s, 3H), 0.83 (s, 9H), 0.04 (s, 6H); ESI-MS (m/z) 386, 388 [(MH)$^+$, Br$^{79,81}$]. |

Intermediate-26a: 5-Bromo-3-methyloxazolo[4,5-b]pyridin-2(3H)-one

And

Intermediate-26b: 6-Bromo-5-cyclopropyl-3-methyl-oxazolo[4,5-b]pyridin-2(3H)-one And Intermediate-26c: 5-Cyclopropyl-3-methyl-6-(4,4,5,5-tetramethyl-1,3,2-dioxaborolan-2-yl)oxazolo[4,5-b]pyridin-2(3H)-one

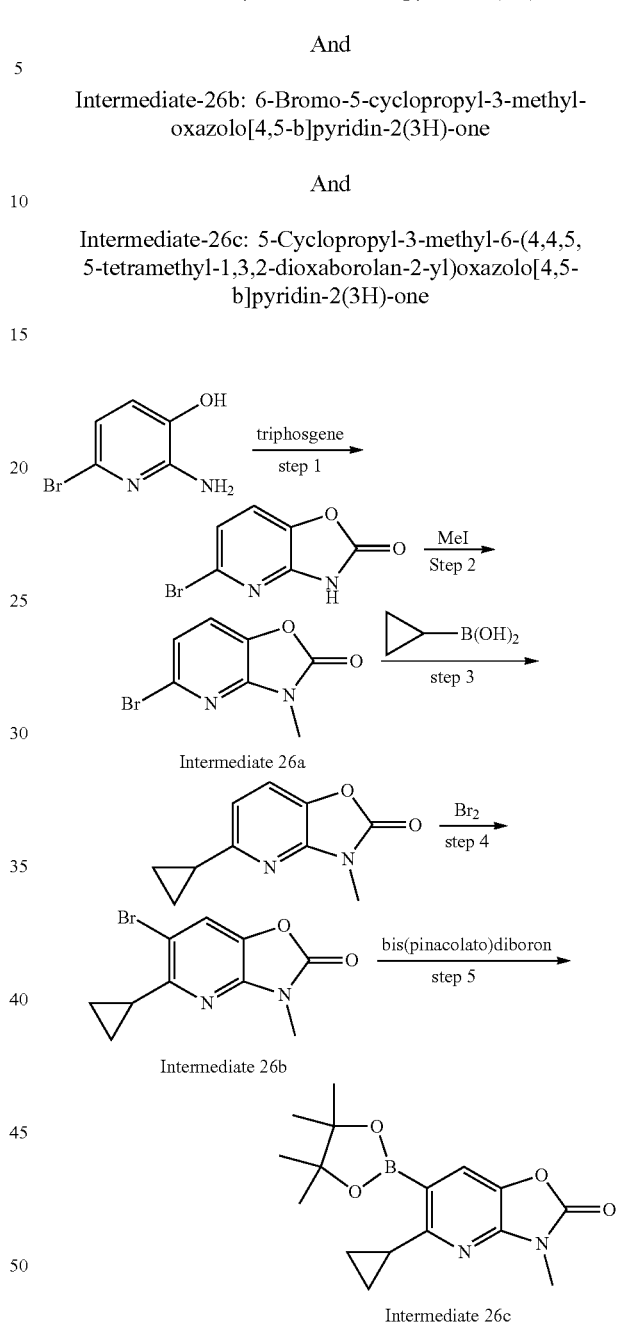

Step-1:

5-Bromooxazolo[4,5-b]pyridin-2(3H)-one: To an ice-cooled solution of 2-amino-bromopyridinate-3-ol (15 g, 79 mmol) and triethylamine (24.33 mL, 175 mmol) in CH$_2$Cl$_2$ (1000 mL) was added drop-wise a solution of triphosgene (9.42 g, 31.7 mmol) in CH$_2$Cl$_2$ (150 mL). The resulting mixture was stirred at room temperature for 2 h, and then diluted with DCM (500 mL). The organic layer was washed water (200 mL), brine (200 mL), dried (Na$_2$SO$_4$) and filtered. The filtrate was rotary evaporated to afford 12 g (70%) of the desired product. ¹HNMR (400 MHz, CDCl$_3$)) δ 7.55 (d, J=8.0 Hz, 1H), 7.26 (d, J=8.0 Hz, 1H), 6.88 (s, 1H, D$_2$O exchangeable); GC-MS (m/z) 214, 216 [M$^+$, Br$^{79, 81}$].

Step-2:

5-Bromo-3-methyloxazolo[4,5-b]pyridin-2(3H)-one: To a solution of step-purged Intermediate (5.60 g, 26.0 mmol) and potassium carbonate (5.40 g, 39.1 mmol) in acetone (25 m) was added methyl iodide (2.44 mL, 39.1 mmol) and the resulting mixture was stirred at room temperature for 16 h. Then the solvent was removed under reduced pressure and the resulting residue was partitioned between ethyl acetate (50 mL) and water (50 mL).

The aqueous layer was extracted with ethyl acetate (2×100 mL) and the combined organic layers were washed with brine (100 mL), dried over ($Na_2SO_4$) and filtered. The filtrate was rotary evaporated and the crude product was purified by flash column chromatography (silica gel, 13% ethyl acetate in hexane system as eluent) to afford 2.20 g (37%) of the desired product as a white solid. $^1$HNMR (400 MHz, CDCl3) δ 7.30 (d, J=8.0 Hz, 1H), 7.25 (d, J=8.0 Hz, 1H), 3.49 (s, 3H); ESI-MS (m/z) 229, 231 [(MH)$^+$, Br$^{79,\ 81}$].

Step-3:

5-Cyclopropyl-3-methyloxazolo[4,5-b]pyridin-2(3H)-one: To a nitrogen purged solution of step-2 Intermediate (550 mg, 2.401 mmol), cyclopropylboronic acid (227 mg, 2.64 mmol), dicyclohexyl(2',6'-diisopropoxy-[1,1'-biphenyl]-2-yl)phosphine (112 mg, 0.24 mmol), and $K_3PO_4$ (1.0 g, 4.80 mmol) in dioxane (15 mL) was added Pd(OAc)$_2$ (54 mg, 0.024 mmol). The resulting mixture was stirred at 100° C. in a sealed-tube for 16 h. The reaction was then cooled to room temperature and filtered through Celite. The residue was washed with ethyl acetate (15 mL) and the combined filtrates were concentrated under reduced pressure. The crude product was purified by flash column chromatography (silica gel, 15% ethyl acetate in hexane system as eluent) to give 333 mg (73%) of the desired product as white solid. $^1$HNMR (400 MHz, CDCl$_3$) δ 7.25 (d, J=8.0 Hz, 1H), 6.90 (d, J=8.0 Hz, 1H), 3.43 (s, 3H), 2.06-2.01 (m, 1H), 1.02-0.96 (m, 4H); GC-MS (m/z) 190 (M)$^+$.

Step-4:

6-Bromo-5-cyclopropyl-3-methyloxazolo[4,5-b]pyridin-2(3H)-one: To a solution of step-3 Intermediate (256 mg, 1.35 mmol) in acetic acid (4 mL), in water bath, was slowly added a solution of bromine (0.07 mL, 1.35 mmol) in acetic acid (1 mL). After stirring at room temperature for 4 h, the solvent was removed under reduced pressure and the residue was purified by flash column chromatography (silica gel, 10% ethyl acetate in hexane system as eluent) to afford 300 mg (83%) of the desired product as white solid. $^1$HNMR (400 MHz, CDCl$_3$) δ 7.54 (s, 1H), 3.41 (s, 3H), 2.55-2.49 (m, 1H), 1.13-0.98 (m, 4H); ESI-MS (m/z) 269, 271 [(MH)$^+$, Br$^{79,\ 81}$].

Step-5:

5-Cyclopropyl-3-methyl-6-(4,4,5,5-tetramethyl-1,3,2-dioxaborolan-2-yl)oxazolo[4,5-b]pyridin-2(3H)-one: The title compound was prepared from step-4 Intermediate by following the similar procedure as described in step-4 of Intermediate-1. $^1$HNMR (400 MHz, CDCl$_3$) δ 7.68 (s, 1H), 3.40 (s, 3H), 2.13-1.89 (m, 1H), 1.37 (s, 12H), 1.10-1.07 (m, 2H), 1.05-0.92 (m, 2H); ESI-MS (m/z) 317 (MH)$^+$.

Intermediate-27a: 6-Bromo-5-ethyl-3-methyloxazolo[4,5-b]pyridin-2(3H)-one

And

Intermediate-27b: 5-Ethyl-3-methyl-6-(4,4,5,5-tetramethyl-1,3,2-dioxaborolan-2-yl)oxazolo[4,5-b]pyridin-2(3H)-one

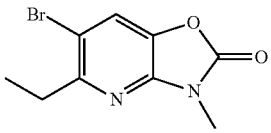

Intermediate 27a

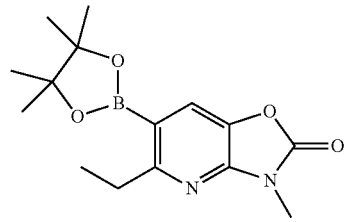

Intermediate 27b

The title compound was prepared by following the similar procedure as described in Intermediate-26.

Intermediate-27a $^1$HNMR (400 MHz, CDCl$_3$) δ 7.56 (s, 1H), 3.48 (s, 3H), 2.96 (q, J=7.5 Hz, 2H), 1.29 (t, J=7.5 Hz, 3H); ESI-MS (m/z) 257, 259 [(MH)$^+$, Br$^{79,\ 81}$].

Intermediate-27b $^1$HNMR (400 MHz, CDCl$_3$) δ 7.73 (s, 1H), 3.49 (s, 3H), 3.10 (q, J=7.5 Hz, 2H), 1.36 (s, 12H), 1.24 (d, J=7.5 Hz, 3H); ESI-MS (m/z) 305 (MH)$^+$.

Intermediate-28: 6-Bromo-3,5-dimethyloxazolo[4,5-b]pyridin-2(3H)-one

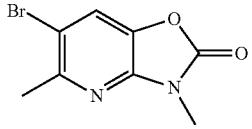

Intermediate 28

The title compound was prepared by following the similar procedure as described in Intermediate-26. $^1$HNMR (400 MHz, CDCl$_3$) δ 7.57 (s, 1H), 3.47 (s, 3H), 2.65 (s, 3H); ESI-MS (m/z) 243, 245 [(MH)$^+$, Br$^{79,\ 81}$].

Intermediate-29: 6-Bromo-1,5-dimethyloxazolo[5,4-b]pyridin-2(1H)-one

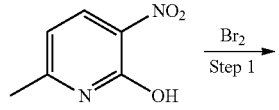

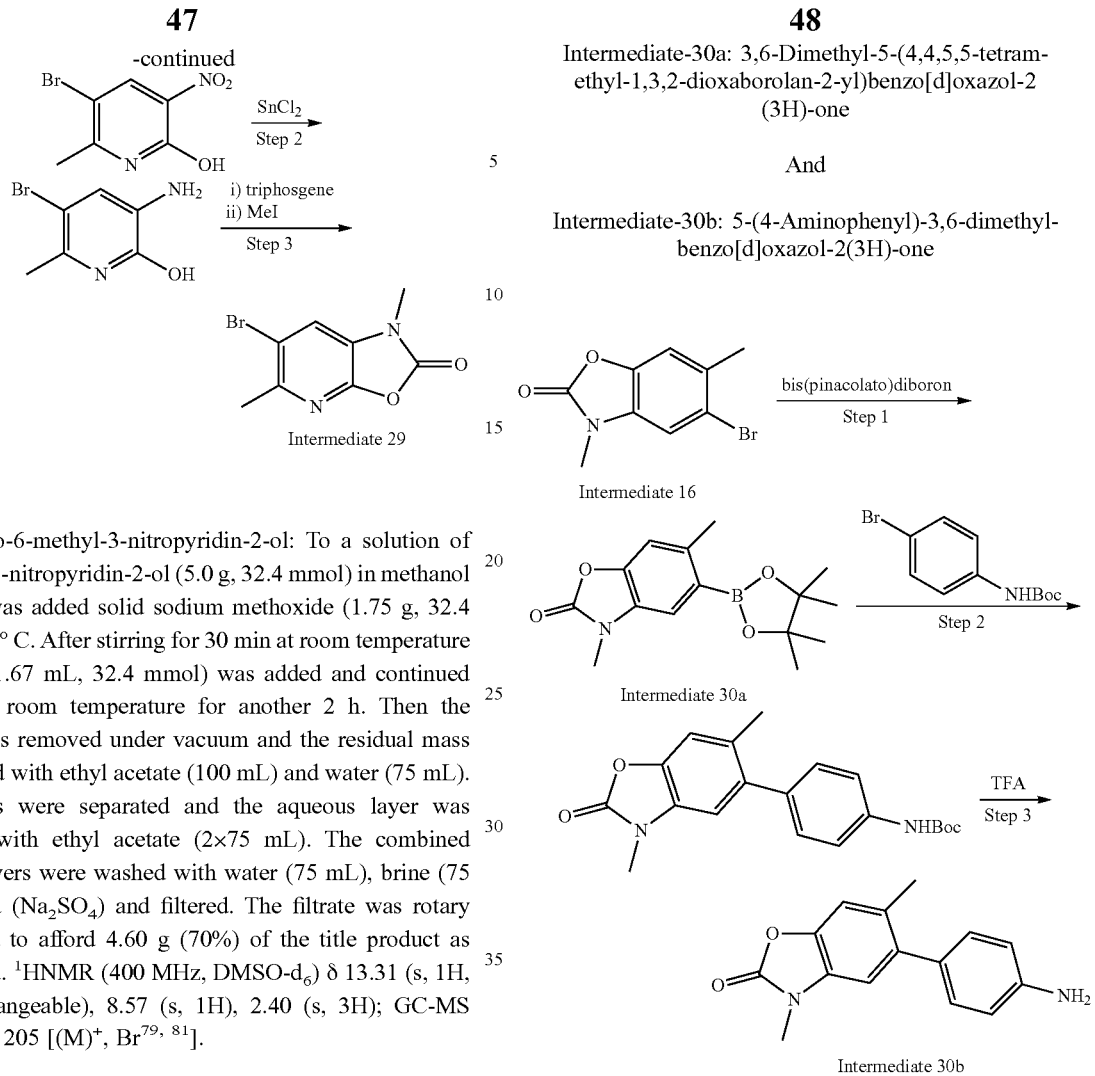

Intermediate-30a: 3,6-Dimethyl-5-(4,4,5,5-tetramethyl-1,3,2-dioxaborolan-2-yl)benzo[d]oxazol-2(3H)-one And Intermediate-30b: 5-(4-Aminophenyl)-3,6-dimethylbenzo[d]oxazol-2(3H)-one Step-1:

5-Bromo-6-methyl-3-nitropyridin-2-ol: To a solution of 6-methyl-3-nitropyridin-2-ol (5.0 g, 32.4 mmol) in methanol (50 mL) was added solid sodium methoxide (1.75 g, 32.4 mmol) at 0° C. After stirring for 30 min at room temperature bromine (1.67 mL, 32.4 mmol) was added and continued stirring at room temperature for another 2 h. Then the solvent was removed under vacuum and the residual mass was diluted with ethyl acetate (100 mL) and water (75 mL). The layers were separated and the aqueous layer was extracted with ethyl acetate (2×75 mL). The combined organic layers were washed with water (75 mL), brine (75 mL), dried ($Na_2SO_4$) and filtered. The filtrate was rotary evaporated to afford 4.60 g (70%) of the title product as white solid. $^1$HNMR (400 MHz, DMSO-$d_6$) δ 13.31 (s, 1H, $D_2O$ exchangeable), 8.57 (s, 1H), 2.40 (s, 3H); GC-MS (m/z) 203, 205 [(M)$^+$, Br$^{79, 81}$].

Step-2:

3-Amino-5-bromo-6-methylpyridin-2-ol: To a solution of step-1 Intermediate (1.50 g, 6.44 mmol) in EtOH/water (30 mL, 2:1) at 0° C. was added solution of $SnCl_2.2H_2O$ (5.81 g, 25.7 mmol) in conc HCl/water (10 mL, 1:1). The resulting mixture was stirred for 2 h at room temperature and then poured into ice cooled water followed by the addition of ethyl acetate (50 mL). The mixture was neutralized with solid sodium bicarbonate and the resulting suspension was filtered. The residue was thoroughly washed with ethyl acetate (2×25 mL) and the combined filtrates were separated. The aqueous layer was extracted with ethyl acetate (50 mL) and the combined organic layers were washed with brine (50 mL), dried ($Na_2SO_4$) and filtered. The filtrate was rotary evaporated to give 0.5 g (39%) of the desired product as white solid. $^1$HNMR (400 MHz, DMSO-$d_6$) δ 11.67 (s, 1H, $D_2O$ exchangeable), 6.50 (s, 1H), 5.12 (s, 2H, $D_2O$ exchangeable), 2.12 (s, 3H); GC-MS (m/z) 232, 234 [(M)$^+$, Br$^{79, 81}$].

Step-3:

6-Bromo-1,5-dimethyloxazolo[5,4-b]pyridin-2(1H)-one: The title compound was prepared by following the similar procedure as described in step-1 and step-2 of Intermediate-26. $^1$HNMR (400 MHz, CDCl$_3$) δ 7.39 (s, 1H), 3.42 (s, 3H), 2.64 (s, 3H); ESI-MS (m/z) 243, 245 [(MH)$^+$, Br$^{79, 81}$].

Step-1:

3,6-Dimethyl-5-(4,4,5,5-tetramethyl-1,3,2-dioxaborolan-2-yl)benzo[d]oxazol-2(3H)-one: In a sealed-tube, to a stirred and nitrogen purged solution of Intermediate-16 (0.9 g, 3.72 mmol) in 1,4-dioxane (25 mL) was added potassium acetate (0.547 g, 5.58 mmol) and bis(pinacolato)diboron (1.13 g, 4.46 mmol) followed by the addition of Pd(OAc)$_2$ (83 mg, 0.37 mmol) and 1,1'-bis(diphenylphosphino)ferrocene (206 mg, 0.37 mmol). The resulting mixture was stirred for 4 h at 100° C. The reaction mass was cooled to room temperature and filtered through Celite bed, and the residue was washed with ethyl acetate (2×40 mL). The combined filtrates were concentrated under vacuum and the crude product was purified by flash column chromatography (silica gel, 30% ethyl acetate in hexane system as eluent) to afford 1.0 g (93%) of the desired product as white solid. $^1$HNMR (400 MHz, CDCl$_3$) δ 7.36 (s, 1H), 7.03 (s, 1H), 3.40 (s, 3H), 2.59 (s, 3H), 1.37 (s, 12H); GC-MS (m/z) 289 (M)$^+$.

Step-2:

tert-Butyl (4-(3,6-dimethyl-2-oxo-2,3-dihydrobenzo[d]oxazol-5-yl)phenyl)carbamate: In a sealed-tube, to a stirred and nitrogen purged solution of 2M aqueous aqueous sodium carbonate (8.3 mL) in 1,4-dioxane (50 mL) was added step-1 Intermediate (2.40 g, 8.30 mmol), tert-butyl (4-bromophenyl)carbamate (2.48 g, 9.13 mmol) followed by the addition of bis(triphenylphosphine) palladium (II) chloride (0.583 g, 0.83 mmol). The resulting mixture was stirred at 100° C. for 6 h. The reaction mass was cooled to room temperature and then filtered through Celite bed, the residue was washed with ethyl acetate (2×50 mL). The combined filtrates were concentrated under reduced pressure and the crude product was purified by flash column chromatography to afford 0.71 g (24%) of the desired product as a white solid. $^1$HNMR (400 MHz, CDCl$_3$) δ 7.45 (d, J=8.0 Hz, 2H), 7.24 (d, J=8.0 Hz, 2H), 7.11 (s, 1H), 6.80 (s, 1H), 6.58 (bs, 1H, D$_2$O exchangeable), 3.39 (s, 3H), 2.27 (s, 3H), 1.56 (s, 9H); ESI-MS (m/z) 355 (MH)$^+$.

Step-3:

5-(4-Aminophenyl)-3,6-dimethylbenzo[d]oxazol-2(3H)-one: To a stirred and cooled solution of step-2 Intermediate (0.7 g, 1.98 mmol) in DCM (5 mL) was added TFA (1.52 mL, 19.75 mmol) and the resulting mixture was stirred at 0° C. for 2 h. The reaction mass was concentrated under reduced pressure at room temperature then diluted with ethyl acetate (80 mL), washed with saturated aqueous solution of NaHCO$_3$ (50 mL) and brine (50 mL). Separated organic layer was dried over anhydrous Na$_2$SO$_4$ and concentrated to afford 0.48 g (98%) as a pale brown solid. $^1$HNMR (400 MHz, CDCl$_3$) δ 7.11 (d, J=8.0 Hz, 2H), 7.09 (s, 1H), 6.81 (s, 1H), 6.76 (d, J=8.0 Hz, 2H), 3.39 (s, 3H), 2.29 (s, 3H); GC-MS (m/z) 254 (M)$^+$.

Intermediate-31:
6-Bromo-7-chloro-3-methylbenzo[d]oxazol-2(3H)-one

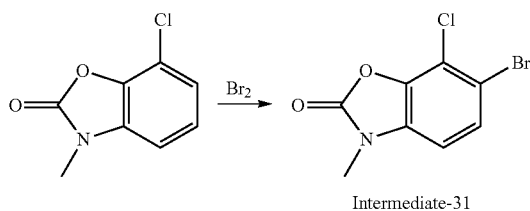

Intermediate-31

To a solution of 7-Chloro-3-methylbenzo[d]oxazol-2 (3H)-one (116 mg, 0.63 mmol, prepared by following the similar procedure as described in WO2006061379) in acetic acid (5 mL) in water bath was slowly added bromine (33 µL, 0.63 mmol). After stirring for 16 h at room temperature the solvent was removed under reduced pressure and the residue was purified by flash column chromatography (silica gel, 15% ethyl acetate in hexane system as eluent) to afford 145 mg (87%) as a white solid. $^1$HNMR (400 MHz, CDCl$_3$) δ 7.51 (d, J=8.0 Hz, 1H), 6.79 (d, J=8.0 Hz, 1H), 3.43 (s, 3H); ESI-MS (m/z) 264 (MH)$^+$.

Intermediate-32a:
4-Bromo-N-(2,6-difluorophenyl)benzamide

And

Intermediate-32b: N-(2,6-Difluorophenyl)-4-(4,4,5, 5-tetramethyl-1,3,2-dioxaborolan-2-yl)benzamide Intermediate 32a

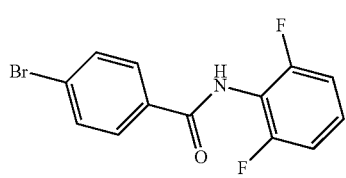

Intermediate 32b

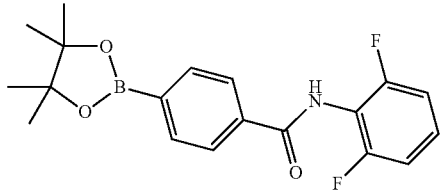

The title compounds were prepared by following the procedure as described in WO2013164769.

Intermediate-33a:
4-Bromo-N-(2,6-difluorobenzyl)aniline

And

Intermediate-33b: N-(2,6-Difluorobenzyl)-4-(4,4,5, 5-tetramethyl-1,3,2-dioxaborolan-2-yl)aniline

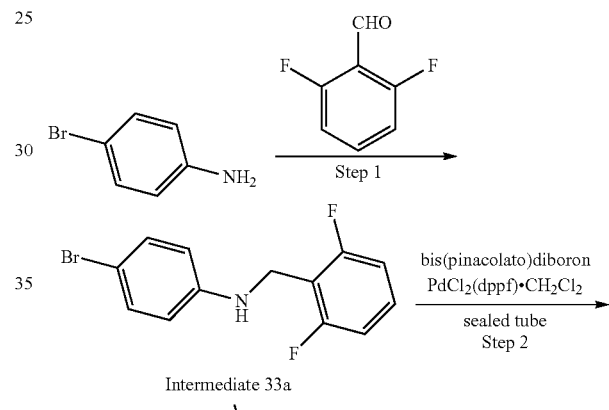

Intermediate 33a

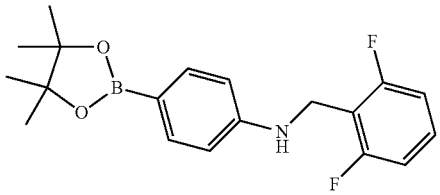

Intermediate 33b

Step-1:

4-Bromo-N-(2,6-difluorobenzyl)aniline: To an ice-cooled solution of 4-bromoaniline (10.0 g, 58.1 mmol) in methanol (100 mL) was added 2,6-difluorobenzaldehyde (6.35 mL, 58.1 mmol) and acetic acid (3.33 mL, 58.1 mmol). The resulting mixture was stirred for 30 min and sodium cyanoborohydride (5.85 g, 93 mmol) was added. The reaction was allowed to stir at room temperature for 6 h. The solvent was evaporated under reduced pressure, diluted with water (50 mL) and extracted with ethyl acetate (2×50 mL). The combined organic layers were washed with water (50 mL), saturated aqueous solution of sodium bicarbonate (50 mL), dried (Na$_2$SO$_4$) and filtered. The filtrate was rotary evaporated and the crude product was purified by flash column chromatography (silica gel, hexane/ethyl acetate 8:2 as eluent) to afford 16.0 g (92%) of the desired product as a white solid. $^1$HNMR (400 MHz, DMSO-d$_6$) δ 7.44-7.37 (m, 1H), 7.21 (d, J=8.5 Hz, 2H), 7.11 (t, J=8.5 Hz, 2H), 6.61 (d, J=8.5 Hz, 2H), 6.24 (t, J=5.5 Hz, 1H, D$_2$O exchangeable), 4.23 (d, J=5.5 Hz, 2H); ESI-MS (m/z) 298, 300 [(MH)$^+$, Br$^{79, 81}$].

Step-2:

N-(2,6-Difluorobenzyl)-4-(4,4,5,5-tetramethyl-1,3,2-dioxaborolan-2-yl)aniline: The title compound was prepared from step-1 Intermediate by following the similar procedure as described in step-4 of Intermediate-1. $^1$HNMR (400 MHz, CDCl$_3$) δ 7.65 (d, J=8.5 Hz, 2H), 7.26-7.18 (m, 1H), 6.88 (t, J=7.0 Hz 2H), 6.73 (d, J=8.5 Hz, 2H), 4.47 (s, 2H), 1.32 (s, 12H). ESI-MS (m/z) 346 (MH)$^+$.

Intermediate-34: 2-Bromo-N-(2,6-difluorophenyl)thiazole-4-carboxamide

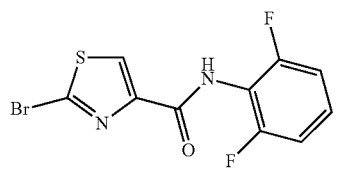 [SMILES: O=C(Nc1c(F)cccc1F)c1csc(Br)n1]

To a stirred solution of 2-bromothiazole-4-carboxylic acid (2.0 g, 9.61 mmol) in DMF (20 mL) was added HATU (5.48 g, 14.4 mmol) followed by DIPEA (5.0 mL, 28.8 mmol) and the resulting mixture was stirred at room temperature for 15 min. Then 2,6-difluoroaniline (1.2 mL, 9.61 mmol) was added to the above stirring mixture and the resulting mixture was continued to stir for another 16 h at room temperature. The reaction mass was then poured into ice-water (50 mL). Solid product precipitated out was filtered off and dried to afford 2.0 g (96%) of the desired product as a white solid. $^1$HNMR (400 MHz, CDCl$_3$) δ 8.55 (brs, 1H, D$_2$O exchangeable), 8.22 (s, 1H), 7.32-7.22 (m, 1H), 7.03 (t, J=8.0 Hz, 2H); ESI-MS (m/z) 319, 321 [(MH)$^+$, Br$^{79, 81}$].

Intermediate-35: 2-Bromo-N-(2,6-difluorophenyl)thiazole-5-carboxamide

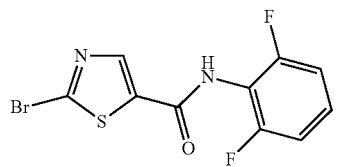 [SMILES: O=C(Nc1c(F)cccc1F)c1cnc(Br)s1]

The title compound was prepared from 2-bromothiazole-5-carboxylic acid by following the similar procedure as described in Intermediate-34. $^1$HNMR (400 MHz, CDCl$_3$) δ 8.09 (s, 1H), 7.66 (brs, 1H, D$_2$O exchangeable), 7.34-7.17 (m, 1H), 6.99 (t, J=8.0 Hz, 2H); ESI-MS (m/z) 319, 321 [(MH)$^+$, Br$^{79, 81}$].

Intermediate-36: 5-Chloro-N-(3,5-difluoropyridin-4-yl)thiophene-2-carboxamide

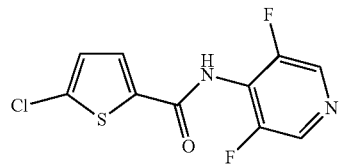 [SMILES: O=C(Nc1c(F)cncc1F)c1ccc(Cl)s1]

To a stirred solution of 5-Chlorothiophene-2-carboxylic acid (250 mg, 1.54 mmol) in CH$_2$Cl$_2$ (20 mL) was added oxalyl chloride (0.27 mL, 3.07 mmol) followed by the catalytic amount of DMF. The resulting mixture was stirred for 1 h at room temperature. The excess of oxalyl chloride and solvent was removed under vacuum to get the corresponding acid chloride. To a suspension of NaH (0.184 g, 4.61 mmol) in DMF (10 mL) was added drop-wise a solution of 3,5-difluoropyridin-4-amine (0.2 g, 1.537 mmol) in DMF (2 mL) at 0° C. A cooled solution of above freshly prepared acid chloride in THF (5 mL) was added to this reaction mixture and the resulting mixture was continued to stir at room temperature for another 16 h. The reaction mixture was then poured into ice cooled water (20 mL) and diluted with ethyl acetate (50 mL). The layers were separated and the organic layer was washed with water (20 mL) and brine (20 mL), dried (Na$_2$SO$_4$) and filtered. The filtrate was concentrated under reduced pressure and the crude product was purified by flash column chromatography to afford 200 mg (47%) as a white solid. $^1$HNMR (400 MHz, CDCl$_3$) δ 8.42 (s, 2H), 7.93 (brs, 1H, D$_2$O exchangeable), 7.59 (d, J=4.0 Hz, 1H), 7.01 (d, J=4.0 Hz, 1H); GC-MS (m/z) 274, 276 [M$^+$, Cl$^{35, 37}$].

Intermediate-37: 5-Bromo-N-(3,5-dichloropyridin-4-yl)thiophene-2-carboxamide

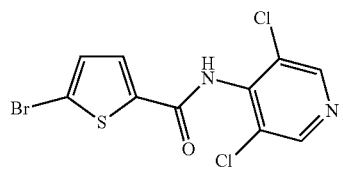

The title compound was prepared by following the similar procedure as described in Intermediate-36. $^1$HNMR (400 MHz, CDCl$_3$) δ 8.57 (s, 2H), 7.94 (brs, 1H, D$_2$O exchangeable), 7.55 (d, J=4.0 Hz, 1H), 7.16 (d, J=4.0 Hz, 1H); ESI-MS (m/z) 351, 353, 355 [(MH)$^+$, Cl$^{35, 37}$ Br$^{79, 81}$].

Intermediate-38: 5-Bromo-N-(3-methylpyridin-4-yl)thiophene-2-carboxamide

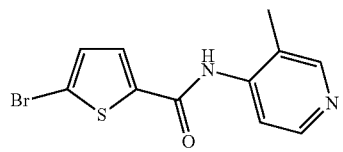 [SMILES: Cc1cnccc1NC(=O)c1ccc(Br)s1]

The title compound was prepared by following the similar procedure as described in Intermediate-36. $^1$H NMR (400 MHz, CDCl$_3$) δ 8.44 (d, J=5.5 Hz, 1H), 8.40 (s, 1H), 8.26 (d, J=5.5 Hz, 1H), 7.50 (d, J=4.0 Hz, 1H), 7.15 (d, J=4.0 Hz, 1H), 2.37 (s, 3H); ESI-MS (m/z) 297, 299 [(MH)$^+$, Br$^{79, 81}$].

Intermediate-39a:
6-Bromo-3,5-dimethylbenzo[d]oxazol-2(3H)-one

And

Intermediate-39b: 3,5-Dimethyl-6-(4,4,5,5-tetramethyl-1,3,2-dioxaborolan-2-yl)benzo[d]oxazol-2(3H)-one

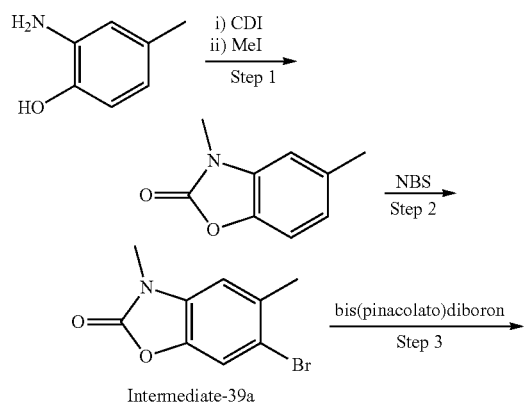

Intermediate-39a

Intermediate-39b

Step-1:
3,5-Dimethylbenzo[d]oxazol-2(3H)-one: To a stirred solution of 2-amino-4-methylphenol (10.0 g, 81 mmol) in THF (100 mL) was added CDI (15.8 g, 97 mmol) at room temperature and then stirred at reflux for 2 h. The reaction mass was allowed to cooled down to room temperature and then diluted with ethyl acetate (200 mL). The combined organic layers were washed with water (100 mL) and brine (100 mL), dried (Na$_2$SO$_4$) and filtered. The filtrate was concentrated under reduced pressure to afford 5-methylbenzo[d]oxazol-2(3H)-one (12.0 g, 99%) as a brown solid. $^1$H NMR (400 MHz, CDCl$_3$) δ 9.50 (s, 1H), 7.06 (d, J=8.0 Hz, 1H), 6.92-6.86 (m, 2H), 2.37 (s, 3H); GC-MS (m/z) 149 (M).

To a stirred solution of 5-Methylbenzo[d]oxazol-2(3H)-one (12.0 g, 80 mmol) in DMF (100 mL) was added potassium carbonate (16.7 g, 121 mmol) and methyl iodide (7.6 mL, 121 mmol) at room temperature. The resulting mixture was stirred for 16 h at room temperature. The reaction mass was diluted with ice-water (300 mL), and the precipitated product was filtered off and dried to afford 10 g (76%) of the title product as white solid. $^1$HNMR (400 MHz, CDCl$_3$) δ 7.08 (d, J=8.0 Hz, 1H), 6.92 (dd, J=8.0 & 2.0 Hz, 1H), 6.79 (d, J=2.0 Hz, 1H), 3.39 (s, 3H), 2.42 (s, 3H); GC-MS (m/z) 163 (M)$^+$.

Step-2:
6-Bromo-3,5-dimethylbenzo[d]oxazol-2(3H)-one: A mixture of step-1 Intermediate (2.0 g, 12.2 mmol), NBS (2.40 g, 13.5 mmol), silica gel (EM Scientific, 230-400 mesh, 11 g) in CH$_2$Cl$_2$ (70 mL) was stirred at room temperature for 16 h. The solvent was removed under vacuum and the residue was subjected to flash column chromatography (silica gel, 2:3 ethyl acetate/hexane system as eluent) to afford 2.10 g (71%) as a white solid. $^1$HNMR (400 MHz, CDCl$_3$) δ 7.39 (s, 1H), 6.85 (s, 1H), 3.39 (s, 3H), 2.44 (s, 3H); GC-MS (m/z) 241, 243 [M$^+$, Br$^{79, 81}$].

Step-3:
3,5-Dimethyl-6-(4,4,5,5-tetramethyl-1,3,2-dioxaborolan-2-yl)benzo[d]oxazol-2(3H)-one: The title compound was prepared from step-2 Intermediate by following the similar procedure as described in step-1 of Intermediate-30. $^1$HNMR (400 MHz, CDCl$_3$) δ 7.58 (s, 1H), 6.77 (s, 1H), 3.39 (s, 3H), 2.60 (s, 3H), 1.36 (s, 12H); GC-MS (m/z) 289 (M)$^+$.

Intermediate-40a:
5-Bromo-6-ethyl-3-methylbenzo[d]oxazol-2(3H)-one

And

Intermediate-40b: 6-Ethyl-3-methyl-5-(4,4,5,5-tetramethyl-1,3,2-dioxaborolan-2-yl)benzo[d]oxazol-2(3H)-one

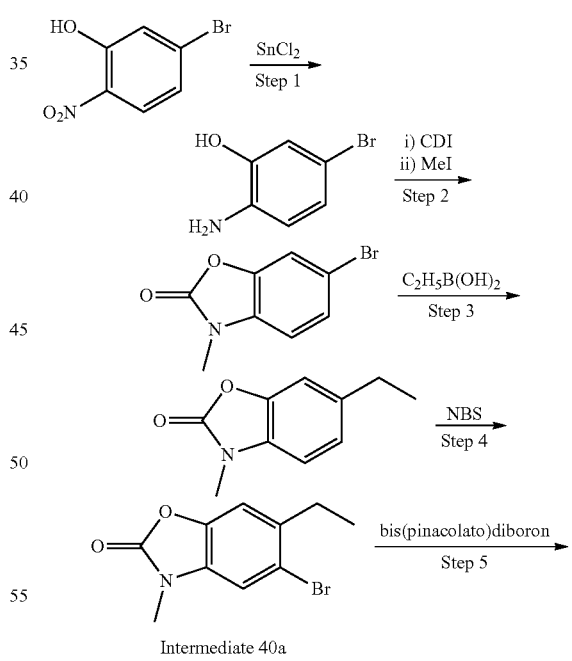

Intermediate 40a

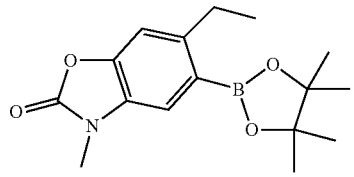

Intermediate 40b

Step-1:

2-Amino-5-bromophenol: The title compound was prepared from 5-bromo-2-nitrophenol by following the similar procedure as described in step-2 of Intermediate-29. $^1$HNMR (400 MHz, DMSO-$d_6$) δ 9.50 (brs, 1H, $D_2O$ exchangeable), 6.75 (d, J=2.0 Hz, 1H), 6.68 (dd, J=8.0 & 2.0 Hz, 1H), 6.51 (d, J=8.0 Hz, 1H), 4.67 (brs, 2H, $D_2O$ exchangeable); GC-MS (m/z) 187, 189 [M+, $Br^{79,81}$].

Step-2:

6-Bromo-3-methylbenzo[d]oxazol-2(3H)-one: The title compound was prepared from step-1 Intermediate by following the similar procedure as described in step-1 of Intermediate-39. $^1$HNMR (400 MHz, $CDCl_3$) δ 7.39 (d, J=2.0 Hz, 1H), 7.36 (dd, J=8.0 & 2.0 Hz, 1H), 6.86 (d, J=8.0 Hz, 1H), 3.42 (s, 3H); GC-MS (m/z) 227, 229 [$M^+$, $Br^{79,81}$].

Step-3:

6-Ethyl-3-methylbenzo[d]oxazol-2(3H)-one: In a sealed-tube, to a stirred and nitrogen purged solution of step-2 Intermediate (4.0 g, 17.5 mmol), ethylboronic acid (1.94 g, 26.3 mmol) and potassium phosphate (7.45 g, 35.1 mmol) in 1,4-dioxane (40 mL) was added dicyclohexyl(2',6'-diisopropoxy-[1,1'-biphenyl]-2-yl)phosphine (0.819 g, 1.754 mmol) and $PdOAc_2$ (0.39 g, 1.75 mmol). The resulting mixture was stirred at 100° C. for 2 h. The reaction mixture was cooled to room temperature and diluted with ethyl acetate (100 mL), filtered through Celite pad and residue was washed with ethyl acetate (100 mL). The filtrate was concentrated under reduced pressure and the crude product was purified by flash column chromatography (silica gel, hexane/ethyl acetate 9:1 as eluent) to afford 3.0 g (97%) as a white solid. $^1$HNMR (400 MHz, $CDCl_3$) δ 7.07 (d, J=2.0 Hz, 1H), 7.03 (dd, J=8.0 & 2.0 Hz, 1H), 6.88 (d, J=8.0 Hz, 1H), 3.40 (s, 3H), 2.69 (q, J=7.5 Hz, 2H), 1.25 (t, J=7.5 Hz, 3H); GC-MS (m/z) 177 ($M^+$).

Step-4:

5-Bromo-6-ethyl-3-methylbenzo[d]oxazol-2(3H)-one: To a stirred solution of step-3 Intermediate (3.0 g, 16.9 mmol) in acetic acid (30 mL) was added NBS (3.31 g, 18.6 mmol) portion wise. The resulting mixture was stirred at 75° C. for 16 h. The reaction mass was cooled to room temperature and then concentrated under reduced pressure. The residue was diluted with ethyl acetate (200 mL), washed with water (100 mL) and brine (100 mL). The organic layer was dried ($Na_2SO_4$) and filtered. The filtrate was rotary evaporated to afford 1.8 g (42%) of the title compound as white solid. $^1$HNMR (400 MHz, $CDCl_3$) δ 7.15 (s, 1H), 7.11 (s, 1H), 3.39 (s, 3H), 2.79 (q, J=7.5 Hz, 2H), 1.24 (t, J=7.5 Hz, 3H); GC-MS (m/z) 255, 257 [$M^+$, $Br^{79,81}$].

Step-5:

6-Ethyl-3-methyl-5-(4,4,5,5-tetramethyl-1,3,2-dioxaborolan-2-yl)benzo[d]oxazol-2(3H)-one: The title compound was prepared by following the similar procedure as described in step-4 of Intermediate-1. $^1$HNMR (400 MHz, $CDCl_3$) δ 7.36 (s, 1H), 7.05 (s, 1H), 3.40 (s, 3H), 2.96 (q, J=7.5 Hz, 2H), 1.36 (s, 12H), 1.19 (t, J=7.5 Hz, 3H); GC-MS (m/z) 303 ($M^+$).

Intermediate-41a: 5-Bromo-6-cyclopropyl-3-methyl-benzo[d]oxazol-2(3H)-one

And

Intermediate-41b: 6-Cyclopropyl-3-methyl-5-(4,4,5,5-tetramethyl-1,3,2-dioxaborolan-2-yl)benzo[d]oxazol-2(3H)-one

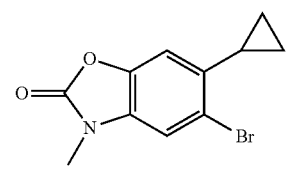

Intermedaite 41a

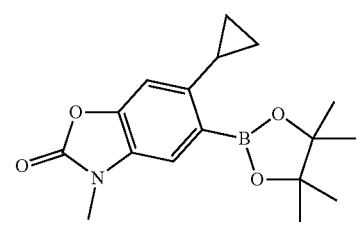

Intermediate 41b

The title compounds were prepared by following the similar procedure as described in Intermediate 40.

Intermediate-41a $^1$HNMR (400 MHz, $CDCl_3$) δ 7.17 (s, 1H), 6.86 (s, 1H), 3.38 (s, 3H), 2.16-2.12 (m, 1H), 1.08-1.01 (m, 2H), 0.69-0.62 (m, 2H); GC-MS (m/z) 269, 271 [$(M)^+$, $Br^{79,81}$].

Intermediate-41b $^1$HNMR (400 MHz, $CDCl_3$) δ 7.33 (s, 1H), 6.73 (s, 1H), 3.41 (s, 3H), 2.77-2.72 (m, 1H), 1.39 (s, 12H), 1.05-0.94 (m, 2H), 0.72-0.60 (m, 2H); GC-MS (m/z) 315 ($M^+$).

Intermediate-42: 3-(Difluoromethyl)-6-methyl-5-(4,4,5,5-tetramethyl-1,3,2-dioxaborolan-2-yl)benzo[d]oxazol-2(3H)-one

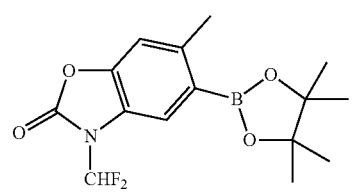

Intermediate 42

The title compound was prepared from Intermediate-21 by following the similar procedure as described in step-1 of Intermediate-30. ESI-MS (m/z) 325 $(MH)^+$.

Intermediate-43: tert-Butyl (4-(4,4,5,5-tetramethyl-1,3,2-dioxaborolan-2-yl)phenyl)carbamate

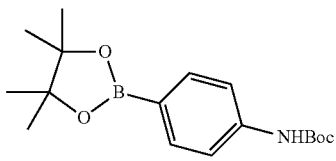

Intermediate-43

The title compound was prepared by following the procedure as described in WO2013164769.

Intermediate-44: 6-(4-Aminophenyl)-3,4-dimethyl-benzo[d]oxazol-2(3H)-one

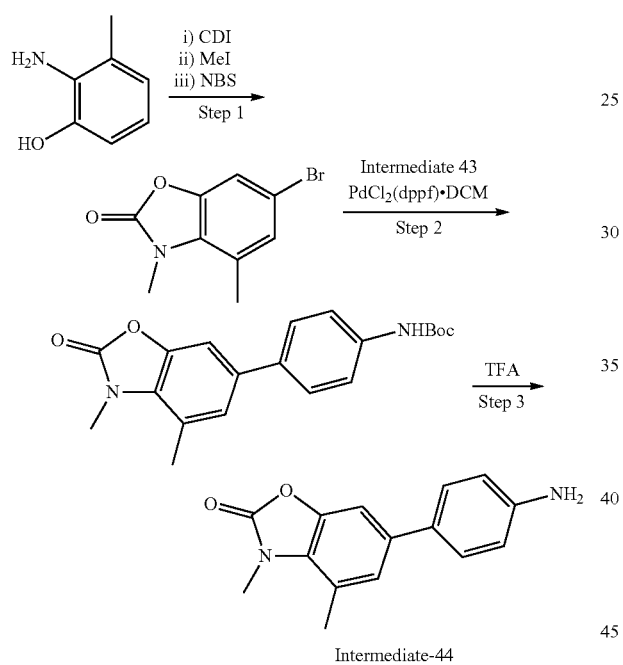

Intermediate-44

Step-1:

6-Bromo-3,4-dimethylbenzo[d]oxazol-2(3H)-one: The title compound was prepared from 2-amino-3-methylphenol by following the similar procedure as described in step-1 and step-2 of Intermediate-39. $^1$HNMR (400 MHz, CDCl$_3$) δ 7.22 (d, J=2.0 Hz, 1H), 7.10 (d, J=2.0 Hz, 1H), 3.62 (s, 3H), 2.56 (s, 3H); GC-MS (m/z) 241, 243 [(M)$^+$, Br$^{79, 81}$].

Step-2:

tert-Butyl (4-(3,4-dimethyl-2-oxo-2,3-dihydrobenzo[d]oxazol-6-yl)phenyl)carbamate: In a sealed tube, to a stirred and nitrogen purged solution of step-1 Intermediate (0.5 g, 2.06 mmol) Intermediate-43 (0.659 g, 2.066 mmol) and 2M aqueous solution of potassium carbonate (2.1 mL, 4.2 mmol) in 1,4-dioxane (20 mL) was added PdCl$_2$(dppf)-CH$_2$Cl$_2$ adduct (0.169 g, 0.207 mmol). The resulting mixture was stirred at 110° C. for 6 h. The reaction mass was diluted with ethyl acetate (50 mL), filtered through Celite bed, the cake was washed with ethyl acetate (2×20 mL). The combined organic layers were washed with water (20 mL), brine (20 mL), dried (Na$_2$SO$_4$) and filtered. The filtrate was concentrated under vacuum and the crude product was purified by flash column chromatography to obtain 0.44 g (60%) of the desired product as a white solid. $^1$HNMR (400 MHz, CDCl$_3$) δ 7.48 (d, J=8.0 Hz, 2H), 7.44 (d, J=8.0 Hz, 2H), 7.25 (d, J=2.0 Hz, 1H), 7.13 (d, J=2.0 Hz, 1H), 6.57 (brs, 1H, D$_2$O exchangeable), 3.66 (s, 3H), 2.63 (s, 3H), 1.55 (s, 9H); ESI-MS (m/z) 355 (M)$^+$.

Step-3:

6-(4-Aminophenyl)-3,4-dimethylbenzo[d]oxazol-2(3H)-one: The title compound was prepared from step-2 Intermediate by following the similar procedure as described in step-3 of Intermediate-30. $^1$HNMR (400 MHz, DMSO-d$_6$) δ 7.36 (d, J=8.0 Hz, 2H), 7.33 (d, J=2.0 Hz, 1H), 7.19 (d, J=2.0 Hz, 1H), 6.64 (d, J=8.0 Hz, 2H), 5.26 (brs, 2H, D$_2$O exchangeable), 3.55 (s, 3H), 2.58 (s, 3H); ESI-MS (m/z) 255 (M)$^+$.

Intermediate-45a: 6-Bromo-5-ethyl-3-methylbenzo[d]oxazol-2(3H)-one

And

Intermediate-45b: 5-Ethyl-3-methyl-6-(4,4,5,5-tetramethyl-1,3,2-dioxaborolan-2-yl)benzo[d]oxazol-2(3H)-one

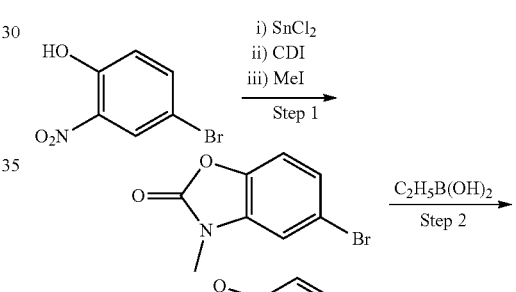

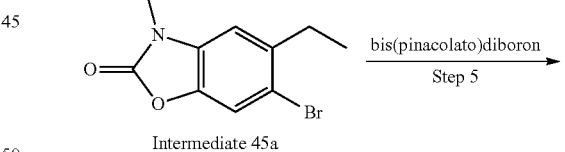

Intermediate 45a

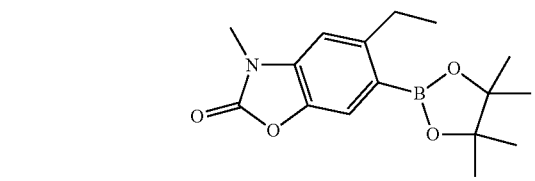

Intermediate 45b

The title compounds were prepared by following the similar procedure as described in Intermediate-40.

Intermediate-45a $^1$HNMR (400 MHz, CDCl$_3$) δ 7.40 (s, 1H), 6.84 (s, 1H), 3.41 (s, 3H), 2.81 (q, J=7.5 Hz, 2H), 1.26 (t, J=7.5 Hz, 3H); GC-MS (m/z) 255, 257 [(M)$^+$, Br$^{79, 81}$].

Intermediate-45b

ESI-MS (m/z) 304 (MH)+.

Intermediate-46a: 6-Bromo-5-cyclopropyl-3-methyl-benzo[d]oxazol-2(3H)-one

And

Intermediate-46b: 5-Cyclopropyl-3-methyl-6-(4,4,5,5-tetramethyl-1,3,2-dioxaborolan-2-yl)benzo[d]oxazol-2(3H)-one

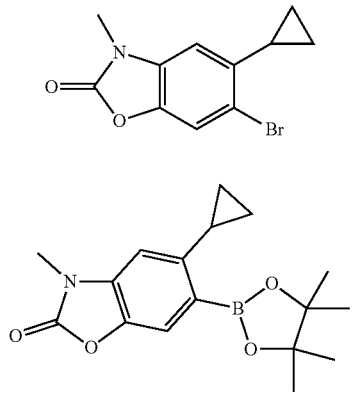

Intermedaite 46a

Intermediate 46b

The title compounds were prepared by following the similar procedure as described in Intermediate-40.

Intermediate-46a

¹HNMR (400 MHz, CDCl₃) δ 7.42 (s, 1H), 6.60 (s, 1H), 3.38 (s, 3H), 2.16-2.15 (m, 1H), 1.12-1.02 (m, 2H), 0.74-0.63 (m, 2H); GC-MS (m/z) 267, 269 [(M)+, Br$^{79, 81}$].

Intermediate-46b

¹HNMR (400 MHz, CDCl₃) δ 7.55 (s, 1H), 6.45 (s, 1H), 3.39 (s, 3H), 2.78-2.69 (m, 1H), 1.36 (s, 12H), 1.02-0.95 (m, 2H), 0.72-0.62 (m, 2H); ESI-MS (m/z) 315 (MH)+.

Intermediate-47: 2,6-Difluoro-N-(3-methyl-4-(4,4,5,5-tetramethyl-1,3,2-dioxaborolan-2-yl)phenyl)benzamide Intermediate 47

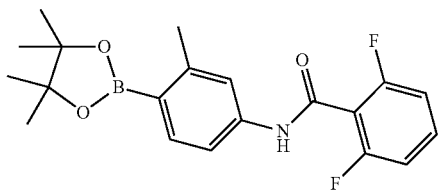

The title compound was prepared by following the known procedure as described in WO2012056478.

Intermediate-48: 6-Bromo-7-cyclopropyl-3-(difluoromethyl)benzo[d]oxazol-2(3H)-one

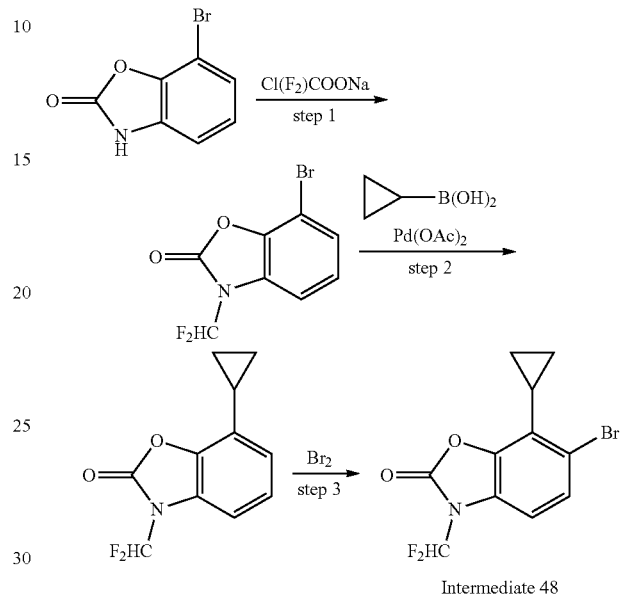

Intermediate 48

Step-1:

7-Bromo-3-(difluoromethyl)benzo[d]oxazol-2(3H)-one: To a solution of 7-bromobenzo[d]oxazol-2(3H)-one (prepared by following the procedure as described in WO2006061379; 3.0 g, 14.02 mmol) and K₂CO₃ (1.94 g, 14.02 mmol) in DMF (20 mL) was added Sodium 2-chloro-2,2-difluoroacetate (3.21 g, 21.03 mmol). The resulting mixture was stirred at 80° C. for 2 h. Then the reaction was diluted with ice water and filtered. The crude solid was washed with water and dried under vacuum to afford 550 mg (15%) of the title product as white solid. ¹HNMR (400 MHz, CDCl3) δ 7.41 (dd, J=8.0, 1.0 Hz, 1H), 7.32 (d, J=8.0 Hz, 1H), 7.22 (t, J=57.0 Hz, 1H), 7.18 (d, J=8.0 Hz, 1H); ESI-MS (m/z) 265, 267 [(MH)+, Br$^{79, 81}$].

Step-2:

7-Cyclopropyl-3-(difluoromethyl)benzo[d]oxazol-2(3H)-one: The title compound was prepared from step-1 Intermediate and cyclopropylboronic acid by following the similar procedure as described in step-1 of Intermediate-4. ¹HNMR (400 MHz, CDCl₃) δ 7.23 (d, J=57.0 Hz, 1H), 7.18-7.12 (m, 2H), 6.82 (d, J=8.0 Hz, 1H), 2.17-2.05 (m, 1H), 1.12-1.05 (m, 2H), 0.93-0.86 (m, 2H); GC-MS (m/z) 225 (M)+.

Step-3:

6-Bromo-7-cyclopropyl-3-(difluoromethyl)benzo[d]oxazol-2(3H)-one: The title compound was prepared from step-2 Intermediate by following the similar procedure as described in step-2 of Intermediate-4. ¹HNMR (400 MHz, CDCl₃) δ 7.28 (s, 1H), 7.23 (d, J=57.0 Hz, 1H), 7.18-7.12 (m, 2H), 6.82 (d, J=8.0 Hz, 1H), 2.17-2.05 (m, 1H), 1.12-1.05 (m, 2H), 0.93-0.86 (m, 2H); ESI-MS (m/z) 304, 306 [(MH)+, Br$^{79, 81}$].

Intermediate-49: 6-(4-Aminophenyl)-7-cyclopropyl-3-methylbenzo[d]oxazol-2(3H)-one

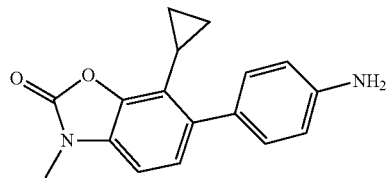

Intermediate-49

The title compound was prepared from Intermediate-14 by following the similar procedure as described for Intermediate-30. ¹HNMR (400 MHz, CDCl₃) δ 7.21 (d, J=8.5 Hz, 2H), 7.08 (d, J=8.0 Hz, 1H), 6.80 (d, J=8.0 Hz, 1H), 6.75 (d, J=8.5 Hz, 2H), 3.75 (s, 2H, D₂O exchangeable), 3.40 (s, 3H), 1.90-1.84 (m, 1H), 1.04-0.01 (m, 2H), 0.81-0.86 (m, 2H); ESI-MS (m/z) 281 (MH)⁺.

Intermediate-50: 2,6-Difluoro-N-(2-methyl-4-(4,4,5,5-tetramethyl-1,3,2-dioxaborolan-2-yl)phenyl)benzamide

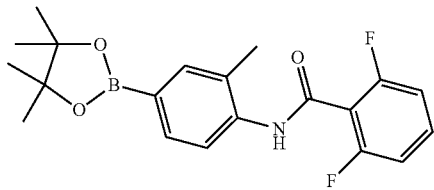

Intermediate 50

The title compound was prepared by following the known procedure as described in WO2012056478.

Intermediate-51: 7-Bromo-4-methyl-2H-pyrido[3,2-b][1,4]oxazin-3(4H)-one

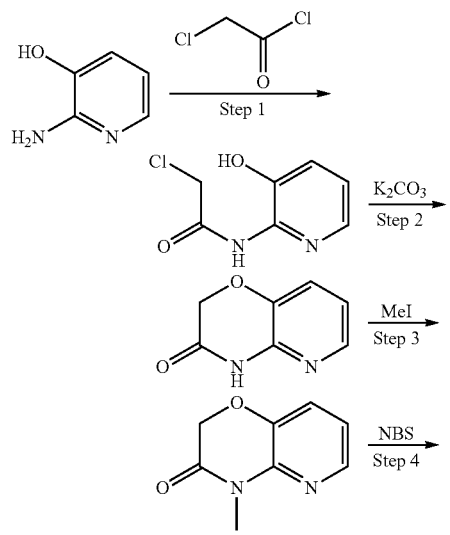

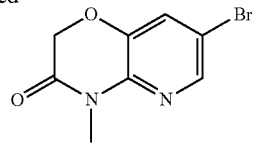

Intermediate 51

Step-1:
2-Chloro-N-(3-hydroxypyridin-2-yl)acetamide: To an ice-cooled solution of 2-amino-pyridin-3-ol (1.0 g, 5.29 mmol) and triethyl amine (1.48 mL, 10.58 mmol) in DMF (10 mL) was added drop-wise a solution of chloroacetyl chloride (0.5 mL, 6.35 mmol) in DMF (1.0 mL). After stirring the resulting mixture at room temperature for 12 h, the reaction was diluted with water (15 mL) and ethyl acetate (15 mL). The aqueous layer was extracted with ethyl acetate (2×10 mL) and the combined organic layers were washed with water (2×20 mL), brine (20 mL), dried (Na₂SO₄) and filtered. The filtrate was concentrated on rotary evaporator and the crude product was purified by flash column chromatography (silica gel, 10% methanol in DCM as eluent) to afford 200 mg (20%) of the title product as a colorless syrup. ¹HNMR (400 MHz, DMSO-d₆) δ 10.36 (s, 1H, D₂O exchangeable), 10.08 (s, 1H, D₂O exchangeable), 7.88 (dd, J=5.0 & 1.5 Hz, 1H), 7.32 (dd, J=8.0 & 1.5 Hz, 1H), 7.16 (dd, J=8.0 & 5.0 Hz, 1H), 4.38 (s, 2H); GC-MS (m/z) 186 (M)⁺.

Step-2:
2(H)-Pyrido[3,2-b][1,4]oxazin-3(4H)-one: To a solution of step-1 Intermediate (0.50 g, 1.88 mmol) in DMF (10 mL) was added potassium carbonate (0.52 g, 3.77 mmol) at room temperature. The resulting mixture was then stirred at 75° C. for 1.5 h. The reaction was then cooled to room temperature, diluted with water (15 mL) and ethyl acetate (15 mL). The aqueous layer was extracted with ethyl acetate (2×15 mL) and the combined organic layers were washed with water (2×20 mL), brine (20 mL), dried (Na₂SO₄) and filtered. The filtrate was concentrated on rotary evaporator and the crude product was purified by flash column chromatography (silica gel, 30% ethyl acetate in hexane system as eluent) to afford 200 mg (71%) of the title product as a white solid. ¹HNMR (400 MHz, DMSO-d₆) δ 11.25 (s, 1H, D₂O exchangeable), 7.89 (dd, J=5.0 & 1.5 Hz, 1H), 7.34 (dd, J=8.0 & 1.5 Hz, 1H), 6.97 (dd, J=8.0 & 5.0 Hz, 1H), 4.64 (s, 2H); GC-MS (m/z) 150 (M)⁺.

Step-3:
4-Methyl-2H-pyrido[3,2-b][1,4]oxazin-3(4H)-one: To a mixture of step-2 Intermediate (0.18 g, 1.20 mmol) and potassium carbonate (0.25 g, 1.8 mmol) in DMF (5 mL) was added methyl iodide (0.11 mL, 1.8 mmol). The resulting mixture was stirred at room temperature for 5 h. The reaction was then diluted with water (10 mL) and the resultant solid obtained was filtered, washed with water (10 mL) and dried to afford 100 mg (51%) of the title compound as white solid. ¹HNMR (400 MHz, CDCl₃) δ 8.05 (d, J=5.0 Hz, 1H), 7.25 (d, J=8.0 Hz, 1H), 6.96 (d, J=5.0 Hz, 1H), 4.70 (s, 2H), 3.50 (s, 3H); GC-MS (m/z) 164 (M)⁺.

Step-4:
7-Bromo-4-methyl-2H-pyrido[3,2-b][1,4]oxazin-3(4H)-one: To a solution of step-3 Intermediate (111 mg, 0.68 mmol) in DMF (5 mL) was added NBS (181 mg, 1.01 mmol) at room temperature. After stirring for 24 h at room temperature, the reaction mixture was diluted with ice-water (10 mL) and the solid obtained was filtered, washed with water and dried to afford 108 mg (65%) of the desired product as a white solid. $^1$HNMR (400 MHz, CDCl$_3$) δ 8.09 (d, J=2.0 Hz, 1H), 7.39 (d, J=2.0 Hz, 1H), 4.71 (s, 2H), 3.47 (s, 3H); GC-MS (m/z) 242, 244 [(M)$^+$, Br$^{79, 81}$].

Intermediate-52a: 7-Bromo-6-cyclopropyl-4-methyl-2H-benzo[b][1,4]oxazin-3(4H)-one And Intermediate-52b: 6-Cyclopropyl-4-methyl-7-(4,4,5,5-tetramethyl-1,3,2-dioxaborolan-2-yl)-2H-benzo[b][1,4]oxazin-3(4H)-one

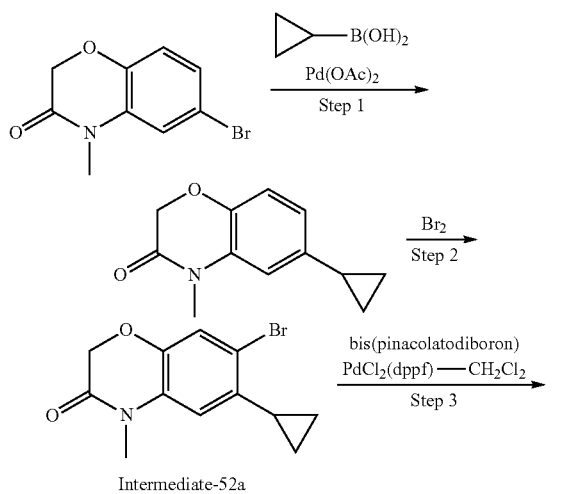

Step-1:

6-Cyclopropyl-4-methyl-2H-benzo[b][1,4]oxazin-3(4H)-one: To a nitrogen purged solution of 6-bromo-4-methyl-2H-benzo[b][1,4]oxazin-3(4H)-one (1.50 g, 6.20 mmol, prepared by following the procedure as described in WO2010128324) in 1,4-dioxane (5 mL) was added RuPhos (75 mg, 0.16 mmol), cyclopropylboronic acid (0.64 g, 7.44 mmol), potassium phosphate (3.29 g, 15.5 mmol) and Pd(OAc)$_2$ (139 mg, 0.62 mmol) sequentially. The resulting mixture was heated in sealed tube at 100° C. for 12 h. The reaction mixture was cooled to room temperature, diluted with ethyl acetate (20 mL) and filtered through celite. The filtrate was concentrated under reduced pressure and the crude product was purified by flash column chromatography (silica gel, 20% ethyl acetate-hexane system as eluent) to afford 200 mg (16%) of the title compound as white solid. $^1$HNMR (400 MHz, CDCl$_3$) δ 6.89 (d, J=8.0 Hz, 1H), 6.77-6.65 (m, 2H), 4.59 (s, 2H), 3.37 (s, 3H), 1.94-1.87 (m, 1H), 0.99-0.94 (m, 2H), 0.68-0.64 (m, 2H); GC-MS (m/z) 203 (M)$^+$.

Step-2:

7-Bromo-6-cyclopropyl-4-methyl-2H-benzo[b][1,4]oxazin-3(4H)-one: To an ice-cooled solution of step-1 Intermediate (0.25 g, 1.23 mmol) in acetic acid (3 mL) was added bromine (0.06 mL, 1.23 mmol). After stirring the resulting mixture at room temperature for 12 h, diluted with ethyl acetate (20 mL) and water (20 mL). The resulting mixture was basified with solid sodium bicarbonate (pH=14.0). The layers were separated and the aqueous layer was extracted with ethyl acetate (2×15 mL). The combined organic layers were washed with brine (15 mL), dried (Na$_2$SO$_4$) and filtered. The filtrate was concentrated over a rotary evaporator. The crude mass was purified by flash column chromatography (silica gel, 25% ethyl acetate in hexane system as eluent) to afford 200 mg (58%) of the desired product as a white solid. $^1$HNMR (400 MHz, CDCl$_3$) δ 7.20 (s, 1H), 6.58 (s, 1H), 4.60 (s, 2H), 3.34 (s, 3H), 2.12-2.05 (m, 1H), 1.11-0.93 (m, 2H), 0.73-0.52 (m, 2H); GC-MS (m/z) 281, 283 [(M)$^+$, Br$^{79, 81}$].

Step-3:

6-Cyclopropyl-4-methyl-7-(4,4,5,5-tetramethyl-1,3,2-dioxaborolan-2-yl)-2H-benzo[b][1,4]oxazin-3(4H)-one: To a degassed solution of 1,4-dioxane (10 mL) in a sealed tube was added step-2 Intermediate (0.5 g, 1.77 mmol) and 4,4,4',4',5,5,5',5'-octamethyl-2,2'-bi(1,3,2-dioxaborolane) (0.54 g, 2.13 mmol) followed by potassium acetate (0.348 g, 3.54 mmol) and PdCl$_2$(dppf)-CH$_2$Cl$_2$ adduct (65 mg, 0.08 mmol). The resulting mixture was heated at 100° C. for 16 h. The reaction mixture was cooled to room temperature and diluted with ethyl acetate (15 mL) and filtered through Celite pad. The residue was washed with ethyl acetate (20 mL). The filtrate was concentrated under rotary evaporator and the crude product was purified by flash column chromatography (silica gel, 10% ethyl acetate in hexane system as eluent) to afford 250 mg (43%) the title product as a white solid. $^1$HNMR (400 MHz, CDCl$_3$) δ 7.37 (s, 1H), 6.46 (s, 1H), 4.57 (s, 2H), 3.34 (s, 3H), 2.66-2.62 (m, 1H), 1.36 (s, 12H), 1.00-0.95 (m, 2H), 0.67-0.61 (m, 2H); ESI-MS (m/z) 330 (MH)$^+$.

The following Intermediates (53-54) were prepared by following the similar procedure as described for Intermediate-52.

Intermediate-53a: 7-Bromo-6-ethyl-4-methyl-2H-benzo[b][1,4]oxazin-3(4H)-one

And

Intermediate-53b: 6-Ethyl-4-methyl-7-(4,4,5,5-tetramethyl-1,3,2-dioxaborolan-2-yl)-2H-benzo[b][1,4]oxazin-3(4H)-one

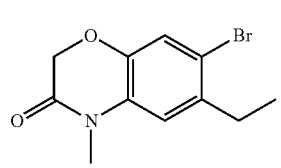

Intermediate-53a

-continued

Intermediate-53b

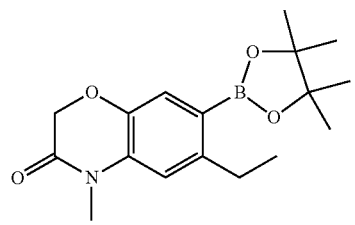

Intermediate-53a

¹HNMR (400 MHz, CDCl₃) δ 7.17 (s, 1H), 6.82 (s, 1H), 4.60 (s, 2H), 3.36 (s, 3H), 2.73 (q, J=7.5 Hz, 2H), 1.23 (t, J=7.5 Hz, 3H); GC-MS (m/z) 269, 271 [(M)⁺, Br⁷⁹, ⁸¹].

Intermediate-53b

¹HNMR (400 MHz, CDCl₃) δ 7.40 (s, 1H), 6.80 (s, 1H), 4.58 (s, 2H), 3.38 (s, 3H), 2.90 (q, J=7.5 Hz, 2H), 1.35 (s, 12H), 1.20 (t, J=7.5 Hz, 3H); ESI-MS (m/z) 318 (MH)⁺.

Intermediate-54a: 7-Bromo-4,6-dimethyl-2H-benzo[b][1,4]oxazin-3(4H)-one

And

Intermediate-54b: 4,6-Dimethyl-7-(4,4,5,5-tetramethyl-1,3,2-dioxaborolan-2-yl)-2H-benzo[b][1,4]oxazin-3(4H)-one

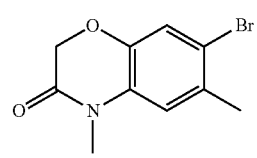

Intermediate-54a

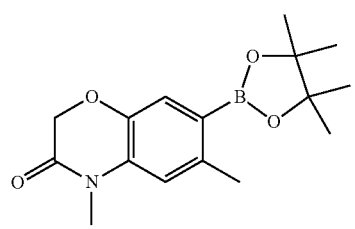

Intermediate-54b

Intermediate-54a

¹HNMR (400 MHz, CDCl₃) δ 7.18 (s, 1H), 6.83 (s, 1H), 4.60 (s, 2H), 3.35 (s, 3H), 2.38 (s, 3H); GC-MS (m/z) 255, 257 [(M)⁺, Br⁷⁹, ⁸¹].

Intermediate-54b

¹HNMR (400 MHz, CDCl₃) δ 7.39 (s, 1H), 6.78 (s, 1H), 4.58 (s, 2H), 3.36 (s, 3H), 2.53 (s, 3H), 1.35 (s, 12H); ESI-MS (m/z) 304 (MH)⁺.

Intermediate-55: 7-Bromo-4,8-dimethyl-2H-benzo[b][1,4]oxazin-3(4H)-one

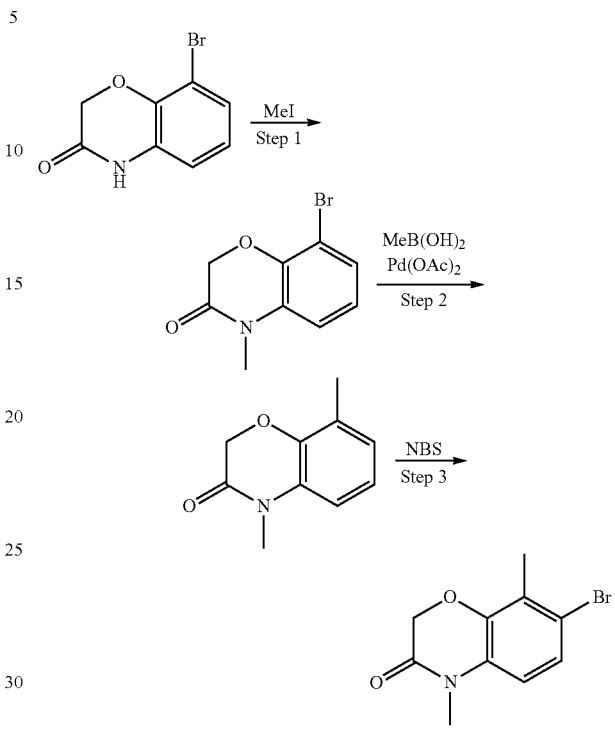

Step-1:

8-Bromo-4-methyl-2H-benzo[b][1,4]oxazin-3(4H)-one: To a solution of 8-bromo-2H-benzo[b][1,4]oxazin-3(4H)-one (2.31 g, 10.1 mmol, prepared by following the procedure as described in WO2013065835) in DMF (20 mL) was added methyl iodide (0.95 ml, 15 mmol) followed by potassium carbonate (2.80 g, 20.3 mmol). The resulting mixture was stirred at room temperature for 6 h and then diluted with ice-water (20 mL). The precipitate was filtered and dried to obtain 2.0 g (82%) of the title compound as a white solid. ¹HNMR (400 MHz, CDCl₃) δ 7.26 (t, J=8.0 Hz, 1H), 6.95 (m, 2H), 4.73 (s, 2H), 3.38 (s, 3H); GC-MS (m/z) 241, 243 [(M)⁺, Br⁷⁹, ⁸¹].

Step-2:

4,8-Dimethyl-2H-benzo[b][1,4]oxazin-3(4H)-one: The title compound was prepared from step-1 Intermediate by following the similar procedure as described in step-1 of Intermediate-52. ¹HNMR (400 MHz, CDCl₃) δ 6.96 (t, J=7.5 Hz, 1H), 6.90 (dd, J=7.5 & 2.0 Hz, 1H), 6.84 (dd, J=7.5 & 2.0 Hz, 1H), 4.64 (s, 2H), 3.37 (s, 3H), 2.26 (s, 3H); GC-MS (m/z) 177 (M)⁺.

Step-3:

7-Bromo-4,8-dimethyl-2H-benzo[b][1,4]oxazin-3(4H)-one: The title compound was prepared from step-2 Intermediate by following the procedure as described in step-4 of Intermediate-51. ¹HNMR (400 MHz, CDCl₃) δ 7.25 (d, J=8.5 Hz, 1H), 6.72 (d, J=8.5 Hz, 1H), 4.64 (s, 2H), 3.35 (s, 3H), 2.33 (s, 3H); GC-MS (m/z) 255, 257 [(M)⁺, Br⁷⁹, ⁸¹].

The following Intermediates (56-57) were prepared by following the similar procedure as described for Intermediate-55.

Intermediate-56: 7-Bromo-8-ethyl-4-methyl-2H-benzo[b][1,4]oxazin-3(4H)-one

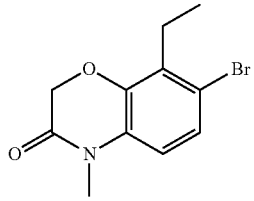

Intermediate-56

$^1$HNMR (400 MHz, CDCl$_3$) δ 7.24 (d, J=8.5 Hz, 1H), 6.72 (d, J=8.5 Hz, 1H), 4.63 (s, 2H), 3.35 (s, 3H), 2.83 (q, J=7.5 Hz, 2H), 1.14 (t, J=7.5 Hz, 3H). GC-MS (m/z) 269, 271 [(M)$^+$, Br$^{79, 81}$].

Intermediate-57a: 7-Bromo-8-cyclopropyl-4-methyl-2H-benzo[b][1,4]oxazin-3(4H)-one And

Intermediate-57b: 8-Cyclopropyl-4-methyl-7-(4,4,5,5-tetramethyl-1,3,2-dioxaborolan-2-yl)-2H-benzo[b][1,4]oxazin-3(4H)-one

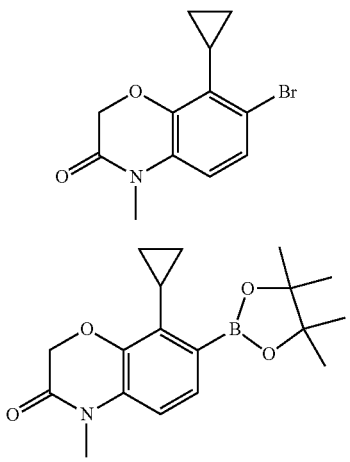

Intermediate-57a

Intermediate-57b

Intermediate-57a $^1$HNMR (400 MHz, CDCl$_3$) δ 7.26 (d, J=8.5 Hz, 1H), 6.73 (d, J=8.5 Hz, 1H), 4.58 (s, 2H), 3.34 (s, 3H), 1.82-1.75 (m, 1H), 1.08-1.03 (m, 2H), 0.86-0.81 (m, 2H). GC-MS (m/z) 281, 283 [(M)$^+$, Br$^{79, 81}$].

Intermediate-57b $^1$HNMR (400 MHz, CDCl$_3$) δ 7.36 (d, J=8.0 Hz, 1H), 6.83 (d, J=8.0 Hz, 1H), 4.57 (s, 2H), 3.35 (s, 3H), 2.17-2.10 (m, 1H), 1.38 (s, 12H), 0.96-0.91 (m, 2H), 0.74-0.69 (m, 2H); ESI-MS (m/z) 330 (MH)$^+$.

Intermediate-58: 7-Bromo-8-cyclopropyl-4-methyl-2H-pyrido[3,2-b][1,4]oxazin-3(4H)-one

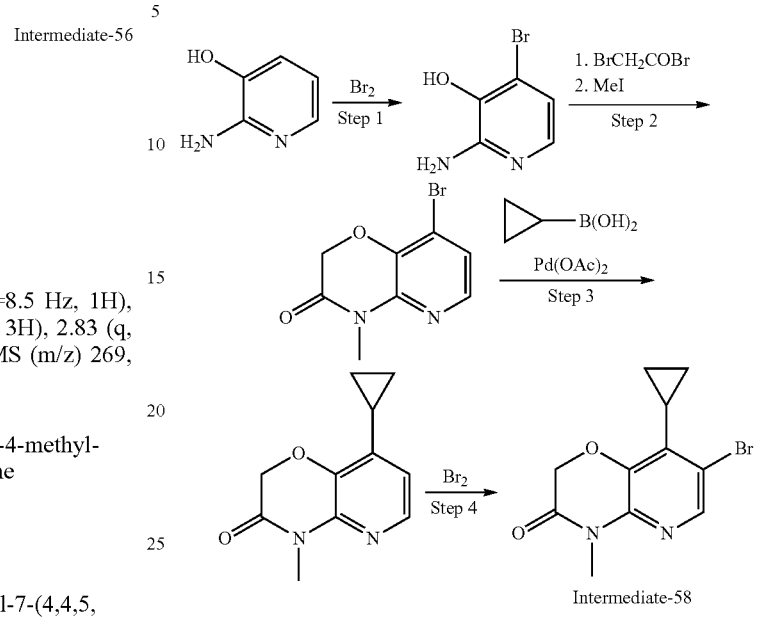

Intermediate-58

Step-1:

2-Amino-4-bromopyridin-3-ol: To an ice-cooled solution of 2-amino-3-pyridinol (15 g, 136 mmol) in ethanol (75 mL) was added bromine (21.8 mL, 136 mmol) over 2 h. Then the resulting mixture was stirred at room temperature for 24 h. The solvent was evaporated under reduced pressure and the residual mass was diluted with ethyl acetate. The organic layer was washed with 5% NaHCO$_3$ solution, dried (Na$_2$SO$_4$) and filtered. The filtrate was rotary evaporated to obtain 4 g (16%) of the desired product, which was used for next step without further purification. $^1$HNMR (400 MHz, DMSO-d$_6$) δ 7.25 (d, J=5.2 Hz, 1H), 6.67 (d, J=5.2 Hz, 1H), 6.03 (bs, 2H, D$_2$O exchangeable), 1.85 (bs, 1H, D$_2$O exchangeable); GC-MS (m/z) 188, 190 [M$^+$, Br$^{79, 81}$].

Step-2:

8-Bromo-4-methyl-2H-pyrido[3,2-b][1,4]oxazin-3(4H)-one: To an ice-cooled solution of step-1 Intermediate (0.850 g, 4.19 mmol) in THF (2 mL) was added triethyl amine (0.7 mL, 5.0 mmol), 2-bromoacetyl bromide (0.55 mL, 4.2 mmol). The resulting reaction mixture was stirred at room temperature for 2 h, then diluted with ethyl acetate (10 mL). The organic layer was washed with water (20 mL), brine (20 mL), dried (Na$_2$SO$_4$) and filtered. The filtrate was concentrated on a rotary evaporator and the crude product was purified by flash column chromatography (silica gel, 25% ethyl acetate in hexane system as eluent) to afford 740 mg (73%) of 8-bromo-2H-pyrido[3,2-b][1,4]oxazin-3(4H)-one as a white solid.

To a solution of 8-Bromo-2H-pyrido[3,2-b][1,4]oxazin-3(4H)-one (700 mg, 2.91 mmol) in DMF (10 mL) was added potassium carbonate (800 mg, 5.83 mmol) at room temperature followed by methyl iodide (0.83 mg, 5.83 mmol). This resulting mixture was stirred at room temperature for 3 h. Then the reaction was diluted with ice-water and the resultant solid was filtered. This crude product was purified by flash column chromatography (eluted with 20-30% ethyl acetate in hexane) to afford 650 mg (89%) of the title product as a white solid. $^1$HNMR (400 MHz, CDCl$_3$) δ 7.86

(d, J=5.5 Hz, 1H), 7.18 (d, J=5.5 Hz, 1H), 4.80 (s, 2H), 3.49 (s, 3H); GC-MS (m/z) 242, 244 [M+, Br$^{79, 81}$].

Step-3:

8-Cyclopropyl-4-methyl-2H-pyrido[3,2-b][1,4]oxazin-3 (4H)-one: The title compound was prepared from step-2 Intermediate by following the procedure as described in step-1 of Intermediate-52. $^1$HNMR (400 MHz, CDCl$_3$) δ 7.90 (d, J=5.5 Hz, 1H), 6.41 (d, J=5.5 Hz, 1H), 4.72 (s, 2H), 3.49 (s, 3H), 2.26-2.19 (m, 1H), 1.12-1.07 (m, 2H), 0.81-0.78 (m, 2H); GC-MS (m/z) 204 (M)+.

Step-4:

7-Bromo-8-cyclopropyl-4-methyl-2H-pyrido[3,2-b][1,4] oxazin-3(4H)-one: The title compound was prepared by following the procedure as described in step-2 of Intermediate-52. $^1$HNMR (400 MHz, CDCl$_3$) δ 8.12 (s, 1H), 4.62 (s, 2H), 3.44 (s, 3H), 2.02-1.84 (m, 1H), 1.11-1.04 (m, 4H); GC-MS (m/z) 282, 284 [(M)+, Br$^{79, 81}$].

Intermediate-59a: 6-Bromo-7-ethyl-4-methyl-2H-benzo[b][1,4]oxazin-3(4H)-one

And

Intermediate-59b: 7-Ethyl-4-methyl-6-(4,4,5,5-tetramethyl-1,3,2-dioxaborolan-2-yl)-2H-benzo[b][1,4]oxazin-3(4H)-one

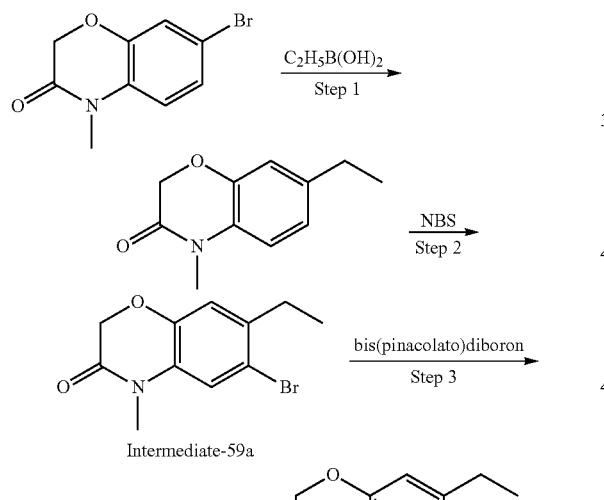

Intermediate-59a

Intermediate-59b

Step-1:

7-Ethyl-4-methyl-2H-benzo[b][1,4]oxazin-3(4H)-one: The title compound was prepared from 7-bromo-4-methyl-2H-benzo[b][1,4]oxazin-3(4H)-one (prepared by following the similar procedure as described in GB2497806) by following the procedure as described in step-1 of Intermediate-52. $^1$HNMR (400 MHz, CDCl$_3$) δ 6.89-6.87 (m, 2H), 6.85-6.82 (m, 1H), 4.61 (s, 2H), 3.36 (s, 3H), 2.61 (q, J=7.5 Hz, 2H), 1.23 (t, J=7.5 Hz, 3H); GC-MS (m/z) 191 (M)+.

Step-2:

6-Bromo-7-ethyl-4-methyl-2H-benzo[b][1,4]oxazin-3 (4H)-one: To a stirred solution of step-1 Intermediate (0.9 g, 4.71 mmol) in acetic acid (20 mL) was added NBS (0.921 g, 5.18 mmol) at room temperature. The resulting mixture was stirred at 75° C. for 16 h. The reaction cooled down to room temperature and the solvent was concentrated under reduced pressure. The crude product was purified by flash column chromatography (silica gel, hexane/ethyl acetate 9:1 system as eluent) to afford 0.88 g (69%) of the title product as white solid. $^1$HNMR (400 MHz, CDCl$_3$) δ 7.12 (s, 1H), 6.87 (s, 1H), 4.61 (s, 2H), 3.34 (s, 3H), 2.69 (q, J=7.5 Hz, 2H), 1.21 (t, J=7.5 Hz, 3H); GC-MS (m/z) 269, 271 [(M)+, Br$^{79, 81}$].

Step-3:

7-Ethyl-4-methyl-6-(4,4,5,5-tetramethyl-1,3,2-dioxaborolan-2-yl)-2H-benzo[b][1,4]oxazin-3(4H)-one: To a stirred and nitrogen purged solution of step-2 Intermediate (0.88 g, 3.26 mmol) in 1,4-dioxane (20 mL) was added bis(pinacolato)diboron (1.241 g, 4.89 mmol) and potassium acetate (0.639 g, 6.52 mmol) followed by the addition of PdCl$_2$(dppf)-CH$_2$Cl$_2$ adduct (0.266 g, 0.326 mmol). The resulting mixture was stirred at 100° C. for 6 h. The reaction mass was filtered off and the residual cake was washed with ethyl acetate (2×30 mL), combined organics were concentrated under reduced pressure and the crude product was purified by flash column chromatography (silica gel, hexane/ethyl acetate 8:2 system as eluent) to obtain 1.0 g (97%) of the desired product as a white solid. $^1$HNMR (400 MHz, CDCl$_3$) δ 7.39 (s, 1H), 6.83 (s, 1H), 4.63 (s, 2H), 3.42 (s, 3H), 2.88 (q, J=7.5 Hz, 2H), 1.36 (s, 12H), 1.19 (t, J=7.5 Hz, 3H); ESI-MS (m/z) 318 (MH)+.

Intermediate-60a: 6-Bromo-7-cyclopropyl-4-methyl-2H-benzo[b][1,4]oxazin-3(4H)-one And Intermediate-60b: 7-Cyclopropyl-4-methyl-6-(4,4,5,5-tetramethyl-1,3,2-dioxaborolan-2-yl)-2H-benzo[b][1,4]oxazin-3(4H)-one

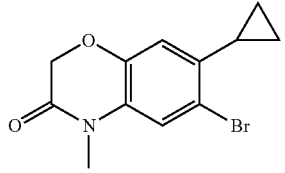

Intermediate-60a

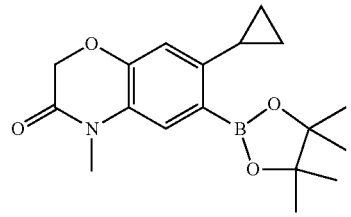

Intermediate-60b

The title compounds were prepared by following the similar procedure as described above for Intermediate-59.

Intermediate-60a

¹HNMR (400 MHz, CDCl₃) δ 7.14 (s, 1H), 6.56 (s, 1H), 4.59 (s, 2H), 3.34 (s, 3H), 2.09-2.06 (m, 1H), 1.08-0.95 (m, 2H), 0.71-0.56 (m, 2H); GC-MS (m/z) 281, 283 [(M)⁺, Br⁷⁹, ⁸¹].

Intermediate-60b

¹HNMR (400 MHz, CDCl₃) δ 7.35 (s, 1H), 6.44 (s, 1H), 4.60 (s, 2H), 3.41 (s, 3H), 2.72-2.70 (m, 1H), 1.37 (s, 12H), 1.02-0.92 (m, 2H), 0.69-0.61 (m, 2H); ESI-MS (m/z) 330 (MH)⁺.

Intermediate-61a: 7-Bromo-2,2,4-trimethyl-2H-benzo[b][1,4]oxazin-3(4H)-one

And

Intermediate-61b: 6-Bromo-2,2,4-trimethyl-2H-benzo[b][1,4]oxazin-3(4H)-one

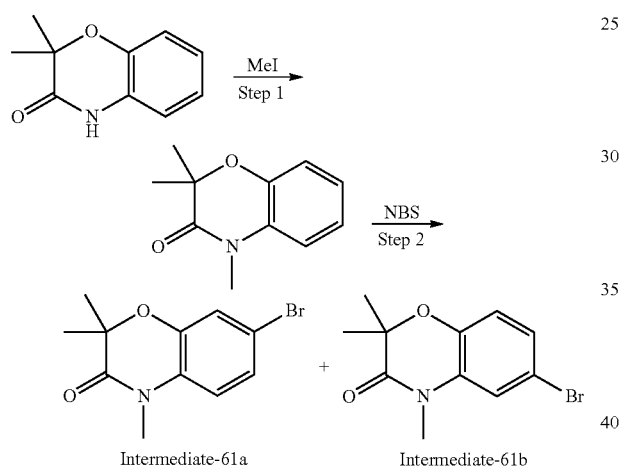

Step-1:

2,2,4-Trimethyl-2H-benzo[b][1,4]oxazin-3(4H)-one: To an ice-cooled solution of 2,2-dimethyl-2H-benzo[b][1,4]oxazin-3(4H)-one (2.0 g, 11.29 mmol, prepared by following the procedure as described in WO2011048112) in DMF (20 mL) was added sodium hydride (0.677 g, 16.93 mmol) portion wise and the reaction mixture was stirred for 15 min at the same temperature. Methyl iodide (0.71 mL, 11.29 mmol) was then added to the above stirring mixture at 0° C. and the resulting mixture was stirred at room temperature for 5 h. The reaction was then cooled to 0° C. and crushed ice was added. The precipitated solid was filtered and washed with cold water. The resulting solid was dried to afford 1.0 g (46%) of the desired product as a white solid. ¹HNMR (400 MHz, CDCl₃) δ 6.80-6.90 (m, 4H), 3.20 (s, 3H), 1.40 (s, 6H); GC-MS (m/z) 191 (M)⁺.

Step-2:

To an ice-cooled solution of step-1 Intermediate (350 mg, 1.83 mmol) in DMF (2 mL) was added NBS (293 mg, 1.65 mmol). The resulting reaction mixture was stirred at room temperature for 2 h, then diluted with water (10 mL) and the extracted with ethyl acetate (2×15 mL). The combined organic layers were washed with water (2×10 mL), brine (10 mL), dried (Na₂SO₄) and filtered. The filtrate was concentrated under reduced pressure and the crude product was purified by flash column chromatography (silica gel, 15% ethyl acetate in hexane system as eluent) to afford 200 mg (41%) of Intermediate-61a and 15 mg (31%) of Intermediate-61b as white solids.

Intermediate-61a

¹HNMR (400 MHz, CDCl₃) δ 7.18-7.11 (m, 2H), 6.80 (d, J=8.0 Hz, 1H), 3.34 (s, 3H), 1.51 (s, 6H); ESI-MS (m/z) 269, 271 [(MH)⁺, Br⁷⁹, ⁸¹].

Intermediate-61b

¹HNMR (400 MHz, CDCl₃) δ 7.20 (dd, J=8.0 & 2.0 Hz, 1H), 7.07 (d, J=2.0 Hz, 1H), 6.85 (d, J=8.0 Hz, 1H), 3.34 (s, 3H), 1.51 (s, 6H); ESI-MS (m/z) 269, 271 [(MH)⁺, Br⁷⁹, ⁸¹].

Intermediate-62: N-(5-Bromopyrazin-2-yl)-2-chloro-6-fluorobenzamide

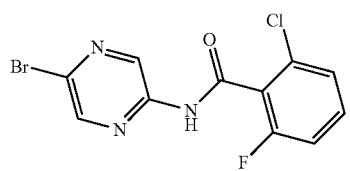

The title compound was prepared by following the similar procedure as described in Intermediate-8. ¹HNMR (400 MHz, CDCl₃) δ 9.52 (s, 1H), 8.56 (s, 1H), 8.19 (s, 1H), 7.48-7.43 (m, 1H), 7.33-7.30 (m, 1H), 7.17-7.12 (m, 1H); ESI-MS (m/z) 330, 332 (MH)⁺.

Intermediate-63: 4-Bromo-N-(3,5-difluoropyridin-4-yl)benzamide

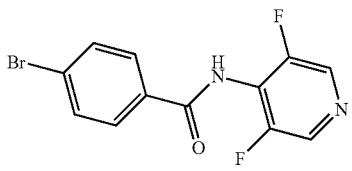 [SMILES: O=C(Nc1c(F)cncc1F)c1ccc(Br)cc1]

The title compound was prepared by following the similar procedure as described in Intermediate-36 by using 4-bromobenzoic acid and 4-amino-3,5-difluoropyridine. ¹HNMR (400 MHz, CDCl₃) δ 8.45 (s, 2H), 7.97 (brs, 1H), 7.86 (d, J=8.0 Hz, 2H), 7.70 (d, J=8.0 Hz, 2H); ESI-MS (m/z) 313, 315 (MH)⁺.

Intermediate-64: 5-Bromo-N-(2,6-difluorophenyl)thiophene-2-carboxamide

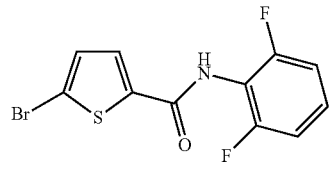 [SMILES: O=C(Nc1c(F)cccc1F)c1ccc(Br)s1]

The title compound was prepared by following the similar procedure as described in WO2012056478.

Intermediate-65:
5-Bromo-3,7-dimethylbenzo[d]oxazol-2(3H)-one

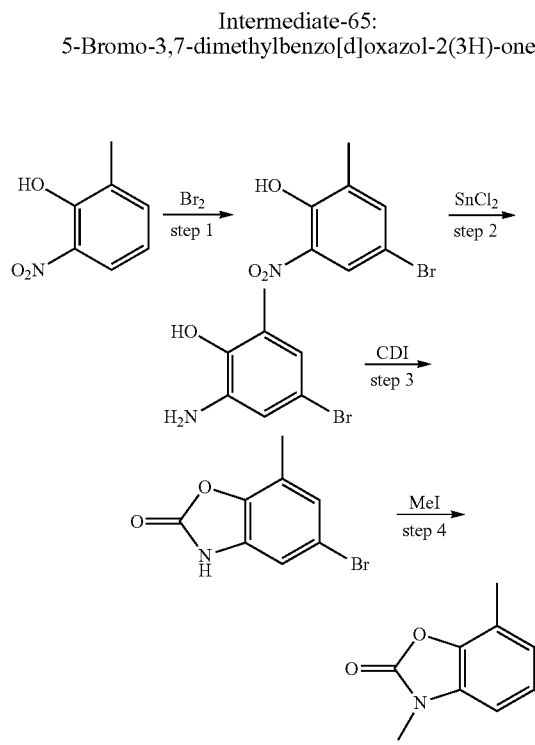

The title compound was prepared from 6-methyl-2-nitrophenol by following the similar procedure as described in Intermediate-16. ¹HNMR (400 MHz, CDCl₃) δ 7.11 (d, J=2.0 Hz, 1H), 6.96 (d, J=2.0 Hz, 1H), 3.39 (s, 3H), 2.37 (s, 3H); GC-MS (m/z) 241, 242 [(M)⁺, Br⁷⁹, ⁸¹].

EXAMPLES

Example-1: N-(4-(3,7-Dimethyl-2-oxo-2,3-dihydrooxazolo[4,5-b]pyridin-6-yl)phenyl)-2,6-difluorobenzamide

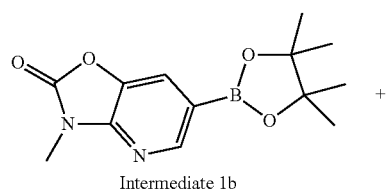

Intermediate 1b

+

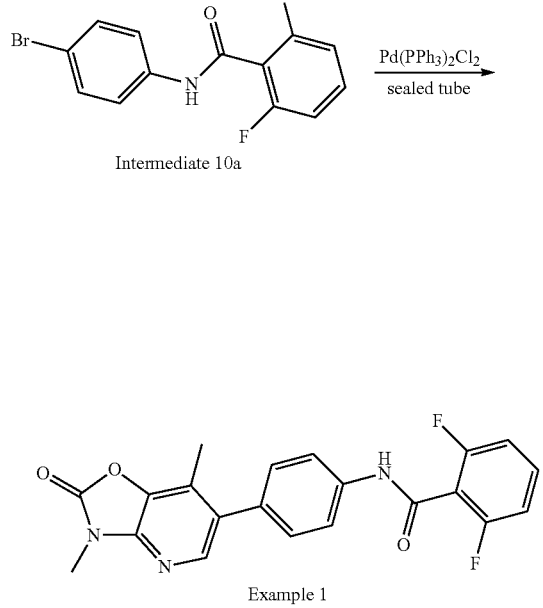

Intermediate 10a

Example 1

In a sealed tube, to a degassed solution of Intermediate-1b (250 mg, 0.862 mmol) and Intermediate-10a (269 mg, 0.862 mmol) in 1,4-dioxane (4 mL) was added 2M aqueous sodium carbonate solution (2 mL), and Pd(PPh₃)₂Cl₂ (30.2 mg, 0.043 mmol). The resulting mixture was thoroughly deoxygenated by purging nitrogen gas for another 5 min and then stirred at 110° C. for 5 h. The reaction mixture was allowed to room temperature and diluted with ethyl acetate (5 mL). The total mass was filtered through celite bed, washed with ethyl acetate (10 mL) and the resultant filtrate was concentrated under reduced pressure. The crude product was purified by flash column chromatography (silica gel, 50% ethyl acetate in hexanes-system as eluent) to afford 150 mg (44%) of the title compound as white solid. ¹HNMR (400 MHz, DMSO-d₆) δ 10.97 (s, 1H, D₂O exchangeable), 8.00 (s, 1H), 7.82 (d, J=8.5 Hz, 2H), 7.64-7.60 (m, 1H), 7.42 (d, J=8.5 Hz, 2H), 7.28 (t, J=8.0 Hz, 2H), 3.35 (s, 3H), 2.28 (s, 3H); ESI-MS (m/z) 396 (MH)⁺.

The below Examples (2-27) given in Table-3 were prepared by following the similar procedure as described in Example-1 from the appropriate Intermediates.

TABLE 3

| Example No: IUPAC name | Structure | NMR /ESI-MS |
|---|---|---|
| Example-2: N-(5-(3,7-Dimethyl-2-oxo-2,3-dihydrooxazolo[4,5-b]pyridin-6-yl)pyrazin-2-yl)-2,6-difluoro benzamide | 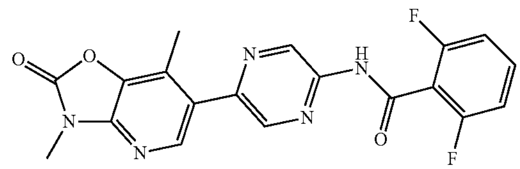 | ¹HNMR (400 MHz, DMSO-d₆) δ 11.84 (s, 1H, D₂O exchangeable), 9.50 (s, 1H), 8.71 (s, 1H), 8.31 (s, 1H), 7.65-7.58 (m, 1H), 7.26 (t, J = 8.0 Hz, 2H), 3.38 (s, 3H), 2.43 (s, 3H); ESI-MS (m/z) 398 (MH)⁺. |

TABLE 3-continued

| Example No: IUPAC name | Structure | NMR /ESI-MS |
|---|---|---|
| Example-3: N-(6-(3,7-Dimethyl-2-oxo-2,3-dihydrooxazolo[4,5-b]pyridin-6-yl)pyridin-3-yl)-2,6-difluorobenzamide | 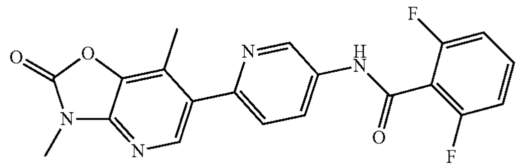 | ¹HNMR (400 MHz, CDCl₃) δ 8.77 (d, J = 2.0 Hz, 1H), 8.49 (dd, J = 8.5 & 2.0 Hz, 1H), 8.20 (s, 1H), 7.94 (s, 1H, D₂O exchangeable), 7.54-7.46 (m, 2H), 7.06 (d, J = 8.5 Hz, 2H), 3.83 (s, 3H), 2.47 (s, 3H); ESI-MS (m/z) 397 (MH)⁺. |
| Example-4: N-(5-(3,7-Dimethyl-2-oxo-2,3-dihydrooxazolo[4,5-b]pyridin-6-yl)pyridin-2-yl)-2,6-difluorobenzamide | 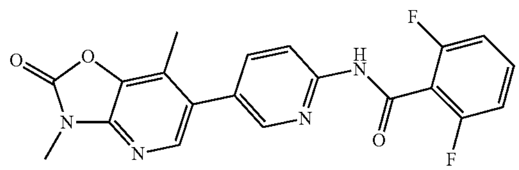 [SMILES: Cc1c(-c2ccc(NC(=O)c3c(F)cccc3F)nc2)cnc2c1oc(=O)n2C] | ¹HNMR (400 MHz, DMSO-d₆) δ 11.52 (s, 1H, D₂O exchangeable), 8.42 (d, J = 2.0 Hz, 1H), 8.29 (d, J = 8.5 Hz, 1H), 8.08 (s, 1H), 7.97 (dd, J = 8.5 & 2.0 Hz, 1H), 7.61-7.57 (m, 1H), 7.24 (t, J = 8.0 Hz, 2H), 3.37 (s, 3H), 2.31 (s, 3H); ESI-MS (m/z) 397 (MH)⁺. |
| Example-5: N-(4-(7-Ethyl-3-methyl-2-oxo-2,3-dihydrooxazolo[4,5-b]pyridin-6-yl)phenyl)-2,6-difluorobenzamide | 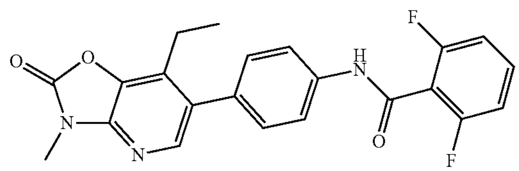 [SMILES: CCc1c(-c2ccc(NC(=O)c3c(F)cccc3F)cc2)cnc2c1oc(=O)n2C] | ¹HNMR (400 MHz, CDCl₃) δ 7.99 (s, 1H), 7.81-7.73 (m, 3H), 7.51-7.43 (m, 1H), 7.37-7.30 (m, 2H), 7.05 (t, J = 8.0 Hz, 2H), 3.53 (s, 3H), 2.76 (q, J = 7.5 Hz, 2H), 1.18 (t, J = 7.5 Hz, 3H); ESI-MS (m/z) 410 (MH)⁺ |
| Example-6: N-(5-(7-Ethyl-3-methyl-2-oxo-2,3-dihydrooxazolo[4,5-b]pyridin-6-yl)pyrazin-2-yl)-2,6-difluorobenzamide | 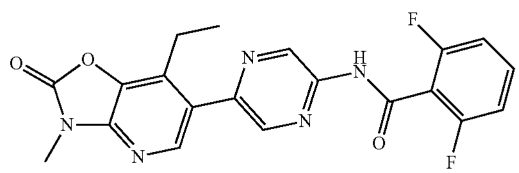 [SMILES: CCc1c(-c2cnc(NC(=O)c3c(F)cccc3F)cn2)cnc2c1oc(=O)n2C] | ¹HNMR (400 MHz, DMSO-d₆) δ 11.86 (s, 1H, D₂O exchangeable), 9.53 (s, 1H), 8.70 (s, 1H), 8.28 (s, 1H), 7.69-7.61 (m, 1H), 7.28 (t, J = 8.0 Hz, 2H), 3.34 (s, 3H), 2.86 (q, J = 7.5 Hz, 2H), 1.15 (t, J = 7.5 Hz, 3H); ESI-MS (m/z) 412 (MH)⁺. |
| Example-7: N-(6-(7-Ethyl-3-methyl-2-oxo-2,3-dihydrooxazolo[4,5-b]pyridin-6-yl)pyridin-3-yl)-2,6-difluorobenzamide | 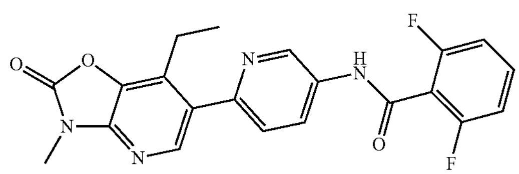 [SMILES: CCc1c(-c2ccc(NC(=O)c3c(F)cccc3F)cn2)cnc2c1oc(=O)n2C] | ¹HNMR (400 MHz, DMSO-d₆) δ 11.22 (s, 1H, D₂O exchangeable), 8.95 (d, J = 2.5 Hz, 1H), 8.28 (dd, J = 8.5, 2.5 Hz, 1H), 8.16 (s, 1H), 7.69-7.61 (m, 2H), 7.31 (t, J = 8.0 Hz, 2H), 3.37 (s, 3H), 2.86 (q, J = 7.5 Hz, 2H), 1.10 (t, J = 7.5 Hz, 3H); ESI-MS (m/z) 411 (MH)⁺. |
| Example-8: N-(5-(7-Ethyl-3-methyl-2-oxo-2,3-dihydrooxazolo[4,5-b]pyridin-6-yl)pyridin-2-yl)-2,6-difluorobenzamide | 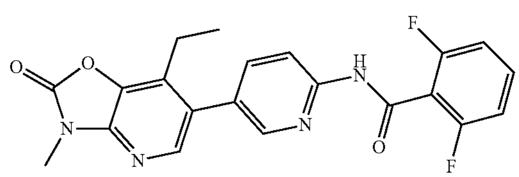 [SMILES: CCc1c(-c2ccc(NC(=O)c3c(F)cccc3F)nc2)cnc2c1oc(=O)n2C] | ¹HNMR (400 MHz, CDCl₃) δ 9.11 (s, 1H, D₂O exchangeable), 8.57 (d, J = 8.5 Hz, 1H), 8.23 (d, J = 2.5 Hz, 1H), 7.98 (s, 1H), 7.81 (dd, J = 8.5 & 2.5 Hz, 1H), 7.51-7.46 (m, 1H), 7.09-7.03 (m, 2H), 3.54 (s, 3H), 2.75 (q, J = 7.5 Hz, 2H), 1.20 (t, J = 7.5 Hz, 3H); ESI-MS 411 (m/z) (MH)⁺. |
| Example-9: N-(4-(7-Cyclopropyl-3-methyl-2-oxo-2,3-dihydrooxazolo[4,5-b]pyridin-6-yl)phenyl)-2,6-difluorobenzamide | 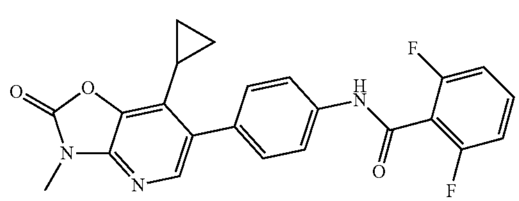 [SMILES: Cn1c(=O)oc2c(C3CC3)c(-c3ccc(NC(=O)c4c(F)cccc4F)cc3)cnc21] | ¹H NMR (400 MHz, CDCl₃) δ 7.96 (s, 1H), 7.82-7.72 (m, 3H), 7.52-7.40 (m, 3H), 7.10-6.99 (m, 2H), 3.49 (s, 3H), 1.86-1.80 (m, 1H), 1.42-1.30 (m, 2H), 1.08-0.96 (m, 2H); ESI-MS (m/z) 422 (MH)⁺ |
| Example-10: 2,6-Difluoro-N-(4-(1-methyl-2-oxo-1,2-dihydrooxazolo[5,4-b]pyridin-6-yl)phenyl)benzamide | 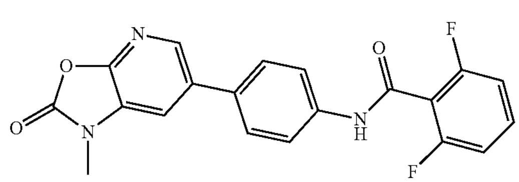 [SMILES: Cn1c(=O)oc2ncc(-c3ccc(NC(=O)c4c(F)cccc4F)cc3)cc21] | ¹HNMR (400 MHz, DMSO-d₆) δ 10.96 (s, 1H, D₂O exchangeable), 8.29 (d, J = 2.0 Hz, 1H), 8.01 (d, J = 2.0 Hz, 1H), 7.82 (d, J = 8.5 Hz, 2H), 7.77 (d, J = 8.5 Hz, 2H), 7.64-7.60 (m, 1H), 7.28 (t, J = 8.0 Hz, 2H), 3.42 (s, 3H); ESI-MS (m/z) 382 (MH)⁺. |

TABLE 3-continued

| Example No: IUPAC name | Structure | NMR /ESI-MS |
|---|---|---|
| Example-11: N-(4-(3,4-Dimethyl-2-oxo-2,3 dihydrobenzo[d]oxazol-5-yl)phenyl)-2,6-difluorobenzamide | 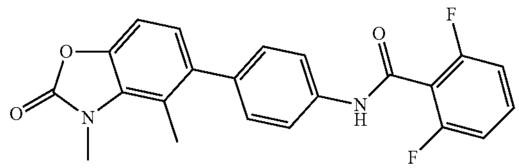 [SMILES: Cc1c(-c2ccc(NC(=O)c3c(F)cccc3F)cc2)ccc2oc(=O)n(C)c12] | $^1$HNMR (400 MHz, DMSO-d$_6$) δ 10.96 (s, 1H, D$_2$O exchangeable), 7.78 (d, J = 8.5 Hz, 2H), 7.63-7.59 (m, 1H), 7.31-7.23 (m, 5H), 7.16 (d, J = 8.5 Hz, 1H), 3.61 (s, 3H), 2.43 (s, 3H); ESI-MS 395 (m/z) (MH)$^+$. |
| Example-12: 2,6-Difluoro-N-(4-(3-methyl-2-oxo-2,3 dihydrobenzo[d]oxazol-5-yl)phenyl)benzamide | 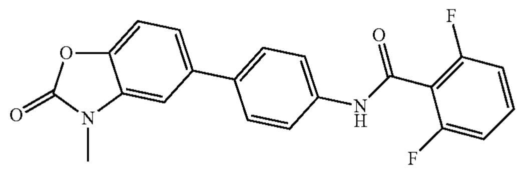 | $^1$HNMR (400 MHz, DMSO-d$_6$) δ 10.92 (s, 1H, D$_2$O exchangeable), 7.81 (d, J = 8.5 Hz, 2H), 7.40 (d, J = 8.5 Hz, 2H), 7.59-7.57 (m, 1H), 7.58 (s, 1H), 7.42 (m, 2H), 7.29-7.25 (m, 2H), 3.36 (s, 3H); ESI-MS (m/z) 381 (MH)$^+$. |
| Example-13: N-(5-(3,7-Dimethyl-2-oxo-2,3-dihydrobenzo[d]oxazol-6-yl)pyrazin-2-yl)-2,6-difluoro benzamide | 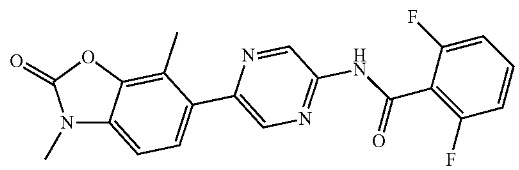 [SMILES: Cc1c(-c2cnc(NC(=O)c3c(F)cccc3F)cn2)ccc2c1oc(=O)n2C] | $^1$HNMR (400 MHz, CDCl$_3$) δ 9.77 (d, J = 1.5 Hz, 1H), 8.49 (s, 1H, D$_2$O exchangeable), 8.40 (d, J = 1.5 Hz, 1H), 7.55-7.49 (m, 1H), 7.36 (d, J = 8.0 Hz, 1H), 7.08 (t, J = 8.0 Hz, 2H), 6.94 (d, J = 8.0 Hz, 1H), 3.47 (s, 3H), 2.47 (s, 3H); ESI-MS (m/z) 397 (MH)$^+$. |
| Example-14: N-(4-(3,7-Dimethyl-2-oxo-2,3-dihydrobenzo[d]oxazol-6-yl)phenyl)-2,6-difluorobenzamide | 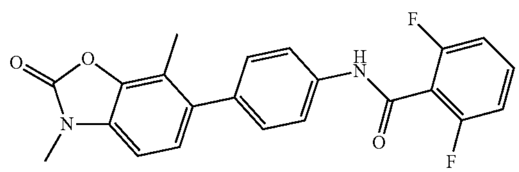 [SMILES: Cc1c(-c2ccc(NC(=O)c3c(F)cccc3F)cc2)ccc2c1oc(=O)n2C] | $^1$HNMR (400 MHz, DMSO-d$_6$) δ 10.93 (s, 1H, D$_2$O exchangeable), 7.81-7.74 (m, 2H), 7.63-7.57 (m, 1H), 7.40-7.34 (m, 2H), 7.28 (t, J = 8.0 Hz, 2H), 7.20-7.10 (m, 2H), 3.44 (s, 3H), 2.25 (s, 3H); ESI-MS (m/z) 395 (MH)$^+$. |
| Example-15: 2,6-Difluoro-N-(4-(3-methyl-2-oxo-2,3-dihydrobenzo[d]oxazol-6-yl)phenyl)benzamide | 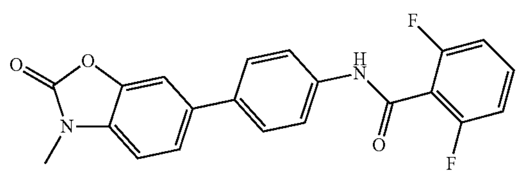 [SMILES: Cn1c(=O)oc2cc(-c3ccc(NC(=O)c4c(F)cccc4F)cc3)ccc21] | $^1$HNMR (400 MHz, DMSO-d$_6$) δ 10.90 (s, 1H, D$_2$O exchangeable), 7.78 (d, J = 8.5 Hz, 2H), 7.69-7.63 (m, 3H), 7.59-7.55 (m, 2H), 7.33 (d, J = 8.0 Hz, 1H), 7.28 (t, J = 8.0 Hz, 2H), 3.38 (s, 3H); ESI-MS (m/z) 381 (MH)$^+$. |
| Example-16: N-(4-(7-Ethyl-3-methyl-2-oxo-2,3-dihydrobenzo[d]oxazol-6-yl)phenyl)-2,6-difluorobenzamide | 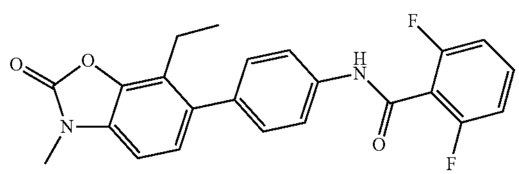 [SMILES: CCc1c(-c2ccc(NC(=O)c3c(F)cccc3F)cc2)ccc2c1oc(=O)n2C] | $^1$HNMR (400 MHz, CDCl$_3$) δ 7.75-7.70 (m, 3H), 7.50-7.44 (m, 1H), 7.35-7.31 (m, 2H), 7.09-7.01 (m, 3H), 6.87 (d, J = 8.0 Hz, 1H), 3.45 (s, 3H), 2.78 (q, J = 7.5 Hz, 2H), 1.15 (t, J = 7.5 Hz, 3H); ESI-MS (m/z) 409 (MH)$^+$. |
| Example-17: N-(5-(3,7-Dimethyl-2-oxo-2,3-dihydrobenzo[d]oxazol-6-yl)pyridin-2-yl)-2,6-difluoro benzamide | 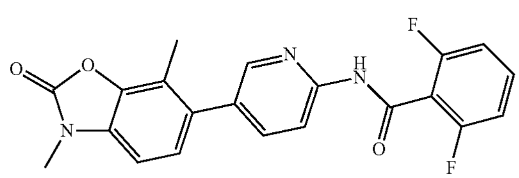 [SMILES: Cc1c(-c2ccc(NC(=O)c3c(F)cccc3F)nc2)ccc2c1oc(=O)n2C] | $^1$HNMR (400 MHz, CDCl$_3$) δ 8.92 (brs, 1H, D$_2$O exchangeable), 8.49 (d, J = 8.0 Hz, 1H), 8.19 (s, 1H), 7.79-7.76 (m, 1H), 7.50-7.42 (m, 1H), 7.10-7.01 (m, 3H), 6.90 (d, J = 8.0 Hz, 1H), 3.46 (s, 3H), 2.33 (s, 3H); ESI-MS (m/z) 396 (M)$^+$. |
| Example-18: N-(6-(3,7-Dimethyl-2-oxo-2,3-dihydrobenzo[d]oxazol-6-yl)pyridin-3-yl)-2,6-difluoro benzamide | 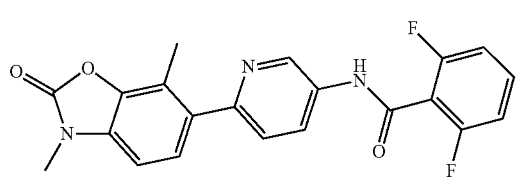 | $^1$HNMR (400 MHz, CDCl$_3$) δ 8.76 (s, 1H), 8.51-8.48 (m, 1H), 7.97 (s, 1H), 7.52-7.46 (m, 2H), 7.36 (d, J = 8.0 Hz, 1H), 7.09 (t, J = 8.0 Hz, 2H), 6.92 (d, J = 8.0 Hz, 1H), 3.46 (s, 3H), 2.45 (s, 3H); ESI-MS (m/z) 396 (MH)$^+$. |

TABLE 3-continued

| Example No: IUPAC name | Structure | NMR /ESI-MS |
|---|---|---|
| Example-19: N-(4-(1,7-Dimethyl-2-oxo-1,2-dihydrooxazolo[5,4-b]pyridin-6-yl)phenyl)-2,6-difluorobenzamide | 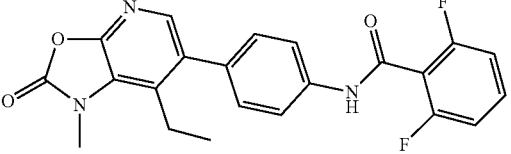 | $^1$HNMR (400 MHz, DMSO-d$_6$) δ 11.02 (s, 1H, D$_2$O exchangeable), 7.81-7.79 (m, 3H), 7.65-7.55 (m, 1H), 7.36 (d, J = 8.0 Hz, 2H), 7.26 (t, J = 8.0 Hz, 2H), 3.62 (s, 3H), 2.44 (s, 3H); ESI-MS (m/z) 396 (MH)$^+$ |
| Example-20: N-(5-(7-Ethyl-3-methyl-2-oxo-2,3-dihydrobenzo[d]oxazol-6-yl)pyrazin-2-yl)-2,6-difluorobenzamide | 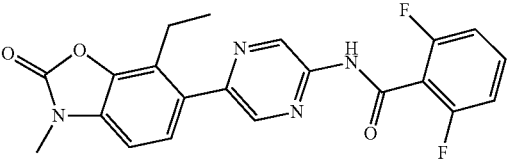 [SMILES: CCc1c(-c2ccc(NC(=O)c3c(F)cccc3F)nc2)ccc2c1oc(=O)n2C] | $^1$HNMR (400 MHz, CDCl$_3$) δ 8.47 (d, J = 1.0 Hz, 1H), 8.20 (s, 1H), 7.75 (d, J = 1.0 Hz, 1H), 7.52-7.44 (m, 1H), 7.12-6.98 (m, 3H), 6.90 (d, J = 8.0 Hz, 1H), 3.46 (s, 3H), 2.73 (q, J = 7.5 Hz, 2H), 1.16 (t, J = 7.5 Hz, 3H); ESI-MS (m/z) 410 (M)$^+$. |
| Example-21: N-(5-(7-Ethyl-3-methyl-2-oxo-2,3-dihydrobenzo[d]oxazol-6-yl)pyridin-2-yl)-2,6-difluorobenzamide | 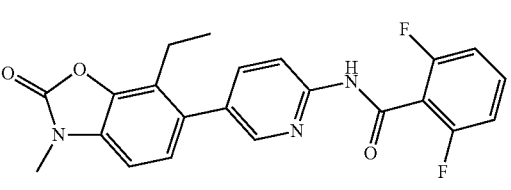 | $^1$HNMR (400 MHz, CDCl$_3$) δ 8.47 (dd, J = 8.3, 1.5 Hz, 1H), 8.20 (dd, J = 2.4, 0.9 Hz, 1H), 7.75-7.74 (m, 1H), 7.47-7.45 (m, 1H), 7.12-6.98 (m, 3H), 6.90 (d, J = 8.0 Hz, 1H), 3.46 (s, 3H), 2.73 (q, J = 7.5 Hz, 2H), 1.16 (t, J = 7.5 Hz, 3H); ESI-MS 410 (m/z) (MH)$^+$. |
| Example-22: N-(6-(7-Ethyl-3-methyl-2-oxo-2,3-dihydrobenzo[d]oxazol-6-yl)pyridin-3-yl)-2,6-difluorobenzamide | 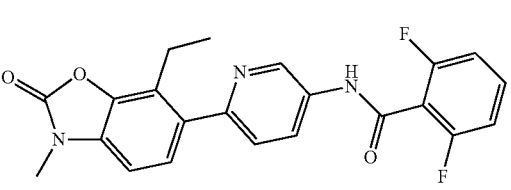 | $^1$HNMR (400 MHz, DMSO-d$_6$) δ 11.21 (s, 1H), 8.92 (s, 1H), 8.43-8.12 (m, 1H), 7.66-7.57 (m, 3H), 7.34-7.21 (m, 3H), 2.84 (q, J = 7.5 Hz, 2H), 1.10 (t, J = 7.5 Hz, 3H); ESI-MS 410 (m/z) (MH)$^+$. |
| Example-23: N-(4-(7-Cyclopropyl-3-methyl-2-oxo-2,3-dihydrobenzo[d]oxazol-6-yl)phenyl)-2,6-difluorobenzamide | 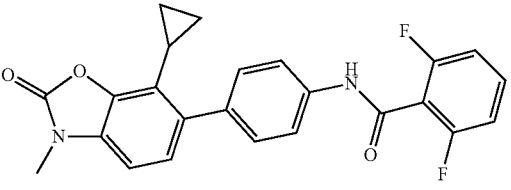 [SMILES: Cn1c(=O)oc2c(C3CC3)c(-c3ccc(NC(=O)c4c(F)cccc4F)cc3)ccc21] | $^1$HNMR (400 MHz, CDCl$_3$) δ 7.75-7.69 (m, 3H), 7.52-7.39 (m, 3H), 7.10 (d, J = 8.0 Hz, 1H), 7.08-7.01 (m, 2H), 6.84 (d, J = 8.0 Hz, 1H), 3.42 (s, 3H), 1.90-1.83 (m, 1H), 1.06-1.01 (m, 2H), 0.91-0.82 (m, 2H); ESI-MS (m/z) 421 (MH)$^+$. |
| Example-24: N-(6-(7-Cyclopropyl-3-methyl-2-oxo-2,3-dihydrobenzo[d]oxazol-6-yl)pyridin-3-yl)-2,6-difluorobenzamide | 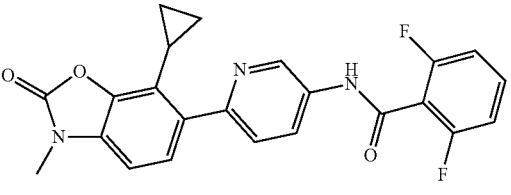 | $^1$HNMR (400 MHz, CDCl$_3$) δ 8.80-8.75 (m, 1H), 8.50 (d, J = 8.0, Hz, 1H), 8.10 (brs, 1H), 7.62 (d, J = 8.0 Hz, 1H), 7.50-7.45 (m, 1H), 7.35 (d, J = 8.0 Hz, 1H), 7.06 (t, J = 8.5 Hz, 2H), 6.90 (d, J = 8.0 Hz, 1H), 3.43 (s, 3H), 2.09-1.97 (m, 1H), 0.95-0.84 (m, 4H); ESI-MS (m/z) 422 (MH)$^+$ |
| Example-25: N-(5-(7-Cyclopropyl-3-methyl-2-oxo-2,3-dihydrobenzo[d]oxazol-6-yl)pyridin-2-yl)-2,6-difluorobenzamide | 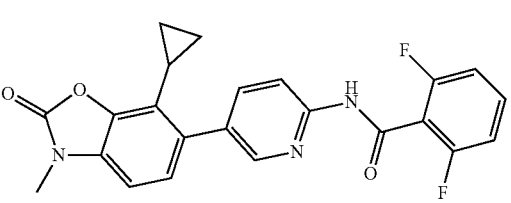 [SMILES: Cn1c(=O)oc2c(C3CC3)c(-c3ccc(NC(=O)c4c(F)cccc4F)nc3)ccc21] | $^1$HNMR (400 MHz, CDCl$_3$) δ 9.29 (brs, 1H), 8.56 (d, J = 8.5 Hz, 1H), 8.35 (d, J = 2.5 Hz, 1H), 8.01-7.93 (dd, J = 8.5 & 2.5 Hz, 1H), 7.52-7.45 (m, 1H), 7.10-7.04 (m, 3H), 6.90 (d, J = 8.0 Hz, 1H), 3.44 (s, 3H), 1.82-1.79 (m, 1H), 0.96-0.91 (m, 4H). ESI-MS (m/z) 422 (MH)$^+$. |
| Example-26: N-(5-(7-Cyclopropyl-3-methyl-2-oxo-2,3-dihydrobenzo[d]oxazol-6-yl)pyrazin-2-yl)-2,6-difluorobenzamide | 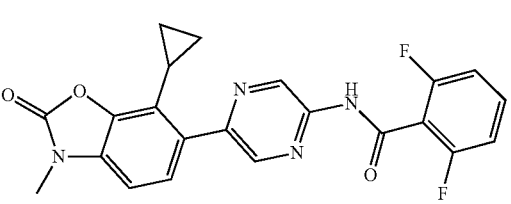 [SMILES: Cn1c(=O)oc2c(C3CC3)c(-c3cnc(NC(=O)c4c(F)cccc4F)cn3)ccc21] | $^1$HNMR (400 MHz, CDCl$_3$) δ 9.77 (d, J = 1.5 Hz, 1H), 8.53 (d, J = 1.5 Hz, 1H), 8.50 (s, 1H), 7.55-7.49 (m, 1H), 7.40 (d, J = 8.0 Hz, 1H), 7.12-7.05 (m, 2H), 6.94 (d, J = 8.0 Hz, 1H), 3.45 (s, 3H), 2.06-2.02 (m, 1H), 0.97-0.90 (m, 2H), 0.88-0.80 (m, 2H); ESI-MS (m/z) 423 (MH)$^+$. |

TABLE 3-continued

| Example No: IUPAC name | Structure | NMR /ESI-MS |
|---|---|---|
| Example-27: N-(4-(3,6-Dimethyl-2-oxo-2,3-dihydrobenzo[d]oxazol-5-yl)phenyl)-2,6-difluorobenzamide | 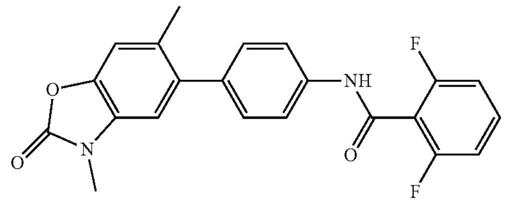 [SMILES: Cc1cc2oc(=O)n(C)c2cc1-c1ccc(NC(=O)c2c(F)cccc2F)cc1] | $^1$HNMR (400 MHz, DMSO-d$_6$) δ 10.91 (s, 1H, D$_2$O exchangeable), 7.78 (d, J = 8.0 Hz, 2H), 7.63-7.59 (m, 1H), 7.38 (d, J = 8.0 Hz, 2H), 7.30 (s, 1H), 7.28 (t, J = 8.0 Hz, 2H), 7.11 (s, 1H), 3.34 (s, 3H), 2.25 (s, 3H); ESI-MS 395 (m/z) (MH)$^+$. |

Example-28: N-(4-(3-Ethyl-6-methyl-2-oxo-2,3-dihydrobenzo[d]oxazol-5-yl)phenyl)-2,6-difluorobenzamide

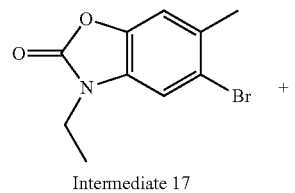

Intermediate 17

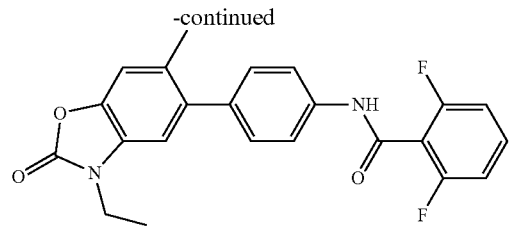

Intermediate 10b

-continued

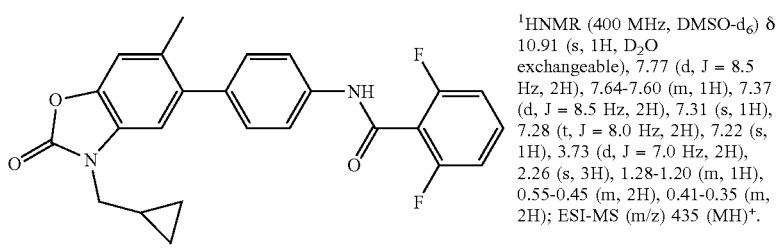

Example-28

In a sealed tube, to a nitrogen purged and stirred solution of Intermediate-17 (0.2 g, 0.78 mmol), Intermediate-10b (0.309 g, 0.86 mmol) and 2M aqueous solution of potassium carbonate (0.78 mL) in 1,4-dioxane (8 mL) and water (2 mL) was added PdCl$_2$(dppf)-CH$_2$Cl$_2$ adduct (64 mg, 0.08 mmol). The resulting mixture was stirred at 100° C. for 6 h. The reaction was cooled to room temperature and filtered through Celite. The residue was washed with ethyl acetate (20 mL) and the combined filtrates were concentrated under vacuum. The crude product was purified by flash column chromatography (silica gel, 30% ethyl acetate in hexane system as eluent) to obtain 130 mg (41%) of the desired product as white solid. $^1$HNMR (400 MHz, DMSO-d$_6$) δ 10.91 (s, 1H, D$_2$O exchangeable), 7.78 (d, J=8.0 Hz, 2H), 7.64-7.61 (m, 1H), 7.38 (d, J=8.0 Hz, 2H), 7.31 (s, 1H), 7.28 (t, J=8.0 Hz, 2H), 7.17 (s, 1H), 3.86 (q, J=7.0 Hz, 2H), 2.25 (s, 3H), 1.25 (t, J=7.0 Hz, 3H); ESI-MS (m/z) 409 (MH)$^+$.

The below Examples (29-44) given in Table-4 were prepared by following the similar procedure as described in Example-28 from the appropriate Intermediates.

TABLE 4

| Example No: IUPAC name | Structure | $^1$H-NMR/ESI-MS |
|---|---|---|
| Example-29: N-(4-(3-(Cyclopropylmethyl)-6-methyl-2-oxo-2,3-dihydrobenzo[d]oxazol-5-yl)phenyl)-2,6-difluorobenzamide | 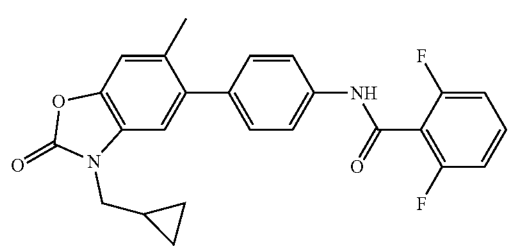 [SMILES: Cc1cc2oc(=O)n(CC3CC3)c2cc1-c1ccc(NC(=O)c2c(F)cccc2F)cc1] | $^1$HNMR (400 MHz, DMSO-d$_6$) δ 10.91 (s, 1H, D$_2$O exchangeable), 7.77 (d, J = 8.5 Hz, 2H), 7.64-7.60 (m, 1H), 7.37 (d, J = 8.5 Hz, 2H), 7.31 (s, 1H), 7.28 (t, J = 8.0 Hz, 2H), 7.22 (s, 1H), 3.73 (d, J = 7.0 Hz, 2H), 2.26 (s, 3H), 1.28-1.20 (m, 1H), 0.55-0.45 (m, 2H), 0.41-0.35 (m, 2H); ESI-MS (m/z) 435 (MH)$^+$. |

TABLE 4-continued

| Example No: IUPAC name | Structure | $^1$H-NMR/ESI-MS |
|---|---|---|
| Example-30: 2,6-Difluoro-N-(4-(3-(2-fluoroethyl)-6-methyl-2-oxo-2,3-dihydrobenzo[d]oxazol-5-yl)phenyl)benzamide | 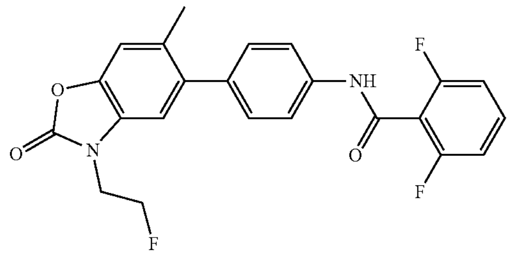 [SMILES: Cc1cc2oc(=O)n(CCF)c2cc1-c1ccc(NC(=O)c2c(F)cccc2F)cc1] | $^1$HNMR (400 MHz, DMSO-$d_6$) δ 10.92 (s, 1H, $D_2O$ exchangeable), 7.77 (d, J = 8.5 Hz, 2H), 7.64-7.60 (m, 1H), 7.36 (d, J = 8.5 Hz, 2H), 7.33 (s, 1H), 7.28 (t, J = 8.0 Hz, 2H), 7.19 (s, 1H), 4.72 (dt, J = 47.0, 4.5 Hz, 2H), 4.17 (dt, J = 27.0, 4.5 Hz, 2H), 2.26 (s, 3H); ESI-MS (m/z) 427 (MH)$^+$. |
| Example-31: 2,6-Difluoro-N-(4-(3-isopropyl-6-methyl-2-oxo-2,3-dihydrobenzo[d]oxazol-5-yl)phenyl)benzamide | 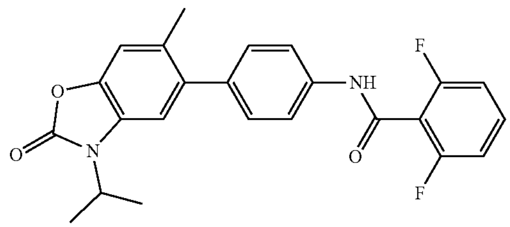 [SMILES: Cc1cc2oc(=O)n(C(C)C)c2cc1-c1ccc(NC(=O)c2c(F)cccc2F)cc1] | $^1$HNMR (400 MHz, DMSO-$d_6$) δ 10.91 (s, 1H, $D_2O$ exchangeable), 7.77 (d, J = 8.0 Hz, 2H), 7.65-7.59 (m, 1H), 7.38 (d, J = 8.0 Hz, 2H), 7.34-7.23 (m, 3H), 7.19 (s, 1H), 4.53-4.46 (m, 1H), 2.24 (s, 3H), 1.46 (d, J = 7.0 Hz, 6H); ESI-MS [(m/z) 423 (MH)$^+$. |
| Example-32: N-(4-(3-(Difluoromethyl)-6-methyl-2-oxo-2,3-dihydrobenzo[d]oxazol-5-yl)phenyl)-2,6-difluorobenzamide | 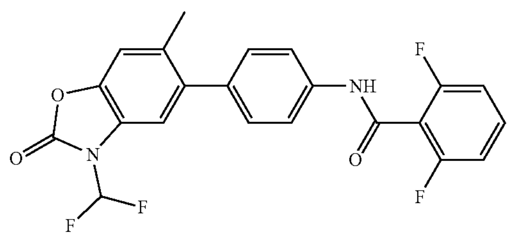 [SMILES: Cc1cc2oc(=O)n(C(F)F)c2cc1-c1ccc(NC(=O)c2c(F)cccc2F)cc1] | $^1$HNMR (400 MHz, DMSO-$d_6$) δ 10.95 (s, 1H, $D_2O$ exchangeable), 7.78 (d, J = 8.0 Hz, 2H), 7.75 (t, J = 57.0 Hz, 1H), 7.67-7.57 (m, 1H), 7.47 (s, 1H), 7.36 (d, J = 8.0 Hz, 2H), 7.28 (t, J = 8.0 Hz, 2H), 7.15 (s, 1H), 2.27 (s, 3H); ESI-MS (m/z) 431 (M + H)$^+$. |
| Example-33: 2,6-Difluoro-N-(4-(6-methyl-2-oxo-3-(3,3,3-trifluoropropyl)-2,3-dihydrobenzo[d]oxazol-5-yl)phenyl)benzamide | 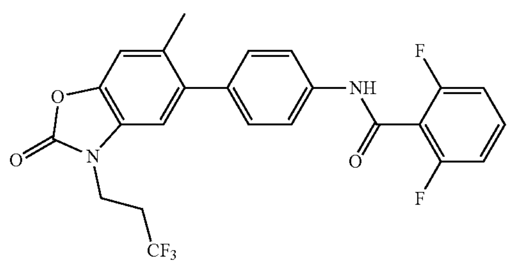 [SMILES: Cc1cc2oc(=O)n(CCC(F)(F)F)c2cc1-c1ccc(NC(=O)c2c(F)cccc2F)cc1] | $^1$HNMR (400 MHz, DMSO-$d_6$) δ 10.92 (s, 1H, $D_2O$ exchangeable), 7.80 (d, J = 8.5 Hz, 2H), 7.64-7.60 (m, 1H), 7.39 (d, J = 8.5 Hz, 2H), 7.33 (s, 1H), 7.28 (d, J = 8.0 Hz, 2H), 7.24 (s, 1H), 4.11 (t, J = 6.5 Hz, 2H), 2.90-2.73 (m, 2H), 2.26 (s, 3H); ESI-MS (m/z) 477 (MH)$^+$. |
| Example-34: 2,6-Difluoro-N-(4-(6-methyl-2-oxo-3-propyl-2,3-dihydrobenzo[d]oxazol-5-371)phenyl)benzamide | 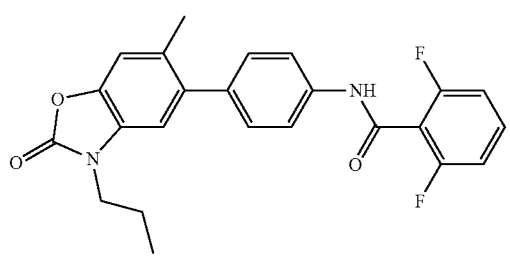 [SMILES: CCCn1c(=O)oc2cc(C)c(-c3ccc(NC(=O)c4c(F)cccc4F)cc3)cc21] | $^1$HNMR (400 MHz, DMSO-$d_6$) δ 10.91 (s, 1H, $D_2O$ exchangeable), 7.77 (d, J = 8.5 Hz, 2H), 7.66-7.57 (m, 1H), 7.37 (d, J = 8.5 Hz, 2H), 7.31 (s, 1H), 7.33-7.24 (t, J = 8.0 Hz, 2H), 7.17 (s, 1H), 3.79 (t, J = 7.0 Hz, 2H), 2.25 (s, 3H), 1.73-1.67 (m, 2H), 0.89 (t, J = 7.0 Hz, 3H); ESI-MS (m/z) 423 (MH)$^+$. |
| Example-35: 2,6-Difluoro-N-(4-(3-isobutyl-6-methyl-2-oxo-2,3-dihydrobenzo[d]oxazol-5-371)phenyl)benzamide | 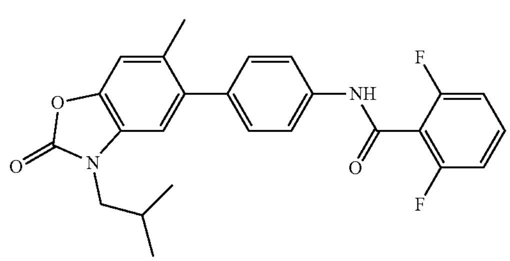 [SMILES: Cc1cc2oc(=O)n(CC(C)C)c2cc1-c1ccc(NC(=O)c2c(F)cccc2F)cc1] | $^1$HNMR (400 MHz, DMSO-$d_6$) δ 10.91 (s, 1H, $D_2O$ exchangeable), 7.77 (d, J = 8.0 Hz, 2H), 7.68-7.57 (m, 1H), 7.36 (d, J = 8.0 Hz, 2H), 7.33-7.24 (m, 3H), 7.17 (s, 1H), 3.64 (d, J = 7.5 Hz, 2H), 2.25 (s, 3H), 2.13-2.10 (m, 1H), 0.90 (d, J = 6.5 Hz, 6H); ESI-MS (m/z) 437 (MH)$^+$. |

TABLE 4-continued

| Example No: IUPAC name | Structure | ¹H-NMR/ESI-MS |
|---|---|---|
| Example-36: N-(4-(5-Cyclopropyl-3-methyl-2-oxo-2,3-dihydro oxazolo [4,5-b]pyridin-6-yl)phenyl)-2,6-difluorobenzamide | 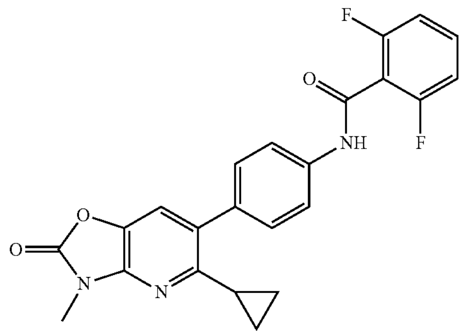 [SMILES: Cn1c(=O)oc2cc(-c3ccc(NC(=O)c4c(F)cccc4F)cc3)c(C3CC3)nc21] | 1HNMR (400 MHz, DMSO-d6) δ 10.96 (s, 1H, D$_2$O exchangeable), 7.81 (d, J = 8.5 Hz, 2H), 7.68-7.57 (m, 1H), 7.56 (s, 1H), 7.46 (d, J = 8.5 Hz, 2H), 7.28 (t, J = 8.0 Hz, 2H), 3.30 (s, 3H), 2.07-2.02 (m, 1H), 1.06-1.03 (m, 2H), 0.91-0.87 (m, 2H); ESI-MS (m/z) 422 (MH)$^+$. |
| Example-37: N-(4-(5-Ethyl-3-methyl-2-oxo-2,3-dihydrooxazolo [4,5-b]pyridin-6-yl)phenyl)-2,6-difluorobenzamide | 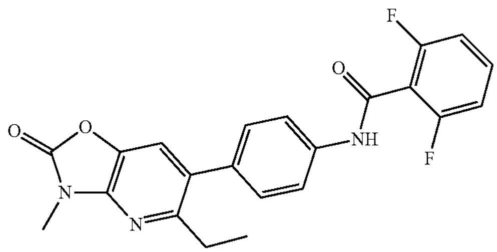 [SMILES: CCc1nc2c(cc1-c1ccc(NC(=O)c3c(F)cccc3F)cc1)oc(=O)n2C] | ¹HNMR (400 MHz, DMSO-d$_6$) δ 10.96 (s, 1H, D$_2$O exchangeable), 7.79 (d, J = 8.0 Hz, 2H), 7.64-7.58 (m, 1H), 7.56 (s, 1H), 7.37 (d, J = 8.0 Hz, 2H), 7.33-7.23 (t, J = 8.0 Hz, 2H), 3.37 (s, 3H), 2.70 (q, J = 7.5 Hz, 2H), 1.15 (t, J = 7.5 Hz, 3H); ESI-MS (m/z) 410 (MH)$^+$. |
| Example-38: N-(4-(3,5-dimethyl-2-oxo-2,3-dihydrooxazolo [4,5-b]pyridin-6-yl)phenyl)-2,6-difluorobenzamide | 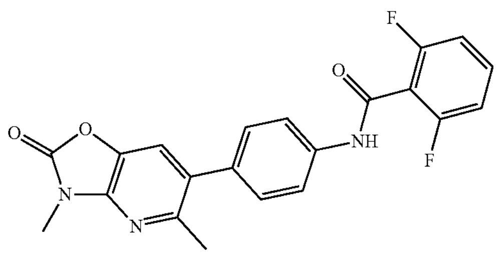 [SMILES: Cc1nc2c(cc1-c1ccc(NC(=O)c3c(F)cccc3F)cc1)oc(=O)n2C] | ¹HNMR (400 MHz, DMSO-d$_6$) δ 10.95 (s, 1H, D$_2$O exchangeable), 7.79 (d, J = 8.0 Hz, 2H), 7.66-7.61 (m, 1H), 7.60 (s, 1H), 7.40 (d, J = 8.0 Hz, 2H), 7.28 (t, J = 8.0 Hz, 2H), 3.36 (s, 3H), 2.44 (s, 3H). ESI-MS (m/z) 396 (MH)$^+$. |
| Example-39: 2,6-Difluoro-N-(4-(3-methyl-2-oxo-2,3-dihydrooxazolo[4,5-b]pyridin-5-yl)phenyl)benzamide | 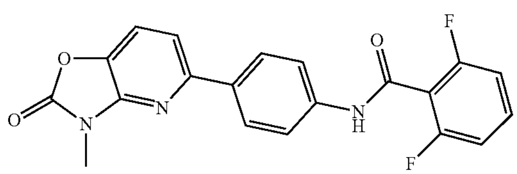 [SMILES: Cn1c(=O)oc2ccc(-c3ccc(NC(=O)c4c(F)cccc4F)cc3)nc21] | ¹HNMR (400 MHz, DMSO-d$_6$) δ 10.98 (s, 1H, D$_2$O exchangeable), 8.11 (d, J = 8.5 Hz, 2H), 7.82 (d, J = 8.5 Hz, 2H), 7.78 (d, J = 8.0 Hz, 1H), 7.72 (d, J = 8.0 Hz, 1H), 7.66-7.60 (m, 1H), 7.28 (d, J = 8.0 Hz, 2H), 3.41 (s, 3H); ESI-MS (m/z) 382 (MH)$^+$. |
| Example-40: N-(4-(1,5-Dimethyl-2-oxo-1,2-dihydrooxazolo [5,4-b]pyridin-6-yl)phenyl)-2,6-difluorobenzamide | 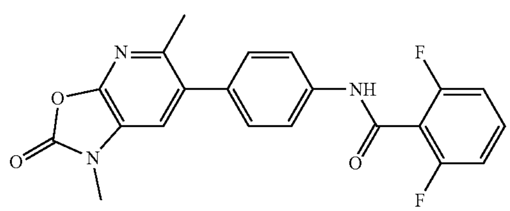 [SMILES: Cc1nc2oc(=O)n(C)c2cc1-c1ccc(NC(=O)c2c(F)cccc2F)cc1] | 1HNMR (400 MHz, DMSO-d6) δ 10.96 (s, 1H, D$_2$O exchangeable), 7.81 (d, J = 8.0 Hz, 2H), 7.62 (m, 1H), 7.57 (s, 1H), 7.43 (d, J = 8.0 Hz, 2H), 7.28 (t, J = 8.0 Hz, 2H), 3.36 (s, 3H), 2.40 (s, 3H); ESI-MS (m/z) 396 (MH)$^+$. |
| Example-41: 4-(5-Cyclopropyl-3-methyl-2-oxo-2,3-dihydro benzo[d]oxazol-6-yl)-N-(2,6-difluorophenyl)benzamide | 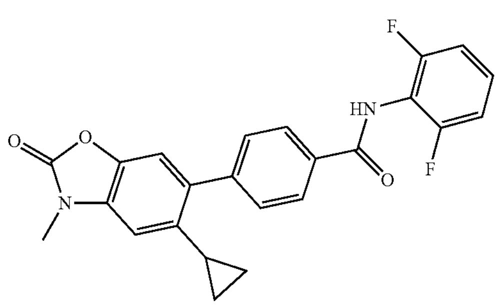 [SMILES: Cn1c(=O)oc2cc(-c3ccc(C(=O)Nc4c(F)cccc4F)cc3)c(C3CC3)cc21] | 1HNMR (400 MHz, CDCl$_3$) δ 8.02 (d, J = 8.0 Hz, 2H), 7.57 (d, J = 8.0 Hz, 2H), 7.50 (s, 1H, D$_2$O exchangeable), 7.34-7.23 (m, 1H), 7.11 (s, 1H), 7.04 (t, J = 8.0 Hz, 2H), 6.61 (s, 1H), 3.44 (s, 3H), 1.92-1.60 (m, 1H), 0.94-0.87 (m, 2H), 0.74-0.64 (m, 2H); ESI-MS (m/z) 421 (MH)$^+$. |

TABLE 4-continued

| Example No: IUPAC name | Structure | ¹H-NMR/ESI-MS |
|---|---|---|
| Example-42: N-(4-(5-Cyclopropyl-3-methyl-2-oxo-2,3-dihydro benzo[d]oxazol-6-yl)phenyl)-2,6-difluorobenzamide | 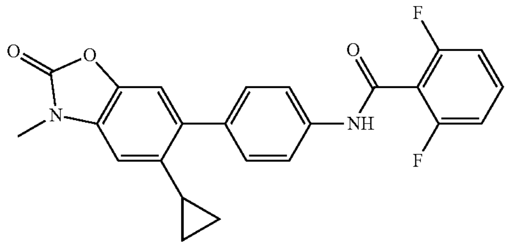 [SMILES: Cn1c(=O)oc2cc(-c3ccc(NC(=O)c4c(F)cccc4F)cc3)c(C3CC3)cc21] | ¹HNMR (400 MHz, DMSO-$d_6$) δ 10.91 (s, 1H), 7.78 (d, J = 8.0 Hz, 2H), 7.64-7.69 (m, 1H), 7.43 (d, J = 8.0 Hz, 2H), 7.28 (t, J = 8.0 Hz, 2H), 7.15 (s, 1H), 6.88 (s, 1H), 3.36 (s, 3H), 1.89-1.85 (m, 1H), 0.93-0.81 (m, 2H), 0.80-0.69 (m, 2H); ESI-MS (m/z) 421 (MH)⁺. |
| Example-43: N-(4-(5-Ethyl-3-methyl-2-oxo-2,3-dihydro benzo[d]oxazol-6-yl)phenyl)-2,6-difluorobenzamide | 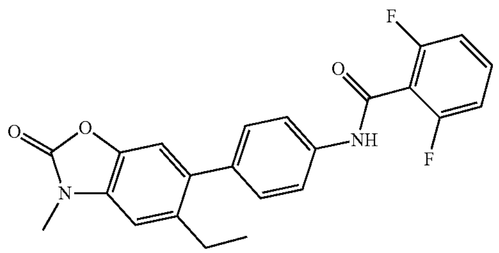 [SMILES: CCc1cc2c(cc1-c1ccc(NC(=O)c3c(F)cccc3F)cc1)oc(=O)n2C] | ¹HNMR (400 MHz, CDCl₃) δ 7.72 (s, 1H), 7.71 (d, J = 8.0 Hz, 2H), 7.49-7.44 (m, 1H), 7.33 (d, J = 8.0 Hz, 2H), 7.08 (s, 1H), 7.07 (t, J = 8.0 Hz, 2H), 6.90 (s, 1H), 3.46 (s, 3H), 2.65 (q, J = 7.5 Hz, 2H), 1.14 (t, J = 7.5 Hz, 3H); ESI-MS (m/z) 409 (MH)⁺. |
| Example-44: N-(4-(7-Chloro-3-methyl-2-oxo-2,3-dihydrobenzo[d]oxazol-6-yl)phenyl)-2,6-difluorobenzamide | 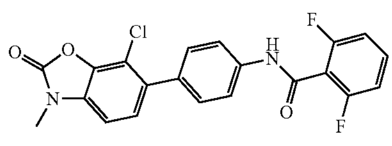 [SMILES: Cn1c(=O)oc2c(Cl)c(-c3ccc(NC(=O)c4c(F)cccc4F)cc3)ccc21] | ¹HNMR (400 MHz, DMSO-$d_6$) δ 10.95 (s, 1H, D₂O exchangeable), 7.80 (d, J = 8.5 Hz, 2H), 7.68-7.55 (m, 1H), 7.45 (d, J = 8.5 Hz, 2H), 7.38-7.23 (m, 4H), 3.39 (s, 3H); ESI-MS (m/z) 415, 417 [(MH)⁺, Cl³⁵,³⁷]. |

Example-45: 2,6-difluoro-N-(4-(3-(2-hydroxyethyl)-6-methyl-2-oxo-2,3-dihydro benzo[d]oxazol-5-yl)phenyl)benzamide

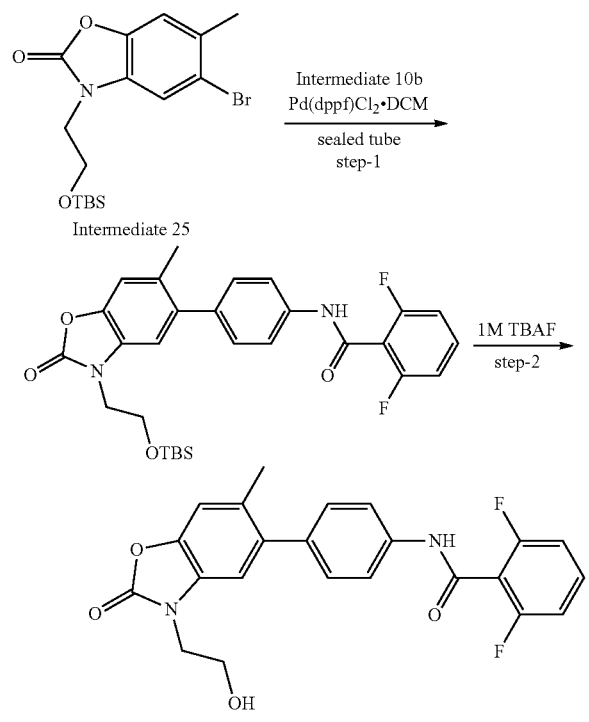

Example-45

Step-1:

N-(4-(3-(2-((tert-Butyldimethylsilyl)oxy)ethyl)-6-methyl-2-oxo-2,3-dihydro benzo[d]oxazol-5-yl)phenyl)-2,6-difluorobenzamide: The title compound was prepared by reacting Intermediate-25 with Intermediate-10b by following the similar procedure as described in Example-28. ¹HNMR (400 MHz, DMSO-$d_6$) δ 10.91 (s, 1H, D₂O exchangeable), 7.76 (d, J=8.0 Hz, 2H), 7.66-7.57 (m, 1H), 7.36-7.25 (m, 4H), 7.14 (s, 1H), 3.98-3.92 (m, 2H), 3.90-3.84 (m, 2H), 2.24 (s, 3H), 0.71 (s, 9H), 0.14 (s, 6H); ESI-MS (m/z) 539 (MH)⁺.

Step-2:

2,6-difluoro-N-(4-(3-(2-hydroxyethyl)-6-methyl-2-oxo-2,3-dihydrobenzo[d]oxazol-5-yl)phenyl)benzamide: To a solution of step-1 Intermediate (0.25 g, 0.46 mmol) in THF at room temperature was added 1M TBAF in THF (0.7 mL, 0.7 mmol). After stirring for 2 h at room temperature the solvent was removed and the residue obtained was purified by flash column chromatography (silica gel, ethyl acetate-hexanes system as eluent) to afford 70 mg (36%) of the desired product as white solid. ¹HNMR (400 MHz, DMSO-$d_6$) δ 10.86 (s, 1H, D₂O exchangeable), 9.81 (s, 1H, D₂O exchangeable), 7.74 (d, J=8.0 Hz, 2H), 7.64-7.59 (m, 1H), 7.33-7.23 (m, 4H), 7.08 (s, 1H), 6.84 (s, 1H), 4.41 (t, J=7.0 Hz, 2H), 3.96-3.84 (m, 2H), 2.19 (s, 3H); ESI-MS (m/z) 426 (MH)⁺.

Example-46: 2-Chloro-N-(4-(3,6-dimethyl-2-oxo-2,3-dihydrobenzo[d]oxazol-5-yl)phenyl)-6-fluorobenzamide

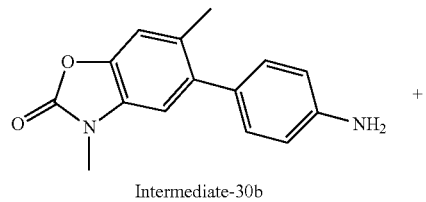

Intermediate-30b

+

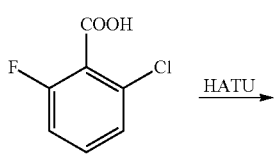

HATU →

-continued

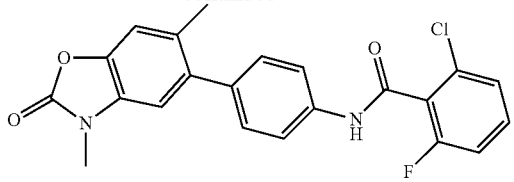

Example-46

To a stirred solution of 2-chloro-6-fluorobenzoic acid (76 mg, 0.43 mmol) in DMF (10 mL) was added HATU (0.18 g, 0.47 mmol), DIPEA (0.10 mL, 0.59 mmol) and stirred for 15 min at room temperature followed by the addition of Intermediate-30b (0.1 g, 0.39 mmol). The resulting mixture was stirred at room temperature for 16 h. The reaction mass was poured into ice cold water (15 mL) and the precipitated solid product was filtered and dried. The residue was triturated with isopropyl alcohol (10 mL) and filtered to afford 80 mg (50%) of the desired product as a white solid. $^1$HNMR (400 MHz, DMSO-d$_6$) δ 10.91 (s, 1H, D$_2$O exchangeable), 7.78 (d, J=8.0 Hz, 2H), 7.62-7.54 (m, 1H), 7.49-7.47 (m, 1H), 7.45-7.38 (m, 1H), 7.37 (d, J=8.0 Hz, 2H), 7.30 (s, 1H), 7.11 (s, 1H), 3.34 (s, 3H), 2.25 (s, 3H); ESI-MS [(m/z) 411, 413 (MH)$^+$, Cl$^{35, 37}$].

The following Examples (47-50) given in Table-5 were prepared from Intermediate-30b or Intermediate-44 by following the similar procedure as described in Example-46

TABLE 5

| Example No: IUPAC name | Structure | $^1$HNMR/ESI-MS |
|---|---|---|
| Example-47: N-(4-(3,6-Dimethyl-2-oxo-2,3-dihydrobenzo[d]oxazol-5-yl)phenyl)-2-fluorobenzamide | 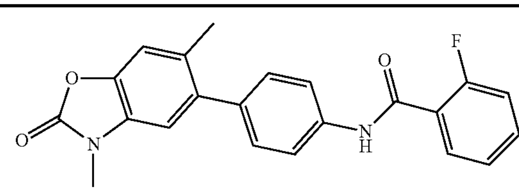 | $^1$HNMR (400 MHz, CDCl$_3$) δ 8.56 (s, 1H), 8.28-8.18 (m, 1H), 7.76 (d, J = 8.0 Hz, 2H), 7.58-7.56 (m, 1H), 7.40-7.36 (m, 1H), 7.34 (d, J = 8.0 Hz, 2H), 7.26-7.21 (m, 1H), 7.13 (s, 1H), 6.84 (s, 1H), 3.41 (s, 3H), 2.30 (s, 3H); ESI-MS (m/z) 377 (MH)$^+$. |
| Example-48: 2-Chloro-N-(4-(3,6-dimethyl-2-oxo-2,3-dihydrobenzo[d]oxazol-5-yl)phenyl)benzamide | 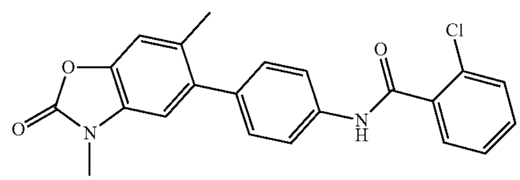 [SMILES: Cc1cc2oc(=O)n(C)c2cc1-c1ccc(NC(=O)c2ccccc2Cl)cc1] | $^1$HNMR (400 MHz, CDCl$_3$) δ 8.01 (s, 1H), 7.85-7.80 (m, 1H), 7.75 (d, J = 8.0 Hz, 2H), 7.51-7.49 (m, 1H), 7.49-7.43 (m, 2H), 7.33 (d, J = 8.0 Hz, 2H), 7.13 (s, 1H), 6.83 (s, 1H), 3.41 (s, 3H), 2.30 (s, 3H); ESI-MS (m/z) 393, 395 [(MH)$^+$Cl $^{35,37}$]. |
| Example-49: N-(4-(3,6-Dimethyl-2-oxo-2,3-dihydrobenzo[d]oxazol-5-yl)phenyl)-2-fluoro-6-methylbenzamide | 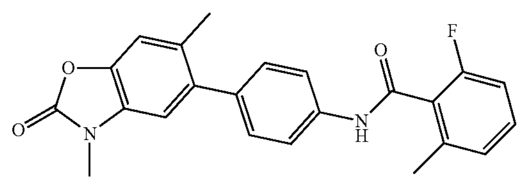 [SMILES: Cc1cc2oc(=O)n(C)c2cc1-c1ccc(NC(=O)c2c(C)cccc2F)cc1] | $^1$HNMR (400 MHz, CDCl$_3$) δ 7.74 (d, J = 8.0 Hz, 2H), 7.60 (brs, 1H, D$_2$O exchangeable), 7.35 (d, J = 8.0 Hz, 2H), 7.37-7.31(m, 1H), 7.13 (s, 1H), 7.10 (d, J = 8.0 Hz, 1H), 7.02 (t, J = 8.0 Hz, 1H), 6.82 (s, 1H), 3.41 (s, 3H), 2.52 (s, 3H), 2.30 (s, 3H); ESI-MS (m/z) 391 (MH)$^+$. |
| Example-50: N-(4-(3,4-Dimethyl-2-oxo-2,3-dihydrobenzo[d]oxazol-6-yl)phenyl)-2,6-difluorobenzamide | 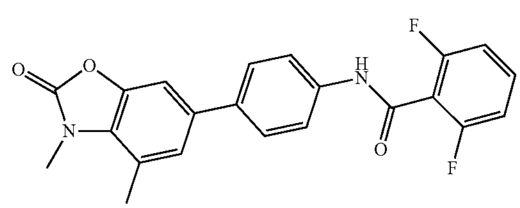 [SMILES: Cc1cc(-c2ccc(NC(=O)c3c(F)cccc3F)cc2)cc2oc(=O)n(C)c12] | $^1$HNMR (400 MHz, CDCl$_3$) δ 7.74 (d, J = 8.0 Hz, 2H), 7.74 (brs, 1H, D$_2$O exchangeable), 7.59 (d, J = 8.0 Hz, 2H), 7.48-7.42 (m, 1H), 7.28 (d, J = 2.0 Hz, 1H), 7.18 (d, J = 2.0 Hz, 1H), 7.04 (t, J = 80 Hz, 2H), 3.67 (s, 3H), 2.65 (s, 3H); ESI-MS (m/z) 395 (M)$^+$. |

Example 51: N-(5-(3,6-dimethyl-2-oxo-2,3-dihydrobenzo[d]oxazol-5-yl)pyrazin-2-yl)-2,6-difluorobenzamide

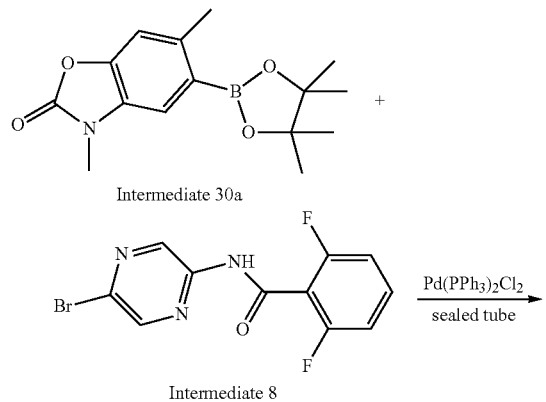

Intermediate 30a

Intermediate 8

Pd(PPh₃)₂Cl₂, sealed tube

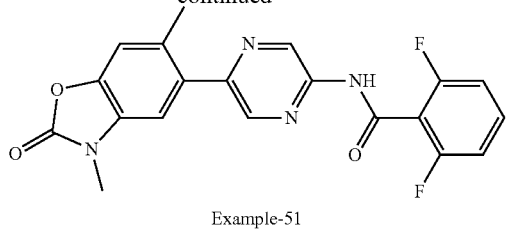

Example-51

The title compound was prepared by reacting Intermediate-30a with Intermediate-8 by following the similar procedure as described in Example-1. ¹HNMR (400 MHz, CDCl₃) δ 9.78 (s, 1H), 8.46 (bs, 1H, D₂O exchangeable), 8.42 (s, 1H), 7.48-7.50 (m, 1H), 7.18 (s, 1H), 7.10 (s, 1H), 7.11-7.07 (t, J=8.0 Hz, 2H), 3.44 (s, 3H), 2.45 (s, 3H); ESI-MS (m/z) 397 (MH)$^+$.

The following Examples (52-62) given in Table-6 were prepared from the appropriate Intermediates by following the similar procedure as described in Example-51.

TABLE 6

| Example No: IUPAC name | Structure | ¹HNMR/ESI-MS |
|---|---|---|
| Example-52: N-(6-(3,6-Dimethyl-2-oxo-2,3-dihydrobenzo[d]oxazol-5-yl)pyridin-3-yl)-2,6-difluoro benzamide | 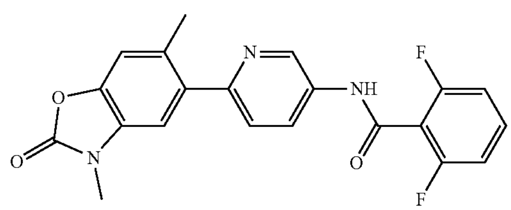 | ¹HNMR (400 MHz, CDCl₃) δ 8.74 (d, J = 2.0 Hz, 1H), 8.46 (dd, J = 8.0 & 2.0 Hz, 1H), 7.83 (brs, 1H, D₂O exchangeable), 7.56-7.52 (m, 1H), 7.48 (d, J = 8.0 Hz, 1H), 7.15 (s, 1H), 7.12-7.04 (m, 3H), 3.43 (s, 3H), 2.41 (s, 3H); ESI-MS (m/z) 396 (MH)$^+$. |
| Example-53: N-(5-(3,6-Dimethyl-2-oxo-2,3-dihydrobenzo[d]oxazol-5-yl)pyridin-2-yl)-2,6-difluoro benzamide | 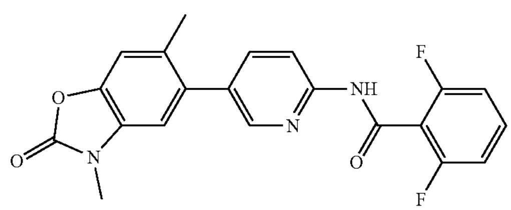 [SMILES: Cc1cc2oc(=O)n(C)c2cc1-c1ccc(NC(=O)c2c(F)cccc2F)nc1] | ¹HNMR (400 MHz, CDCl₃) δ 8.47 (s, 1H, D₂O exchangeable), 8.45 (d, J = 8.5 Hz, 1H), 8.26 (d, J = 2.5 Hz, 1H), 7.75 (dd, J = 8.5 & 2.5 Hz, 1H), 7.50-7.48 (m, 1H), 7.17 (s, 1H), 7.06 (t, J = 8.0 Hz, 2H), 6.82 (s, 1H), 3.43 (s, 3H), 2.31 (s, 3H); ESI-MS 396 (m/z) (MH)$^+$. |
| Example-54: N-(2,6-Difluorophenyl)-4-(3,6-dimethyl-2-oxo-2,3-dihydrobenzo[d]oxazol-5-yl)benzamide | 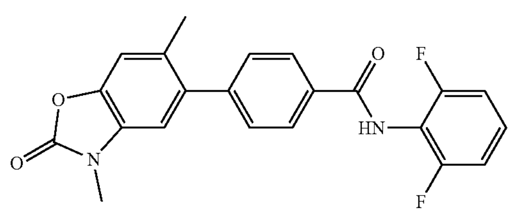 [SMILES: Cc1cc2oc(=O)n(C)c2cc1-c1ccc(C(=O)Nc2c(F)cccc2F)cc1] | ¹HNMR (400 MHz, DMSO-d₆) δ 10.22 (s, 1H, D₂O exchangeable), 8.10 (d, J = 8.0 Hz, 2H), 7.56 (d, J = 8.0 Hz, 2H), 7.45-7.42 (m, 1H), 7.34 (s, 1H), 7.24 (t, J = 8.0 Hz, 2H), 7.19 (s, 1H), 3.36 (s, 3H), 2.26 (s, 3H); ESI-MS (m/z) 395 (MH)$^+$. |
| Example-55: 5-(4-((2,6-Difluoro benzyl)amino)phenyl)-3,6-dimethyl benzo[d]oxazol-2(3H)-one | 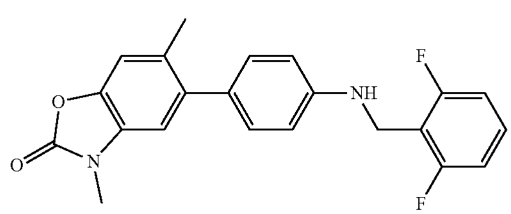 [SMILES: Cc1cc2oc(=O)n(C)c2cc1-c1ccc(NCc2c(F)cccc2F)cc1] | ¹HNMR (400 MHz, DMSO-d₆) δ 7.44-7.39 (m, 1H), 7.22 (s, 1H), 7.13 (t, J = 8.0 Hz, 2H), 7.08 (d, J = 8.0 Hz, 2H), 7.01 (s, 1H), 6.74 (d, J = 8.0 Hz, 2H), 6.16 (t, J = 6.0 Hz, 1H, D₂O exchangeable), 4.30 (d, J = 6.0 Hz, 2H), 3.31 (s, 3H), 2.23 (s, 3H); ESI-MS (m/z) 381 (MH)$^+$. |

TABLE 6-continued

| Example No: IUPAC name | Structure | ¹HNMR/ESI-MS |
|---|---|---|
| Example-56: N-(4-(3,5-Dimethyl-2-oxo-2,3-dihydrobenzo[d]oxazol-6-yl)phenyl)-2,6-difluorobenzamide | 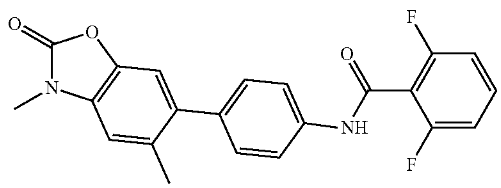 [SMILES: Cc1cc2c(cc1-c1ccc(NC(=O)c3c(F)cccc3F)cc1)oc(=O)n2C] | ¹HNMR (400 MHz, CDCl$_3$) δ 7.72 (d, J = 8.0 Hz, 2H), 7.70 (brs, 1H, D$_2$O exchangeable), 7.54-7.39 (m, 1H), 7.32 (d, J = 8.0 Hz, 2H), 7.09 (s, 1H), 7.05 (t, J = 8.0 Hz, 2H), 6.88 (s, 1H), 3.44 (s, 3H), 2.33 (s, 3H); ESI-MS (m/z) 395 (MH)$^+$. |
| Example-57: N-(2,6-Difluorophenyl)-4-(3,5-dimethyl-2-oxo-2,3-dihydrobenzo[d]oxazol-6-yl)benzamide | 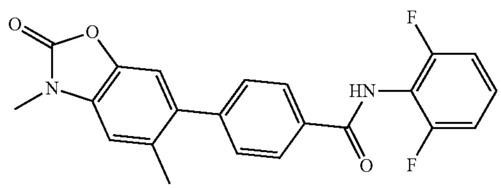 [SMILES: Cc1cc2c(cc1-c1ccc(C(=O)Nc3c(F)cccc3F)cc1)oc(=O)n2C] | ¹HNMR (400 MHz, CDCl$_3$) δ 8.03 (d, J = 8.0 Hz, 2H), 7.46 (d, J = 8.0 Hz, 2H), 7.47 (brs, 1H, D$_2$O exchangeable), 7.34-7.22 (m, 1H), 7.11 (s, 1H), 7.07 (t, J = 8.0 Hz, 2H), 6.91 (s, 1H), 3.45 (s, 3H), 2.33 (s, 3H); ESI-MS (m/z) 395 (MH)$^+$. |
| Example-58: N-(2,6-Difluorophenyl)-2-(3,6-dimethyl-2-oxo-2,3-dihydrobenzo[d]oxazol-5-yl)thiazole-4-carboxamide | 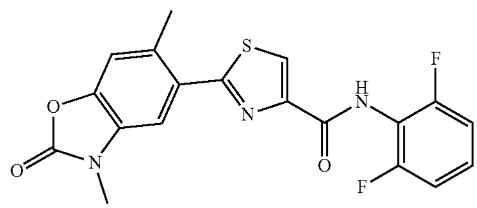 [SMILES: Cc1cc2oc(=O)n(C)c2cc1-c1nc(C(=O)Nc2c(F)cccc2F)cs1] | ¹HNMR (400 MHz, CDCl$_3$) δ 8.76 (s, 1H), 8.37 (s, 1H), 7.38 (s, 1H), 7.29-7.26 (m, 1H), 7.21 (s, 1H), 7.04 (t, J = 8.0 Hz, 2H), 3.48 (s, 3H), 2.66 (s, 3H); ESI-MS (m/z) 402 (MH)$^+$ |
| Example-59: N-(2,6-Difluorophenyl)-2-(3,6-dimethyl-2-oxo-2,3-dihydrobenzo[d]oxazol-5-yl)thiazole-5-carboxamide | 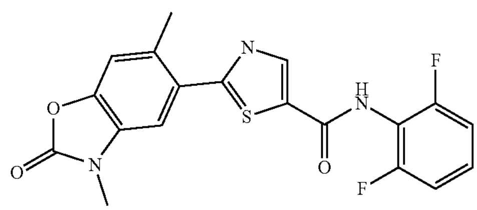 | ¹HNMR (400 MHz, CDCl3) δ 8.43 (s, 1H), 7.52 (s, 1H), 7.35 (brs, 1H, D$_2$O exchangeable), 7.32-7.29 (m, 1H), 7.20 (s, 1H), 7.05 (t, J = 8.0 Hz, 2H), 3.47 (s, 3H), 2.68 (s, 3H); ESI-MS (m/z) 402 (MH)$^+$ |
| Example-60: N-(3,5-Difluoropyridin-4-yl)-5-(3,6-dimethyl-2-oxo-2,3-dihydrobenzo[d]oxazol-5-yl)thiophene-2-carboxamide | 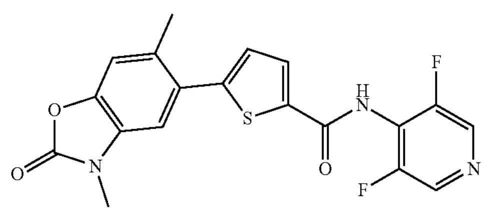 [SMILES: Cc1cc2oc(=O)n(C)c2cc1-c1ccc(C(=O)Nc2c(F)cncc2F)s1] | ¹HNMR (400 MHz, CDCl$_3$) δ 8.46 (s, 2H), 7.75 (d, J = 4.0 Hz, 1H), 7.53 (brs, 1H, D$_2$O exchangeable), 7.17 (s, 1H), 7.12 (d, J = 4.0 Hz, 1H), 6.99 (s, 1H), 3.43 (s, 3H), 2.46 (s, 3H); ESI-MS (m/z) 402 (MH)$^+$. |
| Example-61: N-(3,5-Dichloropyridin-4-yl)-5-(3,6-dimethyl-2-oxo-2,3-dihydrobenzo[d]oxazol-5-yl)thiophene-2-carboxamide | 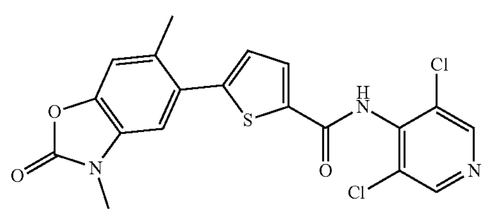 [SMILES: Cc1cc2oc(=O)n(C)c2cc1-c1ccc(C(=O)Nc2c(Cl)cncc2Cl)s1] | HNMR (400 MHz, DMSO-d$_6$) δ 10.77 (brs, 1H, D$_2$O exchangeable), 8.78 (s, 2H), 8.09 (d, J = 4.0 Hz, 1H), 7.39 (s, 1H), 7.38 (s, 1H), 7.35 (d, J = 4.0 Hz, 1H), 3.35 (s, 3H), 2.43 (s, 3H); ESI-MS (m/z) 434, 436 [(MH)$^+$, Cl$^{35,37}$]. |
| Example-62: 5-(3,6-Dimethyl-2-oxo-2,3-dihydrobenzo[d]oxazol-5-yl)-N-(3-methyl pyridin-4-yl)thiophene-2-carboxamide | 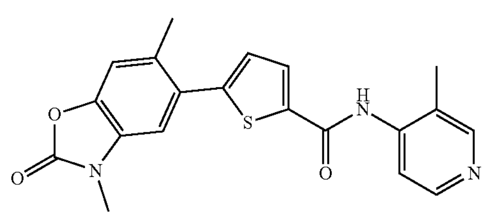 [SMILES: Cc1cnccc1NC(=O)c1ccc(-c2cc3c(cc2C)oc(=O)n3C)s1] | ¹HNMR (400 MHz, DMSO-d$_6$) δ 10.01 (s, 1H, D$_2$O exchangeable), 8.46 (s, 1H), 8.40 (d, J = 5.5 Hz, 1H), 8.06 (d, J = 4.0 Hz, 1H), 7.56 (d, J = 5.5 Hz, 1H), 7.38 (s, 1H), 7.37 (s, 1H), 7.33 (d, J = 4.0 Hz, 1H), 3.36 (s, 3H), 2.43 (s, 3H), 2.30 (s, 3H); ESI-MS (m/z) 380 (MH)$^+$. |

Example-63: N-(5-(3,5-Dimethyl-2-oxo-2,3-dihydrobenzo[d]oxazol-6-yl)pyridin-2-yl)-2,6-difluorobenzamide

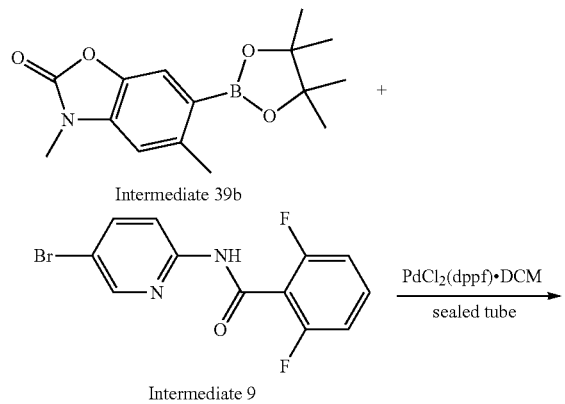

Intermediate 39b

Intermediate 9

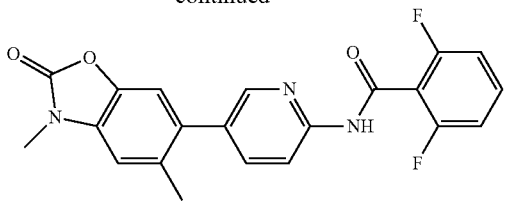

Example 63

The title compound was prepared by reacting Intermediate-39b with Intermediate-9 by following the similar procedure as described in Example-28. $^1$HNMR (400 MHz, CDCl$_3$) δ 8.95 (brs, 1H, D$_2$O exchangeable), 8.51 (d, J=8.0 Hz, 1H), 8.22 (d, J=2.0 Hz, 1H), 7.79 (dd, J=8.0 & 2.0 Hz, 1H), 7.49-7.45 (m, 1H), 7.09 (s, 1H), 7.04 (t, J=8.0 Hz, 2H), 6.92 (s, 1H), 3.45 (s, 3H), 2.33 (s, 3H); ESI-MS (m/z) 396 (MH)$^+$.

The following Examples (64-95) given in Table-7 were prepared by following the similar procedure as described in Example-63 using appropriate Intermediates.

TABLE 7

| Example No: IUPAC name | Structure | $^1$HNMR/ESI-MS |
|---|---|---|
| Example-64: N-(6-(3,5-Dimethyl-2-oxo-2,3-dihydrobenzo[d]oxazol-6-yl)pyridin-3-yl)-2,6-difluorobenzamide | 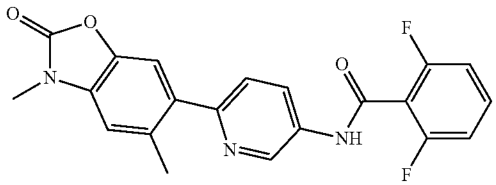 [SMILES: Cc1cc2c(cc1-c1ccc(NC(=O)c3c(F)cccc3F)cn1)oc(=O)n2C] | $^1$HNMR (400 MHz, CDCl$_3$) δ 8.83 (d, J = 2.0 Hz, 1H), 8.58 (d, J = 8.0 Hz, 1H), 7.49 (dd, J = 8.0 & 2.0 Hz, 1H), 7.51-7.29 (m, 1H), 7.29 (s, 1H), 7.06 (t, J = 8.0 Hz, 2H), 6.90 (s, 1H), 3.45 (s, 3H), 2.44 (s, 3H); ESI-MS (m/z) 396 (MH)$^+$. |
| Example-65: N-(5-(3,5-dimethyl-2-oxo-2,3-dihydrobenzo[d]oxazol-6-yl)pyrazin-2-yl)-2,6-difluorobenzamide | 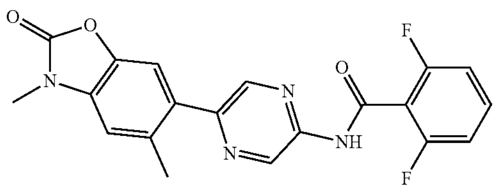 [SMILES: Cc1cc2c(cc1-c1cnc(NC(=O)c3c(F)cccc3F)cn1)oc(=O)n2C] | $^1$HNMR (400 MHz, CDCl$_3$) δ 9.77 (s, 1H), 8.53 (brs, 1H, D$_2$O exchangeable), 8.37 (s, 1H), 7.54-7.49 (m, 1H), 7.30 (s, 1H), 7.10 (t, J = 8.0 Hz, 2H), 6.93 (s, 1H), 3.46 (s, 3H), 2.47 (s, 3H); ESI-MS (m/z) 397 (MH)$^+$. |
| Example-66: N-(4-(3,5-Dimethyl-2-oxo-2,3-dihydrobenzo[d]oxazol-6-yl)-3-methylphenyl)-2,6-difluorobenzamide | 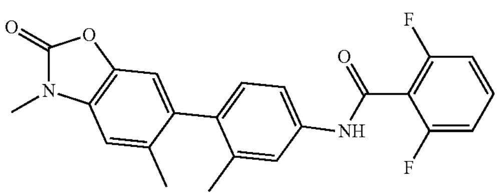 [SMILES: Cc1cc(NC(=O)c2c(F)cccc2F)ccc1-c1cc2oc(=O)n(C)c2cc1C] | $^1$HNMR (400 MHz, CDCl$_3$) δ 7.69 (s, 1H), 7.63 (d, J = 2.0 Hz, 1H), 7.51 (dd, J = 8.0 & 2.0 Hz, 1H), 7.49-7.42 (m, 1H), 7.10 (d, J = 8.0 Hz, 1H), 7.04 (t, J = 8.0 Hz, 2H), 6.96 (s, 1H), 6.89 (s, 1H), 3.44 (s, 3H), 2.11 (s, 3H), 2.08 (s, 3H); ESI-MS (m/z) 409 (MH)$^+$. |
| Example-67: N-(4-(3,5-Dimethyl-2-oxo-2,3-dihydrobenzo[d]oxazol-6-yl)-2-methylphenyl)-2,6-difluorobenzamide | 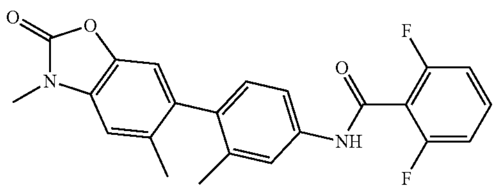 [SMILES: Cc1cc(NC(=O)c2c(F)cccc2F)ccc1-c1cc2oc(=O)n(C)c2cc1C] | $^1$HNMR (400 MHz, CDCl$^3$) δ 8.06 (d, J = 8.0 Hz, 1H), 7.52 (brs, 1H, D$_2$O exchangeable), 7.51-7.41 (m, 1H), 7.22 (dd, J = 8.0 & 2.0 Hz, 1H), 7.18 (d, J = 2.0 Hz, 1H), 7.08 (s, 1H), 7.03 (t, J = 8.0 Hz, 2H), 6.87 (s, 1H), 3.44 (s, 3H), 2.40 (s, 3H), 2.33 (s, 3H); ESI-MS (m/z) 409 (MH)+. |

TABLE 7-continued

| Example No: IUPAC name | Structure | ¹HNMR/ESI-MS |
|---|---|---|
| Example-68: N-(6-(5-Ethyl-3-methyl-2-oxo-2,3-dihydrobenzo[d]oxazol-6-yl)pyridin-3-yl)-2,6-difluoro benzamide | 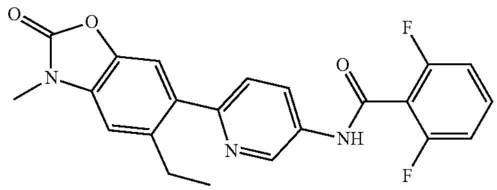 [SMILES: CCc1cc2c(cc1-c1ccc(NC(=O)c3c(F)cccc3F)cn1)oc(=O)n2C] | ¹HNMR (400 MHz, CDCl₃) δ 8.72 (d, J = 2.5 Hz, 1H), 8.44 (dd, J = 8.5 & 2.5 Hz, 1H), 7.83 (brs, 1H), 7.55-7.47 (m, 1H), 7.44 (d, J = 8.5 Hz, 1H), 7.23 (s, 1H), 7.07 (t, J = 8.0 Hz, 2H), 6.92 (s, 1H), 3.46 (s, 3H), 2.78 (q, J = 7.5 Hz, 2H), 1.16 (t, J = 7.5 Hz, 3H); ESI-MS (m/z) 410 (MH)⁺. |
| Example-69: N-(5-(5-Ethyl-3-methyl-2-oxo-2,3-dihydrobenzo[d]oxazol-6-yl)pyridin-2-yl)-2,6-difluoro benzamide | 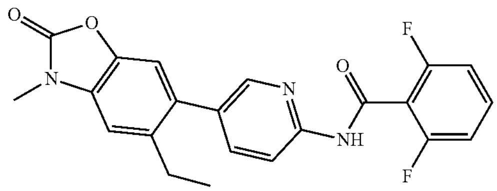 [SMILES: CCc1cc2c(cc1-c1ccc(NC(=O)c3c(F)cccc3F)nc1)oc(=O)n2C] | ¹HNMR (400 MHz, CDCl₃) δ 9.08 (brs, 1H, D₂O exchangeable), 8.52 (d, J = 8.5 Hz, 1H), 8.20 (d, J = 2.5 Hz, 1H), 7.79 (dd, J = 2.5 & 8.5 Hz, 1H), 7.40-7.45 (m, 1H), 7.05 (t, J = 8.0 Hz, 2H), 7.03 (s, 1H), 6.93 (s, 1H), 3.47 (s, 3H), 2.63 (q, J = 7.5 Hz, 2H), 1.15 (t, J = 7.5 Hz, 3H); ESI-MS (m/z) 410 (MH)⁺. |
| Example-70: N-(5-(5-Ethyl-3-methyl-2-oxo-2,3-dihydrobenzo[d]oxazol-6-yl)pyrazin-2-yl)-2,6-difluoro benzamide | 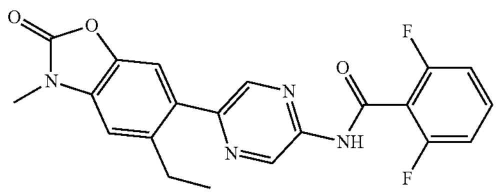 [SMILES: CCc1cc2c(cc1-c1cnc(NC(=O)c3c(F)cccc3F)cn1)oc(=O)n2C] | NMR (400 MHz, CDCl₃) δ 9.77 (s, 1H), 8.44 (s, 1H), 8.38 (s, 1H), 7.55-7.52 (m, 1H), 7.25 (s, 1H), 7.19 (t, J = 8.0 Hz, 2H), 6.96 (s, 1H), 3.48 (s, 3H), 2.80 (q, J = 7.5 Hz, 2H), 1.19 (t, J = 7.5 Hz, 3H); ESI-MS (m/z) 411 (MH)⁺. |
| Example-71: N-(5-(5-Cyclopropyl-3-methyl-2-oxo-2,3-dihydro benzo [d]oxazol-6-yl)pyridin-2-yl)-2,6-difluoro benzamide | 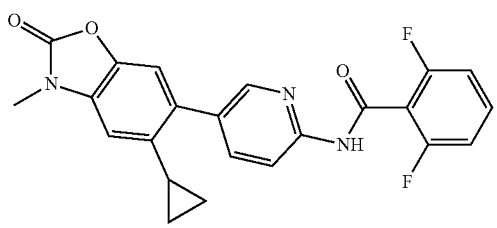 [SMILES: Cn1c(=O)oc2cc(-c3ccc(NC(=O)c4c(F)cccc4F)nc3)c(C3CC3)cc21] | ¹HNMR (400 MHz, CDCl3) δ 9.34 (brs, 1H, D₂O exchangeable), 8.59 (d, J = 8.0 Hz, 1H), 8.35 (d, J = 2.5 Hz, 1H), 7.99 (dd, J = 8.0 & 2.5 Hz, 1H), 7.59-7.45 (m, 1H), 7.09 (s, 1H),7.07 (t, J = 8.0 Hz, 2H), 6.66 (s, 1H), 3.45 (s, 3H), 1.88-1.84 (m, 1H), 0.99-0.88 (m, 2H), 0.69-0.68 (m, 2H); ESI-MS (m/z) 422 (MH)⁺. |
| Example-72: N-(5-(5-Cyclopropyl-3-methyl-2-oxo-2,3-dihydro benzo [d]oxazol-6-yl)pyrazin-2-yl)-2,6-difluorobenzamide | 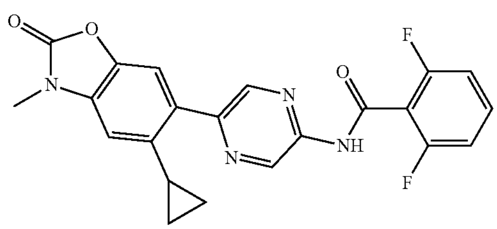 [SMILES: Cn1c(=O)oc2cc(-c3cnc(NC(=O)c4c(F)cccc4F)cn3)c(C3CC3)cc21] | ¹HNMR (400 MHz, DMSO-d₆) δ 11.78 (s, 1H), 9.50 (s, 1H), 8.70 (s, 1H), 7.67-7.63 (m, 1H), 7.44 (s, 1H), 7. 28 (t, = 8.0 Hz, 2H), 7.03 (s, 1H), 3.38 (s, 3H), 2.22-2.08 (m, 1H), 0.87-0.85 (m, 2H), 0.74-0.64 (m, 2H); ESI-MS (m/z) 423 (MH)⁺. |
| Example-73: N-(2,6-Difluorophenyl)-5-(5-ethyl-3-methyl-2-oxo-2,3-dihydrobenzo[d]oxazol-6-yl) thiophene-2-carboxamide | 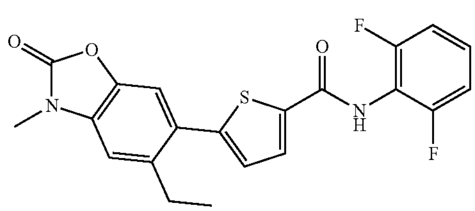 [SMILES: CCc1cc2c(cc1-c1ccc(C(=O)Nc3c(F)cccc3F)s1)oc(=O)n2C] | ¹HNMR (400 MHz, DMSO-d6) δ 10.26 (s, 1H), 8.01 (d, J = 4.0 Hz, 1H), 7.47-7.39 (m, 1H), 7.37 (s, 1H), 7.30 (s, 1H), 7.28-7.21 (m, 3H), 3.35 (s, 3H), 2.76 (q, J = 7.5 Hz, 2H), 1.19 (t, J = 7.5 Hz, 3H); ESI-MS (m/z) 415 (MH)⁺. |
| Example-74: 5-(5-Cyclopropyl-3-methyl-2-oxo-2,3-dihydro benzo [d]oxazol-6-yl)-N-(2,6-difluorophenyl) thiophene-2-carboxamide | 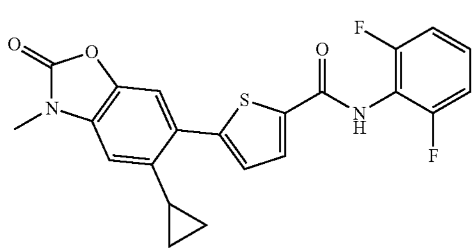 [SMILES: Cn1c(=O)oc2cc(-c3ccc(C(=O)Nc4c(F)cccc4F)s3)c(C3CC3)cc21] | ¹HNMR (400 MHz, DMSO-d₆) δ 10.24 (s, 1H), 8.01 (d, J = 4.0 Hz, 1H), 7.42 (s, 1H), 7.43-7.41 (m, 1H), 7.36 (d, J = 4.0 Hz, 1H), 7.24 (t, J = 8.0 Hz, 2H), 7.01 (s, 1H), 3.37 (s, 3H), 2.14-2.04 (m, 1H), 1.02-0.89 (m, 2H), 0.85-0.77 (m, 2H); ESI-MS (m/z) 427 (MH)⁺. |

| Example No: IUPAC name | Structure | ¹HNMR/ESI-MS |
|---|---|---|
| Example-75: N-(2,6-Difluorophenyl)-5-(3,5-dimethyl-2-oxo-2,3-dihydrobenzo[d]oxazol-6-yl)thiophene-2-carboxamide | 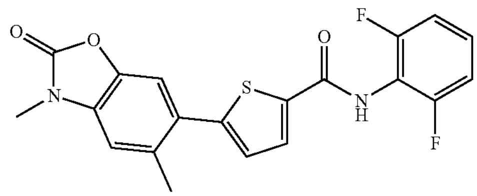 [SMILES: Cc1cc2c(cc1-c1ccc(C(=O)Nc3c(F)cccc3F)s1)oc(=O)n2C] | ¹HNMR (400 MHz, CDCl$_3$) δ 7.70 (d, J = 4.0 Hz, 1H), 7.33-7.28 (m, 1H), 7.25 (s, 1H), 7.07 (d, J = 4.0 Hz, 1H), 7.03 (t, J = 8.0 Hz, 2H), 6.90 (s, 1H), 3.44 (s, 3H), 2.49 (s, 3H); ESI-MS (m/z) 401 (MH)⁺. |
| Example-76: N-(6-(3-(Difluoromethyl)-6-methyl-2-oxo-2,3-dihydrobenzo[d]oxazol-5-yl)pyridin-3-yl)-2,6-difluorobenzamide | 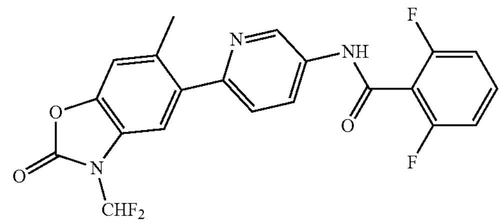 [SMILES: Cc1cc2oc(=O)n(C(F)F)c2cc1-c1ccc(NC(=O)c2c(F)cccc2F)cn1] | ¹HNMR (400 MHz, DMSO-d$_6$) δ 11.23 (s, 1H, D$_2$O exchangeable), 8.94 (d, J = 2.5 Hz, 1H), 8.28 (dd, J = 8.5 & 2.5 Hz, 1H), 7.77 (t, J = 56 Hz, 1H), 7.70-7.58 (m, 1H), 7.65 (d, J = 8.5 Hz, 1H), 7.48 (s, 1H), 7.38 (s, 1H), 7.31 (t, J = 8.0 Hz, 2H), 2.38 (s, 3H); ESI-MS 432 (m/z) (MH)⁺. |
| Example-77: N-(5-(3-(Difluoromethyl)-6-methyl-2-oxo-2,3-dihydrobenzo[d]oxazol-5-yl)pyridin-2-yl)-2,6 difluorobenzamide | 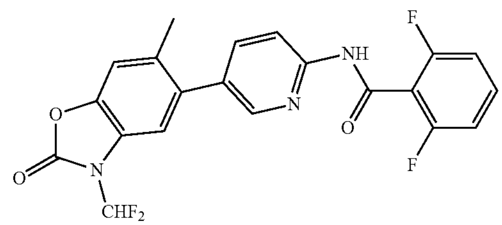 [SMILES: Cc1cc2oc(=O)n(C(F)F)c2cc1-c1ccc(NC(=O)c2c(F)cccc2F)nc1] | ¹HNMR (400 MHz, DMSO-d$_6$) δ 11.50 (s, 1H, D$_2$O exchangeable), 8.37 (d, J = 2.5 Hz, 1H), 8.27 (d, J = 8.5 Hz, 1H), 7.91 (dd, J = 8.5 & 2.5 Hz, 1H), 7.75 (t, J = 56 Hz, 1H), 7.61-7.51 (m, 1H), 7.51 (s, 1H), 7.26 (s, 1H), 7.24 (t, J = 8.0 Hz, 2H), 2.29 (s, 3H); ESI-MS (m/z) 432 (MH)⁺. |
| Example-78: N-(5-(3-(Difluoromethyl)-6-methyl-2-oxo-2,3-dihydrobenzo[d]oxazol-5-yl)pyrazin-2-yl)-2,6-difluorobenzamide | 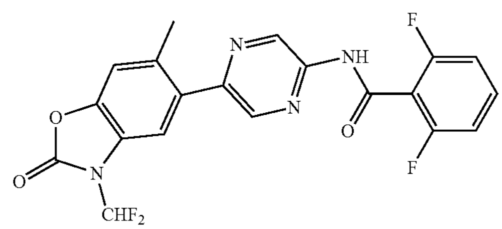 [SMILES: Cc1cc2oc(=O)n(C(F)F)c2cc1-c1cnc(NC(=O)c2c(F)cccc2F)cn1] | ¹HNMR (400 MHz, DMSO-d$_6$) δ 11.83 (s, 1H, D$_2$O exchangeable), 9.51 (s, 1H), 8.67 (s 1H), 7.91 (t, J = 56 Hz, 1H), 7.65-7.63 (m, 1H), 7.53 (s, 1H), 7.48 (s. 1H), 7.28 (t, J = 8.0 Hz, 2H), 2.41 (s, 3H); ESI-MS (m/z) 433 (MH)⁺. |
| Example-79: 5-(4-((2,6-Difluorobenzyl)amino)phenyl)-3-(difluoromethyl)-6-methylbenzo[d]oxazol-2(3H)-one | 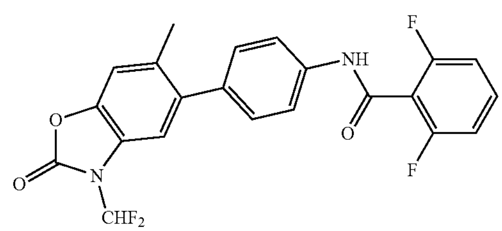 | ¹HNMR (400 MHz, DMSO-d$_6$) δ 7.86 (t, J = 56.0 Hz, 1H), 7.46-7.39 (m, 1H), 7.39 (s, 1H), 7.13 (t, J = 8.0 Hz, 2H), 7.08 (d, J = 8.0 Hz, 2H), 7.06 (s, 1H), 6.73 (d, J = 8.0 Hz, 2H), 6.22 (t, J = 6.0 Hz, 1H), 4.30 (d, J = 6.0 Hz, 2H), 2.25 (s, 3H); ESI-MS (m/z) 417 (MH)⁺. |
| Example-80: N-(5-(6-Ethyl-3-methyl-2-oxo-2,3-dihydrobenzo[d]oxazol-5-yl)pyrazin-2-yl)-2,6-difluoro benzamide | 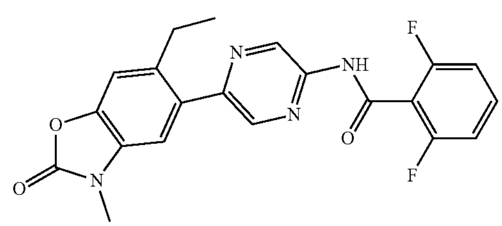 [SMILES: CCc1cc2oc(=O)n(C)c2cc1-c1cnc(NC(=O)c2c(F)cccc2F)cn1] | NMR (400 MHz, DMSO-d$_6$) δ 11.82 (s, 1H, D$_2$O exchangeable), 9.50 (s, 1H), 8.61 (s, 1H), 7.65-7.62 (m, 1H), 7.39 (s, 1H), 7.35 (s, 1H), 7.27 (t, J = 8.0 Hz, 2H), 3.36 (s, 3H), 2.71 (q, J = 7.5 Hz, 2H), 1.08 (t, J = 7.5 Hz, 3H); ESI-MS (m/z) 411 (MH)⁺. |
| Example-81: N-(6-(6-Ethyl-3-methyl-2-oxo-2,3-dihydrobenzo[d]oxazol-5-yl)pyridin-3-yl)-2,6-difluoro benzamide | 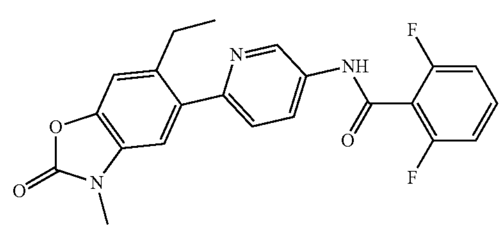 [SMILES: CCc1cc2oc(=O)n(C)c2cc1-c1ccc(NC(=O)c2c(F)cccc2F)cn1] | ¹HNMR (400 MHz, CDCl$_3$) δ 8.76 (d, J = 2.5 Hz, 1H), 8.49 (dd, J = 8.5 & 2.5 Hz, 1H), 7.99 (brs, 1H, D$_2$O exchangeable), 7.50-7.48 (m, 1H), 7.46 (d, J = 8.5 Hz, 1H), 7.19 (s, 1H), 7.07 (t, J = 8.0 Hz, 2H), 7.01 (s, 1H), 3.42 (s, 3H), 2.73 (q, J = 7.5 Hz, 2H), 1.15 (t, J = 7.5 Hz, 3H); ESI-MS (m/z) 410 (MH)⁺. |

TABLE 7-continued

| Example No: IUPAC name | Structure | ¹HNMR/ESI-MS |
|---|---|---|
| Example-82: N-(5-(6-Ethyl-3-methyl-2-oxo-2,3-dihydrobenzo[d]oxazol-5-yl)pyridin-2-yl)-2,6-difluoro benzamide | 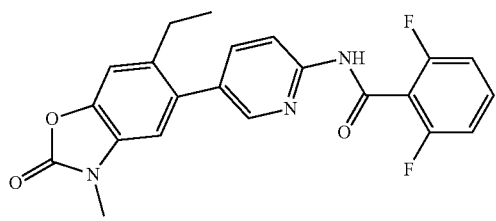 [SMILES: CCc1cc2oc(=O)n(C)c2cc1-c1ccc(NC(=O)c2c(F)cccc2F)nc1] | ¹HNMR (400 MHz, CDCl₃) δ 8.62 (brs, 1H, D₂O exchangeable), 8.49 (d, J = 8.5 Hz, 1H), 8.27 (d, J = 2.5 Hz, 1H), 7.77 (dd, J = 8.5 & 2.5 Hz, 1H), 7.52-7.44 (m, 1H), 7.20 (s, 1H), 7.07 (t, J = 8.0 Hz, 2H), 6.79 (s, 1H), 3.42 (s, 3H), 2.60 (q, J = 7.5 Hz, 2H), 1.13 (t, J = 7.5 Hz, 3H); ESI-MS (m/z) 410 (MH)⁺. |
| Example-83: N-(5-(6-Cyclopropyl-3-methyl-2-oxo-2,3-dihydro benzo [d]oxazol-5-yl)pyridin-2-yl)-2,6-difluorobenzamide | 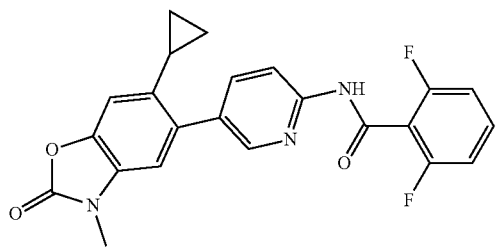 [SMILES: Cn1c(=O)oc2cc(C3CC3)c(-c3ccc(NC(=O)c4c(F)cccc4F)nc3)cc21] | ¹HNMR (400 MHz, DMSO-d₆) δ 11.49 (brs, 1H, D₂O exchangeable), 8.43 (d, J = 2.5 Hz, 1H), 8.27 (d, J = 8.5 Hz, 1H), 7.97 (dd, J = 8.5 & 2.5 Hz, 1H), 7.60-7.56 (m, 1H), 7.23 (t, J = 8.0 Hz, 2H), 7.20 (s, 1H), 7.06 (s, 1H), 3.33 (s, 3H), 1.83-1.82 (m, 1H), 0.83-0.80 (m, 2H), 0.68-0.66 (m, 2H); ESI-MS (m/z) 422 (MH)⁺. |
| Example-84: N-(5-(6-Cyclopropyl-3-methyl-2-oxo-2,3-dihydro benzo [d]oxazol-5-yl)pyrazin-2-yl)-2,6-difluorobenzamide | 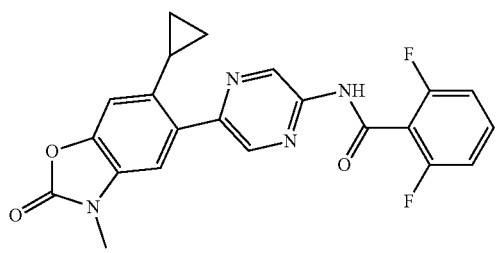 [SMILES: Cn1c(=O)oc2cc(C3CC3)c(-c3cnc(NC(=O)c4c(F)cccc4F)cn3)cc21] | ¹HNMR (400 MHz, DMSO-d₆) δ 11.79 (brs, 1H, D₂O exchangeable), 9.52 (s, 1H), 8.71 (s, 1H), 7.65-7.62 (m, 1H), 7.37 (s, 1H), 7.27 (t, J ? 8.0 Hz, 2H), 7.12 (s, 1H), 3.34 (s, 3H), 2.12-2.10 (m, 1H), 0.90-0.77 (m, 2H), 0.68-0.57 (m, 2H); ESI-MS (m/z) 423 (MH)⁺. |
| Example-85: N-(4-(6-Ethyl-3-methyl-2-oxo-2,3-dihydrobenzo [d]oxazol-5-yl)phenyl)-2,6-difluorobenzamide | 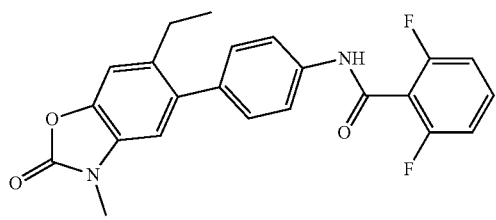 [SMILES: CCc1cc2oc(=O)n(C)c2cc1-c1ccc(NC(=O)c2c(F)cccc2F)cc1] | 1HNMR (400 MHz, CDCl₃) δ 7.75 (brs, 1H, D₂O exchangeable), 7.73 (d, J = 8.0 Hz, 2H), 7.49 (m, 1H), 7.34 (d, J = 8.0 Hz, 2H), 7.16 (s, 1H), 7.07 (t, J = 8.0 Hz, 2H), 6.80 (s, 1H), 3.40 (s, 3H), 2.61(q, J = 7.5 Hz, 2H), 1.12 (t, J = 7.5 Hz, 3H); ESI-MS (m/z) 409 (MH)⁺. |
| Example-86: N-(5-(5-Cyclopropyl-3-methyl-2-oxo-2,3-dihydro oxazolo[4,5-b]pyridin-6-yl)pyrazin-2-yl)-2,6-difluorobenzamide | 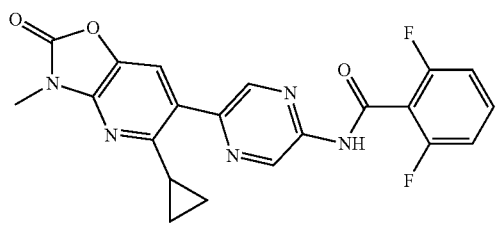 [SMILES: Cn1c(=O)oc2cc(-c3cnc(NC(=O)c4c(F)cccc4F)cn3)c(C3CC3)nc21] | ¹HNMR (400 MHz, DMSO-d₆) δ 11.83 (s, 1H, D₂O exchangeable), 9.53 (s, 1H), 8.71 (s, 1H), 7.80 (s, 1H), 7.72-7.56 (m, 1H), 7.27 (t, J = 8.0 Hz, 2H), 3.32 (s, 3H), 2.35-2.23 (m, 1H), 1.12-1.03 (m, 2H), 0.98-0.90 (m, 2H); ESI-MS (m/z) 424 (MH)⁺. |
| Example-87: N-(5-(5-Ethyl-3-methyl-2-oxo-2,3-dihydrooxazolo [4,5-b]pyridin-6-yl)pyrazin-2-yl)-2,6-difluorobenzamide | 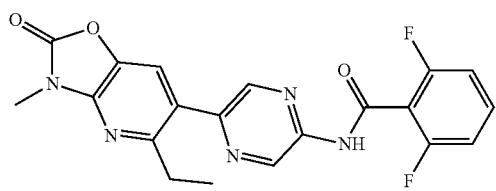 [SMILES: CCc1nc2c(cc1-c1cnc(NC(=O)c3c(F)cccc3F)cn1)oc(=O)n2C] | ¹HNMR (400 MHz, DMSO-d₆) δ 11.83 (s, 1H, D₂O exchangeable), 9.52 (s, 1H), 8.65 (s, 1H), 7.84 (s, 1H), 7.72-7.54 (m, 1H), 7.28 (t, J = 8.0 Hz, 2H), 3.38 (s, 3H), 2.84 (q, J = 7.5 Hz, 2H), 1.20 (d, J = 7.5 Hz, 3H); ESI-MS (m/z) 412 (MH)⁺. |

TABLE 7-continued

| Example No: IUPAC name | Structure | $^1$HNMR/ESI-MS |
|---|---|---|
| Example-88: N-(2,6-Difluorophenyl)-5-(6-ethyl-3-methyl-2-oxo-2,3-dihydrobenzo[d]oxazol-5-yl)thiophene-2-carboxamide | 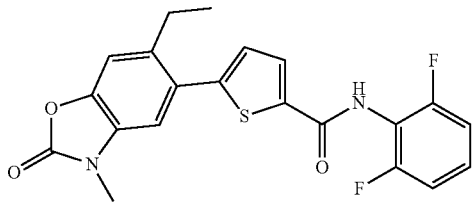 [SMILES: CCc1cc2oc(=O)n(C)c2cc1-c1ccc(C(=O)Nc2c(F)cccc2F)s1] | $^1$HNMR (400 MHz, CDCl$_3$) δ 7.70 (d, J = 4.0 Hz, 1H), 7.32 (brs, 1H, D$_2$O exchangeable), 7.30-7.28 (m, 1H), 7.19 (s, 1H), 7.07 (d, J = 4.0 Hz, 1H), 7.02 (t, J = 8.0 Hz, 2H), 6.96 (s, 1H), 3.42 (s, 3H), 2.77 (q, J = 7.5 Hz, 2H), 1.21 (t, J = 7.5 Hz, 3H); ESI-MS (m/z) 415 (MH)$^+$. |
| Example-89: 5-(6-Cyclopropyl-3-methyl-2-oxo-2,3-dihydrobenzo[d]oxazol-5-yl)-N-(2,6-difluorophenyl)thiophene-2-carboxamide | 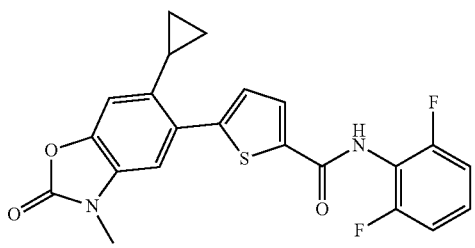 [SMILES: Cn1c(=O)oc2cc(C3CC3)c(-c3ccc(C(=O)Nc4c(F)cccc4F)s3)cc21] | 1HNMR (400 MHz, DMSO-d6) δ 10.25 (brs, 1H, D$_2$O exchangeable), 8.03 (d, J = 4.0 Hz, 1H), 7.43-7.41 (m, 1H), 7.38 (d, J = 4.0 Hz, 1H), 7.35 (s, 1H), 7.24 (t, J = 8.0 Hz, 2H), 7.11 (s, 1H), 3.34 (s, 3H), 2.13-2.02 (m, 1H), 0.98-0.87 (m, 2H), 0.79-0.71 (m, 2H); ESI-MS (m/z) 427 (MH)$^+$. |
| Example-90: N-(3,5-Difluoropyridin-4-yl)-4-(5-ethyl-3-methyl-2-oxo-2,3-dihydrobenzo[d]oxazol-6-yl)benzamide | 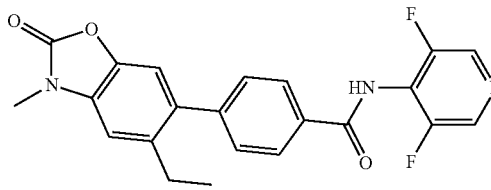 | $^1$HNMR (400 MHz, CDCl$_3$) δ 8.47 (s, 2H), 8.03 (d, J = 8.0 Hz, 2H), 7.64 (s, 1H, D$_2$O exchangeable), 7.47 (d, J = 8.0 Hz, 2H), 7.07 (s, 1H), 6.93 (s, 1H), 3.47 (s, 3H), 2.64 (q, J = 7.5 Hz, 2H), 1.14 (t, J = 7.5 Hz, 3H); ESI-MS (m/z) 410 (MH)$^+$. |
| Example-91: 4-(5-Cyclopropyl-3-methyl-2-oxo-2,3-dihydrobenzo[d]oxazol-6-yl)-N-(3,5-difluoropyridin-4-yl)benzamide | 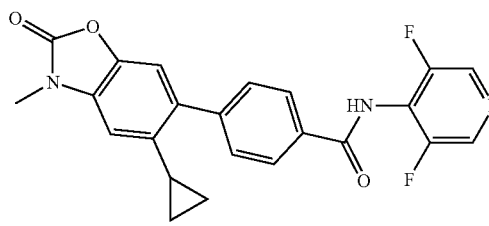 | $^1$HNMR (400 MHz, CDCl$_3$) δ 8.46 (s, 2H), 8.03 (d, J = 8.0 Hz, 2H), 7.77 (s, 1H), 7.60 (d, J = 8.0 Hz, 2H), 7.10 (s, 1H), 6.62 (s, 1H), 3.44 (s, 3H), 1.91-1.87 (m, 1H), 0.94-0.89 (m, 2H), 0.70-0.68 (m, 2H); ESI-MS (m/z) 422 (MH)$^+$. |
| Example-92: N-(3,5-Difluoropyridin-4-yl)-4-(6-ethyl-3-methyl-2-oxo-2,3-dihydrobenzo[d]oxazol-5-yl)benzamide | 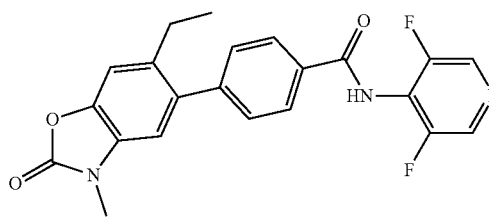 | $^1$HNMR (400 MHz, CDCl$_3$) δ 8.47 (s, 2H), 8.04 (d, J = 8.0 Hz, 2H), 7.71 (brs, 1H, D$_2$O exchangeable), 7.50 (d, J = 8.0 Hz, 2H), 7.20 (s, 1H), 6.80 (s, 1H), 3.42 (s, 3H), 2.60 (q, J = 7.5 Hz, 2H), 1.12 (t, J = 7.5 Hz, 3H); ESI-MS (m/z) 410 (MH)$^+$. |
| Example-93: 4-(6-Cyclopropyl-3-methyl-2-oxo-2,3-dihydrobenzo[d]oxazol-5-yl)-N-(3,5-difluoropyridin-4-yl)benzamide | 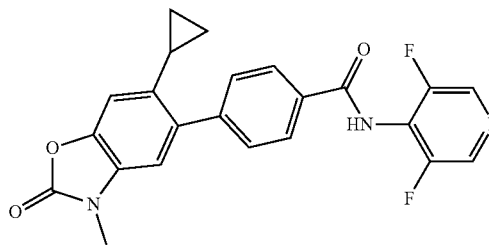 | $^1$HNMR (400 MHz, CDCl$_3$) δ 8.47 (s, 2H), 8.05 (d, J = 8.0 Hz, 2H), 7.66 (brs, 1H, D$_2$O exchangeable), 7.63 (d, J = 8.0 Hz, 2H), 6.89 (s, 1H), 6.83 (s, 1H), 3.42 (s, 3H), 1.89-1.79 (m, 1H), 0.92-0.86 (m, 2H), 0.71-0.63 (m, 2H); ESI-MS (m/z) 422 (MH)$^+$. |

TABLE 7-continued

| Example No: IUPAC name | Structure | ¹HNMR/ESI-MS |
|---|---|---|
| Example-94: N-(4-(6-Cyclopropyl-3-methyl-2-oxo-2,3-dihydro benzo[d]oxazol-5-yl)phenyl)-2,6-difluorobenzamide | 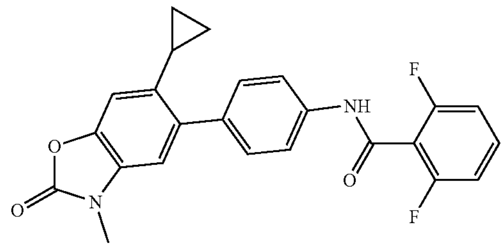 [SMILES: Cn1c(=O)oc2cc(C3CC3)c(-c3ccc(NC(=O)c4c(F)cccc4F)cc3)cc21] | ¹HNMR (400 MHz, DMSO-d6) δ 7.80 (d, J = 8.0 Hz, 2H), 7.63-7.61 (m, 1H), 7.43 (d, J = 8.0 Hz, 2H), 7.30 (t, J = 8.0 Hz, 2H), 7.10 (s, 1H), 6.98 (s, 1H), 3.36 (s, 3H), 1.83-1.84 (m, 1H), 0.89-0.76 (m, 2H), 0.72-0.62 (m, 2H); ESI-MS (m/z) 421 (MH)+. |
| Example-95: N-(4-(7-Cyclopropyl-3-(difluoromethyl)-2-oxo-2,3-dihydro benzo[d]oxazol-6-yl)phenyl)-2,6-difluorobenzamide | 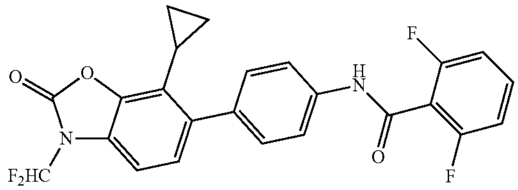 [SMILES: O=C(Nc1ccc(-c2ccc3c(oc(=O)n3C(F)F)c2C2CC2)cc1)c1c(F)cccc1F] | ¹HNMR (400 MHz, DMSO-d₆) δ 10.93 (s, 1H, D2O exchangeable), 7.78 (d, J = 8.0 Hz, 2H), 7.75 (t, J = 57.0 Hz, 1H), 7.67-7.57 (m, 1H), 7.44 (d, J = 8.0 Hz, 2H), 7.32-7.24 (m, 3H), 7.18 (d, J = 8.0 Hz, 1H), 2.01-1.88 (m, 1H), 0.87-0.79 (m, 2H), 0.75-0.69 (m, 2H); ESI-MS (m/z) 457 (MH)+. |

Example-96: 2,6-Difluoro-N-(3-methyl-4-(3-methyl-2-oxo-2,3-dihydrooxazolo[4,5-b]pyridin-6-yl)phenyl)benzamide

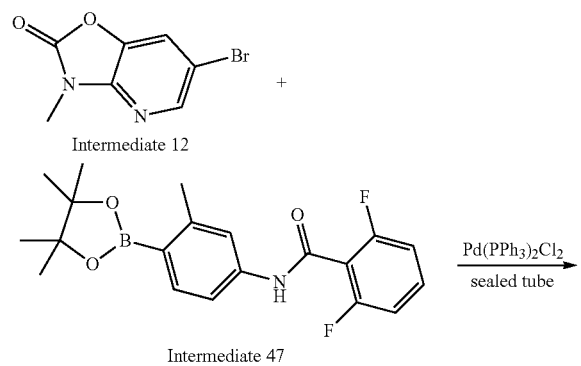

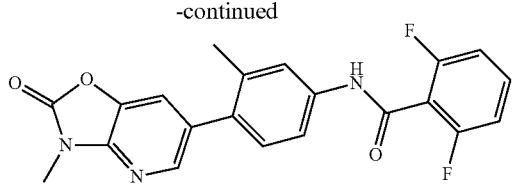

Example 96

The title compound was prepared by reacting Intermediate-12 with Intermediate-47 by following the similar procedure as described for Example-1. ¹HNMR (400 MHz, CDCl₃) δ 8.09 (d, J=2.0 Hz, 1H), 7.72 (s, 1H, D₂O exchangeable), 7.66 (d, J=2.0 Hz, 1H), 7.55 (dd, J=8.0 & 2.0 Hz, 1H), 7.90-7.46 (m, 1H), 7.41 (d, J=2.0 Hz, 1H), 7.28 (s, 1H), 7.08-7.00 (m, 2H), 3.55 (s, 3H), 2.31 (s, 3H); ESI-MS (m/z) 396 (MH)+

The following Examples (97-100) given in Table-8 were by reacting the appropriate Intermediates by following the similar procedure as described for Example-96.

TABLE 8

| Example No: IUPAC name | Structure | ¹H-NMR/ESI-MS |
|---|---|---|
| Example-97: N-(4-(7-Cyclopropyl-3-methyl-2-oxo-2,3-dihydro benzo[d]oxazol-6-yl)-3-methylphenyl)-2,6-difluorobenzamide | 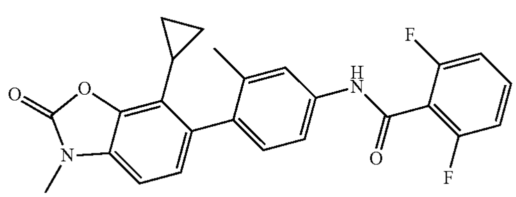 [SMILES: Cc1cc(NC(=O)c2c(F)cccc2F)ccc1-c1ccc2c(oc(=O)n2C)c1C1CC1] | ¹HNMR (400 MHz, CDCl₃) δ 7.66 (s, 1H, D₂O exchangeable), 7.64 (s, 1H), 7.53-7.41 (m, 2H), 7.20 (d, J = 8.0 Hz, 1H), 7.09-7.00 (m, 2H), 6.96 (d, J = 8.0 Hz, 1H), 6.81 (d, J = 8.0 Hz, 1H), 3.42 (s, 3H), 2.17 (s, 3H), 1.57-1.50 (m, 1H), 1.29-1.15 (m, 2H), 0.88-0.72 (m, 2H); ESI-MS (m/z) 435 (MH)+. |

TABLE 8-continued

| Example No: IUPAC name | Structure | ¹H-NMR/ESI-MS |
|---|---|---|
| Example-98: N-(4-(7-Cyclopropyl-3-methyl-2-oxo-2,3-dihydro benzo[d]oxazol-6-yl)-2-methylphenyl)-2,6-difluorobenzamide | 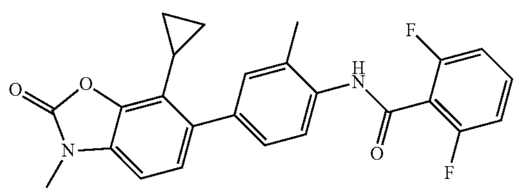 [SMILES: Cc1cc(-c2ccc3c(oc(=O)n3C)c2C2CC2)ccc1NC(=O)c1c(F)cccc1F] | ¹HNMR (400 MHz, DMSO-d₆) δ 10.30 (s, 1H, D₂O exchangeable), 7.64-7.56 (m, 1H), 7.53 (d, J = 8.0 Hz, 1H), 7.33 (d, J = 2.0 Hz, 1H), 7.30-7.23 (m, 3H), 7.12 (t, J = 8.0 Hz, 2H), 3.34 (s, 3H), 2.33 (s, 3H), 1.95-0.88 (m, 1H), 0.84-0.82 (m, 4H); ESI-MS (m/z) 435 (MH)⁺. |
| Example-99: 4-(7-Cyclopropyl-3-methyl-2-oxo-2,3-dihydro benzo[d]oxazol-6-yl)-N-(2,6-difluorophenyl) benzamide | 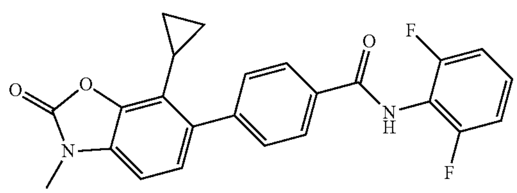 [SMILES: Cn1c(=O)oc2c(C3CC3)c(-c3ccc(C(=O)Nc4c(F)cccc4F)cc3)ccc21] | ¹HNMR (400 MHz, DMSO-d₆) δ 10.22 (s, 1H, D₂O exchangeable), 8.06 (d, J = 8.0 Hz, 2H), 7.66 (d, J = 8.0 Hz, 2H), 7.46-7.40 (m, 1H), 7.28-7.20 (m, 2H), 7.20-7.14 (m, 2H), 3.35 (s, 3H), 1.98-1.90 (m, 1H), 0.87-0.65 (m, 4H); ESI-MS (m/z) 421 (MH)⁺. |
| Example-100: 7-Cyclopropyl-6-(4-((2,6-difluorobenzyl)amino) phenyl)-3-methylbenzo [d]oxazol-2(3H)-one | 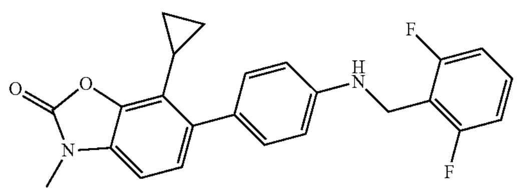 [SMILES: Cn1c(=O)oc2c(C3CC3)c(-c3ccc(NCc4c(F)cccc4F)cc3)ccc21] | ¹HNMR (400 MHz, CDCl₃) δ 7.24 (d, J = 7.0 Hz, 2H), 7.07 (d, J = 8.0 Hz, 1H), 7.00-6.83 (m, 5H), 6.79 (d, J = 8.0 Hz, 1H), 4.51 (s, 2H), 3.40 (s, 3H), 1.94-1.76 (m, 1H), 1.07-0.96 (m, 2H), 0.91-0.79 (m, 2H); ESI-MS (m/z) 407 (MH)⁺. |

Example-101: 2-Chloro-N-(4-(7-cyclopropyl-3-methyl-2-oxo-2,3-dihydrobenzo[d]oxazol-6-yl)phenyl)-6-fluorobenzamide To a nitrogen purged round bottom flask containing 2-chloro-6-fluorobenzoyl chloride (87 mg, 0.45 mmol) in DCM (2 mL) was added Intermediate-49 (120 mg, 0.43 mmol) followed by pyridine (0.04 mL, 0.45 mmol). The resulting mixture was allowed to stir at room temperature for 5 h. Then the reaction was diluted with DCM (10 mL), washed with 10% aqueous HCl (10 mL), followed by saturated aqueous sodium bicarbonate solution (10 mL). The organic layer was dried (Na₂SO₄) and concentrated over rotary evaporator. The crude product was purified by flash column chromatography (silica gel, 50% ethyl acetate in hexane system as eluent) to afford 50 mg (27%) of the desired product as a white solid. ¹HNMR (400 MHz, DMSO-d₆) δ 10.90 (s, 1H, D₂O exchangeable), 7.77 (d, J=8.5 Hz, 2H), 7.60-7.55 (m, 1H), 7.48-7.39 (m, 4H), 7.16-7.09 (m, 2H), 3.31 (s, 3H) 1.94-1.87 (m, 1H), 0.83-0.75 (m, 4H); ESI-MS (m/z) 437, 439 [(MH)⁺, Cl³⁵, ³⁷].

Example-102: N-(4-(7-Cyclopropyl-3-methyl-2-oxo-2,3-dihydrobenzo[d]oxazol-6-yl)phenyl)-2-fluorobenzamide The title compound was prepared by reacting Intermediate-49 with 2-fluorobenzoyl chloride by following the similar procedure as described in Example-101. ¹HNMR (400 MHz, DMSO-d₆) δ 10.53 (s, 1H, D₂O exchangeable), 7.80 (d, J=8.0 Hz, 2H), 7.70-7.67 (m, 1H), 7.62-7.56 (m, 1H), 7.42-7.33 (m, 4H), 7.15-7.09 (m, 2H), 3.34 (s, 3H), 1.96-1.88 (m, 1H), 0.84-0.71 (m, 4H); ESI-MS (m/z) 403 (MH)⁺.

Example-103: 2-Chloro-N-(4-(7-cyclopropyl-3-methyl-2-oxo-2,3-dihydrobenzo[d]oxazol-6-yl)phenyl)benzamide

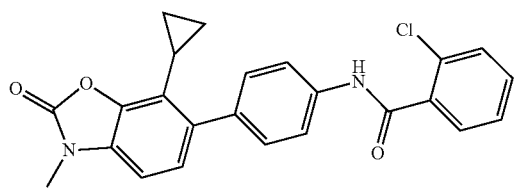

Example-103

The title compound was prepared by reacting Intermediate-49 with 2-chlorobenzoyl chloride by following the similar procedure as described in Example-101. ¹HNMR (400 MHz, DMSO-d₆) δ 10.61 (s, 1H), 7.80 (d, J=8.5 Hz, 2H), 7.62-7.58 (m, 2H), 7.55-7.46 (m, 2H), 7.41 (d, J=8.5 Hz, 2H), 7.12 (m, 2H), 3.34 (s, 3H), 1.95-1.89 (m, 1H), 0.84-0.74 (m, 4H); ESI-MS (m/z) 418, 420 [(MH)⁺, Cl³⁵, ³⁷].

Example-104: 2,6-Difluoro-N-(4-(4-methyl-3-oxo-3,4-dihydro-2H-pyrido[3,2-b][1,4]oxazin-7-yl)phenyl)benzamide

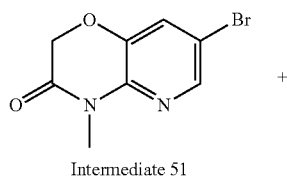

Intermediate 51

+

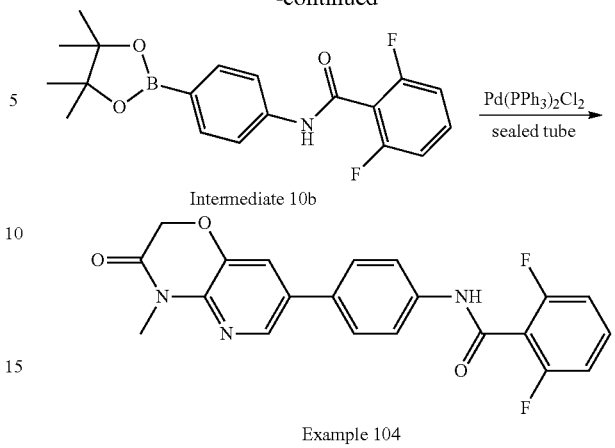

Example 104

To a nitrogen purged solution of Intermediate-51 (110 mg, 0.45 mmol) in 1,4-dioxane:water (5 mL, 4:1) was added Intermediate-10b (163 mg, 0.45 mmol), sodium carbonate (96 mg, 0.91 mmol) and Pd(PPh₃)₂Cl₂ (16 mg, 0.02 mmol) successively. The resulting mixture was stirred in a sealed tube at 110° C. for 15 h. The reaction mixture was then cooled to room temperature and filtered through celite. The residue was washed with ethyl acetate (10 mL) and the combined filtrates were concentrated under reduced pressure. The crude product was purified by flash column chromatography (silica gel, 50% ethyl acetate in hexane system as eluent) followed by preparative HPLC (reverse phase) to give 20 mg (12%) of the title compound as a white solid. ¹HNMR (400 MHz, DMSO-d₆) δ 10.94 (s, 1H, D₂O exchangeable), 8.38 (d, J=2.0 Hz, 1H), 7.83-7.70 (m, 5H), 7.65-7.58 (m, 1H), 7.28 (t, J=8.0 Hz, 2H), 4.82 (s, 2H), 3.38 (s, 3H); ESI-MS (m/z) 396 (MH)⁺.

The below Examples (105-129) given in Table-9 were prepared from the corresponding Intermediates by following the similar procedure as described in Example-104.

TABLE 9

| Example No: IUPAC name | Structure | ¹H-NMR/ESI-MS |
|---|---|---|
| Example-105: N-(4-(4,8-Dimethyl-3-oxo-3,4-dihydro-2H-benzo[b][1,4]oxazin-7-yl)phenyl)-2,6-difluorobenzamide | 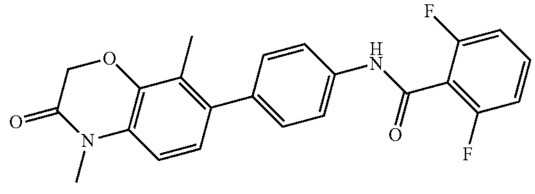 [SMILES: Cc1c(-c2ccc(NC(=O)c3c(F)cccc3F)cc2)ccc2c1OCC(=O)N2C] | ¹HNMR (400 MHz, DMSO-d₆) δ 10.91 (s, 1H, D₂O exchangeable), 7.60 (d, J = 8.0 Hz, 2H), 7.63-7.57 (m, 1H), 7.33 (d, J = 8.0 Hz, 2H), 7.28 (t, J = 8.0 Hz, 2H) 7.09 (d, J = 8.0 Hz, 1H), 6.95 (d, J = 8.0 Hz, 1H), 4.70 (s, 2H), 3.30 (s, 3H), 2.13 (s, 3H); ESI-MS (m/z) 409 (MH)⁺. |
| Example-106: N-(4-(8-Ethyl-4-methyl-3-oxo-3,4-dihydro-2H-benzo[b][1,4]oxazin-7-yl)phenyl)-2,6-difluorobenzamide | 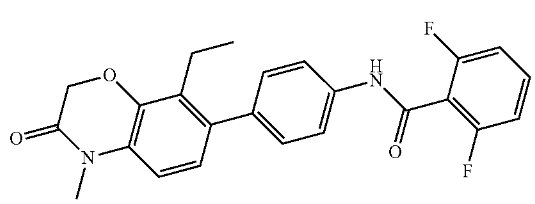 [SMILES: CCc1c(-c2ccc(NC(=O)c3c(F)cccc3F)cc2)ccc2c1OCC(=O)N2C] | ¹HNMR (400 MHz, CDCl₃) δ 7.73 (s, 1H, D₂O exchangeable), 7.71 (d, J = 8.5 Hz, 2H), 7.50-7.42 (m, 1H), 7.32 (d, J = 8.5 Hz, 2H), 7.05 (t, J = 8.0 Hz, 2H), 6.94 (d, J = 8.5 Hz, 1H), 6.89 (d, J = 8.5 Hz, 1H), 4.67 (s, 2H), 3.41 (s, 3H), 2.62 (q, J = 7.5 Hz, 2H), 1.08 (t, J = 7.5 Hz, 3H); ESI-MS (m/z) 423 (MH)⁺. |

TABLE 9-continued

| Example No: IUPAC name | Structure | $^1$H-NMR/ESI-MS |
|---|---|---|
| Example-107: N-(4-(8-Cyclopropyl-4-methyl-3-oxo-3,4-dihydro-2H-benzo[b][1,4]oxazin-7-yl)phenyl)-2,6-difluorobenzamide | 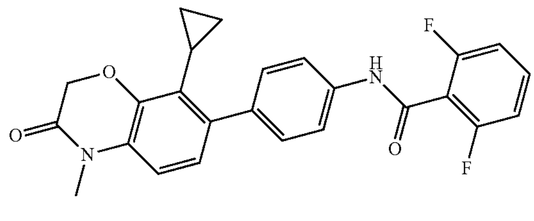 [SMILES: CN1C(=O)COc2c1ccc(-c1ccc(NC(=O)c3c(F)cccc3F)cc1)c2C1CC1] | $^1$HNMR (400 MHz, DMSO-d$_6$) δ 10.89 (s, 1H, D$_2$O exchangeable), 7.74 (d, J = 8.0 Hz, 2H), 7.67-7.57 (m, 1H), 7.41 (d, J = 8.0 Hz, 2H), 7.27 (d, J = 8.0 Hz, 2H), 7.10 (d, J = 8.5 Hz, 1H), 6.96 (d, J = 8.5 Hz, 1H), 4.68 (s, 2H), 3.29 (s, 3H), 1.87-1.80 (m, 1H), 0.72-0.66 (m, 2H), 0.30-0.25 (m, 2H); ESI-MS (m/z) 435 (MH)$^+$. |
| Example-108: N-(5-(8-Cyclopropyl-4-methyl-3-oxo-3,4-dihydro-2H-benzo[b][1,4]oxazin-7-yl)pyridin-2-yl)-2,6-difluorobenzamide | 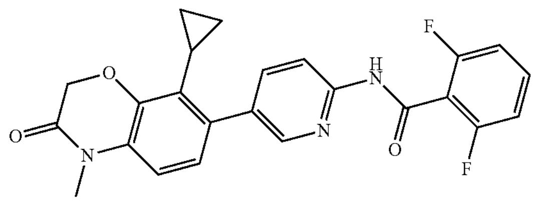 [SMILES: CN1C(=O)COc2c1ccc(-c1ccc(NC(=O)c3c(F)cccc3F)nc1)c2C1CC1] | $^1$HNMR (400 MHz, CDCl$_3$) δ 9.22 (s, 1H, D$_2$O exchangeable), 8.55 (d, J = 8.5 Hz, 1H), 8.34 (s, 1H), 7.95 (d, J = 8.5 Hz, 1H), 7.53-7.46 (m, 1H), 7.06 (t, J = 8.0 Hz, 2H), 6.97 (s, 2H), 4.69 (s, 2H), 3.41 (s, 3H), 1.82-1.76 (m, 1H), 0.86-0.81 (m, 2H), 0.36-0.31 (m, 2H); ESI-MS (m/z) 436 (MH)$^+$. |
| Example-109: N-(5-(8-Cyclopropyl-4-methyl-3-oxo-3,4-dihydro-2H-benzo[b][1,4]oxazin-7-yl)pyrazin-2-yl)-2,6-difluorobenzamide | 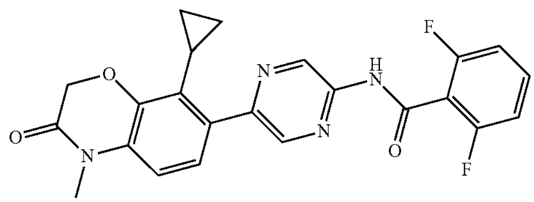 [SMILES: CN1C(=O)COc2c1ccc(-c1cnc(NC(=O)c3c(F)cccc3F)cn1)c2C1CC1] | $^1$HNMR (400 MHz, DMSO-d$_6$) δ 11.74 (s, 1H, D$_2$O exchangeable), 9.48 (s, 1H), 8.72 (s, 1H), 7.64 (m, 1H), 7.30-7.26 (m, 3H), 7.20 (d, J = 8.5 Hz, 1H), 4.73 (s, 2H), 3.31 (s, 3H), 2.06-1.91 (m, 1H), 0.88-0.61 (m, 2H), 0.17-0.16 (m, 2H); ESI-MS (m/z) 437 (MH)$^+$. |
| Example-110: N-(6-(8-Cyclopropyl-4-methyl-3-oxo-3,4-dihydro-2H-benzo[b][1,4]oxazin-7-yl)pyridin-3-yl)-2,6-difluorobenzamide | 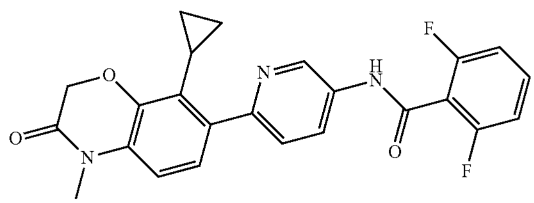 [SMILES: CN1C(=O)COc2c1ccc(-c1ccc(NC(=O)c3c(F)cccc3F)cn1)c2C1CC1] | $^1$HNMR (400 MHz, CDCl$_3$) δ 8.75 (s, 1H), 8.48 (d, J = 8.5 Hz, 1H), 8.07 (s, 1H), 7.59 (d, J = 8.5 Hz, 1H), 7.53-7.45 (m, 1H), 7.23 (d, J = 8.5 Hz, 1H), 7.06 (t, J = 8.0 Hz, 2H), 6.97 (d, J = 8.0 Hz, 1H), 4.67 (s, 2H), 3.40 (s, 3H), 1.93-0.87 (m, 1H), 0.82-0.66 (m, 2H), 0.30-0.26 (m, 2H); ESI-MS (m/z) 436 (MH)$^+$. |
| Example-111: 8-Cyclopropyl-7-(4-((2,6-difluorobenzyl)amino)phenyl)-4-methyl-2H-benzo[b][1,4]oxazin-3(4H)-one | 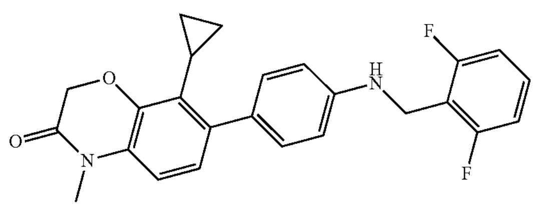 [SMILES: CN1C(=O)COc2c1ccc(-c1ccc(NCc3c(F)cccc3F)cc1)c2C1CC1] | $^1$HNMR (400 MHz, DMSO-d$_6$) δ 7.45-7.38 (m, 1H), 7.16-7.08 (m, 4H), 7.02 (d, J = 8.5 Hz, 1H), 6.87 (d, J = 8.5 Hz, 1H), 6.70 (d, J = 8.0 Hz, 2H), 6.11 (t, J = 8.0 Hz, 1H, D$_2$O exchangeable), 4.62 (s, 2H), 4.28 (s, 2H), 3.26 (s, 3H), 1.83-1.74 (m, 1H), 0.66-0.61 (m, 2H), 0.28-0.24 (m, 2H); ESI-MS (m/z) 421 (MH)$^+$. |
| Example-112: N-(4-(8-Cyclopropyl-4-methyl-3-oxo-3,4-dihydro-2H-pyrido[3,2-b][1,4]oxazin-7-yl)phenyl)-2,6-difluorobenzamide | 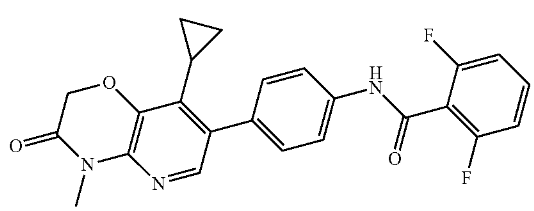 [SMILES: CN1C(=O)COc2c1ncc(-c1ccc(NC(=O)c3c(F)cccc3F)cc1)c2C1CC1] | $^1$HNMR (400 MHz, CDCl$_3$) δ 7.92 (s, 1H), 7.75-7.73 (m, 3H), 7.51-7.45 (m, 1H), 7.42 (d, J = 8.0 Hz, 2H), 7.05 (t, J = 8.0 Hz, 2H), 4.67 (s, 2H), 3.51 (s, 3H), 1.85-1.72 (m, 1H), 0.95-0.68 (m, 4H); ESI-MS (m/z) 436 (MH)$^+$. |
| Example-113: N-(4-(6-Cyclopropyl-4-methyl-3-oxo-3,4-dihydro-2H-benzo[b][1,4]oxazin-7-yl)phenyl)-2,6-difluorobenzamide | 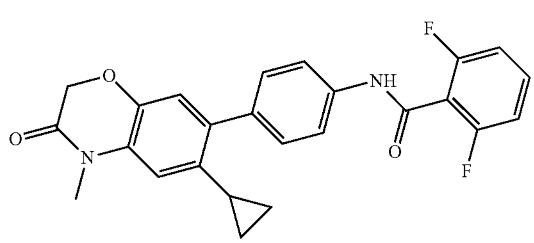 [SMILES: CN1C(=O)COc2cc(-c3ccc(NC(=O)c4c(F)cccc4F)cc3)c(C3CC3)cc21] | $^1$HNMR (400 MHz, CDCl$_3$) δ 7.73-7.70 (m, 3H), 7.50-7.43 (m, 3H), 7.04 (t, J = 8.0 Hz, 2H), 6.91 (s, 1H), 6.59 (s, 1H), 4.63 (s, 2H), 3.39 (s, 3H), 1.97-1.89 (m, 1H), 0.92-0.85 (m, 2H), 0.71-0.59 (m, 2H); ESI-MS (m/z) 435 (MH)$^+$. |

TABLE 9-continued

| Example No: IUPAC name | Structure | ¹H-NMR/ESI-MS |
|---|---|---|
| Example-114: 6-Cyclopropyl-7-(4-((2,6-difluorobenzyl)amino)phenyl)-4-methyl-2H-benzo[b][1,4]oxazin-3(4H)-one | 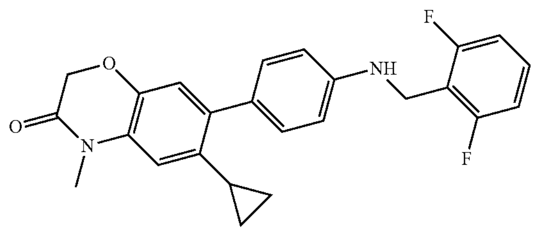 [SMILES: CN1C(=O)COc2cc(-c3ccc(NCc4c(F)cccc4F)cc3)c(C3CC3)cc21] | ¹HNMR (400 MHz, DMSO-d₆) δ 7.46-7.11 (m, 1H), 7.20-7.09 (m, 4H), 6.74 (s, 1H), 6.72 (d, J = 8.5 Hz, 2H), 6.58 (s, 1H), 6.15 (t, J = 6.0 Hz, 1H, D₂O exchangeable), 4.60 (s, 2H), 4.29 (d, J = 5.5 Hz, 2H), 3.28 (s, 3H), 1.90-1.84 (m, 1H), 0.84-0.75 (m, 2H), 0.71-0.63 (m, 2H); ESI-MS (m/z) 421 (MH)⁺. |
| Example-115: N-(5-(6-Cyclopropyl-4-methyl-3-oxo-3,4-dihydro-2H-benzo[b][1,4]oxazin-7-yl)pyridin-2-yl)-2,6-difluorobenzamide | 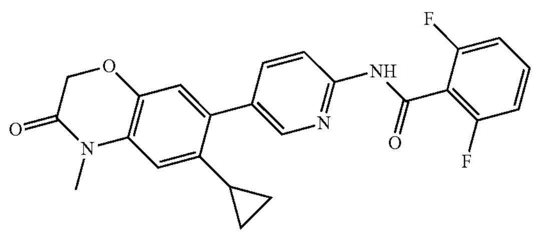 [SMILES: CN1C(=O)COc2cc(-c3ccc(NC(=O)c4c(F)cccc4F)nc3)c(C3CC3)cc21] | ¹HNMR (400 MHz, CDCl₃) δ 8.88 (s, 1H, D₂O exchangeable), 8.50 (d, J = 8.5 Hz, 1H), 8.36 (s, 1H), 7.93 (d, J = 8.5 Hz, 1H), 7.52-7.42 (m, 1H), 7.06 (t, J = 8.5 Hz, 2H), 6.90 (s, 1H), 6.67 (s, 1H), 5.32 (s, 2H), 3.41 (s, 3H), 1.90-1.82 (m, 1H), 0.93-0.88 (m, 2H), 0.66-0.62 (m, 2H); ESI-MS (m/z) 436 (MH)⁺. |
| Example-116: N-(5-(6-Cyclopropyl-4-methyl-3-oxo-3,4-dihydro-2H-benzo[b][1,4]oxazin-7-yl)pyrazin-2-yl)-2,6-difluorobenzamide | 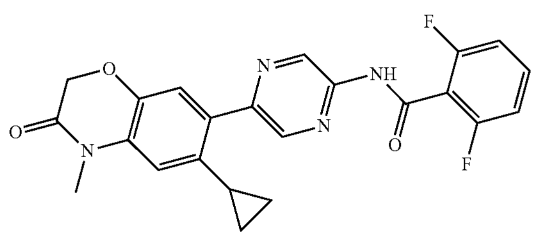 [SMILES: CN1C(=O)COc2cc(-c3cnc(NC(=O)c4c(F)cccc4F)cn3)c(C3CC3)cc21] | ¹HNMR (400 MHz, DMSO-d₆) δ 11.76 (s, 1H, D₂O exchangeable), 9.49 (s, 1H), 8.71 (s, 1H), 7.70-7.60 (m, 1H), 7.27 (t, J = 8.0 Hz, 2H), 7.15 (s, 1H), 6.82 (s, 1H), 3.35 (s, 3H), 4.68 (s, 2H), 2.20-2.13 (m, 1H), 0.88-0.80 (m, 2H), 0.67-0.63 (m, 2H); ESI-MS (m/z) 437 (MH)⁺. |
| Example-117: 2-Chloro-N-(5-(6-cyclopropyl-4-methyl-3-oxo-3,4-dihydro-2H-benzo[b][1,4]oxazin-7-yl)pyrazin-2-yl)-6-fluorobenzamide | 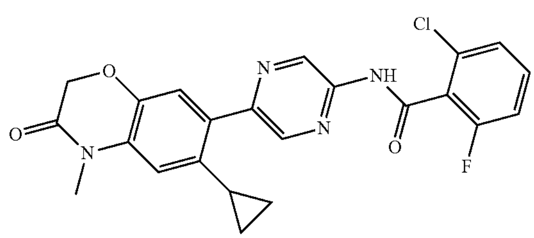 [SMILES: CN1C(=O)COc2cc(-c3cnc(NC(=O)c4c(F)cccc4Cl)cn3)c(C3CC3)cc21] | ¹HNMR (400 MHz, DMSO-d₆) δ 11.78 (s, 1H, D₂O exchangeable), 9.50 (s, 1H), 8.71 (s, 1H), 7.61-7.55 (m, 1H), 7.47 (d, J = 8.0 Hz, 1H), 7.41 (t, J = 7.5 Hz, 1H), 7.15 (s, 1H), 6.81 (s, 1H), 4.68 (s, 2H), 3.33 (s, 3H), 2.19-2.13 (m, 1H), 0.87-0.80 (m, 2H), 0.68-0.62 (m, 2H); ESI-MS (m/z) 453 (MH)⁺. |
| Example-118: N-(6-(6-Cyclopropyl-4-methyl-3-oxo-3,4-dihydro-2H-benzo[b][1,4]oxazin-7-yl)pyridin-3-yl)-2,6-difluorobenzamide | 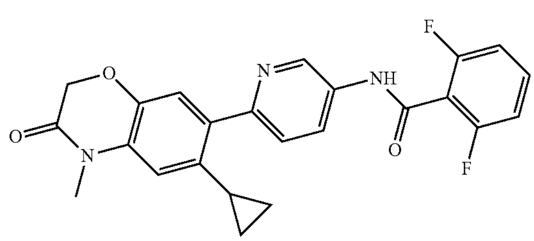 [SMILES: CN1C(=O)COc2cc(-c3ccc(NC(=O)c4c(F)cccc4F)cn3)c(C3CC3)cc21] | ¹HNMR (400 MHz, CDCl₃) δ 8.82 (d, J = 2.5 Hz, 1H), 8.57 (dd, J = 8.5 & 2.5 Hz, 1H), 7.66 (d, J = 8.5 Hz, 1H), 7.50-7.48 (m, 1H), 7.13 (s, 1H), 7.05 (t, J = 8.0 Hz, 2H), 6.69 (s, 1H), 4.62 (s, 2H), 3.40 (s, 3H), 2.14-2.08 (m, 1H), 0.90-0.83 (m, 2H), 0.63-0.55 (m, 2H); ESI-MS (m/z) 436 (MH)⁺. |
| Example-119: 4-(6-Cyclopropyl-4-methyl-3-oxo-3,4-dihydro-2H-benzo[b][1,4]oxazin-7-yl)-N-(3,5-difluoropyridin-4-yl)benzamide | 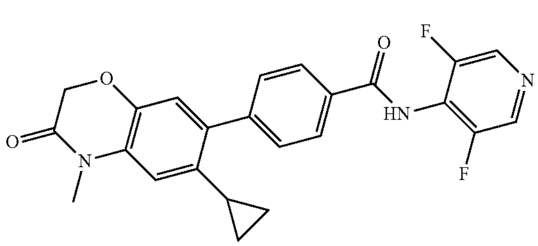 [SMILES: CN1C(=O)COc2cc(-c3ccc(C(=O)Nc4c(F)cncc4F)cc3)c(C3CC3)cc21] | ¹HNMR (400 MHz, DMSO-d₆) δ 10.72 (s, 1H, D₂O exchangeable), 8.64 (s, 2H), 8.08 (d, J = 8.0 Hz, 2H), 7.62 (d, J = 8.0 Hz, 2H), 6.91 (s, 1H), 6.73 (s, 1H), 4.66 (s, 2H), 3.32 (s, 3H), 1.87-1.82 (m, 1H), 0.86-0.78 (m, 2H), 0.77-0.68 (m, 2H); ESI-MS (m/z) 436 (MH)⁺. |

TABLE 9-continued

| Example No: IUPAC name | Structure | ¹H-NMR/ESI-MS |
|---|---|---|
| Example-120: N-(4-(6-Ethyl-4-methyl-3-oxo-3,4-dihydro-2H-benzo[b][1,4]oxazin-7-yl)phenyl)-2,6-difluorobenzamide | 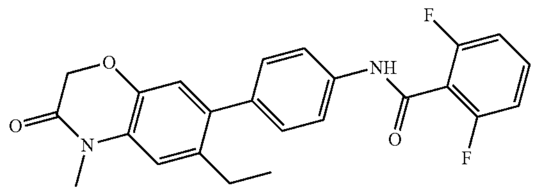 [SMILES: CCc1cc2c(cc1-c1ccc(NC(=O)c3c(F)cccc3F)cc1)OCC(=O)N2C] | ¹HNMR (400 MHz, DMSO-$d_6$) δ 10.92 (s, 1H, $D_2O$ exchangeable), 7.76 (d, J = 8.0 Hz, 2H), 7.65-7.59 (m, 1H), 7.37-7.22 (m, 4H), 7.11 (s, 1H), 6.80 (s, 1H), 4.66 (s, 2H), 3.35 (s, 3H), 2.56 (q, J = 7.0 Hz, 2H), 1.06 (t, J = 7.0 Hz, 3H); ESI-MS (m/z) 423 (MH)⁺. |
| Example-121: N-(5-(6-Ethyl-4-methyl-3-oxo-3,4-dihydro-2H-benzo[b][1,4]oxazin-7-yl)pyrazin-2-yl)-2,6-difluorobenzamide | 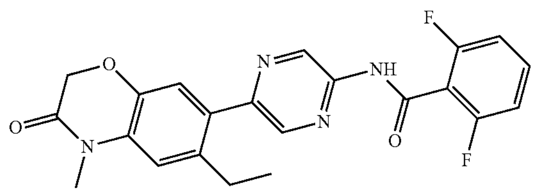 [SMILES: CCc1cc2c(cc1-c1cnc(NC(=O)c3c(F)cccc3F)cn1)OCC(=O)N2C] | ¹HNMR (400 MHz, DMSO-$d_6$) δ 11.77 (s, 1H, $D_2O$ exchangeable), 9.47 (s, 1H), 8.58 (s, 1H), 7.68-7.59 (m, 1H), 7.27 (t, J = 7.5 Hz, 2H), 7.16 (s, 1H), 7.12 (s, 1H), 4.69 (s, 2H), 3.39 (s, 3H), 2.73 (q, J = 7.5 Hz, 2H), 1.09 (t, J = 7.5 Hz, 3H); ESI-MS (m/z) 425 (MH)⁺. |
| Example-122: N-(5-(6-Ethyl-4-methyl-3-oxo-3,4-dihydro-2H-benzo[b][1,4]oxazin-7-yl)pyridin-2-yl)-2,6-difluorobenzamide | 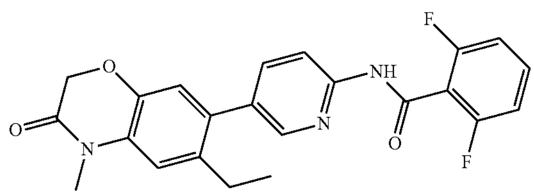 [SMILES: CCc1cc2c(cc1-c1ccc(NC(=O)c3c(F)cccc3F)nc1)OCC(=O)N2C] | ¹HNMR (400 MHz, DMSO-$d_6$) δ 11.46 (s, 1H, $D_2O$ exchangeable), 8.31 (s, 1H), 8.24 (d, J = 8.5 Hz, 1H), 7.5 (d, J = 8.5 Hz, 1H), 7.65-7.55 (m, 1H), 7.24 (t, J = 7.5 Hz, 2H), 7.15 (s, 1H), 6.89 (s, 1H), 4.67 (s, 2H), 3.34 (s, 3H), 2.56 (q, J = 7.5 Hz, 2H), 1.07 (t, J = 7.5 Hz, 3H); ESI-MS (m/z) 424 (MH)⁺. |
| Example-123: N-(4-(4,6-Dimethyl-3-oxo-3,4-dihydro-2H-benzo[b][1,4]oxazin-7-yl)phenyl)-2,6-difluorobenzamide | 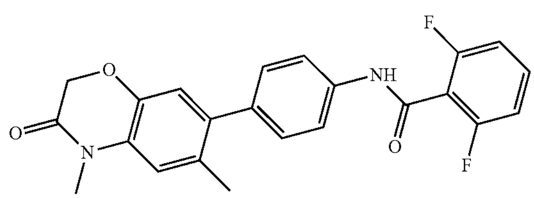 [SMILES: Cc1cc2c(cc1-c1ccc(NC(=O)c3c(F)cccc3F)cc1)OCC(=O)N2C] | ¹HNMR 400 MHz, DMSO) δ 10.91 (s, 1H, $D_2O$ exchangeable), 7.76 (d, J = 8.0 Hz, 2H), 7.58-7.65 (m, 1H), 7.34 (d, J = 8.0 Hz, 2H), 7.28 (t, J = 8.5 Hz, 2H), 7.11 (s, 1H), 6.85 (s, 1H), 4.65 (s, 2H), 3.31 (s, 3H), 2.25 (s, 3H); ESI-MS (m/z) 409 (MH)⁺. |
| Example-124: N-(6-(4,6-Dimethyl-3-oxo-3,4-dihydro-2H-benzo[b][1,4]oxazin-7-yl)pyridin-3-yl)-2,6-difluorobenzamide | 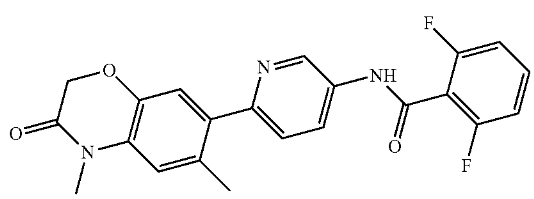 [SMILES: Cc1cc2c(cc1-c1ccc(NC(=O)c3c(F)cccc3F)cn1)OCC(=O)N2C] | ¹HNMR (400 MHz, DMSO-$d_6$) δ 11.15 (s, 1H, $D_2O$ exchangeable), 8.89 (d, J = 2.5 Hz, 1H), 8.22 (dd, J = 8.5 & 2.5 Hz, 1H), 7.68-7.60 (m, 1H), 7.57 (d, J= 8.5 Hz, 1H), 7.30 (t, J = 8.0 Hz, 2H), 7.12 (s, 1H), 7.06 (s, 1H), 4.67 (s, 2H), 3.32 (s, 3H), 2.36 (s, 3H); ESI-MS (m/z) 410 (MH)⁺. |
| Example-125: N-(5-(4,6-Dimethyl-3-oxo-3,4-dihydro-2H-benzo[b][1,4]oxazin-7-yl)pyridin-2-yl)-2,6-difluorobenzamide | 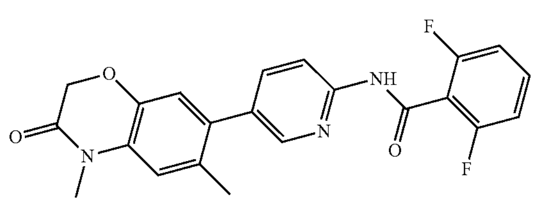 [SMILES: Cc1cc2c(cc1-c1ccc(NC(=O)c3c(F)cccc3F)nc1)OCC(=O)N2C] | ¹HNMR (400 MHz, DMSO-d6) δ 11.45 (s, 1H, $D_2O$ exchangeable), 8.35 (brs, 1H), 8.24 (d, J = 8.5 Hz, 1H), 7.88 (dd, J = 8.5 & 2.5 Hz, 1H), 7.63-7.57 (m, 1H), 7.24 (t, J = 8.0 Hz, 2H), 7.16 (s, 1H), 6.94 (s, 1H), 4.67 (s, 2H), 3.32 (s, 3H), 2.27 (s, 3H); ESI-MS (m/z) 410 (MH)⁺. |
| Example-126: N-(5-(4,6-Dimethyl-3-oxo-3,4-dihydro-2H-benzo[b][1,4]oxazin-7-yl)pyrazin-2-yl)-2,6-difluorobenzamide | 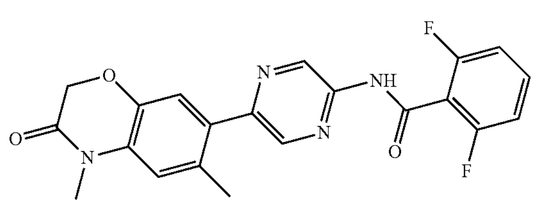 [SMILES: Cc1cc2c(cc1-c1cnc(NC(=O)c3c(F)cccc3F)cn1)OCC(=O)N2C] | ¹HNMR (400 MHz, DMSO-d6) δ 11.77 (s, 1H, $D_2O$ exchangeable), 9.48 (s, 1H), 8.64 (s, 1H), 7.66-7.59 (m, 1H), 7.27 (t, J = 8.0 Hz, 2H), 7.19 (s, 1H), 7.17 (s, 1H), 4.69 (s, 2H), 3.33 (s, 3H), 2.39 (s, 3H); ESI-MS (m/z) 411 (MH)⁺. |

TABLE 9-continued

| Example No: IUPAC name | Structure | 1H-NMR/ESI-MS |
|---|---|---|
| Example-127: 7-(4-((2,6-Difluorobenzyl)amino)phenyl)-4,6-dimethyl-2H-benzo[b][1,4]oxazin-3(4H)-one | 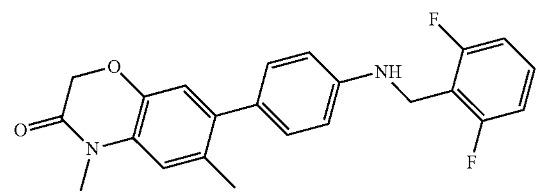 [SMILES: Cc1cc2c(cc1-c1ccc(NCc3c(F)cccc3F)cc1)OCC(=O)N2C] | 1HNMR (400 MHz, DMSO-$d_6$) δ 7.45-7.38 (m, 1H), 7.13 (t, J = 8.0 Hz, 2H), 7.07 (s, 1H), 7.04 (d, J = 8.0 Hz, 2H), 6.74 (s, 1H), 6.70 (d, J = 8.0 Hz, 2H), 6.16 (t, J = 6.0 Hz, 1H, $D_2O$ exchangeable), 4.61 (s, 2H), 4.29 (d, J = 6.0 Hz, 2H), 3.29 (s, 3H), 2.22 (s, 3H); ESI-MS (m/z) 395 (MH)+. |
| Example-128: 2,6-Difluoro-N-(4-(2,2,4-trimethyl-3-oxo-3,4-dihydro-2H-benzo[b][1,4]oxazin-7-yl)phenyl)benzamide | 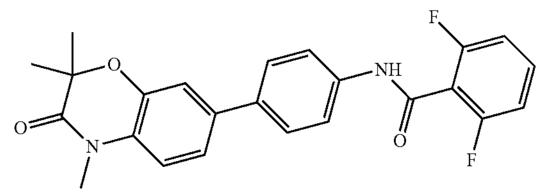 [SMILES: CN1C(=O)C(C)(C)Oc2cc(-c3ccc(NC(=O)c4c(F)cccc4F)cc3)ccc21] | 1HNMR (400 MHz, $CDCl_3$) δ 7.74-7.72 (m, 3H), 7.60 (d, J = 8.0 Hz, 2H), 7.49-7.42 (m, 1H), 7.29-7.23 (m, 2H), 7.06-7.02 (m, 3H), 3.41 (s, 3H), 1.56 (s, 6H); ESI-MS (m/z) 423 (MH)+. |
| Example-129: 2,6-Difluoro-N-(4-(2,2,4-trimethyl-3-oxo-3,4-dihydro-2H-benzo[b][1,4]oxazin-6-yl)phenyl)benzamide | 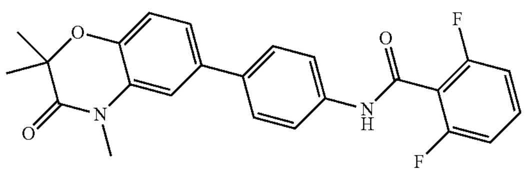 [SMILES: CN1C(=O)C(C)(C)Oc2ccc(-c3ccc(NC(=O)c4c(F)cccc4F)cc3)cc21] | 1HNMR (400 MHz, $CDCl_3$) δ 7.84 (s, 1H), 7.36 (d, J = 8.0 Hz, 2H), 7.57 (d, J = 8.0 Hz, 2H), 748-7.40 (m, 1H), 7.23 (dd, J = 8.0 & 2.0 Hz, 1H), 7.12 (d, J = 2.0 Hz, 1H), 7.04-7.00 (m, 3H), 3.43 (s, 3H), 1.55 (s, 6H); ESI-MS (m/z) 423 (MH)+. |

Example-130a: N-(4-(7-Bromo-4-methyl-3-oxo-3,4-dihydro-2H-benzo[b][1,4]oxazin-6-yl)phenyl)-2,6-difluorobenzamide and Example-130b: N-(4-(4,7-Dimethyl-3-oxo-3,4-dihydro-2H-benzo[b][1,4]oxazin-6-yl)phenyl)-2,6-difluorobenzamide

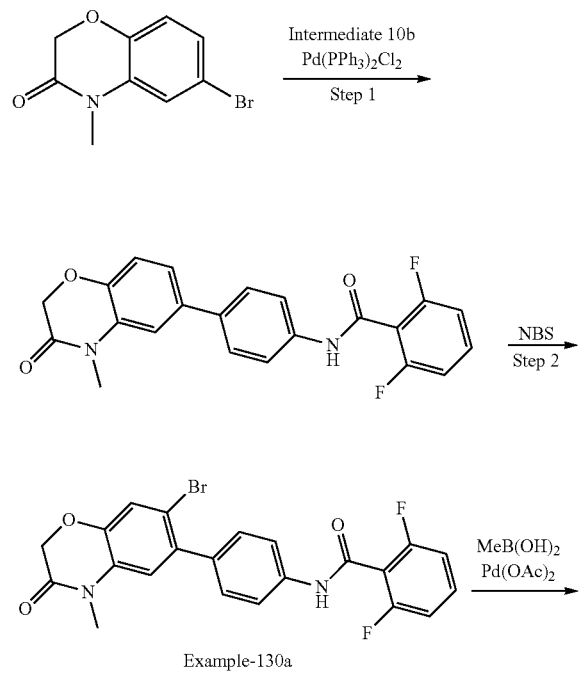

Example-130b

Step-1: 2,6-Difluoro-N-(4-(4-methyl-3-oxo-3,4-dihydro-2H-benzo[b][1,4]oxazin-6-yl)phenyl)benzamide: The title compound was prepared by reacting 6-bromo-4-methyl-2H-benzo[b][1,4]oxazin-3(4H)-one with Intermediate 10b by following the similar procedure as described for Example-104. 1HNMR (400 MHz, DMSO-$d_6$) δ 10.90 (s, 1H, $D_2O$ exchangeable), 7.78 (d, J=8.5 Hz, 2H), 7.72 (d, J=8.5 Hz, 2H), 7.63-7.58 (m, 1H), 7.39 (d, J=2.0 Hz, 1H), 7.35-7.21 (m, 3H), 7.09 (d, J=8.0 Hz, 1H), 4.69 (s, 2H), 3.38 (s, 3H); ESI-MS 395 (m/z) (M)+.

Step-2: N-(4-(7-Bromo-4-methyl-3-oxo-3,4-dihydro-2H-benzo[b][1,4]oxazin-6-yl)phenyl)-2,6-difluorobenzamide:
To an ice-cooled solution of step-1 Intermediate (1.0 g, 2.54 mmol) and silica (2.0 g) in DCM (5 mL) and methanol (1 mL) was added NBS (0.5 g, 2.79 mmol). The resulting mixture was stirred at room temperature for 24 h, then diluted with DCM and filtered through Celite. The residue was washed with 5% methanol in DCM. The combined filtrates were concentrated on a rotary evaporator and the crude product was purified by flash column chromatography (silica gel, 3% methanol in DCM system as eluent) to afford 500 mg (42%) of the title compound as white solid. 1HNMR (400 MHz, DMSO-$d_6$) δ 10.94 (s, 1H, $D_2O$ exchangeable), 7.77 (d, J=8.5 Hz, 2H), 7.65-7.50 (m, 1H), 7.43 (d, J=8.5 Hz, 2H), 7.38 (s, 1H), 7.33-7.24 (m, 2H), 7.13 (s, 1H), 4.74 (s, 2H), 3.29 (s, 3H); ESI-MS (m/z) 473, 475 [(M)+, Br[79, 81]].

Example 130b: N-(4-(4,7-Dimethyl-3-oxo-3,4-dihydro-2H-benzo[b][1,4]oxazin-6-yl)phenyl)-2,6-difluorobenzamide To a degassed solution of step-2 Intermediate (200 mg, 0.42 mmol) in 1,4-dioxane (10 mL) in a sealed tube was added methylboronic acid (25 mg, 0.42 mmol), Ru-Phos (25.6 mg, 0.06 mmol), potassium phosphate (197 mg, 0.93 mmol) and Pd(OAc)$_2$ (10 mg, 0.042 mmol) sequentially. The resulting mixture was heated at 120° C. for 12 h. The reaction mixture was cooled to room temperature, diluted with ethyl acetate (10 mL) and filtered through Celite pad. The residue was washed with ethyl acetate (2×10 mL). The combined filtrates were concentrated on a rotary evaporator and the crude product was purified by flash column chromatography (silica gel, 60% ethyl acetate in hexane system as eluent) followed by preparative HPLC (reverse phase) to afford 30 mg (16%) of the title compound as a white solid. $^1$HNMR (400 MHz, DMSO-d$_6$) δ 10.90 (s, 1H, D$_2$O exchangeable), 7.76 (d, J=8.5 Hz, 2H), 7.65-7.57 (m, 1H), 7.37 (d, J=8.5 Hz, 2H), 7.28 (t, J=8.5 Hz, 2H), 6.96 (s, 2H), 4.66 (s, 2H), 3.28 (s, 3H), 2.19 (s, 3H); ESI-MS (m/z) 408 (MH)$^+$.

Example-131: N-(4-(7-Cyclopropyl-4-methyl-3-oxo-3,4-dihydro-2H-benzo[b][1,4]oxazin-6-yl)phenyl)-2,6-difluorobenzamide

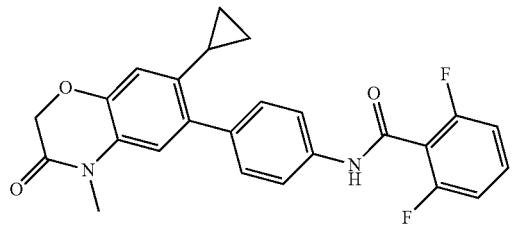

Example-131

The title compound was prepared by following the similar procedure as described in Example-130b by using Example-130a. $^1$HNMR (400 MHz, CDCl$_3$) δ 7.77-7.67 (m, 3H), 7.50-7.44 (m, 3H), 7.05 (t, J=8.0 Hz, 2H), 6.84 (s, 1H), 6.57 (s, 1H), 4.64 (s, 2H), 3.36 (s, 3H), 1.88-1.81 (m, 1H), 0.96-0.80 (m, 2H), 0.76-0.55 (m, 2H); ESI-MS (m/z) 434 (MH)$^+$.

Example-132: N-(4-(7-Ethyl-4-methyl-3-oxo-3,4-dihydro-2H-benzo[b][1,4]oxazin-6-yl)phenyl)-2,6-difluorobenzamide

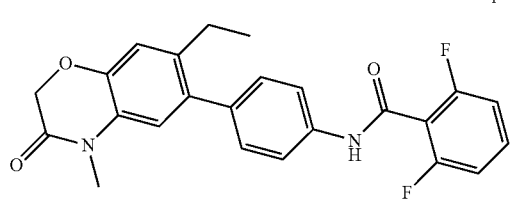

Example-132

The title compound was prepared by following the similar procedure as described in Example-130b by using Example-130a. $^1$HNMR (400 MHz, CDCl$_3$) δ 7.74 (s, 1H, D$_2$O exchangeable), 7.72 (d, J=8.5 Hz, 2H), 7.50-7.42 (m, 1H), 7.32 (d, J=8.5 Hz, 2H), 7.05 (t, J=8.0 Hz, 2H), 6.95 (s, 1H), 6.81 (s, 1H), 4.66 (s, 2H), 3.35 (s, 3H), 2.55 (d, J=7.5 Hz, 2H), 1.11 (t, J=7.5 Hz, 3H); ESI-MS (m/z) 423 (MH)$^+$.

Example-133: N-(5-(7-Ethyl-4-methyl-3-oxo-3,4-dihydro-2H-benzo[b][1,4]oxazin-6-yl)pyrazin-2-yl)-2,6-difluorobenzamide

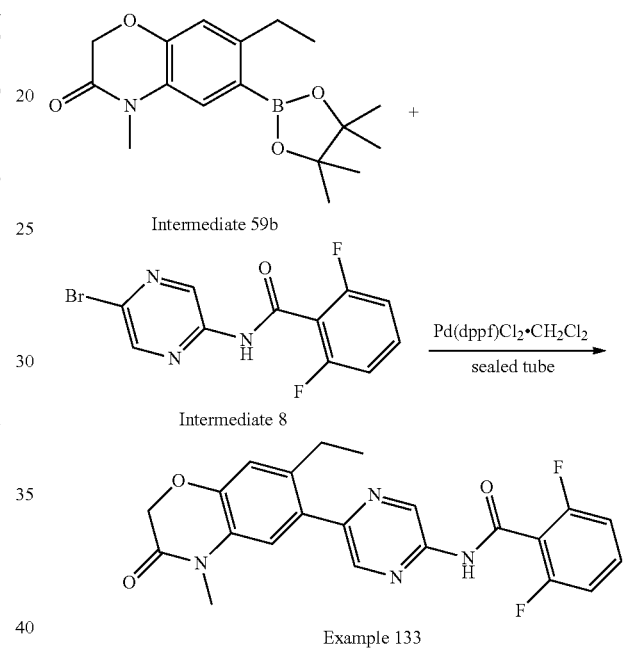

To a stirred and nitrogen purged (in a sealed-tube) solution of Intermediate-59b (0.25 g, 0.788 mmol), Intermediate-8 (0.296 g, 0.946 mmol) and 2M aqueous solution of potassium carbonate (0.8 mL, 1.58 mmol) in 1,4-dioxane (10 mL) was added PdCl$_2$(dppf)-CH$_2$Cl$_2$ adduct (40 mg, 0.08 mmol). The reaction mass was stirred at 100° C. for 6 h. The reaction mixture was cooled to room temperature and filtered through Celite. The celite cake was washed with ethyl acetate (2×30 mL). The filtrate was rotary evaporated and the crude product was purified by flash column chromatography (silica gel, 20% ethyl acetate in hexane system as eluent) to afford 100 mg (30%) of the desired product as a white solid. $^1$HNMR (400 MHz, CDCl$_3$) δ 9.77 (s, 1H), 8.40 (s, 1H), 8.38 (brs, 1H, D$_2$O exchangeable), 7.55-7.50 (m, 1H), 7.12 (t, J=8.0 Hz, 2H), 7.03 (s, 1H), 7.00 (s, 1H), 4.68 (s, 2H), 3.40 (s, 3H), 2.70 (q, J=7.5 Hz, 2H), 1.17 (t, J=7.5 Hz, 3H); ESI-MS (m/z) 425 (MH)$^+$.

The below Examples (134-141) given in Table-10 were prepared from the corresponding Intermediates by following the similar procedure as described in Example-133.

TABLE 10

| Example No: IUPAC name | Structure | ¹HNMR/ESI-MS |
|---|---|---|
| Example-134: N-(5-(7-Ethyl-4-methyl-3-oxo-3,4-dihydro-2H-benzo[b][1,4]oxazin-6-yl)pyridin-2-yl)-2,6-difluorobenzamide | 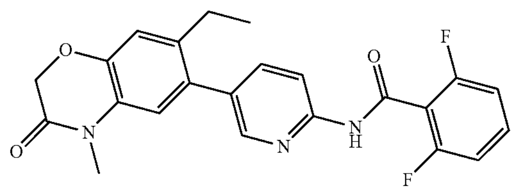 [SMILES: CCc1cc2c(cc1-c1ccc(NC(=O)c3c(F)cccc3F)nc1)N(C)C(=O)CO2] | ¹HNMR (400 MHz, CDCl$_3$) δ 8.52 (brs, 1H, D$_2$O exchangeable), 8.45 (d, J = 8.5 Hz, 1H), 8.24 (d, J = 2.0 Hz, 1H), 7.74 (dd, J = 8.5 & 2.0 Hz, 1H), 7.50-7.46 (m, 1H), 7.08 (t, J = 8.0 Hz, 2H), 6.97 (s, 1H), 6.79 (s, 1H), 4.68 (s, 2H), 3.37 (s, 3H), 2.54 (q, J = 7.5 Hz, 2H), 1.12 (t, J = 7.5 Hz, 3H); ESI-MS (m/z) 424 (MH)⁺. |
| Example-135: N-(3,5-Difluoropyridin-4-yl)-4-(7-ethyl-4-methyl-3-oxo-3,4-dihydro-2H-benzo[b][1,4]oxazin-6-yl)benzamide | 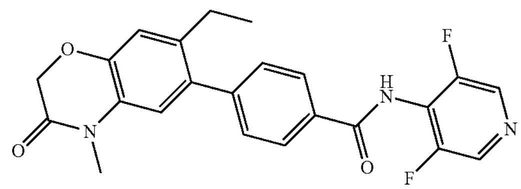 [SMILES: CCc1cc2c(cc1-c1ccc(C(=O)Nc3c(F)cncc3F)cc1)N(C)C(=O)CO2] | ¹HNMR (400 MHz, CDCl$_3$) δ 8.46 (s, 2H), 8.04 (d, J = 8.0 Hz, 2H), 7.67 (brs, 1H, D$_2$O exchangeable), 7.50 (d, J = 8.0 Hz, 2H), 6.98 (s, 1H), 6.81 (s, 1H), 4.68 (s, 2H), 3.37 (s, 3H), 2.54 (q, J = 7.5 Hz, 2H), 1.11 (t, J = 7.5 Hz, 3H); ESI-MS (m/z) 424 (MH)⁺. |
| Example-136: N-(5-(7-Cyclopropyl-4-methyl-3-oxo-3,4-dihydro-2H-benzo[b][1,4]oxazin-6-yl)pyrazin-2-yl)-2,6-difluorobenzamide | 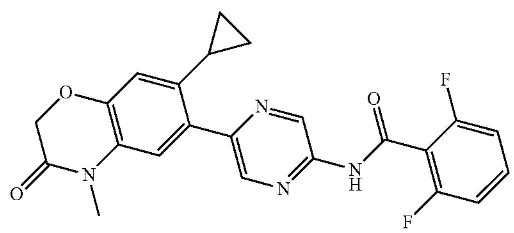 [SMILES: CN1C(=O)COc2cc(C3CC3)c(-c3cnc(NC(=O)c4c(F)cccc4F)cn3)cc21] | ¹HNMR (400 MHz, DMSO-d$_6$) δ 11.77 (s, 1H, D$_2$O exchangeable), 9.51 (s, 1H), 8.72 (s, 1H), 7.65-7.61 (m, 1H), 7.30 (t, J = 8.0 Hz, 2H), 7.24 (s, 1H), 6.71 (s, 1H), 4.69 (s, 2H), 3.30 (s, 3H), 2.16-2.04 (m, 1H), 0.90-0.78 (m, 2H), 0.66-0.57 (m, 2H); ESI-MS (m/z) 437 (MH)⁺. |
| Example-137: 4-(7-Cyclopropyl-4-methyl-3-oxo-3,4-dihydro-2H-benzo[b][1,4]oxazin-6-yl)-N-(3,5-difluoropyridin-4-yl)benzamide | 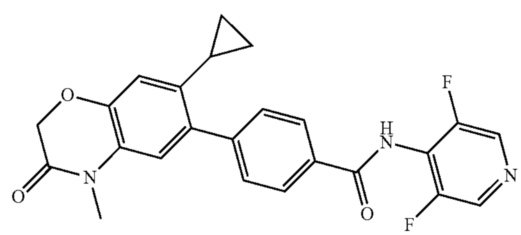 [SMILES: CN1C(=O)COc2cc(C3CC3)c(-c3ccc(C(=O)Nc4c(F)cncc4F)cc3)cc21] | ¹HNMR (400 MHz, CDCl$_3$) δ 8.46 (s, 2H), 8.05 (d, J = 8.0 Hz, 2H), 7.66 (brs, 1H, D$_2$O exchangeable), 7.63 (d, J = 8.0 Hz, 2H), 6.84 (s, 1H), 6.62 (s, 1H), 4.66 (s, 2H), 3.38 (s, 3H), 1.80-1.77 (m, 1H), 0.93-0.85 (m, 2H), 0.73-0.64 (m, 2H); ESI-MS (m/z) 436 (MH)⁺. |
| Example-138: N-(3,5-Difluoropyridin-4-yl)-4-(6-ethyl-4-methyl-3-oxo-3,4-dihydro-2H-benzo[b][1,4]oxazin-7-yl)benzamide | 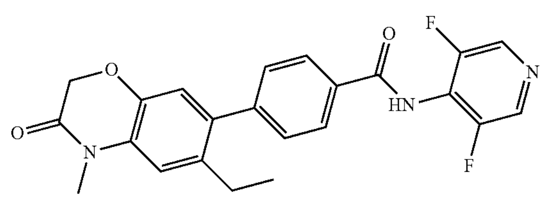 [SMILES: CCc1cc2c(cc1-c1ccc(C(=O)Nc3c(F)cncc3F)cc1)OCC(=O)N2C] | ¹HNMR (400 MHz, DMSO-d6) δ 10.73 (s, 1H, D$_2$O exchangeable), 8.64 (s, 2H), 8.04 (d, J = 8.0 Hz, 2H), 7.50 (d, J = 8.0 Hz, 2H), 7.15 (s, 1H), 6.85 (s, 1H), 4.68 (s, 2H), 2.57 (q, J = 7.5 Hz, 2H), 1.05 (t, J = 7.5 Hz, 3H); ESI-MS (m/z) 424 (MH)⁺. |
| Example-139: N-(5-(7-Cyclopropyl-4-methyl-3-oxo-3,4-dihydro-2H-benzo[b][1,4]oxazin-6-yl)pyridin-2-yl)-2,6-difluorobenzamide | 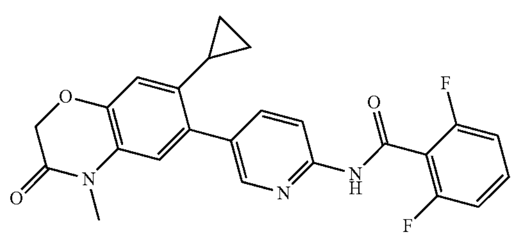 [SMILES: CN1C(=O)COc2cc(C3CC3)c(-c3ccc(NC(=O)c4c(F)cccc4F)nc3)cc21] | ¹HNMR (400 MHz, CDCl$_3$) δ 8.46 (d, J = 8.5 Hz, 1H), 8.45 (brs, 1H, D$_2$O exchangeable), 8.39 (d, J = 2.0 Hz, 1H), 7.88 (dd, J = 8.5 & 2.0 Hz, 1H), 7.55-7.44 (m, 1H), 7.06 (t, J = 8.0 Hz, 2H), 6.83 (s, 1H), 6.63 (s, 1H), 4.65 (s, 2H), 3.38 (s, 3H), 1.81-1.78 (m, 1H), 0.95-0.85 (m, 2H), 0.69-0.67 (m, 2H); ESI-MS (m/z) 436 (MH)⁺. |
| Example-140: N-(2,6-Difluorophenyl)-5-(3,6-dimethyl-2-oxo-2,3-dihydrobenzo[d]oxazol-5-yl)thiophene-2-carboxamide | 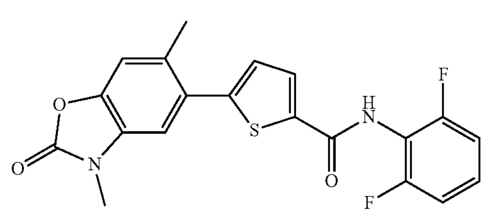 [SMILES: Cc1cc2oc(=O)n(C)c2cc1-c1ccc(C(=O)Nc2c(F)cccc2F)s1] | ¹HNMR (400 MHz, DMSO-d$_6$) δ 10.26 (brs, 1H, D$_2$O exchangeable), 8.04 (d, J = 4.0 Hz, 1H), 7.46-7.42 (m, 1H), 7.38 (s, 1H), 7.37 (s, 1H), 7.33 (d, J = 4.0 Hz, 1H), 7.25 (t, J = 8.0 Hz, 2H), 3.36 (s, 3H), 2.42 (s, 3H); ESI-MS (m/z) 401 (MH)⁺. |

TABLE 10-continued

| Example No: IUPAC name | Structure | ¹HNMR/ESI-MS |
|---|---|---|
| Example-141: N-(4-(3,7-Dimethyl-2-oxo-2,3-dihydrobenzo[d]oxazol-5-yl)phenyl)-2,6-difluorobenzamide | 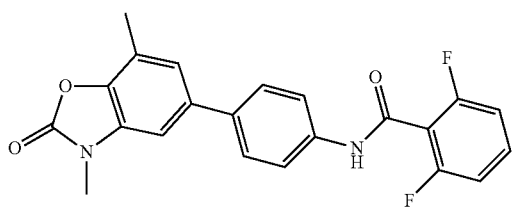 [SMILES: Cc1cc(-c2ccc(NC(=O)c3c(F)cccc3F)cc2)cc2c1oc(=O)n2C] | ¹HNMR (400 MHz, DMSO-$d_6$) δ 10.91 (s, 1H), 7.80 (d, J = 8.0 Hz, 2H), 7.72 (d, J = 8.0 Hz, 2H), 7.64-7.59 (m, 1H), 7.41 (d, J = 2.0 Hz, 1H), 7.30 (d, J = 2.0 Hz, 1H), 7.28 (t, J = 8.0 Hz, 2H), 3.40 (s, 3H), 3.34 (s, 3H); ESI-MS (m/z) 395 (MH)⁺. |

Biological Assays and Utility:

The CRAC channel modulatory activity of the compounds were thus evaluated by measuring the secretion of IL-2 by antigen stimulated T-cells in vitro. Alternatively, such activity can also be evaluated by assay methods known to one skilled in the art.

In Vitro Assay

Example-142

Inhibition of IL-2 secretion: Jurkat T cells were seeded at a density of 0.5 to 1 million cells per well in RPMI medium. Test compounds from this invention were added to the cells at different concentrations. This was followed by the addition of PHA, a T cell mitogen after 10 minutes. The cells were then incubated for 20 to 24 hours in a $CO_2$ incubator at 37° C. After incubation with the compounds, cells were centrifuged, the supernatant was collected and processed for ELISA to quantitate the amount of IL-2 secreted. A commercial ELISA kit (R&D Systems, Inc. Minneapolis, Minn., USA) was used to estimate the IL-2 concentrations. Amount of IL-2 secreted by cells stimulated with PHA was considered as a 100% maximal signal and the decrease in amount of IL-2 secreted by cells treated with the test compounds was expressed as percent inhibition of the maximal signal. The dose response data was analyzed using 4-parametric sigmoidal dose response (variable slope) curve-fit.

In the above IL-2 assay, compounds of the invention were found to have $IC_{50}$ (nM) values as shown below:

| $IC_{50}$ (nM) | Examples |
|---|---|
| <25 nM | 5, 27, 30, 31, 32, 34, 36, 37, 38, 42, 43, 55, 56, 60, 70, 77, 78, 79, 82, 85, 88, 89, 92, 93, 94, 95, 101, 107, 113, 114, 115, 116, 121, 122, 123, 140 |
| 25.01 nM-50 nM | 1, 9, 16, 23, 25, 29, 46, 49, 53, 61, 69, 73, 75, 76, 83, 84, 86, 90, 100, 112, 117, 130, 132 |
| 50.01 nM-100 nM | 14, 28, 51, 72, 74, 80, 81, 103, 109, 127, 131 |
| 100.01 nM-500 nM | 6, 26, 33, 119, 126, 133, 135 |

Thus, compounds of the invention are shown to inhibit IL-2 secretion.

Example-143

SOCE inhibition: Jurkat E6.1 cells were seeded at a density of $1-2\times10^5$ cells per well in calcium-4 dye prepared in calcium free HBSS (Sigma, USA). Test compounds from this invention were added to the cells at different concentrations. This was followed by the addition of Thapsigargin (TG), a SERCA inhibitor, to empty the stores of calcium. Calcium chloride was added to the cells after 10-30 min to induce calcium influx and the fluorescence was measured for 10 min using the FLIPR-Tetra detection system. Fluorescence was also measured using a plate reader at 485 nm excitation and 520 nm emission (Synergy2, Biotek, USA) after 30-90 minutes of calcium addition. Fluorescence observed in cells treated with Thapsigargin and calcium chloride solution was considered 100% maximal signal and the reduced fluorescent signal observed in the presence of test compounds was expressed as percent inhibition of the maximal signal. The dose response data was analyzed using 4-parametric sigmoidal dose response (variable slope) curve-fit.

In the above SOCE inhibition assay, compounds of the invention showed activity less than <1000 nM against SOCE. Thus, compounds of the invention are shown to have CRAC channel modulation activity by inhibition of SOCE.

Example-144

NFAT Transcriptional Activity: HEK 293 cells were stably co-transfected with a NFAT-Firefly Luciferase and Tk-Renilla Luciferase reporter genes 30,000-80,000 cells were seeded per well. Test compounds from this invention were added to the cells at different concentrations. Thapsigargin (TG) was added after 10 mins and the cells were incubated for 4-8 h. The NFAT-Firefly luciferase and Tk-Renilla luciferase activity was measured using Dual-Glo reagent (Promega USA). The Renilla luciferase activity was used for protein normalization. Luminescence observed in cells treated with thapsigargin was considered 100% maximal signal and the reduced fluorescent signal observed in the presence of test compounds was expressed as percent inhibition of the maximal signal. The data was analyzed using 4-parametric sigmoidal dose response (variable slope) curve-fit.

In the above NFAT transcriptional activity assay, compounds of the invention showed activity less than <1000 nM. Thus, compounds of the invention are shown to inhibit NFAT transcription activity.

Thus, the in vitro screening assays showed that the compounds of invention inhibit CRAC channel activity.

As mentioned hereinbefore, the CRAC channel is involved with numerous biological responses through various $Ca^{2+}$ signaling pathways. The compounds of the invention are therefore useful for the treatment and/or prophylaxis of, although not limited to, inflammatory conditions, cancer, rheumatoid arthritis, allergic disorders, immune disorders, cardiovascular diseases, thrombocytopathies and all related conditions which can be benefitted by the CRAC channel modulatory properties of the compounds described herein.

The compounds of the invention can be administered to a warm-blooded animal, including human being, for the treatment and/or prophylaxis of one or many diseases or disorders mentioned hereinabove which can be benefitted by the CRAC channel modulatory properties of the compounds described herein. The compounds may be Formulated according to the methods known in the art as well as by new methods and may be administered to the body system via gastro-intestinal tract as well as via other routes known to a person skilled in the art. Thus, administration of the compounds of the invention via oral route, parenteral route, inhalation and/or topical applications are within the scope of this application. Any combination of a compound of the invention with excipients and/or other therapeutic agents known in the art for the said conditions, diseases and/or disorders are also encompassed by the invention.

Although certain embodiments and Examples have been described in detail above, those having ordinary skill in the art will clearly understand that many modifications are possible in the embodiments and Examples without departing from the teachings thereof. All such modifications are intended to be encompassed within the below claims of the invention.

The invention claimed is:

1. A compound of Formula (I):

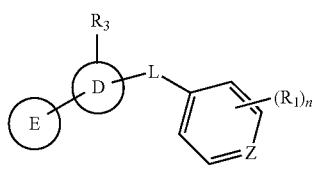

(I)

wherein, ring D is Formula (a) or Formula (b):

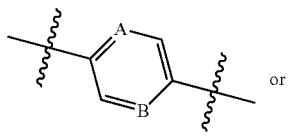

(a)

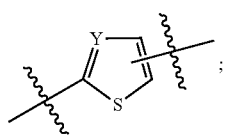

(b)

A and B, which may be same or different, are independently $CR_3$ or N;

Y is $CR_3$ or N;

L is selected from —$NR_2C(O)$—, —$C(O)NR_2$— and —$NR_2CR_aR_b$—;

$R_a$ and $R_b$ are independently hydrogen, halogen or substituted or unsubstituted alkyl;

ring E is selected from the Formula (i) to (vii):

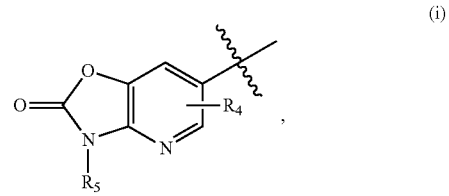

(i)

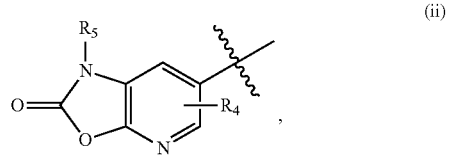

(ii)

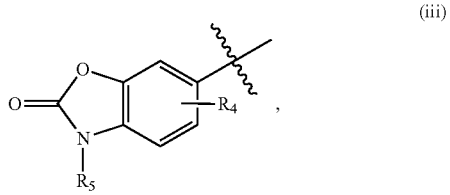

(iii)

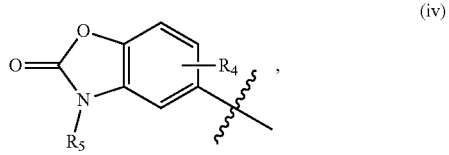

(iv)

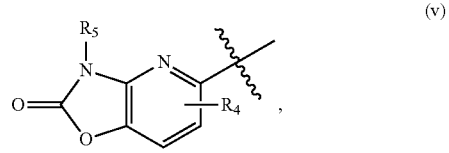

(v)

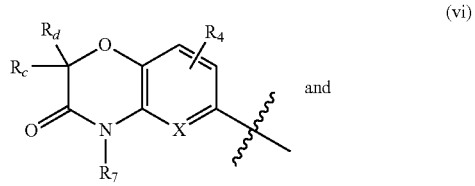

(vi)

and

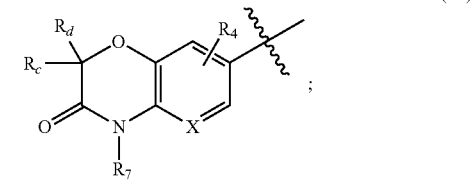

(vii)

;

X is N or $CR_4$;

Z is N or CR where R is selected from hydrogen, halogen or substituted or unsubstituted alkyl;

$R_1$, which may be same or different at each occurrence, is independently selected from halogen, cyano, nitro, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl and substituted or unsubstituted cycloalkoxy;

$R_2$ is hydrogen or substituted or unsubstituted alkyl;

$R_3$ is independently selected from hydrogen, halogen, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl and —C(O)OR$_6$;

R$_4$, which may be same or different at each occurrence, is independently selected from hydrogen, halogen, cyano, nitro, hydroxyl, substituted or unsubstituted alkyl, substituted or unsubstituted haloalkyl, substituted or unsubstituted alkoxy, substituted or unsubstituted haloalkoxy, substituted or unsubstituted cycloalkyl, substituted or unsubstituted cycloalkoxy, —NR$_8$R$_9$, —COOR$_6$ and CONH$_2$;

R$_5$ is selected from substituted or unsubstituted alkyl, substituted or unsubstituted haloalkyl, substituted or unsubstituted hydroxyalkyl, substituted or unsubstituted alkoxyalkyl, substituted or unsubstituted cycloalkyl and substituted or unsubstituted cycloalkylalkyl;

R$_6$ is a hydrogen or substituted or unsubstituted alkyl;

R$_7$ is selected from hydrogen, substituted or unsubstituted alkyl, substituted or unsubstituted haloalkyl, substituted or unsubstituted hydroxyalkyl, substituted or unsubstituted alkoxyalkyl, substituted or unsubstituted cycloalkyl, and substituted or unsubstituted cycloalkylalkyl;

R$_8$ and R$_9$ are independently selected from hydrogen, substituted or unsubstituted alkyl, substituted or unsubstituted haloalkyl, and substituted or unsubstituted cycloalkyl;

R$_c$ and R$_d$ are independently selected from hydrogen or substituted or unsubstituted alkyl, substituted or unsubstituted cycloalkylalkyl, substituted or unsubstituted hydroxyalkyl and substituted or unsubstituted alkoxyalkyl; and 'n' is an integer ranging from 1 to 4, both inclusive;

or a pharmaceutically acceptable salt thereof.

2. The compound of claim 1 having the Formula (II):

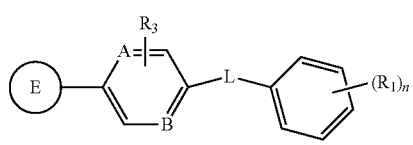

(II)

wherein,

A and B, which may be same or different, are independently CR$_3$ or N, wherein R$_3$ is selected from hydrogen, halogen and substituted or unsubstituted alkyl;

L is selected from —NHC(O)—, —C(O)NH— and —NHCH$_2$—;

ring E is selected from the Formula (i) to (v):

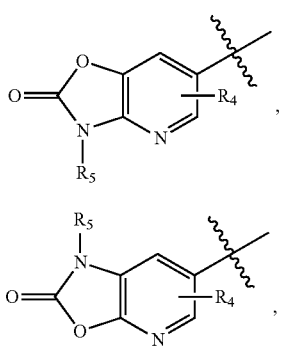

(i)

(ii)

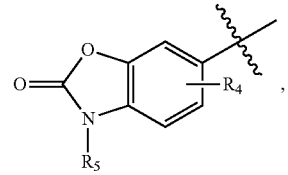

(iii)

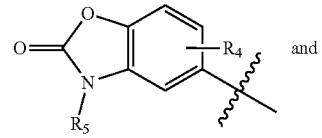

(iv)

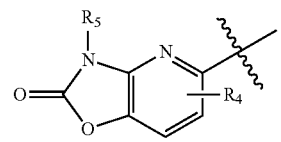

(v)

R$_1$, which may be same or different at each occurrence, is independently selected from halogen, substituted or unsubstituted alkyl and substituted or unsubstituted haloalkyl;

R$_3$ is selected from hydrogen, halogen, or substituted or unsubstituted alkyl;

R$_4$ is independently selected from hydrogen, halogen, substituted or unsubstituted alkyl and substituted or unsubstituted cycloalkyl;

R$_5$ is selected from substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl; and 'n' is an integer ranging from 1 to 2, both inclusive;

or a pharmaceutically acceptable salt thereof.

3. The compound of claim 1 having the Formula (III):

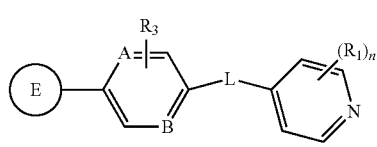

(III)

wherein,

A and B, which may be same or different, are independently CR$_3$ or N, where R$_3$ is selected from hydrogen, halogen and substituted or unsubstituted alkyl;

L is selected from —NHC(O)—, —C(O)NH— and —NHCH$_2$—;

ring E is selected from the Formula (i) to (v):

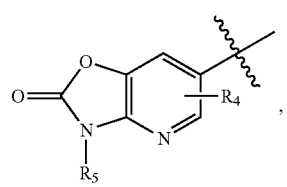

(i)

-continued

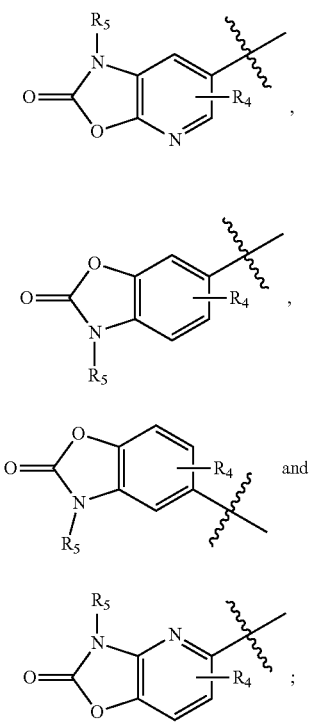

R₁, which may be same or different at each occurrence, is independently selected from halogen, substituted or unsubstituted alkyl and substituted or unsubstituted haloalkyl;

R₃ is selected from hydrogen, halogen and substituted or unsubstituted alkyl;

R₄ is selected from hydrogen, halogen, substituted or unsubstituted alkyl and substituted or unsubstituted cycloalkyl;

R₅ is selected from substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl; and 'n' is an integer ranging from 1 to 2, both inclusive;

or a pharmaceutically acceptable salt thereof.

4. The compound of claim 1 having the Formula (II):

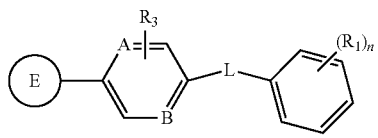

wherein,

A and B, which may be same or different, are independently CR₃ or N, where R₃ is selected from hydrogen, halogen and substituted or unsubstituted alkyl;

L is selected from —NHC(O)—, —C(O)NH— and —NHCH₂—;

ring E is Formula (vi) or (vii):

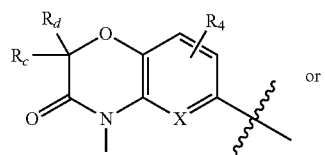

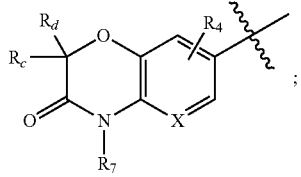

X is N or CR₄ where R₄ is selected from hydrogen, halogen, substituted or unsubstituted alkyl, and substituted or unsubstituted cycloalkyl;

R₁, which may be same or different at each occurrence, is independently selected from halogen, substituted or unsubstituted alkyl and substituted or unsubstituted haloalkyl;

R₃ is selected from hydrogen, halogen and substituted or unsubstituted alkyl;

R₄, which may be same or different at each occurrence, is independently selected from hydrogen, halogen, substituted or unsubstituted alkyl and substituted or unsubstituted cycloalkyl;

R₇ is selected from hydrogen, substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl;

R_c and R_d are hydrogen or substituted or unsubstituted alkyl; and

'n' is an integer ranging from 1 to 2, both inclusive;

or a pharmaceutically acceptable salt thereof.

5. The compound of claim 1 having the Formula (III):

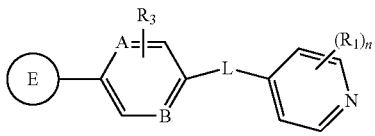

wherein,

A and B, which may be same or different, are independently CR₃ or N, where R₃ is selected from hydrogen, halogen or substituted or unsubstituted alkyl;

L is selected from —NHC(O)—, —C(O)NH— and —NHCH₂—;

ring E is Formula (vi) or (vii):

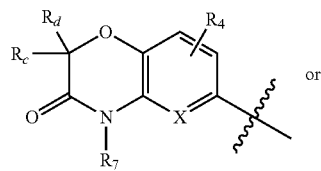

-continued

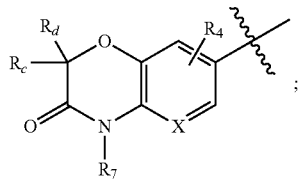
(vii)

X is N or CR₄ where R₄ is selected from hydrogen, halogen, substituted or unsubstituted alkyl, and substituted or unsubstituted cycloalkyl;

R₁, which may be same or different at each occurrence, is independently selected from halogen, substituted or unsubstituted alkyl and substituted or unsubstituted haloalkyl;

R₃ is selected from hydrogen, halogen and substituted or unsubstituted alkyl;

R₄, which may be same or different at each occurrence, is independently selected from hydrogen, halogen, substituted or unsubstituted alkyl and substituted or unsubstituted cycloalkyl;

R₇ is selected from hydrogen, substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl;

R_c and R_d are hydrogen or substituted or unsubstituted alkyl; and

'n' is an integer ranging from 1 to 2, both inclusive;

or a pharmaceutically acceptable salt thereof.

6. The compound of claim 1 having the Formula (IV):

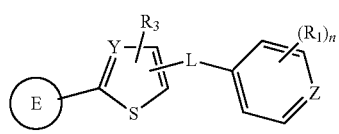
(IV)

wherein,

Y is CR₃ or N, where R₃ is selected from hydrogen, halogen and substituted or unsubstituted alkyl;

Z is CH or N;

L is —NHC(O)— or —C(O)NH—;

ring E is selected from the Formula (i) to (v):

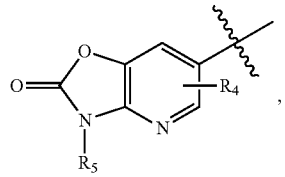
(i)

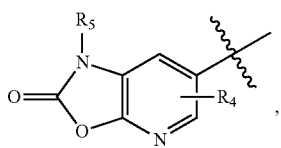
(ii)

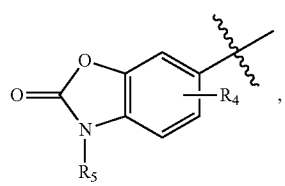
(iii)

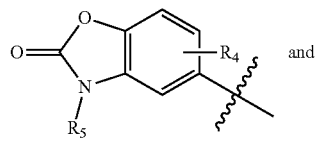
(iv)

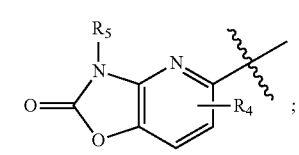
(v)

R₁, which may be same or different at each occurrence, is independently selected from halogen, substituted or unsubstituted alkyl and substituted or unsubstituted haloalkyl;

R₃ is selected from hydrogen, halogen and substituted or unsubstituted alkyl;

R₄ is selected from hydrogen, halogen, substituted or unsubstituted alkyl and substituted or unsubstituted cycloalkyl;

R₅ is selected from substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl; and 'n' is an integer ranging from 1 to 2, both inclusive;

or a pharmaceutically acceptable salt thereof.

7. The compound of claim 1, wherein ring D is Formula (a) or Formula (b):

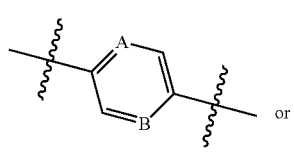
(a)

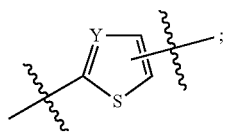
(b)

wherein A and B, which may be same or different, are independently CR₃ or N; Y is CR₃ or N; wherein each of R₃ is selected from hydrogen, halogen and substituted or unsubstituted alkyl.

8. The compound of claim 1, wherein ring E selected from the Formula (i) to (v):

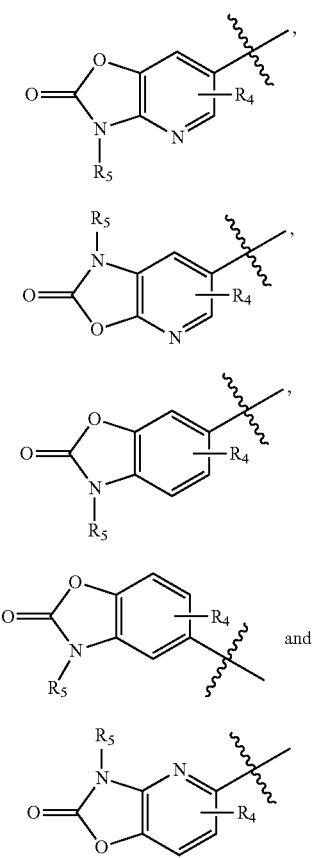

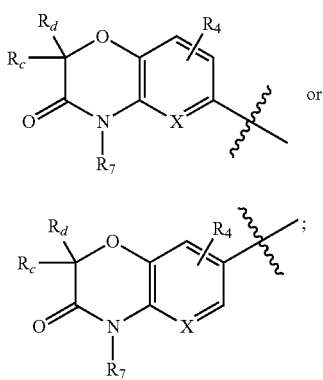

wherein R₄ is selected from hydrogen, halogen, substituted or unsubstituted alkyl, substituted or unsubstituted haloalkyl, and substituted or unsubstituted cycloalkyl; R₅ is selected from substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl.

9. The compound of claim 1 wherein ring E is Formula (vi) or (vii):

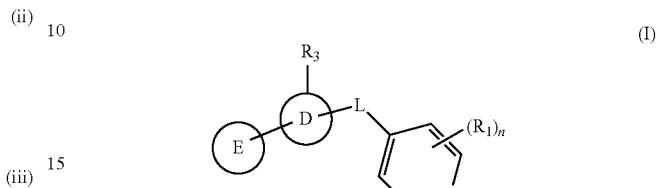

wherein X is N or CR₄ where R₄ is hydrogen, halogen or substituted or unsubstituted alkyl; $R_c$ and $R_d$ are hydrogen or substituted or unsubstituted alkyl; R₄ is selected from hydrogen, halogen, substituted or unsubstituted alkyl, substituted or unsubstituted haloalkyl, and substituted or unsubstituted cycloalkyl; and R₇ is selected from hydrogen, substituted or unsubstituted alkyl, substituted or unsubstituted haloalkyl, substituted or unsubstituted hydroxyalkyl, substituted or unsubstituted cycloalkyl and substituted or unsubstituted cycloalkylalkyl.

10. The compound of claim 1 having the Formula (I):

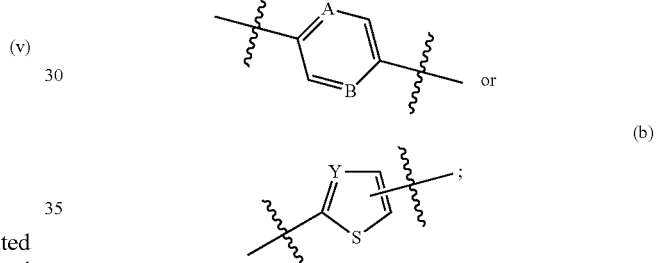

or a pharmaceutically acceptable salt thereof;

wherein L is selected from —NHC(O)—, —C(O)NH— and —NHCH₂—; Z is N or CH; R₁ is halogen or substituted or unsubstituted alkyl; 'n' is 1 or 2; ring D is Formula (a) or Formula (b):

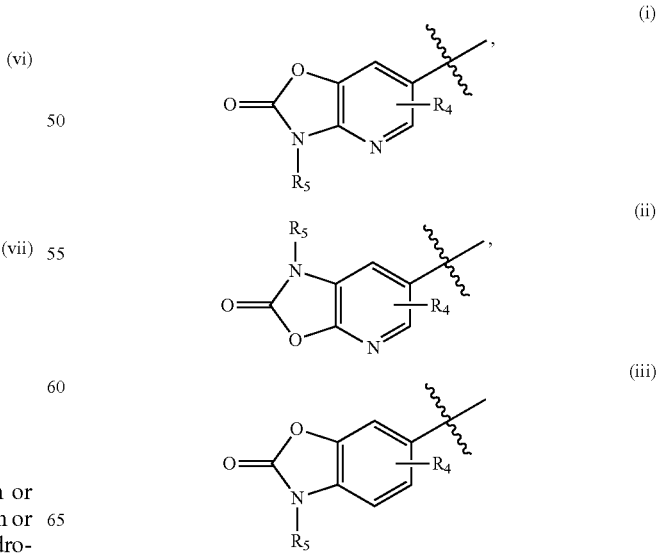

A and B are independently CR₃ or N; Y is CR₃ or N; each of R₃ is independently hydrogen, substituted or unsubstituted alkyl; and ring E is selected from (i) to (v)

-continued

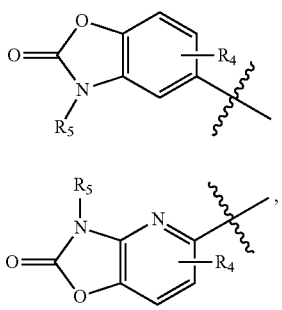

(iv)

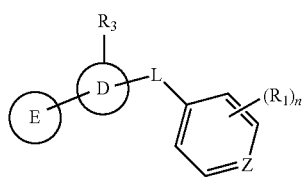

(v)

R<sub>4</sub> is selected from hydrogen, substituted or unsubstituted alkyl and substituted or unsubstituted cycloalkyl; R<sub>5</sub> is selected from substituted or unsubstituted alkyl, substituted or unsubstituted haloalkyl, substituted or unsubstituted hydroxyalkyl and substituted or unsubstituted cycloalkylalkyl.

11. The compound of claim 1 having the Formula (I):

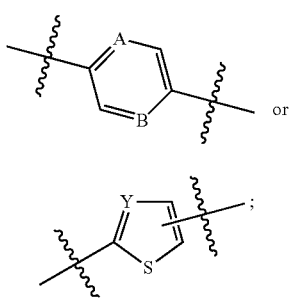

(I)

wherein L is selected from —NHC(O)—, —C(O)NH— and —NHCH$_2$—; Z is N or CH; each of R$_1$ is halogen or substituted or unsubstituted alkyl; 'n' is 1 or 2; ring D is Formula (a) or Formula (b):

(a)

(b)

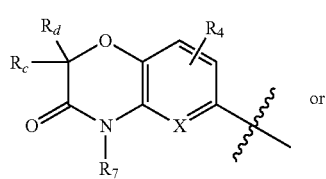

A and B are independently CR$_3$ or N; Y is CR$_3$ or N; each of R$_3$ is selected from hydrogen or substituted or unsubstituted alkyl; and ring E is (vi) or (vii)

(vi)

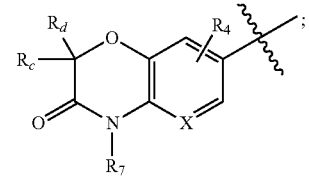

or (vii)

X is N or CR$_4$; R$_4$ is selected from hydrogen, substituted or unsubstituted alkyl and substituted or unsubstituted cycloalkyl; R$_c$ and R$_d$ are hydrogen or substituted or unsubstituted alkyl; and R$_7$ is hydrogen or substituted or unsubstituted alkyl.

12. A compound which is selected from:
N-(4-(3,7-Dimethyl-2-oxo-2,3-dihydrooxazolo[4,5-b]pyridin-6-yl)phenyl)-2,6-difluorobenzamide,
N-(5-(3,7-Dimethyl-2-oxo-2,3-dihydrooxazolo[4,5-b]pyridin-6-yl)pyrazin-2-yl)-2,6-difluoro benzamide,
N-(6-(3,7-Dimethyl-2-oxo-2,3-dihydrooxazolo[4,5-b]pyridin-6-yl)pyridin-3-yl)-2,6-difluoro benzamide,
N-(5-(3,7-Dimethyl-2-oxo-2,3-dihydrooxazolo[4,5-b]pyridin-6-yl)pyridin-2-yl)-2,6-difluoro benzamide,
N-(4-(7-Ethyl-3-methyl-2-oxo-2,3-dihydrooxazolo[4,5-b]pyridin-6-yl)phenyl)-2,6-difluorobenzamide,
N-(5-(7-Ethyl-3-methyl-2-oxo-2,3-dihydrooxazolo[4,5-b]pyridin-6-yl)pyrazin-2-yl)-2,6-difluorobenzamide,
N-(6-(7-Ethyl-3-methyl-2-oxo-2,3-dihydrooxazolo[4,5-b]pyridin-6-yl)pyridin-3-yl)-2,6-difluorobenzamide,
N-(5-(7-Ethyl-3-methyl-2-oxo-2,3-dihydrooxazolo[4,5-b]pyridin-6-yl)pyridin-2-yl)-2,6-difluorobenzamide,
N-(4-(7-Cyclopropyl-3-methyl-2-oxo-2,3-dihydrooxazolo[4,5-b]pyridin-6-yl)phenyl)-2,6-difluorobenzamide,
2,6-Difluoro-N-(4-(1-methyl-2-oxo-1,2-dihydrooxazolo[5,4-b]pyridin-6-yl) phenyl)benzamide,
N-(4-(3,4-Dimethyl-2-oxo-2,3-dihydrobenzo[d]oxazol-5-yl)phenyl)-2,6-difluorobenzamide,
2,6-Difluoro-N-(4-(3-methyl-2-oxo-2,3-dihydrobenzo[d]oxazol-5-yl)phenyl) benzamide,
N-(5-(3,7-Dimethyl-2-oxo-2,3-dihydrobenzo[d]oxazol-6-yl)pyrazin-2-yl)-2,6-difluorobenzamide,
N-(4-(3,7-Dimethyl-2-oxo-2,3-dihydrobenzo[d]oxazol-6-yl)phenyl)-2,6-difluorobenzamide,
2,6-Difluoro-N-(4-(3-methyl-2-oxo-2,3-dihydrobenzo[d]oxazol-6-yl)phenyl) benzamide,
N-(4-(7-Ethyl-3-methyl-2-oxo-2,3-dihydrobenzo[d]oxazol-6-yl)phenyl)-2,6-difluorobenzamide,
N-(5-(3,7-Dimethyl-2-oxo-2,3-dihydrobenzo[d]oxazol-6-yl)pyridin-2-yl)-2,6-difluoro benzamide,
N-(6-(3,7-Dimethyl-2-oxo-2,3-dihydrobenzo[d]oxazol-6-yl)pyridin-3-yl)-2,6-difluoro benzamide,
N-(4-(1,7-Dimethyl-2-oxo-1,2-dihydrooxazolo[5,4-b]pyridin-6-yl)phenyl)-2,6-difluorobenzamide,
N-(5-(7-Ethyl-3-methyl-2-oxo-2,3-dihydrobenzo[d]oxazol-6-yl)pyrazin-2-yl)-2,6-difluorobenzamide,
N-(5-(7-Ethyl-3-methyl-2-oxo-2,3-dihydrobenzo[d]oxazol-6-yl)pyridin-2-yl)-2,6-difluoro benzamide,
N-(6-(7-Ethyl-3-methyl-2-oxo-2,3-dihydrobenzo[d]oxazol-6-yl)pyridin-3-yl)-2,6-difluoro benzamide,
N-(4-(7-Cyclopropyl-3-methyl-2-oxo-2,3-dihydro benzo[d]oxazol-6-yl) phenyl)-2,6-difluorobenzamide,
N-(6-(7-Cyclopropyl-3-methyl-2-oxo-2,3-dihydrobenzo[d]oxazol-6-yl)pyridin-3-yl)-2,6-difluorobenzamide, N-(5-(7-Cyclopropyl-3-methyl-2-oxo-2,3-dihydrobenzo[d]oxazol-6-yl)pyridin-2-yl)-2,6-difluorobenzamide,
N-(5-(7-Cyclopropyl-3-methyl-2-oxo-2,3-dihydrobenzo[d]oxazol-6-yl)pyrazin-2-yl)-2,6-difluorobenzamide,
N-(4-(3,6-Dimethyl-2-oxo-2,3-dihydrobenzo[d]oxazol-5-yl)phenyl)-2,6-difluorobenzamide,
N-(4-(3-Ethyl-6-methyl-2-oxo-2,3-dihydrobenzo[d]oxazol-5-yl)phenyl)-2,6-difluorobenzamide,
N-(4-(3-(Cyclopropylmethyl)-6-methyl-2-oxo-2,3-dihydrobenzo[d]oxazol-5-yl)phenyl)-2,6-difluorobenzamide,
2,6-Difluoro-N-(4-(3-(2-fluoroethyl)-6-methyl-2-oxo-2,3-dihydro benzo[d]oxazol-5-yl)phenyl)benzamide,
2,6-Difluoro-N-(4-(3-isopropyl-6-methyl-2-oxo-2,3-dihydro benzo[d]oxazol-5-yl)phenyl)benzamide,
N-(4-(3-(Difluoromethyl)-6-methyl-2-oxo-2,3-dihydrobenzo[d]oxazol-5-yl)phenyl)-2,6-difluorobenzamide,
2,6-Difluoro-N-(4-(6-methyl-2-oxo-3-(3,3,3-trifluoropropyl)-2,3-dihydrobenzo[d]oxazol-5-yl)phenyl) benzamide,
2,6-Difluoro-N-(4-(6-methyl-2-oxo-3-propyl-2,3-dihydrobenzo[d]oxazol-5-yl) phenyl)benzamide,
2,6-Difluoro-N-(4-(3-isobutyl-6-methyl-2-oxo-2,3-dihydrobenzo[d]oxazol-5-yl) phenyl)benzamide,
N-(4-(5-Cyclopropyl-3-methyl-2-oxo-2,3-dihydro oxazolo[4,5-b]pyridin-6-yl)phenyl)-2,6-difluorobenzamide,
N-(4-(5-Ethyl-3-methyl-2-oxo-2,3-dihydrooxazolo[4,5-b]pyridin-6-yl)phenyl)-2,6-difluorobenzamide,
N-(4-(3,5-dimethyl-2-oxo-2,3-dihydrooxazolo[4,5-b]pyridin-6-yl)phenyl)-2,6-difluorobenzamide,
2,6-Difluoro-N-(4-(3-methyl-2-oxo-2,3-dihydrooxazolo[4,5-b]pyridin-5-yl)phenyl)benzamide,
N-(4-(1,5-Dimethyl-2-oxo-1,2-dihydrooxazolo[5,4-b]pyridin-6-yl)phenyl)-2,6-difluorobenzamide,
4-(5-Cyclopropyl-3-methyl-2-oxo-2,3-dihydro benzo[d]oxazol-6-yl)-N-(2,6-difluorophenyl) benzamide,
N-(4-(5-Cyclopropyl-3-methyl-2-oxo-2,3-dihydro benzo[d]oxazol-6-yl)phenyl)-2,6-difluorobenzamide,
N-(4-(5-Ethyl-3-methyl-2-oxo-2,3-dihydro benzo[d]oxazol-6-yl)phenyl)-2,6-difluorobenzamide,
N-(4-(7-Chloro-3-methyl-2-oxo-2,3-dihydrobenzo[d]oxazol-6-yl)phenyl)-2,6-difluorobenzamide,
2,6-difluoro-N-(4-(3-(2-hydroxyethyl)-6-methyl-2-oxo-2,3-dihydro benzo[d]oxazol-5-yl)phenyl)benzamide,
2-Chloro-N-(4-(3,6-dimethyl-2-oxo-2,3-dihydrobenzo[d]oxazol-5-yl)phenyl)-6-fluorobenzamide,
N-(4-(3,6-Dimethyl-2-oxo-2,3-dihydro benzo[d]oxazol-5-yl)phenyl)-2-fluorobenzamide,
2-Chloro-N-(4-(3,6-dimethyl-2-oxo-2,3-dihydrobenzo[d]oxazol-5-yl)phenyl) benzamide,
N-(4-(3,6-Dimethyl-2-oxo-2,3-dihydrobenzo[d]oxazol-5-yl)phenyl)-2-fluoro-6-methylbenzamide,
N-(4-(3,4-Dimethyl-2-oxo-2,3-dihydrobenzo[d]oxazol-6-yl)phenyl)-2,6-difluorobenzamide,
N-(5-(3,6-dimethyl-2-oxo-2,3-dihydrobenzo[d]oxazol-5-yl)pyrazin-2-yl)-2,6-difluorobenzamide,
N-(6-(3,6-Dimethyl-2-oxo-2,3-dihydrobenzo[d]oxazol-5-yl)pyridin-3-yl)-2,6-difluoro benzamide,
N-(5-(3,6-Dimethyl-2-oxo-2,3-dihydrobenzo[d]oxazol-5-yl)pyridin-2-yl)-2,6-difluoro benzamide,
N-(2,6-Difluorophenyl)-4-(3,6-dimethyl-2-oxo-2,3-dihydrobenzo[d]oxazol-5-yl)benzamide,
5-(4-((2,6-Difluoro benzyl) amino)phenyl)-3,6-dimethyl benzo[d]oxazol-2(3H)-one,
N-(4-(3,5-Dimethyl-2-oxo-2,3-dihydrobenzo[d]oxazol-6-yl)phenyl)-2,6-difluorobenzamide,
N-(2,6-Difluorophenyl)-4-(3,5-dimethyl-2-oxo-2,3-dihydrobenzo[d]oxazol-6-yl)benzamide,
N-(2,6-Difluorophenyl)-2-(3,6-dimethyl-2-oxo-2,3-dihydrobenzo[d]oxazol-5-yl)thiazole-4-carboxamide,
N-(2,6-Difluorophenyl)-2-(3,6-dimethyl-2-oxo-2,3-dihydrobenzo[d]oxazol-5-yl)thiazole-5-carboxamide,
N-(3,5-Difluoropyridin-4-yl)-5-(3,6-dimethyl-2-oxo-2,3-dihydrobenzo[d]oxazol-5-yl) thiophene-2-carboxamide,
N-(3,5-Dichloropyridin-4-yl)-5-(3,6-dimethyl-2-oxo-2,3-dihydrobenzo[d]oxazol-5-yl)thiophene-2-carboxamide,
5-(3,6-Dimethyl-2-oxo-2,3-dihydrobenzo[d]oxazol-5-yl)-N-(3-methyl pyridin-4-yl)thiophene-2-carboxamide,
N-(5-(3,5-Dimethyl-2-oxo-2,3-dihydrobenzo[d]oxazol-6-yl)pyridin-2-yl)-2,6-difluorobenzamide,
N-(6-(3,5-Dimethyl-2-oxo-2,3-dihydrobenzo[d]oxazol-6-yl)pyridin-3-yl)-2,6-difluorobenzamide,
N-(5-(3,5-dimethyl-2-oxo-2,3-dihydrobenzo[d]oxazol-6-yl)pyrazin-2-yl)-2,6-difluorobenzamide,
N-(4-(3,5-Dimethyl-2-oxo-2,3-dihydrobenzo[d]oxazol-6-yl)-3-methylphenyl)-2,6-difluorobenzamide,
N-(4-(3,5-Dimethyl-2-oxo-2,3-dihydrobenzo[d]oxazol-6-yl)-2-methylphenyl)-2,6-difluorobenzamide,
N-(6-(5-Ethyl-3-methyl-2-oxo-2,3-dihydrobenzo[d]oxazol-6-yl)pyridin-3-yl)-2,6-difluoro benzamide,
N-(5-(5-Ethyl-3-methyl-2-oxo-2,3-dihydrobenzo[d]oxazol-6-yl)pyridin-2-yl)-2,6-difluoro benzamide,
N-(5-(5-Ethyl-3-methyl-2-oxo-2,3-dihydrobenzo[d]oxazol-6-yl)pyrazin-2-yl)-2,6-difluoro benzamide,
N-(5-(5-Cyclopropyl-3-methyl-2-oxo-2,3-dihydro benzo[d]oxazol-6-yl)pyridin-2-yl)-2,6-difluoro benzamide,
N-(5-(5-Cyclopropyl-3-methyl-2-oxo-2,3-dihydro benzo[d]oxazol-6-yl)pyrazin-2-yl)-2,6-difluorobenzamide,
N-(2,6-Difluorophenyl)-5-(5-ethyl-3-methyl-2-oxo-2,3-dihydrobenzo[d]oxazol-6-yl) thiophene-2-carboxamide,
5-(5-Cyclopropyl-3-methyl-2-oxo-2,3-dihydro benzo[d]oxazol-6-yl)-N-(2,6-difluorophenyl) thiophene-2-carboxamide,
N-(2,6-Difluorophenyl)-5-(3,5-dimethyl-2-oxo-2,3-dihydrobenzo[d]oxazol-6-yl)thiophene-2-carboxamide,
N-(6-(3-(Difluoromethyl)-6-methyl-2-oxo-2,3-dihydrobenzo[d]oxazol-5-yl)pyridin-3-yl)-2,6-difluorobenzamide,
N-(5-(3-(Difluoromethyl)-6-methyl-2-oxo-2,3-dihydrobenzo[d]oxazol-5-yl)pyridin-2-yl)-2,6-difluorobenzamide,
N-(5-(3-(Difluoromethyl)-6-methyl-2-oxo-2,3-dihydrobenzo[d]oxazol-5-yl)pyrazin-2-yl)-2,6-difluorobenzamide,
5-(4-((2,6-Difluorobenzyl)amino)phenyl)-3-(difluoromethyl)-6-methylbenzo[d]oxazol-2(3H)-one,
N-(5-(6-Ethyl-3-methyl-2-oxo-2,3-dihydrobenzo[d]oxazol-5-yl)pyrazin-2-yl)-2,6-difluoro benzamide,
N-(6-(6-Ethyl-3-methyl-2-oxo-2,3-dihydrobenzo[d]oxazol-5-yl)pyridin-3-yl)-2,6-difluoro benzamide,
N-(5-(6-Ethyl-3-methyl-2-oxo-2,3-dihydrobenzo[d]oxazol-5-yl)pyridin-2-yl)-2,6-difluoro benzamide,
N-(5-(6-Cyclopropyl-3-methyl-2-oxo-2,3-dihydro benzo[d]oxazol-5-yl)pyridin-2-yl)-2,6-difluorobenzamide,
N-(5-(6-Cyclopropyl-3-methyl-2-oxo-2,3-dihydro benzo[d]oxazol-5-yl)pyrazin-2-yl)-2,6-difluorobenzamide, N-(4-(6-Ethyl-3-methyl-2-oxo-2,3-dihydrobenzo[d]oxazol-5-yl)phenyl)-2,6-difluorobenzamide,
N-(5-(5-Cyclopropyl-3-methyl-2-oxo-2,3-dihydro oxazolo[4,5-b]pyridin-6-yl)pyrazin-2-yl)-2,6-difluorobenzamide,
N-(5-(5-Ethyl-3-methyl-2-oxo-2,3-dihydrooxazolo[4,5-b]pyridin-6-yl)pyrazin-2-yl)-2,6-difluorobenzamide,
N-(2,6-Difluorophenyl)-5-(6-ethyl-3-methyl-2-oxo-2,3-dihydrobenzo[d]oxazol-5-yl) thiophene-2-carboxamide,
5-(6-Cyclopropyl-3-methyl-2-oxo-2,3-dihydro benzo[d]oxazol-5-yl)-N-(2,6-difluorophenyl) thiophene-2-carboxamide,
N-(3,5-Difluoropyridin-4-yl)-4-(5-ethyl-3-methyl-2-oxo-2,3-dihydrobenzo[d]oxazol-6-yl) benzamide,
4-(5-Cyclopropyl-3-methyl-2-oxo-2,3-dihydro benzo[d]oxazol-6-yl)-N-(3,5-difluoropyridin-4-yl)benzamide,
N-(3,5-Difluoropyridin-4-yl)-4-(6-ethyl-3-methyl-2-oxo-2,3-dihydrobenzo[d]oxazol-5-yl) benzamide,
4-(6-Cyclopropyl-3-methyl-2-oxo-2,3-dihydro benzo[d]oxazol-5-yl)-N-(3,5-difluoropyridin-4-yl)benzamide,
N-(4-(6-Cyclopropyl-3-methyl-2-oxo-2,3-dihydro benzo[d]oxazol-5-yl)phenyl)-2,6-difluorobenzamide,
N-(4-(7-Cyclopropyl-3-(difluoromethyl)-2-oxo-2,3-dihydro benzo[d]oxazol-6-yl)phenyl)-2,6-difluorobenzamide,
2,6-Difluoro-N-(3-methyl-4-(3-methyl-2-oxo-2,3-dihydrooxazolo[4,5-b]pyridin-6-yl)phenyl)benzamide,
N-(4-(7-Cyclopropyl-3-methyl-2-oxo-2,3-dihydro benzo[d]oxazol-6-yl)-3-methylphenyl)-2,6-difluorobenzamide,
N-(4-(7-Cyclopropyl-3-methyl-2-oxo-2,3-dihydro benzo[d]oxazol-6-yl)-2-methylphenyl)-2,6-difluorobenzamide,
4-(7-Cyclopropyl-3-methyl-2-oxo-2,3-dihydro benzo[d]oxazol-6-yl)-N-(2,6-difluorophenyl) benzamide,
7-Cyclopropyl-6-(4-((2,6-difluorobenzyl)amino)phenyl)-3-methylbenzo[d]oxazol-2(3H)-one,
2-Chloro-N-(4-(7-cyclopropyl-3-methyl-2-oxo-2,3-dihydrobenzo[d]oxazol-6-yl)phenyl)-6-fluorobenzamide,
N-(4-(7-Cyclopropyl-3-methyl-2-oxo-2,3-dihydrobenzo[d]oxazol-6-yl)phenyl)-2-fluorobenzamide,
2-Chloro-N-(4-(7-cyclopropyl-3-methyl-2-oxo-2,3-dihydrobenzo[d]oxazol-6-yl)phenyl)benzamide,
2,6-Difluoro-N-(4-(4-methyl-3-oxo-3,4-dihydro-2H-pyrido[3,2-b][1,4]oxazin-7-yl)phenyl)benzamide,
N-(4-(4,8-Dimethyl-3-oxo-3,4-dihydro-2H-benzo[b][1,4]oxazin-7-yl)phenyl)-2,6-difluorobenzamide,
N-(4-(8-Ethyl-4-methyl-3-oxo-3,4-dihydro-2H-benzo[b][1,4]oxazin-7-yl)phenyl)-2,6-difluorobenzamide,
N-(4-(8-Cyclopropyl-4-methyl-3-oxo-3,4-dihydro-2H-benzo[b][1,4]oxazin-7-yl)phenyl)-2,6-difluorobenzamide,
N-(5-(8-Cyclopropyl-4-methyl-3-oxo-3,4-dihydro-2H-benzo[b][1,4]oxazin-7-yl)pyridin-2-yl)-2,6-difluorobenzamide,
N-(5-(8-Cyclopropyl-4-methyl-3-oxo-3,4-dihydro-2H-benzo[b][1,4]oxazin-7-yl)pyrazin-2-yl)-2,6-difluorobenzamide,
N-(6-(8-Cyclopropyl-4-methyl-3-oxo-3,4-dihydro-2H-benzo[b][1,4]oxazin-7-yl)pyridin-3-yl)-2,6-difluorobenzamide,
8-Cyclopropyl-7-(4-((2,6-difluorobenzyl)amino)phenyl)-4-methyl-2H-benzo[b][1,4]oxazin-3(4H)-one,
N-(4-(8-Cyclopropyl-4-methyl-3-oxo-3,4-dihydro-2H-pyrido[3,2-b][1,4]oxazin-7-yl)phenyl)-2,6-difluorobenzamide,
N-(4-(6-Cyclopropyl-4-methyl-3-oxo-3,4-dihydro-2H-benzo[b][1,4]oxazin-7-yl)phenyl)-2,6-difluorobenzamide,
6-Cyclopropyl-7-(4-((2,6-difluorobenzyl)amino)phenyl)-4-methyl-2H-benzo[b][1,4]oxazin-3(4H)-one,
N-(5-(6-Cyclopropyl-4-methyl-3-oxo-3,4-dihydro-2H-benzo[b][1,4]oxazin-7-yl)pyridin-2-yl)-2,6-difluorobenzamide,
N-(5-(6-Cyclopropyl-4-methyl-3-oxo-3,4-dihydro-2H-benzo[b][1,4]oxazin-7-yl)pyrazin-2-yl)-2,6-difluorobenzamide,
2-Chloro-N-(5-(6-cyclopropyl-4-methyl-3-oxo-3,4-dihydro-2H-benzo[b][1,4]oxazin-7-yl)pyrazin-2-yl)-6-fluorobenzamide,
N-(6-(6-Cyclopropyl-4-methyl-3-oxo-3,4-dihydro-2H-benzo[b][1,4]oxazin-7-yl)pyridin-3-yl)-2,6-difluorobenzamide,
4-(6-Cyclopropyl-4-methyl-3-oxo-3,4-dihydro-2H-benzo[b][1,4]oxazin-7-yl)-N-(3,5-difluoropyridin-4-yl)benzamide,
N-(4-(6-Ethyl-4-methyl-3-oxo-3,4-dihydro-2H-benzo[b][1,4]oxazin-7-yl)phenyl)-2,6-difluorobenzamide,
N-(5-(6-Ethyl-4-methyl-3-oxo-3,4-dihydro-2H-benzo[b][1,4]oxazin-7-yl)pyrazin-2-yl)-2,6-difluorobenzamide,
N-(5-(6-Ethyl-4-methyl-3-oxo-3,4-dihydro-2H-benzo[b][1,4]oxazin-7-yl)pyridin-2-yl)-2,6-difluorobenzamide,
N-(4-(4,6-Dimethyl-3-oxo-3,4-dihydro-2H-benzo[b][1,4]oxazin-7-yl)phenyl)-2,6-difluorobenzamide,
N-(6-(4,6-Dimethyl-3-oxo-3,4-dihydro-2H-benzo[b][1,4]oxazin-7-yl)pyridin-3-yl)-2,6-difluorobenzamide,
N-(5-(4,6-Dimethyl-3-oxo-3,4-dihydro-2H-benzo[b][1,4]oxazin-7-yl)pyridin-2-yl)-2,6-difluorobenzamide,
N-(5-(4,6-Dimethyl-3-oxo-3,4-dihydro-2H-benzo[b][1,4]oxazin-7-yl)pyrazin-2-yl)-2,6-difluorobenzamide,
7-(4-((2,6-Difluorobenzyl) amino)phenyl)-4,6-dimethyl-2H-benzo[b][1,4]oxazin-3(4H)-one,
2,6-Difluoro-N-(4-(2,2,4-trimethyl-3-oxo-3,4-dihydro-2H-benzo[b][1,4]oxazin-7-yl) phenyl)benzamide,
2,6-Difluoro-N-(4-(2,2,4-trimethyl-3-oxo-3,4-dihydro-2H-benzo[b][1,4]oxazin-6-yl)phenyl)benzamide,
N-(4-(4,7-Dimethyl-3-oxo-3,4-dihydro-2H-benzo[b][1,4]oxazin-6-yl)phenyl)-2,6-difluorobenzamide,
N-(4-(7-Cyclopropyl-4-methyl-3-oxo-3,4-dihydro-2H-benzo[b][1,4]oxazin-6-yl)phenyl)-2,6-difluorobenzamide,
N-(4-(7-Ethyl-4-methyl-3-oxo-3,4-dihydro-2H-benzo[b][1,4]oxazin-6-yl)phenyl)-2,6-difluorobenzamide,
N-(5-(7-Ethyl-4-methyl-3-oxo-3,4-dihydro-2H-benzo[b][1,4]oxazin-6-yl)pyrazin-2-yl)-2,6-difluorobenzamide,
N-(5-(7-Ethyl-4-methyl-3-oxo-3,4-dihydro-2H-benzo[b][1,4]oxazin-6-yl)pyridin-2-yl)-2,6-difluorobenzamide,
N-(3,5-Difluoropyridin-4-yl)-4-(7-ethyl-4-methyl-3-oxo-3,4-dihydro-2H-benzo[b][1,4]oxazin-6-yl)benzamide,
N-(5-(7-Cyclopropyl-4-methyl-3-oxo-3,4-dihydro-2H-benzo[b][1,4]oxazin-6-yl)pyrazin-2-yl)-2,6-difluorobenzamide,
4-(7-Cyclopropyl-4-methyl-3-oxo-3,4-dihydro-2H-benzo[b][1,4]oxazin-6-yl)-N-(3,5-difluoropyridin-4-yl)benzamide,
N-(3,5-Difluoropyridin-4-yl)-4-(6-ethyl-4-methyl-3-oxo-3,4-dihydro-2H-benzo[b][1,4]oxazin-7-yl)benzamide,
N-(5-(7-Cyclopropyl-4-methyl-3-oxo-3,4-dihydro-2H-benzo[b][1,4]oxazin-6-yl)pyridin-2-yl)-2,6-difluorobenzamide,
N-(2,6-Difluorophenyl)-5-(3,6-dimethyl-2-oxo-2,3-dihydrobenzo[d]oxazol-5-yl)thiophene-2-carboxamide and N-(4-(3,7-Dimethyl-2-oxo-2,3-dihydrobenzo[d]oxazol-5-yl)phenyl)-2,6-difluorobenzamide or a pharmaceutically acceptable salt thereof.

13. A pharmaceutical composition comprising one or more compounds of Formula (I) according to claim 1 and one or more pharmaceutically acceptable excipients.

14. A method of treating, managing and/or lessening diseases or disorders, syndromes or conditions associated with the modulation of calcium release-activated calcium (CRAC) channel in a subject in need thereof wherein the method comprises administering to the subject a therapeutically effective amount of a compound of claim 1 or a pharmaceutically acceptable salt thereof.

15. The method of claim 14, wherein the diseases, disorders, syndromes or conditions associated with the modulation of calcium release-activated calcium (CRAC) channel are selected from the group consisting of inflammatory diseases, autoimmune diseases, allergic disorders, organ transplant, cancer and cardiovascular disorders.

16. The method of claim 14, wherein the disease is rheumatoid arthritis, multiple sclerosis and psoriasis.

17. The method of claim 15, wherein the allergic disorders are selected from asthma, chronic obstructive pulmonary disorder (COPD) or respiratory disorders.

18. The method of claim 15, wherein inflammatory diseases are selected from rheumatoid arthritis, osteoarthritis, ankylosing spondylitis, psoriatic arthritis, chronic obstructive pulmonary disease (COPD), inflammatory bowel diseases, pancreatitis, peripheral neuropathy, multiple sclerosis (MS) and inflammation associated with cancer.

19. A process for the preparation of compound of Formula (I):

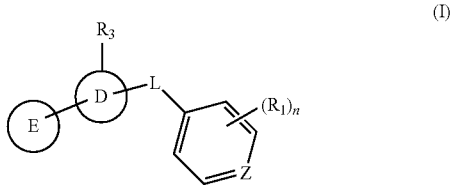

where ring D, ring E, L, Z, $R_1$, $R_2$, $R_3$, and "n" are as described in claim 1;

the process comprising any of the method (A) to (D):

method (A):

reacting a borate compound of Formula (1) with various halobenzamides of Formula (2) where X' is halogen or OTf, to give compound of Formula (1) by using suitable reagents $Pd(PPh_3)_2Cl_2$, $Pd_2dba_3$, $Pd(PPh_3)_4$, or $Pd(OAc)_2$ and suitable ligand 2,2'-bis(diphenylphosphino)-1,1'-binaphthyl (BINAP), xanthophos, or triphenylphosphine

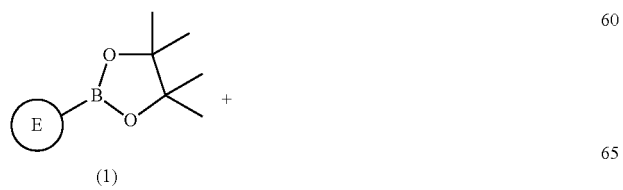

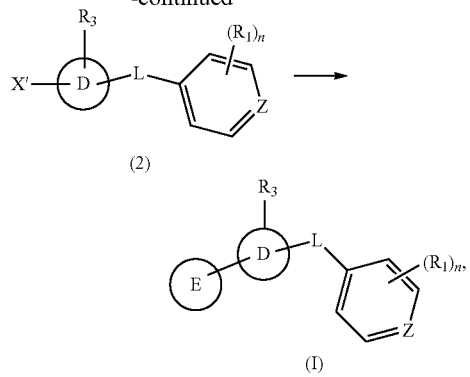

method (B)

reacting a compound of Formula (3) where X' is halogen or OTf, with compound of Formula (4) where P is pinacolatoboronate or stannane, to give compound of Formula (I) by using suitable reagents $Pd(PPh_3)_2Cl_2$, $Pd_2dba_3$, $Pd(PPh_3)_4$, or $Pd(OAc)_2$ and a suitable ligand 2,2'-bis(diphenylphosphino)-1,1'-binaphthyl (BINAP), xanthophos, or triphenylphosphine

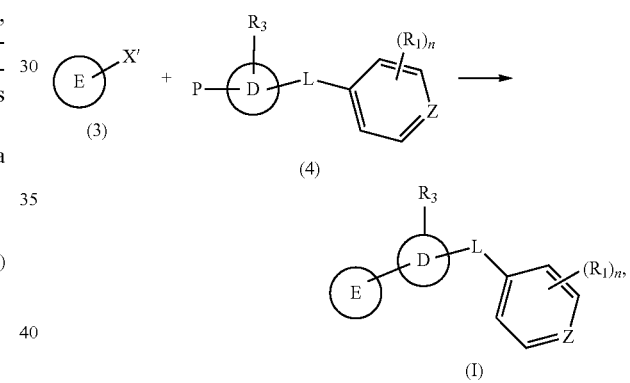

method (C), which comprising the steps of a) reacting a borate derivative of Formula (1) with compound of Formula (5) where X' is halogen or OTf, and Y' is $NHR_2$, or COOH, COOalkyl or COCl, to give compound of Formula (7) by using suitable reagents $Pd(PPh_3)_2Cl_2$, $Pd_2dba_3$, $Pd(PPh_3)_4$, or $Pd(OAc)_2$ and suitable ligand 2,2'-bis(diphenylphosphino)-1,1'-binaphthyl (BINAP), xanthophos, or triphenylphosphine

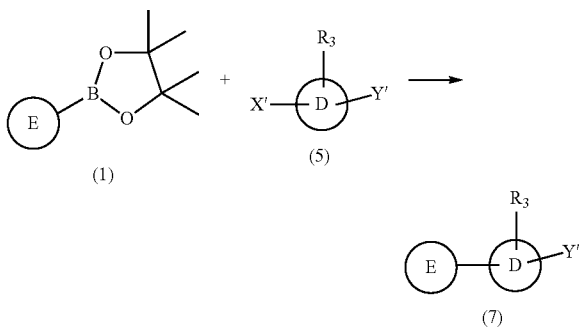

b) coupling of compound of said compound of Formula (7), with compound of Formula (8) Y″ is COOH, COOalkyl, COCl or NHR2, to give compound of Formula (1) using suitable coupling reagents

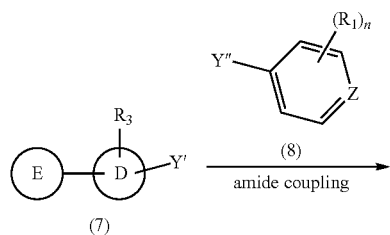

(7)

amide coupling (8)

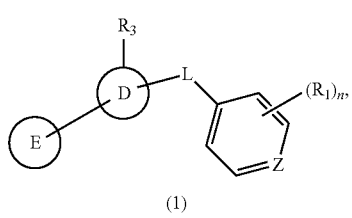

(1)

method (D), which comprising the steps of
c) reacting a Formula (3) where X' is halogen or OTf, with compound of Formula (6) where P is pinacolatoboronate or stannane and Y' is NHR$_2$, or COOH, COOalkyl or COCl, to give compound of Formula (7) by using suitable reagents Pd(PPh$_3$)$_2$Cl$_2$, Pd$_2$dba$_3$, Pd(PPh$_3$)$_4$, or Pd(OAc)$_2$ and suitable ligand 2,2'-bis(diphenylphosphino)-1,1'-binaphthyl (BINAP), xanthophos, or triphenylphosphine

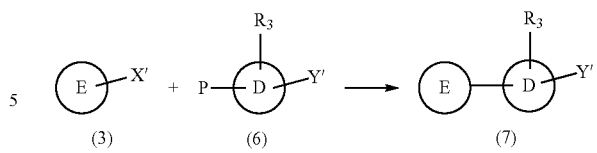

(3)   (6)   (7)

d) coupling of compound of said compound of Formula (7) with compound of Formula (8) where Y″ is COOH, COOalkyl, COCl or NHR$_2$, to give compound of Formula (1) using suitable coupling reagents

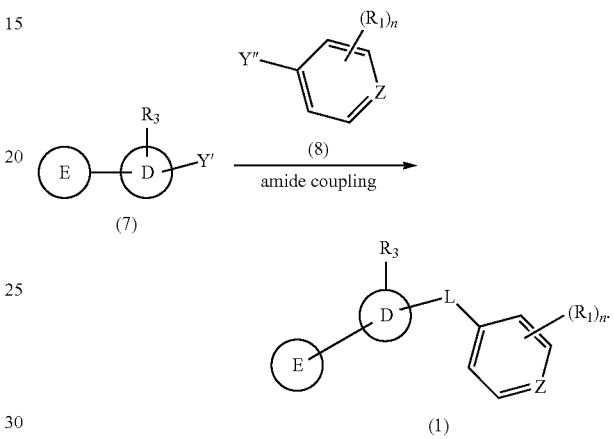

* * * * *